United States Patent [19]
Shiraishi et al.

[11] Patent Number: 5,716,971
[45] Date of Patent: Feb. 10, 1998

[54] PYRIDINE DERIVATIVES, THEIR PRODUCTION AND USE

[75] Inventors: Mitsuru Shiraishi, Amagasaki; Toshifumi Watanabe, Kawachinagano, both of Japan

[73] Assignee: Takeda Chemical Industries, Ltd., Osaka, Japan

[21] Appl. No.: 694,834

[22] Filed: Aug. 9, 1996

Related U.S. Application Data

[63] Continuation of Ser. No. 233,966, Apr. 28, 1994, abandoned.

[30] Foreign Application Priority Data

Apr. 28, 1993 [JP] Japan ................. 5-102880
Mar. 25, 1994 [JP] Japan ................. 6-055756

[51] Int. Cl.$^6$ .......... C07D 213/63; C07D 213/79; C07D 213/84; C07D 213/89
[52] U.S. Cl. .......... 514/336; 514/346; 514/352; 514/357; 514/344; 546/283.7; 546/286; 546/287; 546/289; 546/315; 546/318; 546/326; 546/330; 546/297; 546/300
[58] Field of Search .......... 546/286, 287, 546/289, 315, 318, 326, 330, 283.7, 297, 300; 514/344, 346, 336, 352, 357

[56] References Cited

U.S. PATENT DOCUMENTS

| | | | |
|---|---|---|---|
| 4,297,359 | 10/1981 | Van Zorge | 514/336 |
| 4,798,841 | 1/1989 | Downs et al. | 514/357 |
| 4,971,985 | 11/1990 | Otsuka et al. | 514/357 |
| 5,039,685 | 8/1991 | Knutsen et al. | 514/326 |
| 5,071,860 | 12/1991 | Alig et al. | 514/332 |
| 5,086,051 | 2/1992 | James et al. | 514/228.2 |

FOREIGN PATENT DOCUMENTS

| | | | |
|---|---|---|---|
| 0 366 006 | 5/1990 | European Pat. Off. | 546/333 |
| 2 413 986 | 11/1974 | Germany | 546/18 |
| 4-99767 | 8/1990 | Japan | 546/333 |
| 1 510 977 | 5/1978 | United Kingdom | 546/268.1 |
| WO93/21146 | 10/1993 | WIPO . | |

OTHER PUBLICATIONS

"The Merck Index", Eleventh Edition, Merck & Co., U.S.A. *Progabide, entry 7782 (1989).
Cameron et al., Chemical Abstracts, vol. 97, No. 25, 1982, Columbus, Ohio USA Abstract No. 215955df.
Hodogaya Chemical Co., Chemical Abstracts, vol. 97, No. 24, 1982, Columbus, Ohio USA Abstract No. 199542j.
Duennenberger et al., Chemical Abstracts, vol. 55, No. 20, 2 Oct., 1961, Columbus, Ohio Abstract No. 19747i.
Sidgwick, The Organic Chemistry Of Nitrogen, p. 382 Clarendon Press Oxford 1966.

*Primary Examiner*—Alan L. Rotman
*Attorney, Agent, or Firm*—Wenderoth, Lind & Ponack

[57] ABSTRACT

Pyridine derivatives of the formula

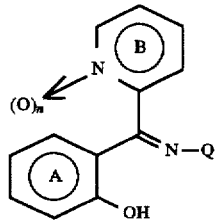

wherein the ring A stands for an optionally further substituted benzene ring; the ring B stands for an optionally substituted pyridine ring; Q stands for hydroxyl group, or $OQ^1$ or $Q^1$ wherein $Q^1$ stands for an optionally substituted aliphatic hydrocarbon group; and n denotes 0 or 1, or their salts, which have potassium.channel opening activity and are useful as therapeutic agents of circulatory diseases such as angina pectoris, hypertension, etc.

40 Claims, No Drawings

PYRIDINE DERIVATIVES, THEIR PRODUCTION AND USE

This application is a continuation of now abandoned application Ser. No. 233,966, filed Apr. 28, 1994.

This invention relates to novel pyridine derivatives useful as medicines, a method of producing them and pharmaceutical compositions containing them.

The novel pyridine derivatives of this invention have smooth muscle relaxation activities, coronary blood flow increasing activities and antihypertensive activities, and have therapeutic and prophylactic effects against, for example, circulatory diseases such as angina pectoris, cardiac infarction, cardiac insufficiency, arrhythmia and hypertension; respiratory diseases such as asthma; cerebral diseases such as cerebrovascular contraction, apoplectic stroke and epilepsy; enuresis; peptic ulcer; hypersensitive intestinal disturbances; and alopecia.

Recently, drugs of a new type called a potassium channel opener exhibiting smooth muscle relaxation activities by opening (activating) the potassium channel have attracted attention. For example, chroman-3-ol derivatives which have the potassium channel opening (activating)activity and exhibit antihypertensive activity on spontaneous hypertensive rats are disclosed in JPA S58(1983)-67683 corresponding to EPA 76075, J. Med. Chem., 29, pp. 2194–2201 (1986) and Br. J. Pharmac. 88, pp. 103–111 (1986). In U.S. Pat. No. 4057636, cyanoguanidine derivatives having antihypertensive activities is disclosed. However, 2-(2-hydroxybenzoyl) pyridine derivatives having potassium channel opening activities have not been known yet.

And, benzoyl pyridine O-substituted oxime derivatives are disclosed in JPA S55(1980)-19288 corresponding to EPA 7679, JPA H2(1990)-115166 corresponding to EPA 366006 and JPA H4(1992)-99767.

In JPA S55(1980)-19288, there is disclosed a compound having the activity of suppressing ulcer, which is represented by the formula Het—(CH₂)ₘ—C—(CH₂)ₙ—Ar
          ‖
          N
          |
          OR wherein Het stands for 2-, 3- or 4-pyridinyl group which is, in some cases, substituted with one or more of a halogen atom, a $C_{1-6}$ alkyl group or a $C_{1-6}$ alkoxy group; Ar stands for phenyl group or 5- or 6-membered monocyclic heterocyclic group which are, in some cases, substituted with a halogen atom, a $C_{1-6}$ alkyl group, a $C_{1-6}$ alkoxy group, trifluoromethyl group or hydroxymethyl group; R stands for a $C_{1-3}$ alkyl group; and m and n each denotes 0 or 1, provided that, in no case, m+n=2, or its N-oxide or its pharmaceutically acceptable salts.

In JPA H2(1990)-115166, there is disclosed a compound having the calmodulin-antagonistic activity, which is represented by the formula

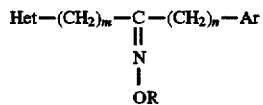

wherein Ar stands for an optionally substituted aromatic cyclic group or heterocyclic group; X stands for —(CH₂)ₘ—, —(CH₂)ₘ—Y— or —CH₂—(CH—CH)ₙ—, wherein m denotes an integer of 1 to 5, n denotes an integer of 1 to 2 and Y stands for O or S; and R stands for an optionally substituted phenyl group, naphthyl group, cycloalkyl group or heterocyclic group, or its salts.

In JPA H4(1992)-99767, there is disclosed a herbicidal composition, which is characterized by containing 3-benzoylpyridine O-benzyl oximes as an active principle, represented by the formula

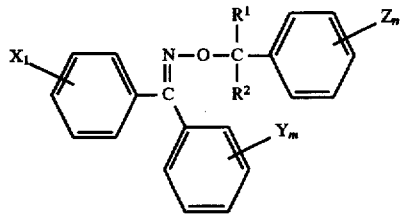

wherein $R^1$ stands H, a $C_{1-4}$ alkyl group or a halogen atom; $R^2$ stands for H or methyl group; X stands for a halogen atom; l denotes 0, 1 or 2; Y stands for a halogen atom, a $C_{1-4}$ alkyl group or phenyl group; m denotes 0, 1 or 2; Z stands for a halogen atom, a $C_{1-4}$ alkyl group, a $C_{1-4}$ alkoxy group, a $C_{1-4}$ haloalkoxy group, a $C_{1-4}$ haloalkylthio group, a $C_{1-4}$ alkylsulfonyl group, a $C_{1-4}$ alkoxy-carbonyl group, cyano group or nitro group, and n denotes 0, 1 or 3, provided that, when n is 2, two Z's can stands for 4-methylenedioxy group.

In JPA S51(1976)-48673 corresponding to GBA 1510977, there is disclosed 4-, 3- or 2-(O-hydroxybenzoyl)-pyridine, etc., as the materials employed for the production of a compound represented by the formula

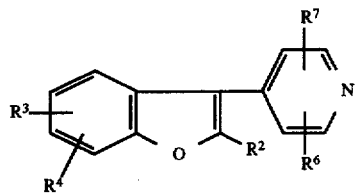

wherein $R^2$ stands for H or a lower alkyl group; $R^3$ and $R^4$ independently stand for H, a lower alkyl group, a lower alkoxy group, a halogen atom whose atomic number is up to 35; and $R^3$ can also stand for trifluoromethyl group, a lower 1-hydroxyalkyl group, a lower alk-1-enyl group or respectively $C_{5-8}$ hydroxyalkyl group, cycloalk-1-enyl group or cycloalkyl group; and $R^3$ and $R^4$, taken together, form 1,3-butadienylene group corresponding to trimethylene group, tetramethylene group or condensed benzene nucleus; $R^6$ and $R^7$ each stands for H or both stand for an alkyl group having not more than 6 carbon atoms.

However, no concrete disclosure that benzoyl group in these benzoyl pyridine O-substituted oxime derivatives is optionally substituted with hydroxyl group is given at all, and, besides, no disclosure that these O-substituted oxime derivatives have potassium channel opening activity is given at all.

The present invention is to provide novel pyridine derivatives and their salts which have smooth muscle relaxation activities, coronary blood flow increasing activities and antihypertensive activities, and have therapeutic and prophylactic activities against circulatory diseases such as angina pectoris, arrhythmia, cardiac insufficiency, cardiac infarction and hypertension, cerebral diseases such as cerebrovascular contraction, apoplectic stroke and epilepsia, asthma and urinary incontinence, and, besides, are useful for topical therapy of alopecia.

The present inventors studied intensively on benzoyl pyridine derivatives, and, as the result, synthesized new pyridine derivatives represented by

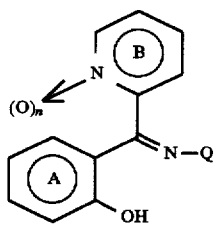

[I]

wherein the ring A stands for an optionally further substituted benzene ring;

the ring B stands for an optionally substituted pyridine ring;

Q stands for a hydroxyl group, $OQ^1$ or $Q^1$ wherein $Q^1$ stands for an optionally substituted aliphatic hydrocarbon group; and n denotes 0 or 1, or their salts (hereinafter simply called Compound [I]) having the chemical structure characterized by having hydroxyl group at the 2-position of the benzoyl group, and found that this Compound [I] or its salt has, unexpectedly, excellent potassium channel opening activities. Based on this finding, the present invention was accomplished.

More specially, the present invention relates to:

1) a compound represented by the formula [I] or its salt, 2) a compound as described in the above 1), wherein the substituent on the benzene ring is selected from the group consisting of (1) a halogen, (2) cyano group, (3) nitro group, (4) an acyl group, (5) an optionally substituted amino group, (6) an optionally substituted alkoxy group, (7) an optionally esterified or amidated carboxyl group, (8) an optionally esterified or amidated sulfinic acid or sulfonic acid, (9) an optionally substituted mercapto group, (10) an optionally substituted hydrocarbon group, (11) a divalent hydrocarbon group which may be bonded through carbonyl group, and (12) =N—O—N=, 3) a compound as discribed in the above 1), wherein the substituent on the benzene ring is selected from the group consisting of (i) a halogen, (ii) cyano group, (iii) nitro group, (iv) an acyl group, (v) an optionally substituted amino group, (vi) an optionally substituted alkoxy group, (vii) an optionally substituted mercapto group, or (viii) an optionally substituted hydrocarbon group, 4) a compound as described in the above 1), wherein the substituent on the benzene ring is selected from the group consisting of (i) a halogen, (ii) cyano group, (iii) nitro group, (iv) a $C_{1-10}$ acyl group, (v) an amino group which may be substituted with a $C_{1-4}$ alkyl, (vi) a $C_{1-4}$ alkoxy group which may be substituted with halogen, (vii) a $C_{1-4}$ alkylthio group, or (viii) a $C_{1-4}$ hydrocarbon group which may be substituted with a halogen, 5) a compound as described in the above 1), wherein the benzene ring is substituted with a halogen or cyano, 6) a compound as described in the above 1), wherein the ring A stands for

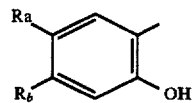

wherein Ra stands for a halogen, cyano group, nitro group, a $C_{1-10}$ acyl group, a $C_{1-4}$ alkoxy group, a halogeno-$C_{1-4}$ alkoxy group, a $C_{1-4}$ alkylthio group, a halogeno-$C_{1-4}$ alkyl group or a hydrocarbon group; and Rb stands for H, a halogen, cyano group, nitro group, a $C_{1-4}$ acyl group, an amino group, a $C_{1-4}$ alkylamino group, a $C_{1-4}$ alkoxy group, a $C_{1-4}$ alkylthio group, a $C_{1-4}$ hydrocarbon group or halogeno-$C_{1-4}$ alkyl group, 7) a compound as described in the above 1), wherein the benzene ring may be substituted with 1 to 3 electron-attracting groups, 8) a compound as described in the above 1), wherein the ring A stands for

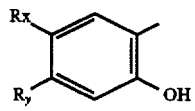

wherein Rx and Ry each stands for an electron-attracting group, 9) a compound as described in the above 7) and 8), wherein the electron-attracting group stands for a halogen, cyano group, nitro group, trifluoromethyl group, pentafluoroethyl group, trifluoromethoxy group, pentafluoroethoxy group or a $C_{1-10}$ acyl group, 10) a compound as described in the above 1), wherein the ring B stands for a substituted pyridine ring, 11) a compound as described in the above 1) and 10), wherein the substituent on the ring B is selected from the group consisting of (1) a halogen, (2) cyano group, (3) an optionally substituted amino group, (4) an acyl group, (5) an optionally esterified or amidated carboxyl group, (6) an optionally substituted alkoxy group, (7) an optionally substituted mercapto group, (8) an optionally substituted hydrocarbon group, and (9) $OR^2$ wherein $R^2$ stands for H or a hydroxyl-protecting group, 12) a compound as described in the above 1) and 10), wherein the substituent on the ring B is selected from the group consisting of (1) a halogen, (2) cyano group, (3) an amino group, (4) a $C_{1-10}$ acyl or 1,3-dioxolan-2-yl group, (5) a carboxyl, carbamoyl or $C_{1-4}$ alkoxycarbonyl group, (6) a $C_{1-4}$ alkoxy group, (7) a $C_{1-4}$ alkylthio group, (8) a $C_{1-4}$ hydrocarbon group which may be substituted with a hydroxyl, hydroxylmino, halogen or $C_{1-4}$ alkoxy, and (9) $OR^2$ wherein $R^2$ stands for H or a hydroxyl-protecting group, 13) a compound as described in the above 1) and 10), wherein the ring B stands for

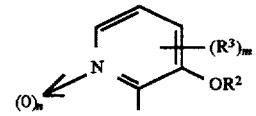

wherein $R^2$ stands for H or a hydroxyl-protecting group; $R^3$ stands for a halogen, cyano, $C_{1-4}$ alkoxy, $C_{1-4}$ alkyl or halogeno-$C_{1-4}$ alkyl group; and m and n each denotes 0 or 1, 14) a compound as described in the above 13), wherein m is 0.

15) a compound as described in the above 1), wherein the ring B stands for a pyridine ring which may be substituted with 1 or 2 substituents selected a halogen, $C_{1-4}$ alkoxy group, $C_{1-4}$ alkyl, halogeno-$C_{1-4}$ alkyl and $OR^2$ wherein $R^2$ stands for H or a hydroxyl-protecting group, 16) a compound as described in the above 1), which is a Z-isomer.

17) a compound as described in the above 1), which is a compound of the formula:

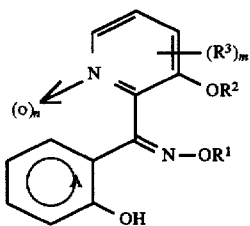

wherein the ring A stands for an optionally further substituted benzene ring; $R^1$ stands for H or an optionally substituted aliphatic hydrocarbon group; $R^2$ stands for H or a hydroxyl-protecting group; $R^3$ stands for a halogen, cyano, $C_{1-4}$ alkoxy, $C_{1-4}$ alkyl or halogeno-$C_{1-4}$ alkyl group; and m and n each denotes 0 or 1.

18) a compound as described in the above 17), wherein $R^3$ stands for a halogen, $C_{1-4}$ alkoxy group, $C_{1-4}$ alkyl or halogeno-$C_{1-4}$ alkyl group.

19) a compound as described in the above 17), wherein $R^1$ stands for H, $C_{1-10}$ alkyl, $C_{3-10}$ alkenyl, $C_{3-10}$ alkynyl, $C_{3-8}$ cycloalkyl, $C_{5-8}$ cycloalkenyl or benzyl group.

20) a compound as described in the above 17), wherein $R^1$ is t-butyl group.

21) a compound as described in the above 17), wherein m is 0.

22) a compound as described in the above 17), wherein the ring A stands for

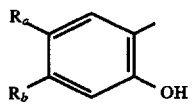

wherein Ra stands for a halogen, cyano group, nitro group, a $C_{1-10}$ acyl group, a $C_{1-4}$ alkoxy group, a halogeno-$C_{1-4}$ alkoxy group, a $C_{1-4}$ alkylthio group, a halogeno-$C_{1-4}$ alkyl group or a $C_{1-4}$ hydrocarbon-group; and Rb stands for H, a halogen, cyano group, nitro group, a $C_{1-10}$ acyl group, an amino group, a $C_{1-4}$ alkylamino group, a $C_{1-4}$ alkoxy group, a $C_{1-4}$ alkylthio group, a $C_{1-4}$ hydrocarbon group or a halogeno-$C_{1-4}$ alkyl group.

23) a compound as described in the above 22), wherein Ra stands for a halogen, cyano group, nitro group, a $C_{1-4}$ alkoxy group, a halogeno-$C_{1-4}$ alkyl group or a $C_{1-4}$ alkyl group; and Rb stands for H, a halogen or a $C_{1-4}$ alkyl group.

24) a compound as described in the above 1), which is a compound of the formula:

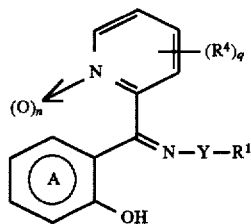

wherein the ring A stands for an optionally further substituted benzene ring; $R^1$ stands for H or an optionally substituted aliphtic hydrocarbon group; $R^4$ stands for (1) a halogen, (2) cyano group, (3) an amino group, (4) a $C_{1-10}$ acyl or 1,3-dioxolan-2-yl group, (5) a carboxyl, carbamoyl or $C_{1-4}$ alkoxycarbonyl group, (6) a $C_{1-4}$ alkoxy group, (7) a $C_{1-4}$ alkylthio group, or (8) a $C_{1-4}$ hydrocarbon group which may be substituted with a hydroxyl, a hydroxylmino, a halogen or $C_{1-4}$ alkoxy; Y stands for O or $CH_2$; n denotes 0 or 1; and q denotes 0, 1 or 2.

25) a compound as described in the above 24), wherein n denotes 1.

26) a compound as described in the above 24), wherein q denotes 0 or 1.

27) a compound as described in the above 24), wherein $R^4$ stands for a halogen, a $C_{1-4}$ alkyl group or a $C_{1-4}$ alkoxy group.

28) a compound as described in the above 24), wherein $R^1$ stands for a branched $C_{3-8}$ alkyl or cycloalkyl group.

29) a compound as described in the above 24), wherein $R^1$ is t-butyl group.

30) a compound as described in the above 24), wherein the ring A stands for

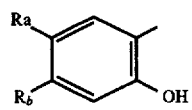

wherein Ra stands for a halogen, cyano group, nitro group, a $C_{1-10}$ acyl group, a $C_{1-4}$ alkoxy group, a halogeno-$C_{1-4}$ alkoxy group, a $C_{1-4}$ alkylthio group, a halogeno-$C_{1-4}$ alkyl group or a $C_{1-4}$ hydrocarbon group; and Rb stands for H, a halogen, cyano group, nitro group, a $C_{1-4}$ acyl group, an amino group, a $C_{1-4}$ alkylamino group, a $C_{1-4}$ alkoxy group, a $C_{1-4}$ alkylthio group, a $C_{1-4}$ hydrocarbon group or a halogeno-$C_{1-4}$ alkyl group.

31) a compound as described in the above 30), wherein Ra stands for a halogen, cyano group, nitro group, a $C_{1-4}$ alkoxy group, a halogeno-$C_{1-4}$ alkyl group or a alkyl group; and Rb stands for H, a halogen or a $C_{1-4}$ alkyl group.

32) a compound as described in the above 1), which is (Z)-2-(5-chloro-4-fluoro-2-hydroxybenzoyl)-3-hydroxypyridine N-oxide O-t-butyloxime or its salt, (Z)-2-(5-bromo-4-chloro-2-hydroxybenzoyl)-3-hydroxypyridine N-oxide O-t-butyloxime or its salt, (Z)-2-(5-bromo-4-fluoro-2-hydroxybenzoyl)-3-hydroxypyridine N-oxide O-t-butyloxime or its salt, (Z)-2-(5-bromo-4-cyano-2-hydroxybenzoyl)-3-hydroxypyridine O-t-butyloxime or its salt, (Z)-2-(5-bromo-4-cyano-2-hydroxybenzoyl)-3-hydroxypyridine N-oxide O-t-butyloxime or its salt, (Z)-2-(5-chloro-4-cyano-2-hydroxybenzoyl)-3-hydroxypyridine N-oxide O-t-butyloxime or its salt,
(Z)-2-(5-cyano-4-chloro-2-hydroxybenzoyl)-3-hydroxypyridine N-oxide O-t-butyloxime or its salt,
(Z)-2-(5-fluoro-4-cyano-2-hydroxybenzoyl)-3-hydroxypyridine N-oxide O-t-butyloxime or its salt,
(Z)-2-(5-cyano-4-fluoro-2-hydroxybenzoyl)-3-hydroxypyridine N-oxide O-t-butyloxime or its salt, or
(Z)-2-(4,5-dicyano-2-hydroxybenzoyl)-3-hydroxypyridine N-oxide O-t-butyloxime or its salt, 33) a compound as described in the above 1), which is (Z)-2-(5-chloro-4-fluoro-2-hydroxybenzoyl)-3-acetoxypyridine N-oxide O-t-butyloxime or its salt,
(Z)-2-(5-bromo-4-chloro-2-hydroxybenzoyl)-3-acetoxypyridine N-oxide O-t-butyloxime or its salt,
(Z)-2-(5-bromo-4-fluoro-2-hydroxybenzoyl)-3-acetoxypyridine N-oxide O-t-butyloxime or its salt,
(Z)-2-(5-bromo-4-cyano-2-hydroxybenzoyl)-3-acetoxypyridine O-t-butyloxime or its salt,
(Z)-2-(5-bromo-4-cyano-2-hydroxybenzoyl)-3-acetoxypyridine N-oxide O-t-butyloxime or its salt,
(Z)-2-(5-chloro-4-cyano-2-hydroxybenzoyl)-3-acetoxypyridine N-oxide O-t-butyloxime or its salt,
(Z)-2-(5-cyano-4-chloro-2-hydroxybenoyl)-3-acetoxypyridine N-oxide O-t-butyloxime or its salt,
(Z)-2-(5-fluoro-4-cyano-2-hydroxybenzoyl)-3-acetoxypyridine N-oxide O-t-butyloxime or its salt,
(Z)-2-(5-cyano-4-fluoro-2-hydroxybenzoyl)-3-acetoxypyridine N-oxide O-t-butyloxime or its salt,
or (Z)-2-(4,5-dicyano-2-hydroxybenzoyl)-3-acetoxypyridine N-oxide O-t-butyloxime or its salt, 34) a compound as described in the above 1), which is (Z)-2-(5-chloro-4-fluoro-2-hydroxybenzoyl)-3-pivaloyloxypyridine N-oxide O-t-butyloxime or its salt,
(Z)-2-(5-bromo-4-chloro-2-hydroxybenzoyl)-3-pivaloyloxypyridine N-oxide O-t-butyloxime or its salt,
(Z)-2-(5-bromo-4-fluoro-2-hydroxybenzoyl)-3-pivaloyloxypyridine N-oxide O-t-butyloxime or its salt,
(Z)-2-(5-bromo-4-cyano-2-hydroxybenzoyl)-3-pivaloyloxypyridine O-t-butyloxime or its salt,
(Z)-2-(5-bromo-4-cyano-2-hydroxybenzoyl)-3-pivaloyloxypyridine N-oxide O-t-butyloxime or its salt,
(Z)-2-(5-chloro-4-cyano-2-hydroxybenzoyl)-3-pivaloyloxypyridine N-oxide O-t-butyloxime or its salt,
(Z)-2-(5-cyano-4-chloro-2-hydroxybenzoyl)-3-pxvaloyloxypyridine N-oxide O-t-butyloxime or its salt,
(Z)-2-(5-fluoro-4-cyano-2-hydroxybenzoyl)-3-pivaloyloxypyridine N-oxide O-t-butyloxime or its salt,
(Z)-2-(5-cyano-4-fluoro-2-hydroxybenzoyl)-3-pivaloyloxypyridine N-oxide O-t-butyloxime or its salt,
or (Z)-2-(4,5-dicyano-2-hydroxybenzoyl)-3-pivaloyloxypyridine N-oxide O-t-butyloxime or its salt, 35) a compound of the formula:

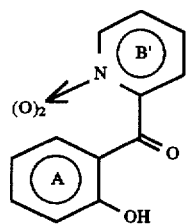

wherein the ring A stands for an optionally further substituted benzene ring; the ring B' stands for a substituted pyridine ring; and n denotes 0 or 1.

36) a compound as described in the above 35), wherein the ring B' stands for

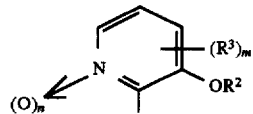

wherein $R^2$ stands for H or a hydroxyl-protecting group; $R^3$ stands for a halogen, cyano group, a $C_{1-4}$ alkoxy group, a $C_{1-4}$ alkyl group or a halogeno-$C_{1-4}$ alkyl group; and n and m each denotes 0 or 1, 37) a compound as described in the above 35), wherein the ring B' stands for

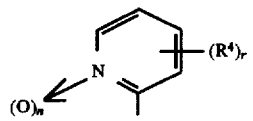

wherein $R^4$ stands for (1) a halogen, (2) cyano group, (3) an amino group, (4) a $C_{1-10}$ acyl or 1,3-dioxolan-2-yl group, (5) a carboxyl, carbamoyl or $C_{1-4}$ alkoxycarbonyl group, (6) a $C_{1-4}$ alkoxy group, (7) a $C_{1-4}$ alkylthio group, or (8) a $C_{1-4}$ hydrocarbon group which may be substituted with a hydroxyl, a hydroxylmino, a halogen or a $C_{1-4}$ alkoxy; n denotes 0 or 1; and r denotes 1 or 2, 38) a method of producing a compound as described in the above 1), which comprises reacting a compound represented by the formula:

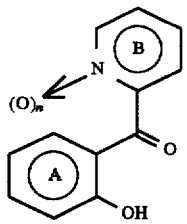

wherein the ring A stands for an optionally further substituted benzene ring; the ring B stands for an optionally substituted pyridine ring; and n denotes 0 or 1, or its salt with a compound represented by the formula:

wherein Q stands for a hydroxyl group, $OQ^1$ or $Q^1$ wherein $Q^1$ stands for an optionally substituted aliphatic hydrocarbon group, or its salt, 39) an agent for treating cardiovascular disease which comprises a compound as described in claim the above 1), 40) an anti-angina pectoris composition which comprises a compound as described in the above 1), 41) an anti-hypertension composition which comprises a compound as described in the above 1) and so on.

In the above-mentioned formulae, the ring A stands for an optionally further substituted benzene ring.

The benzene ring shown by the ring A may be substituted at replaceable positions with 1 to 3 substituents, preferably 1 or 2 substituents, which substituents are the same or different, selected from the group consisting of, for example, (1) a halogen, (2) cyano group, (3) nitro group, (4) an acyl group, (5) an optionally substituted amino group, (6) an optionally substituted alkoxy group, (7) an optionally esterified or amidated carboxyl group, (8) an optionally esterified or amidated sulfinic acid or sulfonic acid, (9) an optionally substituted mercapto group and (10) an optionally substituted hydrocarbon group, or (11) a divalent hydrocarbon group which may be bonded through carbonyl group and (12) =N—O—N=, etc.

In the above case, as (1) a halogen, use is made of, for example, fluorine, chlorine, bromine, iodine, etc., preferably, for example, fluorine, chlorine, bromine, etc.

As the acyl group in (4) an acyl group, use is made of, for example, acyl group derived from, carboxylic acid, sulfinic acid or sulfonic acid, preferably a $C_{1-10}$ acyl group derived from carboxylic acid.

As the $C_{1-10}$ acyl group derived from carboxylic acid, use is made of, for example, a $C_{1-8}$ alkanoyl (e.g. formyl, acetyl, propionyl, butyryl, isobutyryl, valeryl, pivaloyl, etc.), $C_{3-6}$ cycloalkyl-carbonyl (e.g. cyclopropylcarbonyl, cyclopentylcarbonyl, cyclohexylcarbonyl, etc.), benzoyl, etc., preferably, use is made of, for example, a $C_{1-8}$ alkanoyl, etc.

As the acyl group derived from sulfinic acid, use is made of, for example, a $C_{1-6}$ alkylsulfinyl (e.g. methylsulfinyl, ethylsulfinyl, propylsulfinyl, isopropylsulfinyl, butylsulfinyl, isobutylsulfinyl, t-butylsulfinyl, etc.), $C_{3-6}$ cycloalkylsulfinyl (e.g. cyclopropylsulfinyl, cyclopentylsulfinyl, cyclohexylsulfinyl, etc.), phenylsulfinyl, etc., preferably, for example, a lower alkylsulfinyl (e.g. a $C_{1-4}$ alkylsulfinyl such as methylsulfinyl, ethyl sulfinyl, etc.).

As the acyl group derived from sulfonic acid, use is made of, for example, a $C_{1-6}$ alkyl sulfonyl (e.g. methylsulfonyl, ethylsulfonyl, propylsulfonyl, isopropylsulfonyl, butylsulfonyl, isobutylsulfonyl, t-butylsulfonyl, etc.), $C_{3-6}$ cycloalkylsulfonyl (e.g. cyclopropylsulfonyl, cyclopenylsulfonyl, cyclohexylsulfonyl, etc.), phenylsulfonyl, etc., preferably, a lower alkylsulfonyl (e.g. $C_{1-4}$ alkylsulfonyl such as methylsulfonyl, ethylsulfonyl, etc.).

Such an acyl group as above may be substituted with, for example, a nitroxy (—O—NO$_2$), phenyl, etc. at replaceable positions.

As (5) an optionally substituted amino group, use is made of an amino group which may be substituted with 1 or 2 groups selected from, for example, a $C_{1-6}$ alkyl (e.g. methyl, ethyl, propyl, isopropyl, butyl, isobutyl, t-butyl, etc.), $C_{1-6}$ alkoxy (e.g. methoxy, ethoxy, propoxy, isopropoxy, butoxy, isobutoxy, t-butoxy, etc.), halogeno-$C_{1-4}$ alkyl (e.g. CF$_3$, etc.), $C_{3-6}$ cycloalkyl (e.g. cyclopropyl, cyclopentyl, cyclohexyl, etc.), hydroxyl, carbamoyl, phenyl, phenyl-$C_{1-4}$ alkyl (e.g. benzyl, phenethyl, etc.), $C_{1-6}$ alkanoyl (e.g. formyl, acetyl, propionyl, butyryl, isobutyryl, valeryl, pivaloyl, etc.), nitroxy-$C_{2-4}$ alkanoyl (e.g. 2-nitroxyacetyl, 3-nitroxypropionyl, etc.), $C_{3-6}$ cycloalkyl-carbonyl (e.g. cyclopropylcarbonyl, cyclopentylcarbonyl, cyclohexylcarbonyl, etc.), benzoyl, phenyl-$C_{2-4}$ alkanoyl (e.g. phenylacetyl, phenylpropionyl, etc.), $C_{1-6}$ alkoxycarbonyl (e.g. methoxycarbonyl, ethoxycarbonyl, propoxycarbonyl, isopropoxycarbonyl, butoxycarbonyl, isobutoxycarbonyl, t-butoxycarbonyl, etc.), nitroxy-$C_{1-4}$ alkoxy-carbonyl (e.g. 2-nitroxyethoxycarbonyl, 3-nitroxypropoxycarbonyl, etc.), phenoxycarbonyl, phenyl-$C_{1-4}$ alkoxy-carbonyl (e.g. benzyloxycarbonyl, phenylethoxycarbonyl, etc.), $C_{1-6}$ alkylsulfinyl (e.g. methylsulfinyl, ethylsulfinyl, propylsulfinyl, isopropylsulfinyl, butylsulfinyl, isobutylsulfinyl, t-butylsulfinyl, etc.), nitroxy-$C_{1-4}$ alkylsulfinyl (e.g. 2-nitroxyethylsulfinyl, 3-nitroxypropylsulfinyl, etc.), $C_{3-6}$ cycloalkylsulfinyl (e.g. cyclopropylsulfinyl, cyclopentylsulfinyl, cyclohexylsulfinyl, etc.), phenylsulfinyl, $C_{1-6}$ alkylsulfonyl(e.g. methylsulfonyl, ethylsulfonyl, propylsulfonyl, isopropylsulfonyl, butylsulfonyl, isobutylsulfonyl, t-butylsulfonyl, etc.), nitroxy-$C_{1-4}$ alkylsulfonyl (e.g. 2-nitroxyethylsulfonyl, 3-nitroxypropylsulfonyl, etc.), $C_{3-6}$ cycloalkylsulfonyl (e.g. cyclopropylsulfonyl, cyclopentylsulfonyl, cyclohexylsulfonyl, etc.), $C_{1-6}$ alkoxysulfonyl (e.g. methoxysulfonyl, ethoxysulfonyl, propoxysulfonyl, isopropoxysulfonyl, butoxysulfonyl, isobutoxysulfonyl, t-butoxysulfonyl, etc.) and phenylsulfonyl, etc. And, two of such substituents may, in some instance, form a cyclic amino group taken together with nitrogen atom. As such cyclic amino groups, use is made of, for example, pyrrolidino, piperidino, morpholino, thiomorpholino, etc. Preferable examples of an optionally substituted amino group include, an amino group optionally substituted with, for example, a lower alkyl (e.g. $C_{1-4}$ alkyl such as methyl, ethyl, etc.).

As the alkoxy group in (6) an optionally substituted alkoxy group, use is made of, for example, a $C_{1-6}$ alkoxy (e.g. methoxy, ethoxy, propoxy, isopropoxy, butoxy, isobutoxy, t-butoxy, etc.), preferably, for example, lower alkoxy (e.g. $C_{1-4}$ alkoxy such as methoxy, ethoxy, etc.). Such alkoxy groups may be optionally substituted with 1 to 3 groups, at replaceable positions, the same or different, selected from, for example, a lower alkoxy (e.g. $C_{1-4}$ alkoxy such as methoxy, ethoxy, etc.), phenyl, phenoxy, hydroxyl group, nitro, nitroxy (—O—NO$_2$), halogen (e.g. fluorine, chlorine, bromine, iodine, etc.), halogeno-lower alkoxy (e.g. halogeno-$C_{1-4}$ alkoxy such as CF$_3$O, HCF$_2$O, etc.) and cyano. Preferable examples of the optionally substituted alkoxy group include a lower alkoxy optionally substituted with halogen.

As the esterified carboxyl group in (7) an optionally esterified or amidated carboxyl group, use is made of, for example, a $C_{1-6}$ alkoxy-carbonyl (e.g. methoxycarbonyl, ethoxycarbonyl, propoxycarbonyl, isopropoxycarbonyl, butoxycarbonyl, isobutoxycarbonyl, t-butoxycarbonyl, etc.), nitroxy-$C_{1-4}$ alkoxycarbonyl (e.g. 2-nitroxyethoxycarbonyl, 3-nitroxypropoxycarbonyl, etc.), $C_{3-6}$ cycloalkoxy-carbonyl (e.g. cyclopentyloxycarbonyl, cyclohexyloxycarbonyl etc.), phenyl-$C_{1-4}$ alkoxycarbonyl(e.g. benzyloxycarbonyl, phenethyloxycarbonyl, etc.).

As the amidated carboxyl group, use is made of, for example, a carbamoyl, $C_{1-6}$ alkylaminocarbonyl (e.g. methylaminocarbonyl, ethylaminocarbonyl, propylaminocarbonyl, isopropylaminocarbonyl, butylaminocarbonyl, isobutylaminocarbonyl, t-butylaminocarbonyl, etc.), $C_{3-6}$ cycloalkylaminocarbonyl (e.g. cyclopropylaminocarbonyl, cyclopentylaminocarbonyl, cyclohexylaminocarbonyl, etc.), nitroxy-$C_{1-4}$ alkylaminocarbonyl (e.g. 2-nitroxyethylaminocarbonyl, 3-nitroxypropylaminocarbonyl, etc.), cyclic aminocarbonyl (e.g. morpholinocarbonyl, piperidinocarbonyl, pyrrolidinocarbonyl, thiomorpholinocarbonyl, etc.), anilinocarbonyl and phenyl-$C_{1-4}$ alkylaminocarbonyl (e.g. benzylaminocarbonyl, phenethylaminocarbonyl, etc.)

In (8) an optionally esterified or amidated sulfinic acid or sulfonic acid group, as the esterified sulfinic acid, use is made of, for example, a $C_{1-6}$ alkoxysulfinyl (e.g. methoxysulfinyl, ethoxysulfinyl, propoxysulfinyl, isopropoxysulfinyl, butoxysulfinyl, isobutoxysulfinyl, t-butoxysulfinyl, etc.), $C_{3-6}$ cycloalkoxysulfinyl (e.g. cyclopentyloxysulfinyl, cyclohexyloxysulfinyl, etc.), phenyl-$C_{1-4}$ alkoxysulfinyl (e.g. benzyloxysulfinyl, phenethyloxysulfinyl, etc.).

As the amidated sulfinic acid group, use is made of, for example, a sulfimamoyl, $C_{1-6}$ alkylaminosulfinyl (e.g. methylaminosulfinyl, ethylaminosulfinyl, propylaminosulfinyl, isopropylaminosulfinyl, butylaminosulfninyl, isobutylaminosulfinyl, t-butylaminosulfinyl, etc.), $C_{3-6}$ cycloalkylaminosulfinyl (e.g. cyclopropylaminosulfinyl, cyclopentylaminosulfinyl, cyclohexylaminosulfinyl, etc.), nitroxy-$C_{1-4}$ alkylaminosulfinyl (e.g. 2-nitroxyethylaminosulfinyl, 3-nitroxypropylaminosulfinyl, etc.), cyclic aminosulfinyl (e.g. morpholinosulfinyl, piperidinosulfinyl, pyrrolidinosulfinyl, thiomorpholinosulfinyl, etc.), anilinosulfininyl, phenyl-$C_{1-4}$ alkylaminosulfinyl (e.g. benzylaminosulfinyl, phenethylaminosulfinyl, etc.).

As the esterified sulfonic acid group, use is made of, for example, a $C_{1-6}$ alkoxysulfonyl (e.g. methoxysulfonyl, ethoxysulfonyl, propoxysulfonyl, isopropoxysulfonyl, butoxysulfonyl, isobutoxysulfonyl, t-butoxysulfonyl, etc.), $C_{3-6}$ cycloalkoxysulfonyl (e.g. cyclopentyloxysulfonyl, cyclohexyloxysulfonyl, etc.), phenyl-$C_{1-4}$ alkoxysulfonyl (e.g. benzyloxysulfonyl, phenethyloxysulfonyl, etc.).

As the amidated sulfonic acid group, use is made of, for example, a sulfamoyl, $C_{1-6}$ alkylaminosulfonyl (e.g. methylaminosulfonyl, ethylaminosulfonyl, propylaminosulfonyl, isopropylaminosulfonyl, butylaminosulfonyl, isobutylaminosulfonyl, t-butylaminosulfonyl, etc.), $C_{3-6}$ cycloalkylaminosulfonyl (e.g. cyclopropylaminosulfonyl, cyclopentylaminosulfonyl, cyclohexylaminosulfonyl, etc.), nitroxy-$C_{1-4}$ alkylaminosulfonyl (e.g. 2-nitroxyethylaminosulfonyl, 3-nitroxypropylaminosulfonyl, etc.), cyclic aminosulfonyl (e.g. morpholinosulfonyl, piperidinosulfonyl, pyrrolidinosulfonyl, thiomorpholinosulfonyl, etc.), anilinosulfonyl and phenyl-$C_{1-4}$ alkyklaminosulfonyl (e.g. benzylaminosulfonyl, phenethylaminosulfonyl etc.).

As (9) an optionally substituted mercapto group, use is made of, for example, a mercapto group optionally substituted with, for example, a $C_{1-6}$ alkyl (e.g. methyl ethyl, propyl, isopropyl, butyl, isobutyl, t-butyl, etc), nitroxy-$C_{1-4}$ alkyl (e.g. 2-nitroxyethyl, 3-nitroxypropyl, etc.), $C_{3-6}$ cycloalkyl (e.g. cyclopropyl, cyclopentyl, cyclohexyl, etc.), phenyl, phenyl-$C_{1-4}$ alkyl (e.g. benzyl, phenethyl, etc.), halogeno-$C_{1-4}$ alkyl (e.g. $CF_3$, etc.). Preferably, use is made of, for example, a lower alkylthio (e.g. $C_{1-4}$ alkylthio such as methylthio, ethylthio, etc.), nitroxy $C_{2-4}$ alkylthio (e.g. 2-nitroxyethylthio, 3-nitroxypropylthio, etc.), $C_{3-6}$ cycloalkylthio (e.g. cyclopropylthio, cyclopentylthio, cyclohexylthio, etc.), phenylthio (optionally substituted with 1 to 2 substituents selected from, for example, methyl, methoxy, halogen, nitro, $CF_3$ or cyano, etc.), phenyl-$C_{1-2}$ alkylthio (optionally substituted with 1 to 2 substituents selected from, for example, methyl, methoxy, halogen, nitro, $CF_3$ or cyano, etc.) such as benzylthio, etc. (optionally substituted with 1 to 2 substituents selected from, for example, methyl, methoxy, halogen, nitro, $CF_3$ or cyano, etc.), halogeno-$C_{1-2}$ alkylthio (e.g. trifluoromethylthio, pentafluoroethylthio, etc.), more preferably, for example, lower alkylthio, etc.

As the hydrocarbon group in (10) an optionally substituted hydrocarbon group, use is made of, for example, a $C_{1-6}$ alkyl (e.g. methyl, ethyl, propyl, butyl, isobutyl, isopropyl, t-butyl, etc.), $C_{2-6}$ alkenyl (e.g. vinyl, allyl, isopropenyl, 3-methyl-2-butenyl, etc.), $C_{2-6}$ alkynyl (e.g. ethynyl, 1-propynyl, 2-propynyl, etc.), $C_{3-6}$ cycloalkyl (e.g. cyclopropyl, cyclopentyl, cyclohexyl, etc.), $C_{6-10}$ aryl (e.g. phenyl, etc.), preferably, use is made of, for example, lower alkyl (e.g. $C_{1-4}$ alkyl group such as methyl, ethyl, etc.).

Such hydrocarbon groups as above may be substituted, at replaceable positions, the same or different, with 1 to 3 substituents selected from, for example, a lower alkyl (e.g. $C_{1-4}$ alkyl such as methyl, ethyl, etc.), lower alkoxy (e.g. $C_{1-4}$ alkoxy such as methoxy, ethoxy, etc.), phenyl, phenoxy, hydroxyl group, nitro, nitroxy, halogen (e.g. fluorine, chlorine, bromine, iodine, etc.), halogeno-lower alkoxy (e.g halogeno-$C_{1-4}$ alkoxy such as $CF_3O$, $HCF_2O$, etc,) and cyano, etc. The phenyl in these substituents may further be substituted at replaceable positions, the same or different, with 1 to 3 substituents selected from a lower alkyl (e.g. $C_{1-4}$ alkyl such as methyl, ethyl, etc.), lower alkoxy (e.g. $C_{1-4}$ alkoxy such as methoxy, ethoxy, etc.), hydroxyl group, nitro, halogen (e.g. fluorine, chlorine, bromine, iodine, etc.), halogeno-lower alkyl (e.g. halogeno-$C_{1-4}$ alkyl such as $CF_3$, $CF_3CF_2$, $CH_2F$, $CHF_2$, etc.), cyano and halogeno-lower alkoxy (e.g. halogeno-$C_{1-4}$ alkoxy such as $CF_3O$, $HCF_2O$, etc.). Among them, as the substituent of a $C_{1-6}$ alkyl, use is made of 1 to 3 groups selected from, for example, a lower alkoxy, phenyl, phenoxy, hydroxyl, nitro, nitroxy, halogen, halogeno-lower alkoxy and cyano. As the substituents of a $C_{2-6}$ alkenyl and $C_{3-6}$ cycloalkyl, use is made of 1 to 3 groups selected from, for example, a lower alkyl, halogen and phenyl. And, as the substituents of a $C_{2-6}$ alkynyl, use is made of 1 to 3 groups selected from, for example, a lower alkyl, halogen and phenyl, besides, use is made of trimethylsilyl group.

Preferable examples of the optionally substituted hydrocarbon group include lower hydrocarbon groups optionally substituted with halogen (e.g. fluorine, chlorine, bromine, iodine, etc.), for example, a lower alkyl (e.g. $C_{1-4}$ alkyl such as methyl, ethyl, etc.) optionally substituted with halogen, lower alkynyl (e.g. $C_{2-4}$ alkynyl such as ethynyl, 1-propynyl, etc.) optionally substituted with halogen, lower alkenyl (e.g. $C_{2-4}$ alkenyl such as vinyl, allyl, etc.) optionally substituted with halogen, etc., and, for example, halogeno-lower alkyl (e.g. halogeno-$C_{1-4}$ alkyl such as $CF_3$, $CF_3CF_2$, $CH_2F$, $CHF_2$, etc.), etc. are more preferable. And, as the optionally substituted hydrocarbon groups, use is also made of a substituted iminomethyl group. As the substituents of the imino of these substituted iminomethyl, use is made of, for example, a hydroxyl, amino, $C_{1-6}$ alkyl (e.g. methyl, ethyl, propyl, isopropyl, butyl, isobutyl, t-butyl, etc.), $C_{3-6}$ cycloalkyl (e.g. cyclopropyl, cyclopentyl, cyclohexyl, etc.), $C_{1-6}$ alkoxy (e.g. methoxy, ethoxy, propoxy, isopropoxy, butoxy, isobutoxy, t-butoxy, etc.), $C_{3-6}$ cycloalkoxy (e.g. cyclopropoxy, cyclopentyloxy, cyclohexyloxy, etc.), phenyl-$C_{1-4}$ alkyl (e.g. benzyl, phenethyl, etc.), phenyl-$C_{1-4}$ alkoxy (e.g. benzyloxy, pheneloxy, etc.), etc., and, as the substituted iminomethyl, for example, hydroxylminomethyl, etc. are preferable.

As (11) the divalent hydrocarbon group which may be bonded through carbonyl group, use is made of, for example, —CH=CH—CH=CH— (here, this group may be substituted with 1 to 3 groups selected from a $C_{1-4}$ alkyl, $C_{1-4}$ alkoxy, nitro, halogen, $CF_3$, $C_{1-4}$ alkoxycarbonyl and cyano), —$(CH_2)_a$— (a denotes 3 or 4) or —$(CH_2)_b$—CO—(b denotes 2 or 3), etc. and, preferably, use is made of, for example —CH=CH—CH=CH—, —$(CH_2)_3$—, —$(CH_2)_4$—, —$(CH_2)_2$—CO—, —$(CH_2)_4$—CO—, etc. (optionally substituted with, for example, methyl, methoxy, nitro, halogen, $CF_3$, cyano, etc.).

And, in the case where the ring A is substituted with (12) =N—O—N==, the ring A shows the rings represented by the following formula,

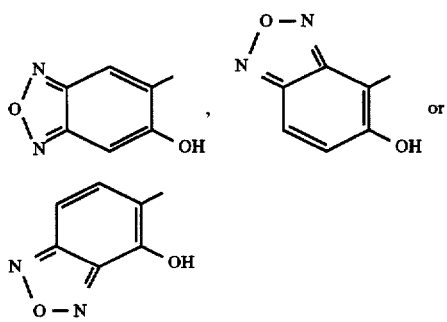

Preferable examples of the substituents of the benzene ring include, from the viewpoint of the effect, (1) a halogen, (2) cyano group, (3) nitro group, (4) an acyl group, (5) an optionally substituted amino group, (6) an optionally substituted alkoxy group, (7) an optionally substituted mercapto group, (8) an optionally substituted hydrocarbon group, etc., and, for example, (1) a halogen, (2) cyano group, (3) nitro group, (4) a $C_{1-10}$ acyl group, (5) amino group optionally substituted with lower alkyl, (6) lower alkoxy optionally substituted halogen, (7) lower alkylthio group, (8) lower hydrocarbon groups optionally substituted with halogen are more preferable, and, among them, halogen, cyano, etc. are further preferable.

As the ring A, rings represented by, for example, the following formula

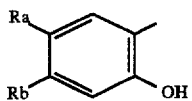

wherein Ra stands for a halogen, cyano group, nitro group, a $C_{1-10}$ acyl group, a lower alkoxy group, a halogeno-lower alkoxy group, a lower alkylthio group, a halogeno-lower alkyl or a lower hydrocarbon group; Rb stands for H, a halogen, cyano group, nitro group, a $C_{1-10}$ acyl group, an amino group, a lower alkylamino group, a lower alkoxy group, a lower alkylthio group, a lower hydrocarbon group or a halogeno-lower alkyl group, are preferable. As the halogen, $C_{1-10}$ acyl group $C_{1-10}$ acyl group derived from carboxylic acid, sulfinic acid or sulfonic acid), lower alkoxy group, halogeno-lower alkoxy group, lower alkylthio group, halogeno-lower alkyl group and lower hydrocarbon group, use is made of those similar to the groups mentioned above referring to the substituent on the benzene ring shown by the ring A.

As substituents of the benzene ring, an electron-attracting group, for example, is preferable, and, as the ring A, a ring represented by, for example, the formula

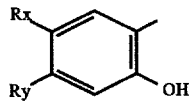

wherein Rx and Ry each stands for an electron-attracting group, or the like are also preferable. As such electron-attracting groups, are more preferable, for example, a halogen, cyano group, nitro group, trifluoromethyl group, pentafluoroethyl group, trifluoromethoxy group, pentafluoroethoxy group, a $C_{1-10}$ acyl group, etc. As the halogen and the $C_{1-10}$ acyl group shown as an electron-attracting group herein, use is made of similar groups to halogen and the $C_{1-10}$ acyl group shown by the above-mentioned Ra or Rb.

In the above-mentioned formula [I], the ring B stands for an optionally substituted pyridine ring.

The pyridine ring shown by the ring B may be substituted at replaceable positions, the same or different, with 1 or 2 groups selected from, for example, (1) a halogen, (2) cyano group, (3) an optionally substituted amino group, (4) an acyl group, (5) an esterified or amidated carboxyl group, (6) an optionally substituted alkoxy group, (7) an optionally substituted mercapto group, (8) an optionally substituted hydrocarbon group and (9) $OR^2$ wherein $R^2$ stands for H or a hydroxyl-protecting group.

Herein, as (1) a halogen, (3) an optionally substituted amino group, (5) an esterified or amidated carboxyl group, (6) an optionally substituted hydrocarbon group, (7) an optionally substituted mercapto group and (8) an optionally substituted hydrocarbon group, use is made of groups similar to substituents of the benzene ring shown by the above-mentioned ring A.

As (4) an acyl group, use is made of groups similar to those mentioned above as substituents on the benzene ring represented by the ring A, and, besides, 1,3-dioxolan-2-yl group or the like, for example, can be employed.

As the hydroxyl-protecting group represented by $R^2$, any one which leaves in a living body can be used, as exemplified by $C_{1-6}$ acyl groups such as formyl, acetyl, propionyl, succinyl, butyryl, isobutyryl, pivaloyl, etc., $SO_3H$, benzyl group, etc.

Preferable examples of the substituents of the pyridine ring represented by the ring B include, from the viewpoint of the effect, (1) a halogen, (2) cyano group, (3) an amino group, (4) a $C_{1-10}$ acyl or 1,3-dioxolan-2-yl group, (5) a carboxyl, carbamoyl or lower alkoxycarbonyl group, (6) a lower alkoxy group, (7) a lower alkylthio group, (8) a lower hydrocarbon group optionally substituted with a hydroxy, hydroxyimino, halogen or lower alkoxy group, and (9) $OR^2$ wherein $R^2$ stands for H or a hydroxyl-protecting group.

Herein, as (4) a $C_{1-10}$ acyl, (6) a lower alkoxy group, and (7) a lower alkylthio group, use is made of groups similar to the substituents on the benzene ring represented by ring A.

As (5) a lower alkoxycarbonyl group, use is made of, for example, $C_{1-6}$ alkoxycarbonyl such as methoxycarbonyl, ethoxycarbonyl, etc.

As (8) a lower hydrocarbon group optionally substituted with a hydroxy, hydroxylmino, halogen (e.g. fluorine, chlorine, bromine, iodine, etc.) or lower alkoxy group (e.g. $C_{1-4}$ alkoxy such as methoxy, ethoxy, etc.), for example, a lower alkyl (e.g. $C_{1-4}$ alkyl such as methyl, ethyl, etc.), lower alkynyl (e.g. alkynyl such as ethynyl, 2-propynyl, etc.), lower alkenyl (e.g. $C_{2-6}$ alkenyl such as vinyl, allyl, etc.), use is made of, for example, a lower alkyl, halogeno-lower alkyl (e.g. halogeno-$C_{1-4}$ alkyl such as $CF_3$, $CF_3CF_2$, $CH_2F$, $CHF_2$, etc.), hydroxy-lower alkyl (e.g. hydroxy-$C_{1-4}$ alkyl such as hydroxymethyl, 1-hydroxyethyl, 2-hydroxyethyl, etc.), hydroxylmino-lower alkyl (e.g. hydroxylmino-$C_{1-4}$ alkyl such as hydroxylminomethyl, etc.), a lower alkoxy-lower alkyl (e.g. $C_{1-4}$ alkoxy-$C_{1-4}$ alkyl such as methoxymethyl, ethoxyethyl, etc.), lower alkenyl, halogeno-lower alkenyl (e.g. halogeno-$C_{2-4}$ alkenyl such as $CF_2$=CF, etc), lower alkynyl, etc.

As the ring B, are preferable, for example, rings represented by the formula

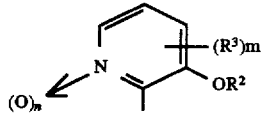

wherein $R^2$ stands for H or a hydroxyl-protecting group; $R^3$ stands for a halogen, cyano, lower alkoxy, lower alkyl or halogeno-lower alkyl group; and m and n each denotes 0 or 1.

As the halogen, lower alkoxy group, lower alkyl group and halogeno-lower alkyl group represented by $R^3$, use is made of groups similar to the substituents on the pyridine ring represented by the above-mentioned ring B.

The symbol m is preferably 0.

And, the ring B is also preferable when it is pyridine ring may be substituted with 1 or 2 groups selected from a halogen, lower alkoxy, lower alkyl, halogeno-lower alkyl group and $OR^2$ wherein $R^2$ stands for H or a hydroxyl-protecting group.

Q stands for a hydroxyl group, $OQ^1$ or $Q^1$ wherein $Q^1$ stands for an optionally substituted aliphatic hydrocarbon group. As the aliphatic hydrocarbon group in the optionally substituted aliphatic hydrocarbon group shown by $Q^1$, use is made of a $C_{1-10}$ aliphatic hydrocarbon group such as a $C_{1-10}$ alkyl (e.g. methyl, ethyl, propyl, isopropyl, butyl, isobutyl, t-butyl, s-butyl, pentyl, isopentyl, neopentyl, t-pentyl, 1-methylbutyl, 2-methylbutyl, 1,2-dimethylpropyl, 1-ethylpropyl, hexyl, isohexyl, 1-methylpentyl, 2-methylpentyl, 3-methylpentyl, 1,1-dimethylbutyl, 1,2-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, etc.), $C_{3-10}$ alkenyl (e.g. alkyl, 2-butenyl, 3-butenyl, 3-methyl-3-butenyl, 2-pentenyl, 3-pentenyl, 4-pentenyl, 4-methyl-3-pentenyl, 2-hexenyl, 3-hexenyl, 4-hexenyl, 5-hexenyl, etc.), $C_{3-10}$ alkynyl (e.g. 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 1,1-dimethyl-2-butynyl, 1,1-dimethyl-3-butynyl, 2,2-dimethyl- 3-butynyl, 1-ethyl-2-butynyl, 2-ethyl-3-butynyl, 1-propyl-2-propynyl, 1-isopropyl-2-propynyl, 1-ethyl-1-methyl-2-propynyl, 1-ethyl-1-methyl-2-propynyl, etc.), $C_{3-8}$ cycloalkyl (e.g. cyclopropyl, cyclobutyl, cyclopentyl, cyclohexyl, etc.), and $C_{5-8}$ cycloalkenyl (e.g. 2-cyclopenten-1-yl, 3-cyclopenten-1-yl, 2-cyclohexen-1-yl, 3-cyclohexen-1-yl, etc.).

As the substituents in the optionally substituted aliphatic hydrocarbon group shown by $Q^1$, use is made of 1 to 3 groups selected from (i) a halogen, (ii) a halogeno-$C_{1-4}$ alkyl (e.g. $CF_3$, etc.), (iii) a $C_{1-4}$ alkoxy (e.g. methoxy, ethoxy, etc.) and (iv) a phenyl group optionally substituted with 1 to 3 groups selected from a $C_{1-4}$ alkyl (e.g. methyl, ethyl, etc.), $C_{1-4}$ alkoxy (e.g. methoxy, ethoxy, etc.), hydroxyl, nitro, halogen, halogeno-$C_{1-4}$ alkyl (e.g. $CF_3$, etc.), cyano and halogeno-$C_{1-4}$ alkoxy (e.g. $CF_3O$, etc.).

Preferable examples of $Q^1$ include a $C_{3-8}$ alkyl (e.g. propyl, etc.), $C_{3-8}$ alkenyl (e.g. allyl, etc.), $C_{3-8}$ alkynyl (e.g. propynyl, etc.), $C_{3-6}$ cycloalkyl (e.g. cyclohexyl, etc.), $C_{5-6}$ cycloalkenyl (e.g. cyclohexenyl, etc.) and benzyl optionally substituted with methyl, methoxy, halogen, nitro, $CF_3$ or cyano. More preferable examples are $C_{3-6}$ alkyl having branched chain (e.g. isopropyl, isobutyl, s-butyl, t-butyl, isopentyl, neopentyl, t-pentyl, 1,2-dimethylpropyl, 1-ethylpropyl, 1-methylbutyl, 2-methylbutyl, 1,1-dimethylbutyl, 1,2-dimethylbutyl, 2,2-dimethylbutyl, 1-ethyl-1-methylpropyl, 2-ethyl-1-methylpropyl, 1,1,2-trimethylpropyl, 1,2,2-trimethylpropyl, etc.) or $C_{3-6}$ cycloalkyl (e.g. cyclopropyl, cyclopentyl, cyclohexyl, etc.). Especially, isopropyl, t-butyl, neopentyl, t-pentyl, 1,2-dimethylpropyl, 1,2,2-trimethylpropyl, cyclopropyl, cyclobutyl, cyclopentyl and cyclohexyl are often used.

As typical compounds represented by the formula [I], use is made of compounds represented by the formula [Ia]:

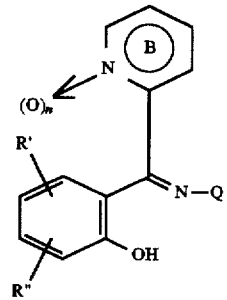

[Ia]

wherein R' and R" each stand for H, a halogen atom, nitro, cyano, optionally substituted $C_{1-6}$ alkyl, optionally substituted $C_{1-6}$ alkoxy, optionally substituted $C_{2-6}$ alkenyl, optionally substituted $C_{2-6}$ alkynyl, optionally substituted $C_{3-6}$ cycloalkyl, optionally substituted $C_{3-6}$ cycloalkoxy, optionally substituted amino, optionally substituted $C_{1-10}$ acyl, optionally esterified or amidated carboxyl, optionally esterified or amidated sulfonic acid, substituted iminomethyl or optionally substituted mercapto, or, R' and R" may be combined with each other to form —CH=CH—CH=CH— (optionally substituted with 1 to 3 groups selected from a $C_{1-4}$ alkyl, $C_{1-4}$ alkoxy, nitro, halogen, $CF_3$, $C_{1-4}$ alkoxycarbonyl and cyano), =N—O—N=, —($CH_2$)$_a$— (a denotes 3 or 4) or —($CH_2$)$_b$—CO— (b denotes 2 or 3), and other symbols are of the same meaning as defined above or their salts.

The R' and R" in the compound [Ia] are preferably located at 4- and 5-positions of the in the benzene nucleus (for convenience' sake, the hydroxyl group on the benzene nucleus is supposed to be located at 2-position). However, these groups may be located at 3- and 4-positions, 3- and 5-positions, 3- and 6-positions, 4- and 6-positions or 5- and 6-positions. In the case where either one of R' and R" is H and the other one is a group other than H, this other one is preferably located at 5-position, while it may be located at 3-, 4- or 6-position. Or, in the case where neither R' nor R" is H or R' and R" are combined to each other, they are preferably located at 4- and 5-positions, while they may be located at 3- and 4-positions or 5- and 6-positions.

As the substituents in the optionally substituted $C_{1-6}$ alkyl (e.g. methyl, ethyl, propyl, isopropyl, butyl, isobutyl, t-butyl, etc.) and the optionally substituted $C_{1-6}$ alkoxy (e.g. methoxy, ethoxy, propoxy, isopropoxy, butoxy, isobutoxy, t-butoxy, etc.), mention is made of 1 to 3 groups selected from, for example, $C_{1-4}$ alkoxy (e.g. methoxy, ethoxy, etc.), phenyl, phenoxy, hydroxyl, nitro, nitroxy, halogen, halogeno $C_{1-4}$ alkoxy (e.g. $CF_3O$, etc.) and cyano. The phenyl in these substituents may further be substituted with 1 to 3 groups selected from a $C_{1-4}$ alkyl (e.g. methyl, ethyl, etc.), $C_{1-4}$ alkoxy (e.g. methoxy, ethoxy, etc.), hydroxy, nitro, halogen, halogeno-$C_{1-4}$ alkyl (e.g. $CF_3$, etc.), cyano and halogeno-$C_{1-4}$ alkoxy (e.g. $CF_3O$, etc.).

As the substituents in the optionally substituted $C_{2-6}$ alkenyl group (e.g. vinyl, aryl, isopropenyl, 3-methyl-2-butenyl, etc.), mention is made of 1 to 3 groups selected from a $C_{1-4}$ alkyl (e.g. methyl, ethyl, etc.), halogen and phenyl.

As the substituents in the optionally substituted $C_{2-6}$ alkynyl group (e.g. ethynyl, 1-propynyl, 2-propynyl, etc.), mention is made of trimethyl silyl group or the like, besides 1 to 3 groups selected from, for example, a $C_{1-4}$ alkyl (e.g. methyl, ethyl, etc.), halogen and phenyl.

As the substituents in the optionally substituted $C_{3-6}$ cycloalkyl group (e.g. cyclopropyl, cyclopentyl, cyclohexyl, etc.), mention is made of 1 to 3 groups selected from a $C_{1-4}$ alkyl (e.g. methyl, ethyl, etc.), halogen and phenyl.

As the substituents in the optionally substituted amino, use is of the same optionally substituted amino, as described substituents on the ring A in the formula [I].

As the $C_{1-10}$ acyl group in the optionally substituted $C_{1-10}$ acyl group, mention is made of a $C_{1-8}$ alkanoyl (e.g. formyl, acetyl, propionyl, butyryl, isobutyryl, valeryl, pivaloyl, etc.), $C_{3-6}$ cycloalkylcarbonyl (e.g. cyclopropylcarbonyl, cyclopentylcarbonyl cyclohexylcarbonyl, etc.), benzoyl, $C_{1-6}$ alkylsulfinyl (e.g. methylsulfinyl, ethylsulfinyl, propylsulfinyl, isopropylsulfinyl, etc.), $C_{3-6}$ cycloalkylsulfinyl (e.g. cyclopropylsulfinyl, cyclopentylsulfinyl, cyclohexylsulfinyl, etc.), phenylsulfinyl, $C_{1-6}$ alkylsulfonyl (e.g. methylsulfonyl, ethylsulfonyl, propylsulfonyl, isopropylsulfonyl, butylsulfonyl, isobutylsulfonyl, t-butylsulfonyl, etc.), $C_{3-8}$ cycloalkylsulfonyl (e.g. cyclopropylsulfonyl, cyclopentylsulfonyl, cyclohexylsulfonyl, etc.), phenylsulfonyl, etc. As substituents of the $C_{1-10}$ acyl group, mention is made of, for example, nitroxy (—O—$NO_2$) and phenyl.

As the esterified or amidated carboxyl group, use is of the same esterified or amidated carboxyl group, as described substituents on the ring A in the formula [I].

As the esterified or amidated sulfonic acid, use is of the same esterified or amidated sulfonic acid, as described substituents on the ring A in the formula [I].

As the substituents in the imino of the substituted iminomethyl, use is of the same substituents in the imino of the substituted iminomethyl, as described substituents on the ring A in the formula [I].

As the substituents in the optionally substituted mercapto group, use is of the same substituents in the optionally substituted mercapto group, as described substituents on the ring A in the formula [I].

Preferable examples of R' and R" each includes a $C_{1-4}$ alkyl (e.g. methyl, ethyl, etc.), $C_{3-6}$ cycloalkyl (e.g. cyclopropyl, cyclopentyl, cyclohexyl, etc.), hydroxy-$C_{1-4}$ alkyl (e.g. hydroxymethyl, 1-hydroxyethyl, 2-hydroxyethyl, etc.), nitro-$C_{1-4}$ alkyl (e.g. nitromethyl, 2-nitroethyl, etc.), cyano-$C_{1-4}$ alkyl (e.g. cyanomethyl, 2-cyanoethyl, etc.), nitroxy-$C_{1-4}$ alkyl (e.g. nitroxymethyl, 2-nitroxyethyl, etc.), nitroxy-$C_{1-4}$ alkoxy-$C_{1-2}$ alkyl (e.g. 2-nitroxyethoxymethyl, 2-nitroxyethoxyethyl, 3-nitroxypropoxymethyl, 3-nitroxypropoxyethyl, etc.), optionally substituted phenyl-$C_{1-2}$ alkyl (e.g. benzyl, wherein optionally substituted with 1 to 2 of methyl, methoxy, halogen, nitro, $CF_3$ or cyano, etc.), $C_{1-4}$ alkoxy (e.g. methoxy, ethoxy, etc.), $C_{3-6}$ cycloalkoxy (e.g. cyclopropoxy, cyclopentyloxy, cyclohexyloxy, etc.), hydroxy-$C_{1-4}$ alkoxy (e.g. 2-hydroxyethoxy, 3-hydroxypropoxy, etc.), nitroxy-$C_{1-4}$ alkoxy (e.g. 2-nitroxyethoxy, 3-nitroxypropoxy, etc.), optionally substituted phenyl-$C_{1-2}$ alkoxy (e.g. benzyloxy, wherein optionally substituted with 1 to 2 of methyl, methoxy, halogen, nitro, $CF_3$ or cyano, etc.), $C_{2-6}$ alkenyl (e.g. vinyl, allyl, isopropenyl, 3-methyl-2-butenyl, etc.), optionally substituted phenyl-$C_{2-3}$ alkenyl (e.g. styryl, wherein optionally substituted with 1 to 2 of methyl, methoxy, halogen, nitro, $CF_3$ or cyano, etc.), $CF_3$, $CF_3CF_2$, $CF_3O$, $HCF_2O$, $CF_2$=$CF$, $C_{2-4}$ alkynyl (e.g. ethynyl, 1-propynyl, 2-propynyl, etc.), optionally substituted phenyl-$C_{2-3}$ alkynyl (e.g. phenylethynyl, wherein optionally substituted with 1 to 2 of methyl, methoxy, halogen, nitro, $CF_3$ or cyano, etc.), trimethylsilylethynyl, $C_{1-6}$ alkanoyl (e.g. formyl, acetyl, propionyl, butyryl, isobutyryl, valeryl, pivaloyl, etc.), $C_{3-6}$ cycloalkylcarbonyl (e.g. cyclopropylcarbonyl, cyclopentylcarbonyl, cyclohexylcarbonyl, etc.), nitroxy-$C_{2-4}$ alkanoyl (e.g. 2-nitroxyacetyl, 3-nitroxypropionyl, 4-nitroxybutyryl, etc.), benzoyl (optionally substituted with methyl, methoxy, halogen, nitro, $CF_3$ or cyano), optionally substituted phenyl-$C_{2-3}$ alkanoyl (e.g. phenylacetyl, wherein optionally substituted with 1 to 2 of methyl, methoxy, halogen, nitro, $CF_3$ or cyano, etc.), $C_{1-4}$ alkylsulfinyl (e.g. methylsulfinyl, ethylsulfinyl, etc.), nitroxy-$C_{2-4}$ alkylsulfinyl (e.g. 2-nitroxyethylsulfinyl, 3-nitroxypropylsulfinyl, etc.), $C_{3-6}$ cycloalkylsulfinyl (e.g. cyclopropylsulfinyl, cyclopentylsulfinyl, cyclohexylsulfinyl, etc.), phenylsulfinyl (optionally substituted with 1 to 2 of methyl, methoxy, halogen, nitro, CF3 or cyano), optionally substituted phenyl-$C_{1-2}$ alkylsulfinyl (e.g. benzylsulfinyl, wherein optionally substituted with methyl, methoxy, halogen, nitro, $CF_3$ or cyano, etc.), $C_{1-4}$ alkylsulfonyl (e.g. methylsulfonyl, ethylsulfonyl, propylsulfonyl, etc.), nitroxy-$C_{2-4}$ alkylsulfonyl (e.g. 2-nitroxyethylsulfonyl, 3-nitroxypropylsulfonyl, etc.), $C_{3-6}$ cycloalkylsulfonyl (e.g. cyclopropylsulfonyl, cyclopentylsulfonyl, cyclohexylsulfonyl, etc.), phenylsulfonyl (optionally substituted with 1 or 2 of methyl, methoxy, halogen, nitro, $CH_3$ or cyano), optionally substituted phenyl-$C_{1-2}$ alkylsulfonyl (e.g. benzylsulfonyl, wherein optionally substituted with 1 to 2 of methyl, methoxy, halogen, nitro, $CF_3$ or cyano, etc.), $C_{1-4}$ alkxoy-carbonyl (e.g. methoxycarbonyl, ethoxycarbonyl, etc.), nitroxy-$C_{2-4}$ alkoxy-carbonyl (e.g. 2-nitroxyethoxycarbonyl, 3-nitroxypropoxyccarbonyl etc.), optionally substituted phenyl-$C_{1-2}$ alkoxy-carbonyl (e.g. benzyloxycarbonyl, wherein optionally substituted with 1 to 2 of methyl, methoxy, halogen, nitro, $CF_3$ or cyano, etc.), carbamoyl, $C_{1-4}$ alkylaminocarbonyl (e.g. methylaminocarbonyl, ethylaminocarbonyl, etc.), $C_{3-6}$ cycloalkylaminocarbonyl (e.g. cyclopropylaminocarbonyl, cyclopentylaminocarbonyl, cyclohexylaminocarbonyl, etc.), nitroxy-$C_{2-4}$ alkylaminocarbonyl (e.g. 2-nitroxyethylaminocarbonyl, 3-nitroxypropylaminocarbonyl, etc.), anilinocarbonyl (optionally substituted with 1 to 2 of methyl, methoxy, halogen, nitro, $CF_3$ or cyano), optionally substituted phenyl-$C_{1-2}$ alkylaminocarbonyl (e.g. benzylaminocarbonyl, wherein optionally substituted with 1 to 2 of methyl, methoxy, halogen, nitro, $CF_3$ or cyano, etc.), $C_{1-4}$ alkoxysulfonyl (e.g. methoxysulfonyl, ethoxysulfonyl, etc.), optionally substituted phenyl-$C_{1-2}$ alkoxysulfonyl (e.g. benzyloxysulfonyl, wherein optionally substituted with 1 to 2 of methyl, methoxy, halogen, nitro, CF3 or cyano, etc.), sulfamoyl, $C_{1-4}$ alkylaminosulfonyl (e.g.

methylaminosulfonyl, ethylaminosulfonyl, etc.), $C_{3-6}$ cycloalkylaminosulfonyl (e.g. cyclopropylaminosulfonyl, cyclopentylaminosulfonyl, cyclohexylaminosulfonyl, etc.), nitroxy-$C_{2-4}$ alkylaminosulfonyl (e.g. 2-nitroxyethylaminosulfonyl, 3-nitroxypropylaminosulfonyl, etc.), anilinosulfonyl (optionally substituted with 1 to 2 of methyl, methoxy, halogen, nitro, $CF_3$ or cyano), optionally substituted phenyl-$C_{1-2}$ alkylaminosulfonyl (e.g. benzylaminosulfonyl, wherein optionally substituted with 1 to 2 of methyl, methoxy, halogen, nitro and $CF_3$, etc.), $C_{1-4}$ alkylamino (e.g. methylamino, ethylamino, etc.), cyclic amino (e.g. morpholino, piperazino, pyrrolidino, thiomorpholino, etc.), halogeno-$C_{1-2}$ alkylamino (e.g. trifluoromethylamino, pentafluoroethylamino, etc.), $C_{3-6}$ cycloalkylamino (e.g. cyclopropylamino, cyclopentylamino, cyclohexylamino, etc.), ureido, anilino (optionally substituted with 1 to 2 of methyl, methoxy, halogen, nitro, $CF_3$ or cyano), optionally substituted phenyl-$C_{1-2}$ alkylamino (e.g. benzylamino, wherein optionally substituted with 1 to 2 of methyl, methoxy, halogen, nitro, $CF_3$ or cyano, etc.), $C_{1-4}$ alkanoylamino (e.g. formylamino, acetylamino, etc.), $C_{3-6}$ cycloalkylcarbonylamino (e.g. cyclopropylcarbonylamino, cyclopentylcarbonylamino, cyclohexylcarbonylamino etc.), benzamido (optionally substituted with 1 to 2 of methyl, methoxy, halogen, nitro, $CF_3$ or cyano), optionally substituted phenyl-$C_{2-3}$ alkanoylamino (e.g. phenylacetamido, wherein optionally substituted with 1 to 2 of methyl, methoxy, halogen, nitro, $CF_3$ or cyano, etc.), nitroxy-$C_{2-4}$ alkanoylamino (e.g. 2-nitroxyacetylamino, 3-nitroxypropionylamino, etc.), $C_{1-4}$ alkoxycarbonylamino (e.g. methoxycarbonylamino, ethoxycarbonylamino, etc.), nitroxy-$C_{2-4}$ alkoxycarbonylamino (e.g. 2-nitroxyethoxycarbonylamino, 3-nitroxypropoxycarbonylamino, etc.), phenoxycarbonylamino (optionally substituted with 1 to 2 of methyl, methoxy, halogen, nitro, $CF_3$ or cyano), optionally substituted phenyl-$C_{1-2}$ alkoxycarbonylamino (e.g. benzyloxycarbonylamino, wherein optionally substituted with 1 to 2 of methyl, methoxy, halogen, nitro, $CF_3$ or cyano, etc.), $C_{1-4}$ alkylsulfinylamino (e.g. methylsulfinylamino, ethylsulfinylamino, etc.), nitroxy-$C_{2-4}$ alkylsulfinylamino (e.g. 2-nitroxyethylsulfinylamino, 3-nitroxypropylsulfinylamino, etc.), cycloalkylsulfinylamino (e.g. cyclopropylsulfinylamino, cyclopentylsulfinylamino, cyclohexylsulfinylamino, etc.), phenylsulfinylamino (optionally substituted with 1 to 2 of methyl, methoxy, halogen, nitro, $CF_3$ or cyano), $C_{1-4}$ alkylsulfonylamino (e.g. methylsulfonylamino, ethylsulfonylamino, etc.), $C_{3-6}$ cycloalkylsulfonylamino (e.g. cyclopropylsulfonylamino, cyclopentylsulfonylamino, cyclohexylsulfonylamino, etc.), nitroxy-$C_{2-4}$ alkylsulfonylamino (e.g. 2-nitroxyethylsulfonylamino, 3-nitroxypropylsulfonylamino, etc.), $C_{1-4}$ alkoxysulfonylamino (e.g. methoxysulfonylamino, ethoxysulfonylamino, etc.), phenylsulfonylamino (optionally substituted with 1 to 2 of methyl, ethoxy, halogen, nitro, $CF_3$ or cyano), hydroxyiminomethyl, hydrazinomethyl, $C_{1-4}$ alkyliminomethyl (e.g. methyliminomethyl, ethyliminomethyl, etc.), $C_{3-6}$ cycloalkyliminomethyl (e.g. cyclopropyliminomethyl, cyclopentyliminomethyl, cyclohexyliminomethyl, etc.), $C_{1-4}$ alkoxyliminomethyl (e.g. methoxyliminomethyl, ethoxyliminomethyl, isopropoxyliminomethyl, isobutoxyliminomethyl, t-butoxyliminomethyl, etc.), $C_{3-6}$ cycloalkoxyliminomethyl (e.g. cyclopropyloxyliminomethyl, cyclopentyloxyliminomethyl, cyclohexyloxyliminomethyl, etc.), optionally substituted phenyl-$C_{1-2}$ alkyliminomethyl (e.g. benzyliminomethyl, wherein optionally substituted with 1 to 2 of methyl, methoxy, halogen, nitro, $CF_3$ or cyano, etc.), optionally substituted phenyl-$C_{1-2}$ alkoxyliminomethyl (e.g. benzyloxyliminomethyl, wherein optionally substituted with 1 to 2 of methyl, methoxy, halogen, nitro, $CF_3$ or cyano, etc.), $C_{1-4}$ alkylthio (e.g. methylthio, ethylthio, etc.), nitroxy-$C_{2-4}$ alkylthio (e.g. 2-nitroxyethylthio, 3-nitroxypropylthio, etc.), $C_{3-6}$ cycloalkylthio (e.g. cyclopropylthio, cyclopentylthio, cyclohexylthio, etc.), phenylthio (optionally substituted with 1 to 2 of methyl, methoxy, halogen, nitro, $CF_3$ or cyano), optionally substituted phenyl $C_{1-2}$ alkylthio (e.g. benzylthio, wherein optionally substituted with 1 to 2 of methyl, methoxy, halogen, nitro, $CF_3$ or cyano, etc.), halogeno-$C_{1-2}$ alkylthio (e.g. trifluoromethylthio, pentafluoroethylthio, etc.), nitro, cyano, halogen, amino, $CO_2H$ or SH. The phenyl in these substituents may further be substituted with 1 to 3 groups selected from $C_{1-4}$ alkyl (e.g. methyl, ethyl, etc.), $C_{1-4}$ alkoxy (e.g. methoxy, ethoxy, etc.), hydroxy, nitro, halogen, halogeno-$C_{1-4}$ alkyl (e.g. $CF_3$, etc.), cyano and halogeno-$C_{1-4}$ alkoxy (e.g. $CF_3O$, etc.).

More preferable examples of R' and R" include methyl, ethyl, nitroxymethyl, 2-nitroxyethyl, 2-nitroxyethoxymethyl, nitromethyl, cyanomethyl, methoxy, ethoxy, vinyl, $CF_3$, $CF_3CF_2$, $CH_3O$, $CF_2=CF$, ethynyl, formyl, acetyl, propionyl, isobutyryl, cyclopropylcarbonyl, 2-nitroxyacetyl, 3-nitroxypropionyl, benzoyl (optionally substituted with 1 to 2 of methyl, methoxy, halogen, nitro, $CF_3$ or cyano), methylsulfonyl, ethylsulfonyl, propylsulfonyl, 2-nitroxyethylsulfonyl, 3-nitroxypropylsulfonyl, phenylsulfonyl (optionally substituted with 1 to 2 of methyl, ethoxy, halogen, nitro, $CF_3$ or cyano), methoxycarbonyl, ethoxycarbonyl, 2-nitroxyethoxycarbonyl, carbamoyl, methylaminocarbonyl, ethylaminocarbonyl, 2-nitroxyethylaminocarbonyl, methoxysulfonyl, ethoxysulfonyl, sulfamoyl, methylaminosulfonyl, ethylaminosulfonyl, 2-nitroxyethylaminosulfonyl, methylamino, ethylamino, formylamino, acetylamino, methylsulfonylamino, 2-nitroxyethylsulfonylamino, hydroxylminomethyl, methoxylminomethyl, 2-nitroxyethylthio, nitro, cyano, halogen or amino.

In the case where R' and R" are combined with each other, preferable examples of them include —CH=CH—CH=CH— (optionally substituted with methyl, methoxy, halogen, nitro, $CF_3$ or cyano), =N—O—N=, —$(CH_2)_3$—, —$(CH_2)_4$—, —$(CH_2)_2CO$— or —$(CH_2)_3CO$—.

The ring B in the compound [Ia] stands for pyridine ring optionally substituted with one or two of the groups selected from H, a halogen, a lower alkyl group, a halogeno-lower alkyl group, a lower alkoxy group and $OR^2$ ($R^2$ stands for H or a hydroxyl-protecting group). As the halogeno-lower alkyl group, use is made of, for example, a halogeno-$C_{1-4}$ alkyl group such as $CF_3$ or $CF_3CF_2$. As the lower alkyl group, use is made of a $C_{1-4}$ alkyl group such as methyl or ethyl. As the lower alkoxy group, use is made of a $C_{1-4}$ alkoxy group such as methoxy or ethoxy. As the hydroxyl-protecting group shown by $R^2$ may be any one so long as it leaves in a living body, and use is made of, for example, a $C_{1-6}$ acyl group such as formyl, acetyl and pivaloyl, $SO_3H$, benzyl group, etc.

Q in the compound [Ia] is of the same meaning as Q in the formula [I] as described above.

Especially preferable examples of the compound [I] include a compound represented by the formula [I']:

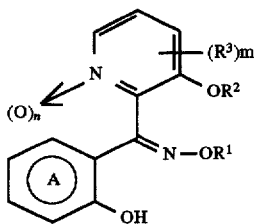

[I']

wherein $R^1$ stands for H or an optionally substituted aliphatic hydrocarbon group; and other symbols are of the same meaning as defined above, or its salt; and a compound represented by the formula [I"]:

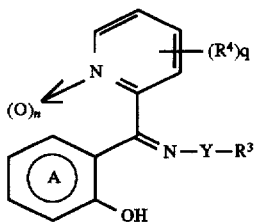

[I"]

wherein $R^4$ stands for (1) a halogen, (2) cyano group, (3) amino group, (4) a $C_{1-10}$ acyl or 1,3-dioxolan-2-yl group, (5) a carboxyl, carbamoyl or a lower alkoxy carbonyl group, (6) a lower alkoxy group, (7) a lower alkylthio, (8) a lower alkoxy group optionally substituted with hydroxy, hydroxylmino, halogen or a lower alkoxy; Y stands for O or $CH_2$; q denotes an integer of 0 to 2; and other symbols are of the same meaning as defined above, or its salt.

As the optionally substituted hydrocarbon group represented by $R^1$ in the formula [I'] and [I"], use is made of those similar to Q in the formula [I].

Preferable examples of $R^1$ in the formula [I'] include H, a $C_{1-10}$ alkyl group, a $C_{3-10}$ alkenyl group, a $C_{3-10}$ alkynyl group, a $C_{3-8}$ cycloalkyl group, a $C_{5-8}$ cycloalkenyl group or benzyl group, especially preferable one being, for example, t-butyl group.

Preferable examples of $R^1$ in the formula [I"] include branched $C_{3-8}$ alkyl groups (e.g. isopropyl, isobutyl, s-butyl, t-butyl, isopentyl, neopentyl, t-pentyl, 1,2-dimethylpropyl, 1-ethylpropyl, 1-methylbutyl, 2-methylbutyl, 1,1-dimethylbutyl, 1,2-dimethylbutyl, 2,2-dimethylbutyl, 1-ethyl-1-methylpropyl, 2-ethyl-1-methylpropyl, 1,1,2-trimethylpropyl, 1,2,2-tripropyl, etc.), cycloalkyl (e.g. $C_{3-8}$ cycloalkyl groups such as cyclopropyl, cyclobutyl, cyclopentyl, cyclohexyl, etc.), especially preferable one being, for example, t-butyl group.

As $R^2$ and the hydroxyl-protecting groups shown by $R^2$ in the formula [I'], use is made of groups similar to the above-mentioned $R^2$ and hydroxyl-protecting groups shown by $R^2$ in the substituents of the ring B in the formula [Ia].

As the halogen, the lower alkyl group, halogeno lower alkyl group shown by $R^3$ in the formula [I'], use is made of groups similar to the above mentioned halogen, the lower alkoxy group, the lower alkyl group and the halogeno-lower alkyl group, etc. as the substituents of the ring B in the formula [I] or [Ia]. As m, 0 is preferable, and, in the case of m being 1, preferable examples of $R^3$ include halogen, a lower alkoxy group, a lower alkyl group, halogeno-lower alkyl group, more preferably halogen, $CF_3$, methyl, methoxy, etc. being employed.

As (1) the halogen, (4) the $C_{1-10}$ acyl group, (5) the lower alkoxy carbonyl group, (6) the lower alkoxy group, (7) the lowerhydrocarbonand (8) the lower hydrocarbon group optionally substituted with hydroxy, hydroxylmino, halogen or a lower alkoxy group, shown by $R^4$ in the formula [I"], use is made of groups similar to the above-mentioned substituents of the ring B. The symbol q denotes preferably 0 or 1 and q is also preferably 0. preferable examples of $R^4$ include a halogen, a lower alkyl group, a lower alkoxy group, etc.

Preferable examples of the ring A in the formula [I'] include rings represented by the formula

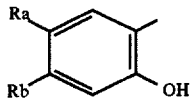

wherein Ra stands for a halogen, cyano group, nitro group, $C_{1-10}$ acyl group, lower alkoxy group, halogeno-lower alkoxy group, lower alkylthio group, lower hydrocarbon group or halogeno-lower alkyl group; and Rb stands for H, a halogen, cyano group, nitro group, $C_{1-10}$ acyl group, amino group, lower hydrocarbon group or halogeno-lower alkyl group, and preferable examples of the ring A in the formula [I"] include rings represented by the formula

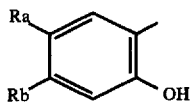

wherein symbols are of the same meaning as defined above.

Ra and Rb are of the same meaning as defined referring to Ra and Rb shown as substituents of the benzene ring represented by the above-mentioned ring A. It is also preferable that Ra stands for a nitro group, cyano group, halogen, lower alkyl group, lower alkoxy group or halogeno-lower alkyl group, and Rb stands for H, a halogen or lower alkoxy group.

The compound [I] of this invention has geometrical isomers, in the structure portion of oxime or imine, based on the steric configuration of pyridyl group and Q group, and it can exist as E- and Z-isomers or a mixture of them. The present compounds of this invention include each of the isomers and a mixture of them preferably a Z-isomer and a mixture of E and Z, and more preferably the Z-isomer.

Preferred practical examples of the compound [I] of this invention include, as those represented by the formula [I']:

(Z)-2-(5-bromo-2-hydroxybenzoyl)-3-hydroxypyridine O-t-butyloxime, (Z)-2-(5-bromo-2-hydroxybenzoyl)-3-hydroxypyridine N-oxide O-t-butyloxime, (Z)-2-(5-trifluoromethyl-2-hydroxybenzoyl)-3-hydroxypyridine O-t-butyloxime, (Z)-2-(5-trifluoromethyl-2-hydroxybenzoyl)-3-hydroxypyridine N-oxide O-t-butyloxime, (Z)-2-(5-fluoro-2-hydroxybenzoyl)-3-hydroxypyridine O-t-butyloxime, (Z)-2-(5-fluoro-2-hydroxybenzoyl)-3-hydroxypyridine N-oxide O-t-butyloxime, (Z)-2-(5-cyano-2-hydroxybenzoyl)-3-hydroxypyridine O-t-butyloxime, (Z)-2-(5-cyano-2-hydroxybenzoyl)-3-hydroxypyridine N-oxide O-t-butyloxime, -(5-chloro-2-hydroxybenzoyl)-3-hydroxypyridine O-t-butyloxime, 2-(5-chloro-2-hydroxybenzoyl)-3-hydroxypyridine N-oxide-t-butyloxime, 2-(5-trifluoromethoxy-2-hydroxybenzoyl)-3-hydroxypyridine O-t-butyloxime, 2-(5-trifluoromethoxy-2-hydroxybenzoyl)-3-hydroxypyridine N-oxide O-t-butyloxime,
(Z)-2-(5-bromo-2-hydroxybenzoyl)-3-hydroxypyridine O-i-propyloxime,
(Z)-2-(5-bromo-2-hydroxybenzoyl)-3-hydroxypyridine N-oxide O-i-propyloxime,
(Z)-2-(5-bromo-2-hydroxybenzoyl)-3-hydroxypyridine O-ethyloxime,
(Z)-2-(5-bromo-2-hydroxybenzoyl)-3-hydroxypyridine N-oxide O-ethyloxime,
(Z)-2-(2-hydroxy-5-methylbenzoyl)-3-hydroxypyridine O-t-butyloxime,
(Z)-2-(2-hydroxy-5-methylbenzoyl)-3-hydroxypyridine N-oxide O-t-butyloxime,
(Z)-2-(2-hydroxy-5-nitrobenzoyl)-3-hydroxypyridine O-t-butyloxime,
(Z)-2-(2-hydroxy-5-nitrobenzoyl)-3-hydroxypyridine N-oxide O-t-butyloxime,
(Z)-2-(4-fluoro-2-hydroxybenzoyl)-3-hydroxypyridine O-t-butyloxime,
(Z)-2-(4-fluoro-2-hydroxybenzoyl)-3-hydroxypyridine N-oxide O-t-butyloxime,
(Z)-2-(4,5-dichloro-2-hydroxybenzoyl)-3-hydroxypyridine O-t-butyloxime,
(Z)-2-(4,5-dichloro-2-hydroxybenzoyl)-3-hydroxypyridine N-oxide O-t-butyloxime,
(Z)-2-(4,5-difluoro-2-hydroxybenzoyl)-3-hydroxypyridine O-t-butyloxime,
(Z)-2-(4,5-difluoro-2-hydroxybenzoyl)-3-hydroxypyridine N-oxide O-t-butyloxime,
(Z)-2-(5-chloro-4-fluoro-2-hydroxybenzoyl)-3-hydroxypyridine O-t-butyloxime,
(Z)-2-(5-chloro-4-fluoro-2-hydroxybenzoyl)-3-hydroxypyridine N-oxide O-t-butyloxime,
(Z)-2-(5-bromo-4-chloro-2-hydroxybenzoyl)-3-hydroxypyridine O-t-butyloxime,
(Z)-2-(5-bromo-4-chloro-2-hydroxybenzoyl)-3-hydroxypyridine N-oxide O-t-butyloxime,
(Z)-2-(4-chloro-5-fluoro-2-hydroxybenzoyl)-3-hydroxypyridine O-t-butyloxime,
(Z)-2-(4-chloro-5-fluoro-2-hydroxybenzoyl)-3-hydroxypyridine N-oxide O-t-butyloxime,
(Z)-2-(5-bromo-2-hydroxy-4-methylbenzoyl)-3-hydroxypyridine O-t-butyloxime,
(Z)-2-(5-bromo-2-hydroxy-4-methylbenzoyl)-3-hydroxypyridine N-oxide O-t-butyloxime,
(Z)-2-(5-bromo-4-fluoro-2-hydroxybenzoyl)-3-hydroxypyridine O-t-butyloxime,
(Z)-2-(5-bromo-4-fluoro-2-hydroxybenzoyl)-3-hydroxypyridine N-oxide O-t-butyloxime,
(Z)-2-(2-hydroxy-4,5-dimethylbenzoyl)-3-hydroxy pyridine O-t-butyloxime,
(Z)-2-(2-hydroxy-4,5-dimethyl-benzoyl)-3-hydroxy pyridine N-oxide O-t-butyloxime,
(Z)-2-(4-fluoro-2-hydroxy-5-methylbenzoyl)-3-hydroxy pyridine O-t-butyloxime,
(Z)-2-(4-fluoro-2-hydroxy-5-methylbenzoyl)-3-hydroxy pyridine N-oxide O-t-butyloxime,
(Z)-2-(5-fluoro-2-hydroxy-4-methylbenzoyl)-3-hydroxy pyridine O-t-butyloxime,
(Z)-2-(5-fluoro-2-hydroxy-4-methylbenzoyl)-3-hydroxy pyridine N-oxide O-t-butyloxime,
(Z)-2-(2-hydroxy-4-methoxy-5-nitrobenzoyl)-3-hydroxy pyridine N-oxide O-t-butyloxime,
(Z)-2-(5-bromo-2-hydroxy-4-methoxybenzoyl)-3-hydroxy pyridine N-oxide O-t-butyloxime,
(Z)-2-(5-bromo-4-cyano-2-hydroxybenzoyl)-3-hydroxy pyridine O-t-butyloxime,
(Z)-2-(5-bromo-4-cyano-2-hydroxybenzoyl)-3-hydroxy pyridine N-oxide O-t-butyloxime,
(Z)-2-(4-chloro-5-cyano-2-hydroxybenzoyl)-3-hydroxy pyridine O-t-butyloxime,
(Z)-2-(4-chloro-5-cyano-2-hydroxybenzoyl)-3-hydroxy pyridine N-oxide O-t-butyloxime,
2-(5-chloro-2-hydroxy-4-methylaminobenzoyl)-3-hydroxy pyridine O-t-butyloxime,
2-(5-chloro-2-hydroxy-4-methylthiobenzoyl)-3-hydroxy pyridine O-t-butyloxime,
(Z)-2-(5-chloro-2-hydroxy-4-methylsulfinylbenzoyl)-3-hydroxypyridine O-t-butyloxime,
(Z)-2-(5-chloro-2-hydroxy-4-methylsulfonylbenzoyl)-3-hydroxypyridine N-oxide O-t-butyloxime,
(Z)-2-(5-chloro-4-cyano-2-hydroxybenzoyl)-3-hydroxy pyridine O-t-butyloxime,
(Z)-2-(5-chloro-4-cyano-2-hydroxybenzoyl)-3-hydroxy pyridine N-oxide O-t-butyloxime,
(Z)-2-(5-cyano-4-fluoro-2-hydroxybenzoyl)-3-hydroxy pyridine O-t-butyloxime,
(Z)-2-(5-cyano-4-fluoro-2-hydroxybenzoyl)-3-hydroxy pyridine N-oxide O-t-butyloxime,
(Z)-2-(4-cyano-5-fluoro-2-hydroxybenzoyl)-3-hydroxy pyridine O-t-butyloxime,
(Z)-2-(4-cyano-5-fluoro-2-hydroxybenzoyl)-3-hydroxy pyridine N-oxide O-t-butyloxime,
(Z)-2-(4,5-dicyano-2-hydroxybenzoyl)-3-hydroxypyridine O-t-butyloxime,
(Z)-2-(4,5-dicyano-2-hydroxybenzoyl)-3-hydroxypyridine N-oxide O-t-butyloxime, and their salts.

Or, use is made of the 3-acetoxy compound and the 3-pivaloyloxy compound of them.

And, as compounds represented by the formula [I″], (Z)-2-(5-bromo-2-hydroxybenzoyl)pyridine N-oxide O-t-butyloxime,
2-(5-trifluoromethyl-2-hydroxybenzoyl)pyridine N-oxide O-t-butyloxime,
(Z)-2-(5-fluoro-2-hydroxybenzoyl)pyridine N-oxide O-t-butyloxime,
(Z)-2-(5-cyano-2-hydroxybenzoyl)pyridine N-oxide O-t-butyloxime,
(Z)-2-(2-hydroxy-5-nitrobenzoyl)pyridine N-oxide O-t-butyloxime,
(Z)-2-(4,5-dichloro-2-hydroxybenzoyl)pyridine N-oxide O-t-butyloxime,
(Z)-2-(4,5-difluoro-2-hydroxybenzoyl)pyridine N-oxide O-t-butyloxime,
(Z)-2-(5-bromo-4-chloro-2-hydroxybenzoyl)pyridine N-oxide O-t-butyloxime,
(Z)-2-(4-chloro-5-fluoro-2-hydroxybenzoyl)pyridine N-oxide O-t-butyloxime,
(Z)-2-[(5-bromo-2-hydroxy)-α-neopentyliminobenzyl] pyridine N-oxide,
(Z)-2-(5-bromo-2-hydroxybenzoyl)-3-fluoromethyl pyridine O-t-butyloxime,
(Z)-2-(5-bromo-2-hydroxybenzoyl)-3-formyl pyridine O-t-butyloxime,
(Z)-2-(5-bromo-2-hydroxybenzoyl)-3-hydroxymethyl pyridine O-t-butyloxime,
(Z)-2-(5-bromo-2-hydroxybenzoyl)-3-trifluoromethyl pyridine O-t-butyloxime,
(Z)-2-(5-bromo-2-hydroxybenzoyl)-3-hydroxyIminomethyl pyridine O-t-butyloxime,
(Z)-2-(5-bromo-2-hydroxybenzoyl)-3-cyano pyridine N-oxide O-t-butyloxime, (Z)-2-(5-bromo-2-hydroxybenzoyl)-3-vinyl pyridine O-t-butyloxime,
(Z)-2-(5-chloro-2-hydroxybenzoyl)-3-chloro pyridine O-t-butyloxime,
(Z)-2-(5-bromo-2-hydroxybenzoyl)-3-ethoxycarbonyl pyridine O-t-butyloxime,
(Z)-2-(5-bromo-2-hydroxybenzoyl)-3-fluoro pyridine O-t-butyloxime,
(Z)-2-(5-bromo-2-hydroxybenzoyl)-3-difluoromethyl pyridine O-t-butyloxime,
(Z)-2-(5-bromo-2-hydroxybenzoyl)-3-fluoromethyl pyridine O-t-butyloxime,
(Z)-3-carbamoyl-2-(5-chloro-2-hydroxybenzoyl)pyridine O-t-butyloxime,
(Z)-3-cyano-2-(2-hydroxy-5-methylbenzoyl)pyridine O-t-butyloxime,
(Z)-2-(5-chloro-4-fluoro-2-hydroxybenzoyl)-3-cyano pyridine O-t-butyloxime,
(Z)-2-(5-cyano-2-hydroxybenzoyl)-3-cyano pyridine O-t-butyloxime,
(Z)-2-(5-bromo-2-hydroxybenzoyl)-3-methoxymethyl pyridine O-t-butyloxime,
(Z)-3-cyano-2-(5-fluoro-2-hydroxybenzoyl)-3-pyridine O-t-butyloxime,
(Z)-3-cyano-2-(2-hydroxy-5-triluoromethoxybenzoyl) pyridine O-t-butyloxime,
(Z)-3-cyano-2-(2-hydroxy-5-trifluoromethylbenzoyl) pyridine O-t-butyloxime,
(Z)-3-cyano-2-(2-hydroxy-5-nitrobenzoyl)pyridine O-t-butyloxime, and their salts.

More preferable examples the compound [I] include (Z)-2-(5-chloro-4-fluoro-2-hydroxybenzoyl)-3-hydroxypyridine N-oxide O-t-butyloxime,
(Z)-2-(5-bromo-4-chloro-2-hydroxybenzoyl)-3-hydroxypyridine N-oxide O-t-butyloxime,
(Z)-2-(5-bromo-4-fluoro-2-hydroxybenzoyl)-3-hydroxypyridine N-oxide O-t-butyloxime,
(Z)-2-(5-bromo-4-cyano-2-hydroxybenzoyl)-3-hydroxypyridine O-t-butyloxime,
(Z)-2-(5-bromo-4-cyano-2-hydroxybenzoyl)-3-hydroxypyridine N-oxide O-t-butyloxime,
(Z)-2-(5-chloro-4-cyano-2-hydroxybenzoyl)-3-hydroxypyridine N-oxide O-t-butyloxime,
(Z)-2-(5-cyano-4-chloro-2-hydroxybenzoyl)-3-hydroxypyridine N-oxide O-t-butyloxime,
(Z)-2-(5-fluoro-4-cyano-2-hydroxybenzoyl)-3-hydroxypyridine N-oxide O-t-butyloxime,
(Z)-2-(5-cyano-4-fluoro-2-hydroxybenzoyl)-3-hydroxypyridine N-oxide O-t-butyloxime,
(Z)-2-(4,5-dicyano-2-hydroxybenzoyl)-3-hydroxypyridine N-oxide O-t-butyloxime,
(Z)-2-(5-chloro-4-fluoro-2-hydroxybenzoyl)-3-acetoxypyridine N-oxide O-t-butyloxime,
(Z)-2-(5-bromo-4-chloro-2-hydroxybenzoyl)-3-acetoxypyridine N-oxide O-t-butyloxime,
(Z)-2-(5-bromo-4-fluoro-2-hydroxybenzoyl)-3-acetoxypyridine N-oxide O-t-butyloxime,
(Z)-2-(5-bromo-4-cyano-2-hydroxybenzoyl)-3-acetoxypyridine O-t-butyloxime,
(Z)-2-(5-bromo-4-cyano-2-hydroxybenzoyl)-3-acetoxypyridine N-oxide O-t-butyloxime,
(Z)-2-(5-chloro-4-cyano-2-hydroxybenzoyl)-3-acetoxypyridine N-oxide O-t-butyloxime,
(Z)-2-(5-cyano-4-chloro-2-hydroxybenoyl)-3-acetoxypyridine N-oxide O-t-butyloxime,
(Z)-2-(5-fluoro-4-cyano-2-hydroxybenzoyl)-3-acetoxypyridine N-oxide O-t-butyloxime,
(Z)-2-(5-cyano-4-fluoro-2-hydroxybenzoyl)-3-acetoxypyridine N-oxide O-t-butyloxime,
(Z)-2-(4,5-dicyano-2-hydroxybenzoyl)-3-acetoxypyridine N-oxide O-t-butyloxime,
(Z)-2-(5-chloro-4-fluoro-2-hydroxybenzoyl)-3-pivaloyloxypyridine N-oxide O-t-butyloxime,
(Z)-2-(5-bromo-4-chloro-2-hydroxybenzoyl)-3-pivaloyloxypyridine N-oxide O-t-butyloxime,
(Z)-2-(5-bromo-4-fluoro-2-hydroxybenzoyl)-3-pivaloyloxypyridine N-oxide O-t-butyloxime,
(Z)-2-(5-bromo-4-cyano-2-hydroxybenzoyl)-3-pivaloyloxypyridine O-t-butyloxime,
(Z)-2-(5-bromo-4-cyano-2-hydroxybenzoyl)-3-pivaloyloxypyridine N-oxide O-t-butyloxime,
(Z)-2-(5-chloro-4-cyano-2-hydroxybenzoyl)-3-pivaloyloxypyridine N-oxide O-t-butyloxime,
(Z)-2-(5-cyano-4-chloro-2-hydroxybenzoyl)-3-pivaloyloxypyridine N-oxide O-t-butyloxime,
(Z)-2-(5-fluoro-4-cyano-2-hydroxybenzoyl)-3-pivaloyloxypyridine N-oxide O-t-butyloxime,
(Z)-2-(5-cyano-4-fluoro-2-hydroxybenzoyl)-3-pivaloyloxypyridine N-oxide O-t-butyloxime,
(Z)-2-(4,5-dicyano-2-hydroxybenzoyl)-3-pivaloyloxypyridine N-oxide O-t-butyloxime, and their salts.

In this specification, the object compound [I] or a salt thereof or the starting or intermediate compound therefor or a salt thereof may occasionally be abbreviated only as the object compound [I] or the starting or intermediate compound with the omission of "a salt thereof".

The compound [I] of this invention can be produced by, for example, allowing a compound represented by the formula [II]:

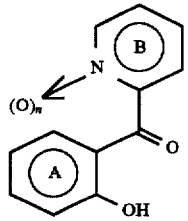

wherein symbols are of the same meaning as defined above, or a salt thereof to react with a compound represented by the formula [III]:

Q—NH$_2$    [III]

wherein the symbol is of the same meaning as defined above or a salt thereof. The compound [III] or a salt thereof is employed usually in an amount ranging from about 1 to 2 moles relative to one mole of the compound [II] or a salt thereof. This reaction can be allowed to proceed smoothly by, upon necessity, adding triethylamine, pyrrolidine, sodium acetate, boron trifluoride.diethylether, etc. as the catalyst in an amount ranging from ⅒ to 3 times as much moles.

For example, this condensation reaction can be conducted in an inert solvent such as methanol, ethanol, propanol, isopropanol, n-butanol, tetrahydrofuran, diethylether, dimethoxyethane, 1,4-dioxane, toluene, benzene, xylene, dichloromethane, chloroform, 1,2-dichloroethane, DMF, DMSO, acetic acid, pyridine and water, or a mixture solvent of them. The reaction is conducted at temperatures ranging from about 0° to 180° C.

The compound [II] to be employed as the starting substance can be produced by a known method and the following method or can be produced by, for example, methods disclosed by the following reference examples.

The compound [II] include a novel compound represented by the formula [II$^a$]

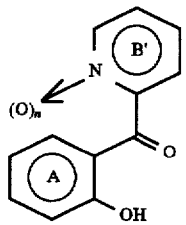

[II$^a$]

wherein the ring A stands for optionally further substituted benzene ring; the ring B' stands for substituted pyridine ring; and n denotes 0 or 1, or a salt thereof, and, as the substituents on the substituted pyridine ring shown by the ring B', use is made of groups similar to the substituents in the optionally substituted pyridine ring shown by the above-mentioned B.

Preferable examples of the compound represented by the formula [II$^a$] include those in which the ring B' is a ring represented by, for example, the formula [II$^b$]

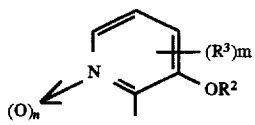

[II$^b$]

wherein R$^2$ stands for H or a hydroxy-protecting group; R$^3$ stands for halogen, cyano group, a lower alkoxy group, a lower alkyl group or a halogeno lower alkyl group; n and m each denotes 0 or 1, or the ring B' is a ring represented by, for example, the formula [II$^c$]

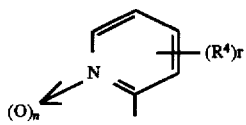

[II$^c$]

wherein R$^4$ stands for (1) a halogen, (2) cyano group, (3) an amino group, (4) a C$_{1-10}$ acyl or 1,3-dioxolan-2-yl group, (5) a carboxyl, carbamoyl or a lower alkoxycarbonyl group, (6) a lower alkoxy group, (7) a lower alkylthio group or (8) a lower hydrocarbon group which may be substituted with a hydroxy, hydroxylmino, halogen or a lower alkoxy; n denotes 0 or 1; r denotes 1 or 2.

Further, one or more groups of R' and/or R" in the compound [I] can be converted into different groups of R' and/or R". For example, following per se known methods, a hydrogen atom can be substituted with a halogen atom by halogenation or a nitro group by nitration, and reduction of the nitro group can lead to an amino group, and acylation or sulfonation of the amino group can lead to an acylamino group or sulfonylamino group. A cyano group can be converted into carbamoyl group when necessary, by processing it with an aqueous solution of sodium hydroxide/a 30% aqueous solution of hydrogen peroxide. A cyano group can also be converted into carboxyl group by, for example, heating in an aqueous solution of sodium hydroxide to hydrolyze, and, it can also be converted into a formyl group by using Raney's nickel in water/acetic acid/pyridine in the presence of sodium phosphate. The formyl group can be converted into a vinyl group by Wittig reaction, and to hydroxyliminomethyl group by the reaction with hydroxylamine. A hydroxyalkyl group can be converted into a nitroxyalkyl group by processing with sulfuric acid/nitric acid.

And, the pyridyl group can be converted into a pyridine-N-oxide group by oxidation with m-chloroperbenzoic acid, perbenzoic acid, p-nitroperbenzoic acid, pentafluoroperbenzoic acid, monoperphthalic acid, magnesium monoperoxyphthalate, peracetic acid, hydrogen peroxide or the like.

Desirably, the conditions of this oxidation reaction are appropriately changed depending upon an oxidant then employed. For example, when m-chloroperbenzoic acid is employed, the reaction is carried out in an inert solvent such as dichloromethane, chloroform, 1,2-dichloroethane, diethylether, acetone, ethyl acetate and the like, or a mixed solvent thereof. The oxidant is employed in an amount ranging from about 1 to 2 moles relative to one mole of the pyridine derivative. The reaction is carried out at temperatures usually ranging from −25° C. to 80° C., preferably ranging from −25° to 25° C.

And, the compound [I'] or a salt thereof, for example, can be produced by, for example, a reaction as shown in the Reaction Scheme I.

Reaction Scheme I

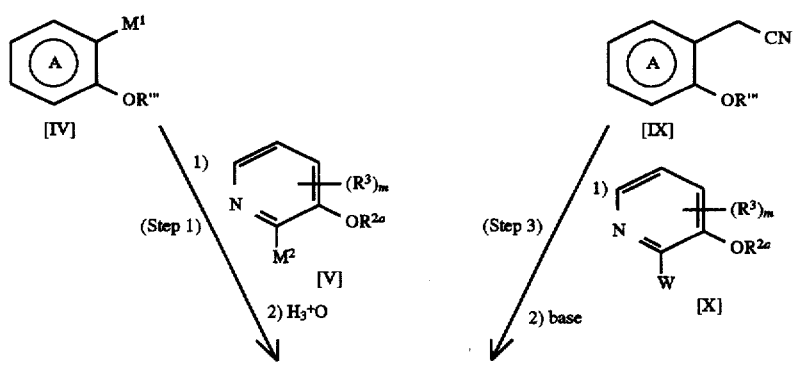

-continued
Reaction Scheme I

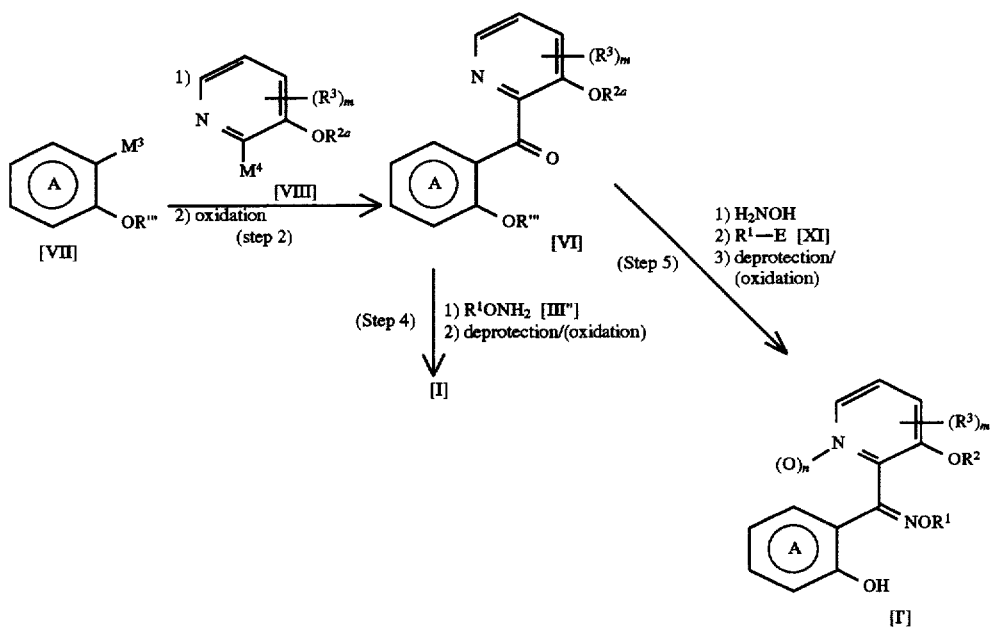

More specificaily, the compound [I'] can be produced by allowing a compound represented by the formula [IV]:

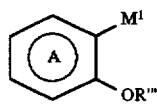   [IV]

to react with a compound represented by the general formula [V]:

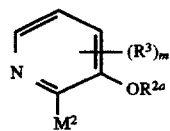   [V]

wherein either one of $M^1$ and $M^2$ stands for CN and the other stands for a leaving group; $R^{2a}$ and $R'''$ each stands for a hydroxyl-protecting group; other symbols are of the same meaning as defined above, then by subjecting the reaction product to acid-hydrolysis to give a ketone compound represented by the formula [VI]:

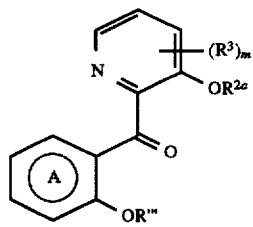   [VI]

wherein symbols are of the same meaning as defined above, then by allowing the ketone compound to react with a compound represented by the formula [III"]:

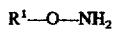   [III"]

wherein $R^1$ is of the same meaning as defined above, or a salt thereof, followed by subjecting the reaction product to deprotection or deprotection/oxidation.

The ketone compound represented by the formula [VI] can also be produced by, for example, allowing a compound represented by the formula [VII]:

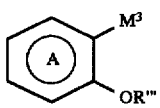   [VII]

to react with a compound represented by the formula [VIII]:

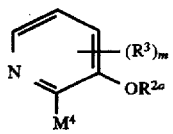   [VIII]

wherein either one of $M^3$ and $M^4$ stands for CHO and the other stands for a leaving group, and other symbols are of the same meaning as defined above, followed by subjecting the reaction product to oxidation.

And, the compound represented by the formula [VI] can also be produced by allowing a compound represented by the formula [IX]:

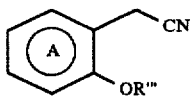   [IX]

wherein symbols are of the same meaning as defined above, to react with a compound represented by the formula [X]:

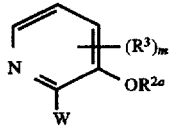   [X]

wherein W stands for halogen; $R^3$, $R^{2a}$ and m are of the same meaning as defined above, in the presence of a basic catalyst, followed by subjecting the reaction product to oxidative decyanation.

Further, the compound [I] can also be produced by allowing the compound [VI] to react with hydroxylamine, then by allowing the reaction product to react with a compound represented by the formula [XI]

$R^1$—E    [XI]

wherein E stands for halogen or an esterified hydroxyl group; and $R^1$ is of the same meaning as defined above, followed by subjecting the reaction product to deprotection or deprotection/oxidation.

In the above formulae, preferable examples of leaving groups represented by $M^1$ to $M^4$ include alkali metals, alkaline earth metals or their halogenides (e.g. Li, Na, K, Ca (½), MgCl, MgBr, MgI, etc.), zinc compounds (e.g. ZnCl, etc.) and tin compounds (e.g. SnCl etc.).

Preferable examples of the hydroxyl-protecting groups shown by R'" in the formulae [IV], [VI], [VII] and [IX] and shown by $R^{2a}$ in the formulae [V], [VI], [VIII] and [X] include per se known protecting groups of phenolic hydroxyl groups, such as methoxydimethylmethyl group, trimethylsilyl group, t-butyldimethylsilyl group, trimethylsilylethoxymethyl (SEM) group, methoxymethyl (MOM) group, benzyloxymethyl group and tetrahydropyranyl (THP) group.

Preferable examples of halogen shown by W in the formula [X] include chlorine, bromine or iodine.

In the formula [XI], preferable examples of halogen shown by E include chlorine, bromine or iodine, and preferable examples of the esterified hydroxyl groups include hydroxyl groups esterified with a reactive group such as trifluoromethanesulfonyl, methanesulfonyl or p-toluenesulfonyl.

Each step is illustrated below in detail.

(Step 1)

This condensation reaction is carried out in an inert solvent such as tetrahydrofuran, diethyl ether, dimethoxyethane, hexane, toluene, benzene and methylene chloride or a mixed solvent thereof at temperatures ranging from about −80° C. to 70° C. This reaction is conducted preferably under atmosphere of an inert gas (e.g. nitrogen or argon or the like).

Imine compounds then produced are converted into ketone compounds by a per se known means, for example, hydrolysis or alcoholysis.

(Step 2)

This condensation reaction is also conducted in substantially the same manner as in Step 1. Oxidation reaction of the benzyl alcohol compound then produced is conducted by a per se known method, for example, by using an about 2 to 10 times as much weight of activated manganese dioxide as an oxidizing agent in an inert solvent such as benzene, toluen, chloroform, dichloromethane, 1,2-dichloroethane, tetrahydrofuran, diethyl ether and hexane, or a mixed solvent thereof, at temperatures ranging from about 0° C. to 100° C.

(Step 3)

The condensation reaction of the benzyl cyanide compound [IX] with the halogenopyridine compound [X] is carried out in an inert solvent such as benzene, toluene, chloroform, dichloromethane, 1,2-dichloroethane, diethyl ether, tetrahydrofuran and DMF or a mixed solvent thereof in the presence of a base at temperatures ranging from about 0° C. to 100° C. As the base, use is made of lithium hydride, sodium hydride, sodium methoxide, sodium ethoxide, potassium t-butoxide or the like. This reaction can be allowed to proceed smoothly by, upon necessity, adding about 1 to 3 times as much moles of sodium benzenesulfinate, sodium p-toluenesulfinate or the like. This reaction is carried out, preferably, under atmosphere of an inert gas (e.g. nitrogen, argon or the like).

The oxidative decyanation to be followed is carried out, preferably, for example, in an inert organic solvent such as dichloromethane, 1,2-dichloroethane, chloroform, benzene, toluene, DMF and DMSO, or a mixed solvent (a hydrated solvent) thereof, in the presence of a base (sodium hydroxide, potassium hydroxide, sodium carbonate, potassium carbonate or the like), by, upon necessity, adding a phase-transfer catalyst (tetrabutyl ammonium hydrogensulfate, benzyl triethyl ammonium chloride or the like), at temperatures ranging from about 10° C. to 50° C.

The ketone compound [VI] obtained in the steps 1, 2 and 3 can be also used in the next reaction even without purification and isolation thereof.

(Step 4)

The condensation reaction between the ketone compound [VI] and the hydroxylamine compound [III"], and the oxidation of pyridyl group are carried out in substantially the same manner as described above.

The deprotection reaction is carried out, in accordance with a conventional manner, by acid hydrolysis or by using a fluorinating reagent such as tetrabutyl ammonium fluoride, potassium fluoride or the like.

(Step 5)

The condensation reaction between the ketone compound [VI] and hydroxylamine is carried out in substantially the same manner as described above. The reaction between the resulting hydroxime compound and the halogeno (or active ester) compound [XI] is carried out in an inert solvent, for example, methanol, ethanol, propanol, benzene, toluene, diethyl ether, tetrahydrofuran, DMF,and DMSO or a mixed solvent thereof in the presence of a base at temperatures ranging from about 0° C. to 100° C. As the base, use can be made of lithium hydride, sodium hydride, sodium methoxide, sodium ethoxide, potassium t-butoxide, sodium carbonate, triethylamine, pyridine or the like. This reaction is carried out, preferably, under atmosphere of an inert gas (e.g. nitrogen, argon or the like).

The oxidation of pyridyl group and the deprotection reaction are carried out in substantially the same manner as described above.

The starting material in the reaction scheme I is a known compound or can be produced by, for example, the procedure described in the Reference Examples given hereinafter.

Further, the compound [I"] or a salt thereof can also be produced by a reaction as shown in the reaction scheme II.

Reaction Scheme II

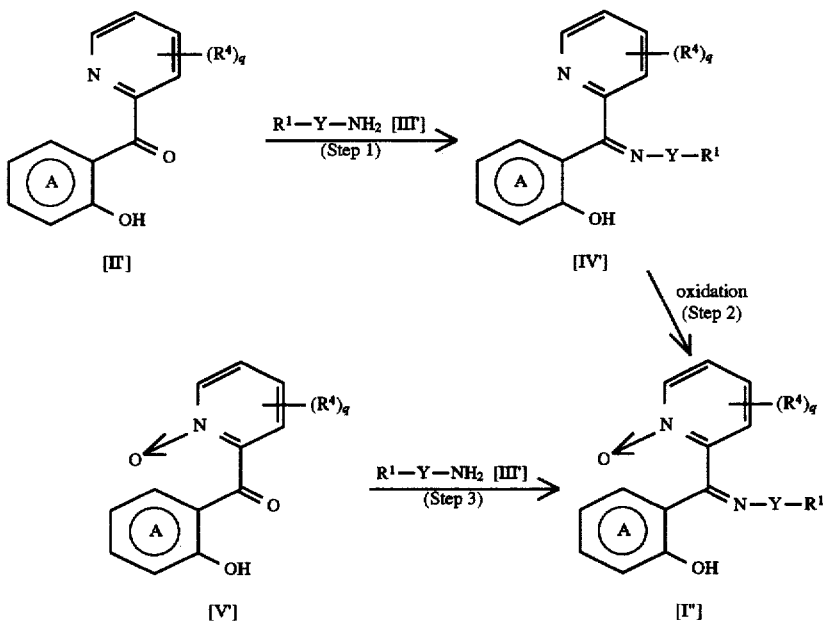

More specifically, the desired compound can be produced by allowing the compound represented by the formula [II']:

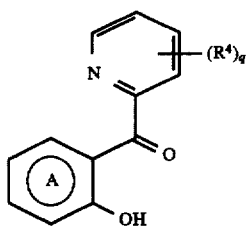

[II']

wherein symbols are of the same meaning as defined above, to react with a compound represented by the formula [III']:

R¹—Y—NH₂     [III']

wherein R¹ and Y are of the same meaning as defined above, or a salt thereof to give a compound represented by the formula [IV']

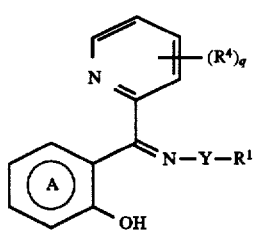

[IV']

wherein symbols are of the same meaning as defined above, followed by subjecting the compound [IV'] to oxidation.

Further, the compound [I] can be produced also by allowing a compound represented by the formula [V']

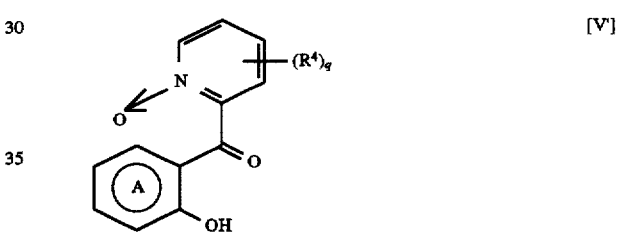

[V']

wherein symbols are of the same meaning as defined above, to react with the compound [III"] or a salt thereof.

Each step is illustrated in detail as follows.

(Step 1)

This condensation reaction is carried out in an inert solvent, for example, methanol, ethanol, propanol, isopropanol, n-butanol, tetrahydrofuran, diethyl ether, dimethoxyethane, 1,4-dioxane, toluene, benzene, xylene, dichloromethane, chloroform, 1,2-dichloroethane, DMF, DMSO, acetic acid, pyridine and water, or a mixed solvent thereof at temperatures ranging from about 0° C. to 180° C.

And, this reaction can be allowed to proceed smoothly by, upon necessity, adding about a ¹/₁₀ to 3-fold molar amount of triethylamine, pyrrolidine, sodium acetate, borontrifluoride.diethyl ether as the catalyst.

(Step 2)

As the oxidizing agent to be employed in this reaction, mention is made of, for example, m-chloroperbonzoic acid, perbenzoic acid, p-nitroperbenzoic acid, pentafluoroperbenzoic acid, permonophthalic acid, magnesium monoperoxyphthalate, peracetic acid and hydrogen peroxide.

The conditions of this reaction are desirably changed depending on the oxidizing agent then employed. For example, in the case where m-chloroperbenzoic acid is employed, the reaction is carried out in an inert solvent such as dichloromethane, chloroform, 1,2-dichloroethane, diethyl ether, acetone and ethyl acetate and the like, or a mixed solvent thereof at temperatures ranging from −25° C. to 80° C.

(Step 3)

This condensation reaction is conducted in substantially the same manner as described in Step 1 of the Reaction Scheme II described above.

The starting material in the Reaction Scheme II can be produced by a known method and the following method or can be produced by, for example, the procedure described in the Reference Examples given hereinafter. Provided that, in all the production methods mentioned above, when the benzene ring of ring A or the pyridine ring of ring B has a carbonylacyl group as the substituent, the carbonyl moiety is protected with, for example, 1,3-dioxolan-2-yl by a per se conventional method, which is then subjected to acid-hydrolysis, followed by deprotection to thereby revert to carbonylacyl group.

In the case where an amino-, hydroxyl- or carboxyl-protecting group is contained in the reaction product, the protecting group can be removed by suitably selecting from known means, for example, a method using an acid, a method using a base, a method using hydrazine, a method resorting to reduction, a method using sodium N-methyldithiocarbamate, or the like.

Among the above-mentioned object compounds or starting compounds, basic compounds can be converted into salts thereof by using an acid, in accordance with a conventional procedure. Suitable acids for this reaction are preferably those which can give pharmaceutically acceptable salts. They include inorganic acids such as hydrochloric acid, hydrobromic acid, phosphoric acid, sulfuric acid, nitric acid and sulfamic acid, and organic acids such as acetic acid, tartaric acid, citric acid, fumaric acid, maleic acid, p-toluenesulfonic acid, methanesulfonic acid and glutamic acid. And, when the compound thus obtained is a salt, it may be converted into a free base in a conventional manner.

And, the above-mentioned object compounds or starting or intermediate compounds therefor having acid groups such as —COOH, —SO$_2$H and —SO$_3$H can be converted into salts thereof, in accordance with the conventional method.

Preferable examples of salts include salts with bases such as alkali metals, alkaline earth metals, ammonium or substituted ammonium, more specially, salts with sodium, potassium, lithium, calcium, magnesium, aluminum, zinc, ammonium, tri-C$_{1-4}$ alkylammonium (e.g. trimethylammonium, triethylammonium, etc.), triethanolammonium, etc.

In each reaction described above, unless otherwise mentioned, the starting materials are used in an equimolar amount, and the reaction times ranges usually from 1 to 24 hours.

The object compound [I] or its starting compounds thus obtained can be isolated from a reaction mixture by conventional isolation and purification procedures, for example, extraction, concentration, neutralization, filtration, recrystallization and column (or thin-layer) chromatography.

The compounds [I] of this invention exhibit smooth muscle relaxation activity, coronary blood-flow increasing activity, antihypertensive activity in animals, especially mammals (e.g. human, monkey, dog, cat, rabbit, guinea pig, rat and mouse, etc.), which is considered to be based on potassium channel opening (activating) activity, and they are useful as therapeutic and prophylactic agents against angina pectoris, myocardial infarction, congestlye heart failure, hypertension, asthma, cerebrovascular contraction, arrhythmia, cerebral hemorrhage, dysmenorrhea, renal insufficiency, peripheral angiemphraxis, enuresis, gastrointestinal disorders (especially irritable intestinal syndrome), epilepsia, alopecia, among others.

The compounds [I] of this invention are low in toxicity, well absorbed even through oral administration and high in stability. Therefore, when the compounds [I] are used as the medicines as described above, they can be safely administered orally or non-orally as they are, or in the form of a pharmaceutical composition prepared by admixing them with suitable pharmaceutically acceptable carriers, excipients or diluents, as exemplified by powders, granules, tablets, capsules (including soft capsules and microcapsules), liquids, injections, suppositories and the like. The dosage varies with subject patients, administration routes and conditions of diseases to be treated. In the case of oral administration to an adult patient for the treatment of, for example, angina pectoris or hypertension, one dosage ranges usually from about 0.001 to 10 mg/kg, preferably from 0.001 to 0.2 mg/kg, more preferably from 0.001 to 0.02 mg/kg. It is desirable to administer the above dosage about one to three times a day depending on symptoms of the patients.

The following Reference Examples describing the production of the starting materials, Examples describing the object compounds [I] of this invention and Experimental Examples describing pharmacological actions of the compounds [I] further illustrate the present invention in more detail, but they are not to be construed to limit the scope of this invention.

Reference Example 1 (Production of Compound A-1)

2,4-Dibromophenol (25.7 g) and 2-methoxypropene (10 ml) were stirred for one hour at room temperature. To the mixture was added diethyl ether (300 ml). The mixture was cooled at −78° C. under atmosphere of argon. Then, to the resultant mixture, a 1.6M solution of n-butyl lithium haxane solution (70 ml) was added dropwise. The mixture was stirred for one hour while maintaining the temperature. Then, 2-cyano-3-trimethylsilyloxy pyridine (19.1 g) was added dropwise to the reaction mixture. The cooling bath was then removed, and the reaction mixture was stirred for 3 hours while warming the reaction system to room temperature. Then, methanol (10 ml) was added to the reaction system, and the mixture was stirred for several minutes, followed by distilling off the solvent under reduced pressure. To the residue were added methanol (50 ml), THF (tetrahydrofuran) (15 ml) and 2N HCl (60 ml), and the mixture was stirred for 2 hours at room temperature. The resultant mixture was neutralized with sodium hydrogencarbonate, followed by extraction with ethyl acetate. The organic layer was dried (anhydrous magnesium sulfate), then the solvent was distilled off under reduced pressure. The residue was subjected to a silica gel column chromatography, eluting with ethyl acetate/hexane, followed by purification to give 2-(5-bromo-2-hydroxybenzoyl)-3-hydroxypyridine (19.9 g) (Compound A-1). Physical properties and spectrum data of the compound are shown in Table 1 and Table 3.

In substantially the same procedure as above, Compounds A-2 and A-3 shown in Table 1 were produced.

Reference Example 2 (Production of Compound B-1).

In dichloromethane (150 ml) were dissolved 2-bromo-4-methylphenol (16.6 g) and N-ethyl diisopropylamine (20 ml). The solution was cooled to 0° C., to which was added dropwise chloromethyl methyl ether (7.5 ml). The mixture was warmed up to room temperature, which was stirred for 7.5 hours. To the reaction mixture was added water to quench the reaction, which was subjected to extraction with chloroform. The organic layer was dried (anhydrous magnesium sulfate), then the solvent was distilled off under reduced pressure. The residue was purified by means of a silica gel column chromatography (eluted with ethyl acetate/hexane) to give 2-bromo-4-methylphenol methoxy methyl ether (19.8 g) (Compound B-1). The physical properties are shown in Table 7.

By substantially the same procedure as described above, Compounds B-14, B-22, B-28 and B-30 shown in Table 7 and Table 8 were produced.

Reference Example 3 (Production of Compound B-2)

In dichloromethane (150 ml) was dissolved 3-chloro-4-fluorophenol (10.0 g). To the solution was added dropwise a solution of bromine (3.7 ml) in dichloromethane (10 ml). The mixture was stirred for 4 days at room temperature, to which was then added an aqueous solution of sodium hydrogensulfite. The mixture was stirred for 20 minutes at room temperature, which was subjected to extraction with chloroform. The extract was dried (anhydrous magnesium sulfate), then the solvent was distilled off under reduced pressure. To the residue were added N-ethyl diisopropylamine (18 ml) and dichloromethane (200 ml). The mixture was cooled to 0° C., to which was then added dropwise chloromethyl methyl ether (6.5 ml). The mixture was warmed up to room temperature, which was stirred overnight. To the mixture was added water to quench the reaction, and the reaction mixture was subjected to extraction with chloroform. The organic layer was dried (anhydrous magnesium sulfate). The solvent was then distilled off under reduced pressure. The residue was purified by means of a silica gel column chromatography (eluted with ethyl acetate/hexane) to give 2-bromo-5-chloro-4-fluorophenol methoxymethyl ether (12.4 g) (Compound B-2), whose physical properties are shown in Table 7.

By substantially the same procedure as described above, Compounds B-3, B-16 to B-18, B-20, B-42, B-44 and B-52 shown in Table 7 and Table 8 were produced.

Reference Example 4 (Production of Compound A-4)

A solution of 2-bromo-4-methylphenol methoxymethyl ether (9.49 g) in diethyl ether (170 ml) was cooled to −78° C. To the solution was added dropwise a 1.6M solution of n-butyl lithium hexane solution (30 ml) under argon atmosphere. The mixture was stirred for 45 minutes, to which was then added dropwise 2-cyano-3-trimethylsilyloxy pyridine (8.13 g) at −78° C. Then, the cooling bath was removed, and the mixture was stirred for 3 hours while warming up to room temperature. To the reaction mixture was added methanol (10 ml) to quench the reaction, then the solvent was distilled off under reduced pressure. To the residue were added methanol (100 ml), THF (25 ml) and 2N HCl (60 ml). The mixture was stirred overnight at room temperature, which was then heated for 2 hours under reflux. The reaction mixture was cooled by aeration, which was neutralized with an aqueous solution of sodium hydroxide, which was concentrated, followed by extraction with ethyl acetate. The extract was dried (anhydrous magnesium sulfate), then the solvent was distilled off, and the residue was purified by means of a silica gel column chromatography (eluted with ethyl acetate/hexane) to give 2-(2-hydroxy-5-methylbenzoyl)-3-hydroxypyridine (7.72 g) (Compound A-4), whose physical properties and spectrum data are shown in Table 1 and Table 3.

By substantially the same procedure as described above, Compounds A-5, A-6 and A-18 to A-20 shown in Table 1 were produced.

Reference Example 5 (Production of Compound B-4)

A solution of 4-methoxysalicylaldehyde (7.54 g) and N-ethyl diisopropylamine (17 ml) in dichloromethane (250 ml) was cooled to 0° C., to which was added dropwise chloromethyl methyl ether (6.0 ml). The mixture was then warmed up to room temperature, which was stirred overnight. To the reaction mixture was added water to quench the reaction, which was subjected to extraction with chloroform. The organic layer was dried (anhydrous magnesium sulfate), then the solvent was distilled off under reduced pressure. The residue was purified by means of a silica gel column chromatography (eluted with ethyl acetate/hexane) to give 4-methoxy-2-methoxymethoxy benzaldehyde (8.82 g) (Compound B-4), whose physico-chemical properties are shown in Table 5.

By substantially the same procedure as described above, Compounds B-5, B-13, B-24 and B-47 shown in Table 7 and Table 8 were produced.

Reference Example 6 (Production of Compound B-7)

A solution of 4-methyl salicyclic acid (50.0 g) and N-ethyl diisopropylamine (170 ml) in dichloromethane (500 ml) was cooled to 0° C., to which was added dropwise chloromethyl methyl ether (60 ml). The mixture was then warmed up to room temperature, which was stirred overnight. To the reaction mixture was added water to quench the reaction, followed by extraction with chloroform. The organic layer was dried (anhydrous magnesium sulfate), then the solvent was distilled off under reduced pressure. The residue was purified by means of a silica gel column chromatography (eluted with ethyl acetate/hexane) to give the methoxymethyl ether compound. A solution of this compound in THF (150 ml) was added dropwise at 0° C. to a solution of aluminum lithium hydride (12.5 g) in THF (350 ml). The mixture was stirred for one hour while warming up to room temperature. The reaction mixture was poured into ice-water, to which was added ethyl acetate. The mixture was subjected to filtration by using celite to separate insolubles. The filtrate was subjected to extraction with ethyl acetate. The organic layer was washed with a saturated aqueous saline solution, which was dried (anhydrous magnesium sulfate), followed by distilling off the solvent under reduced pressure. The residue was dissolved in dichloromethane (500 ml), to which was added activated manganese dioxide (92.0 g). The mixture was stirred overnight at room temperature. The reaction mixture was subjected to filtration using celite to remove manganese dioxide. The filtrate was concentrated under reduced pressure. The residue was purified by means of a silica gel column chromatography (eluted with ethyl acetate/hexane) to give 4-methyl-2-methoxymethoxy benzaldehyde (54.4 g) (Compound B-7), whose physical properties are shown in Table 7.

Reference Example 7 (Compound B-8)

5-Bromosalicylaldehyde (25.0 g) was dissolved in DMF (100 ml), to which was added cuprous cyanide (14.4 g). The mixture was heated under reflux for 3 hours under argon atmosphere. To the reaction mixture were added ferric chloride hexahydrate (55.2 g), conc. HCl (13 ml) and water (160 ml). The mixture was stirred for 40 minutes at room temperature, followed by extraction with ethyl acetate. The organic layer was washed successively with a saturated aqueous solution of potassium hydrogensulfate and a saturated aqueous saline solution, which was dried (anhydrous magnesium sulfate), followed by distilling off the solvent under reduced pressure. To the residue were added N-ethyl diisopropylamine (40 ml) and dichloromethane (500 ml) to dissolve. The solution was cooled to 0° C., to which was added dropwise chloromethyl methyl ether (15 ml). The mixture was then warmed up to room temperature, which was stirred overnight. To the reaction mixture was added water to quench the reaction, which was subjected to extraction with chloroform. The organic layer was dried (anhydrous magnesium sulfate), followed by distilling off the solvent under reduced pressure. The residue was purified by means of a silica gel column chromatography (eluted with ethyl acetate/hexane) to give 5-cyano-2-methoxybenzaldehyde (Compound B-8), whose physical properties are shown in Table 7.

Reference Example 8 (Production of Compound B-9)

To a solution of 4-methoxysalicylaldehyde (9.33 g) in dichloromethane (100 ml) was added dropwise a solution of bromine (3.1 ml) in dichloromethane (5 ml) at room temperature. The mixture was stirred for one hour at room temperature, to which was added an aqueous solution of sodium hydrogensulfite. The mixture was stirred for 20 minutes, which was subjected to extraction with chloroform. The organic layer was dried (anhydrous magnesium sulfate), then the solvent was distilled off under reduced pressure. The residue and N-ethyl diisopropylamine (20 ml) were dissolved in dichloromethane (300 ml), to which was added dropwise at 0° C. chloromethyl methyl ether (7.0 ml). The mixture was warmed up to room temperature, which was stirred overnight. To the reaction mixture was added water to quench the reaction. The mixture was subjected to extraction with chloroform, and the extract was dried (anhydrous magnesium sulfate), then the solvent was distilled off under reduced pressure. The residue was purified by means of a silica gel column chromatography (eluted with ethyl acetate/hexane) to give 5-bromo-4-methoxy-2-methoxymethoxybenzaldehyde (13.9 g) (Compound B-9), whose physical properties are shown in Table 7.

By substantially the same procedure as described above, Compounds B-10 and B-15 shown in Table 7 were produced.

Reference Example 9 (Production of Compound B-11)

To a solution of 4-methoxysalicylaldehyde (9.58 g) in acetic acid (50 ml) was added dropwise gradually nitric acid (10 ml) at 0° C. The mixture was stirred for 80 minutes, which was subjected to extraction with ethyl acetate. The organic layer was washed with a saturated aqueous saline solution, which was dried (anhydrous magnesium sulfate), followed by distilling off the solvent under reduced pressure. To the residue were added N-ethyl diisopropylamine (20 ml) and dichloromethane (300 ml) to dissolve. To the solution was added dropwise at 0° C. chloromethyl methyl ether (7.5 ml). The mixture was then warmed up to room temperature, which was stirred overnight. To the reaction mixture was added water to quench the reaction, followed by extraction with chloroform. The extract was dried (anhydrous magnesium sulfate), then the solvent was distilled off under reduced pressure. The residue was subjected to a silica gel column chromatography (eluted with ethyl acetate/hexane) to give 4-methoxy-5-nitro-2-methoxymethoxybenzaldehyde (5.67 g) (Compound B-11), whose physical properties are shown in Table 7.

By substantially the same procedure as described above, Compound B-12 shown in Table 7 was produced.

Reference Example 10 (Production of Compound C-1)

To a solution of 2-bromo-3-(β-trimethylsilyl ethoxymethoxy)pyridine (9.13 g) in THF (100 ml) was added dropwise, under argon atmosphere, a 1.7M solution of t-butyl lithium pentane solution (38 ml) at −78° C. The mixture was stirred for 20 minutes, to which was added dropwise at −78° C. a solution of 5-methoxy-2-methoxymethoxybenzaldehyde (6.0 g) in THF (40 ml). The mixture was then warmed up to room temperature, followed by stirring for 3 hours. To the reaction mixture was added water to quench the reaction, which was neutralized with a saturated aqueous solution of potassium hydrogensulfate, followed by extraction (ethyl acetate). The extract was dried (anhydrous magnesium sulfate), concentrated and, then, purified by means of a silica gel column chromatography (eluted with ethyl acetate/hexane) to give the benzyl alcohol compound (7.40 g) (Compound C-1), whose physical properties and spectrum data are shown in Table 9 and Table 10.

By substantially the same procedure as described above, Compound C-2 shown in Table 9 was produced.

Reference Example 11 (Production of Compound C-3)

To a solution of 5-bromo-4-methoxy-2-methoxymethoxybenzaldehyde (5.56 g) in THF (100 ml) was added dropwise, under argon atmosphere at −78° C., a solution of 2-lithio-3-semoxypyridine (20.2 mmol) in THF (150 ml) prepared in advance [prepared by adding dropwise a 1.7M t-butyl lithium pentane solution (26 ml) to a solution of 2-bromo-3-β-trimethylsilyl ethoxymethoxy)pyridine (6.13 g) in THF (150 ml)]. The mixture was then stirred for 90 minutes, to which was added water to quench the reaction. The reaction mixture was neutralized with a saturated aqueous solution of potassium hydrogensulfate, which was subjected to extraction (ethyl acetate). The extract was dried (anhydrous magnesium sulfate), concentrated and purified by means of a silica gel column chromatography (eluted with ethyl acetate/hexane) to give the benzyl alcohol compound (8.56 g) (Compound C-3), whose physical properties and spectrum data are shown in Table 9 and Table 10.

By substantially the same procedure as described above, Compounds C-4 to C-13 and C-19 shown in Table 9 were produced.

Reference Example 12 (Production of Compound A-7)

To a solution of Compound C-1 (7.40 g) in dichloromethane (200 ml) was added activated manganese dioxide (20.3 g). The mixture was stirred for 4.5 hours at room temperature. The reaction mixture was subjected to filtration with celite to remove manganese dioxide. The filtrate was concentrated under reduced pressure. To the concentrate were added acetone (50 ml) and 1N-sulfuric acid (36 ml). The mixture was stirred for 6 hours at temperatures ranging from 50° to 60° C. The reaction mixture was neutralized with a saturated aqueous solution of sodium hydrogencarbonate, which was concentrated. The concentrate was then subjected to extraction with chloroform. The extract was dried (anhydrous magnesium sulfate) and concentrated. The concentrate was purified by subjecting to a silica gel column chromatography, eluting with ethyl acetate/hexane to give 2-(2-hydroxy-5-methoxybenzoyl)-3-hydroxypyridine (3.32 g) (Compound A-7), whose physical properties and spectrum data are shown in Table 1 and Table 3.

By substantially the same procedure as described above, Compounds A-8 to A-16, A-22 and A-23 shown in Table 1 were produced.

Reference Example 13 (Production of Compound A-17)

To a solution of 4-ethylphenol methoxymethyl ether (4.64 g) in diethyl ether (120 ml) was added dropwise, under argon atmosphere at −78° C., a 1.7M t-butyl lithium pentane solution (18 ml). The mixture was stirred for one hour, to which was then added dropwise 2-cyano-3-trimethylsilyloxypyridine (4.91 g), followed by removing the cooling bath. The reaction mixture was stirred for 3 hours while warming up to room temperature. To the reaction mixture was added methanol (10 ml) to quench the reaction, then the solvent was distilled off. To the residue were added acetone (200 ml), conc. sulfuric acid (4 ml) and water (40 ml), then the mixture was heated for 5 hours under reflux. The reaction mixture was cooled, neutralized with an aqueous solution of sodium hydroxide, and concentrated. The concentrate was subjected to extraction with chloroform, and the extract was dried (anhydrous magnesium sulfate), then the solvent was distilled off. The residue was purified by means of a silica gel column chromatography (eluted with ethyl acetate/hexane) to give 2-(5-ethyl-2-hydroxybenzoyl)-3-hydroxypyridine (4.40 g) (Compound A-17), whose physical propertphysical properties and spectrum data are shown in Table 1 and Table 4.

Reference Example 14

Employing 2-cyanopyridine in place of 2-cyano-3-triemthylsilyloxypyridine in the production of Compound A-4 in Reference Example 4, reaction was conducted in substantially the same manner as in Reference Example 4 to thereby obtain 2-(4-chloro-5-fluoro-2-hydroxybenzoyl) pyridine (3.59 g, m.p. 122°–123° C.) from 2-bromo-5-chloro-4-fluorophenol (4.92 g). The spectrum data are shown below.

$^1$H-NMR(CDCl$_3$); δ7.12(1H,d,J=6.4 Hz), 7.58(1H,ddd,J= 1.4, 4.8 & 8.7 Hz), 7.94–8.03(1H,m), 8.07–8.11(1H,m), 8.27(1H,d,J=10.4 Hz), 8.72(1H,m), 12.74(1H,s). IR(KBr); 3440, 3090, 1840, 1625, 1590, 1480, 1455, 1430, 1400, 1040 (cm$^{-1}$)

Reference Example 15

To a solution of 5-bromo-2-methoxymethoxybenzaldehyde (5.00 g) in methanol (50 ml) was added, at 0° C., sodium borohydride (0.46 g). The mixture was stirred for 30 minutes at the same temperature, which was then concentrated. To the concentrate was added ethyl acetate, and the mixture was washed with an aqueous solution of potassium hydrogensulfate and a saturated aqueous saline solution, successively. The organic layer was dried (anhydrous magnesium sulfate), which was then concentrated to leave 5-bromo-2-methoxymethoxybenzyl alcohol (5.04 g) as a pale yellow oily product.

By substantially the same procedure as described above, Compound B-21 shown in Table 7 was produced.

Reference Example 16

60% Sodium hydride (1.22 g) was washed with hexane, which was suspended in DMF (30 ml). To the suspension was added, at 0° C., 5-bromosalicylic acid (3.00 g). The mixture was stirred for one hour while warming up to room temperature. To the mixture was then added chloromethyl methyl ether (3.06 g), which was stirred for one hour at room temperature. The reaction mixture was poured into water, which was subjected to extraction with ethyl acetate. The extract solution was washed with water, dried (anhydrous magnesium sulfate) and concentrated to give an oily product (3.88 g). A solution of this oily product in THF (5 ml) was added to a suspension of lithium aluminum hydride (0.32 g) in THF (70 ml) at room temperature, and the mixture was stirred for one hour. The reaction mixture was poured into a saturated aqueous saline solution, to which was added ethyl acetate. The mixture was subjected to filtration through celite. The organic layer was washed with a saturated aqueous saline solution, dried (anhydrous magnesium sulfate), and concentrated to give an oily product. The oily product was purified by means of a silica gel column chromatography (eluted with ethyl acetate/hexane) to give 5-bromo-2-methoxymethoxybenzyl alcohol (2.83 g) as an oily product.

Reference Example 17

To a solution of 5-bromo-2-methoxymethoxybenzyl alcohol (27.2 g) and triethylamine (23 ml) in dichloromethane (550 ml) was added, at 0° C., methanesulfonyl chloride (13.9 g). The mixture was stirred for 15 hours, while warming up to room temperature. The reaction mixture was poured into water, which was subjected to extraction with ethyl acetate. The extract solution was washed with an aqueous saline solution, which was then dried (anhydrous magnesium sulfate), followed by concentration to give an oily product. The oily product was purified by means of a silica gel column chromatography (eluted with ethyl acetate/hexane) to give 5-bromo-2-methoxymethoxybenzyl chloride (21.6 g) as an oily product.

Reference Example 18

To a mixture of 5-bromo-2-methoxymethoxybenzyl chloride (21.6 g), sodium cyanide (8.33 g) and dichloromethane (10 ml) was added, at 15° to 20° C., DMSO (80 ml), followed by stirring for 3 hours at room temperature. The mixture was poured into water, which was subjected to extraction with ethyl acetate. The extract solution was washed with water, dried (anhydrous magnesium sulfate) and concentrated to leave an oily product. The oily product was purified by means of a silica gel column chromatography (eluted with ethyl acetate/hexane) to give 5-bromo-2-methoxymethoxybenzyl cyanide (20.4 g), whose spectrum data are shown below.

$^1$H-NMR (CDCl$_3$): δ3.49(3H,s), 3.67(2H,s), 5.22(2H,s), 7.03(1H,d,J=8.8 Hz), 7.40(1H,dd,J=8.8 & 2.4 Hz), 7.48(1H, d,J=2.4 Hz).

IR(neat); 2250, 1600, 1490(cm$^{-1}$).

Reference Example 19 (Production of Compound C-14)

To a mixture of 5-bromo-2-methoxymethoxybenzyl cyanide (2.10 g), 2-bromo-3-methoxymethoxypyridine (1.79 g), sodium p-toluenesulfinate (0.44 g) and THF (30 ml) was added, at room temperature, 60% sodium hydride (0.69 g), followed by heating for 2 hours under reflux under argon atmosphere. The reaction mixture was poured into a saturated aqueous saline solution, which was subjected to extraction with ethyl acetate. The extract solution was washed with a saturated aqueous saline solution, dried (anhydrous sodium sulfate), and concentrated. The concentrate was purified by means of a silica gel column chromatography (eluted with ethyl acetate/hexane) to give 2-(5-bromo-α-cyano-2-methoxymethoxybenzyl)-3-methoxymethoxypyridine (2.58 g), whose physical properties and spectrum data are shown in Table 9 and Table 12.

By substantially the same procedure as described above, Compound D-3 shown in Table 13 was produced.

Reference Example 20

A mixture of 2-(5-bromo-α-cyano-2-methoxymethoxybenzyl)-3-methoxymethoxypyridine (2.40 g), potassium carbonate (2.53 g), tetrabutylammonium hydrogensulfate (0.41 g) and DMF (24 ml) was stirred for 38 hours at room temperature. The reaction mixture was poured into water, which was subjected to extraction with ethyl acetate. The extract solution was washed with water, dried (anhydrous sodium sulfate), and concentrated to leave an oily product. The oily product was purified by means of a silica gel column chromatography (eluted with ethyl acetate/hexane) to give 2-(5-bromo-2-methoxymethoxybenzoyl)-3-methoxymethoxypyridine (2.03 g) as an oily product, whose spectrum data are shown below.

$^1$H-NMR(CDCl$_3$); δ3.19(3H,s), 3.44(3H,s), 4.83(2H,s), 5.21(2H,s), 7.03(1H,d,J=8.8 Hz), 7.34(1H,dd,J=8.4 & 4.8 Hz), 7.55(1H,dd,J=8.8 & 2.6 Hz), 7.58(1H,dd,J=8.4 & 1.4), 7.87(1H,d,J=2.6 Hz), 8.25(1H,dd,J=4.8 & 1.4 Hz).

By substantially the same procedure as described above, Compound E-3 shown in Table 16 was produced.

Reference Example 21 (Production of Compound A-1)

A mixture of 2-(5-bromo-2-methoxymethoxybenzoyl)-3-methoxymethoxypyridine (1.89 g), hydrochloric acid (10 ml) and methanol (80 ml) was stirred for 70 hours at room temperature. The reaction mixture was concentrated, which was partitioned with ethyl acetate-water. The organic layer was washed with a saturated aqueous saline solution, dried (anhydrous sodium sulfate) and concentrated. The concentrate was purified by means of a silica gel column chromatography (eluted with ethyl acetate/hexane) to give 2-(5-bromo-2-hydroxybenzoyl)-3-hydroxypyridine (1.34 g) (Compound A-1).

By substantially the same procedure as described above, Compounds A-25 to A-30, E-4, E-6, E-8 and E-21 shown in Table 2 and Table 16 were produced.

Reference Example 22 (Production of Compound D-1)

To a solution of 2-bromopyridine (5.75 g) in THF (125 ml) was added, under argon atmosphere at −78° C., a 1.6M n-butyl lithium hexane solution (40.0 ml). The mixture was stirred for 15 minutes at the same temperature. To the reaction mixture was added a solution of 5-bromosalicylaldehyde (3.65 g) in THF (20 ml), which was stirred for 20 minutes at the same temperature, then for further 15 minutes while warming up to room temperature. The reaction mixture was poured into 3N HCl, which was washed with diethyl ether, followed by rendering the pH to alkaline side with the addition of 3N sodium hydroxide. The resultant was washed with diethyl ether, followed by being acidified to about pH 5 with 3N HCl. The weakly acodofoed reaction mixture was subjected to extraction with ethyl acetate, washed with water, dried (anhydrous sodium sulfate), and concentrated to dryness to give 5-bromo-2-hydroxy-α-(2-pyridyl)benzyl alcohol (3.50 g) (Compound D-1), whose phisical properties and spectrum data are shown in Table 13 and Table 14.

Reference Example 23

To a solution of 5-bromo-2-hydroxy-α-(2-pyridyl)-benzyl alcohol (3.18 g) in chloroform (60 ml) was added at 0° C. 70% m-chloroperbenzoic acid (3.30 g). The mixture was stirred for 10 minutes at the same temperature, then for further 3.5 hours while warming up to room temperature. The reaction mixture was poured into an aqueous solution of sodium sulfite, followed by extraction with ethyl acetate. The extract solution was washed with an aqueous solution of sodium carbonate and a saturated aqueous saline solution, successively, dried (anhydrous sodium sulfate), and concentrated. The concentrate was purified by means of a silica gel column chromatography (eluted with ethyl acetate/hexane) to give 2-(5-bromo-2, α-dihydroxybenzyl)pyridine N-oxide (2.50 g, m.p.188°–189° C.), whose spectrum data are shown below.

$^1$H-NMR(DMSO-d$_6$); δ6.37(1H,d,J=4.4 Hz), 6.49(1H,dd, J=8.4 & 2.6 Hz), 6.72(1H,d,J=8.4 Hz), 7.24(1H,dd,J=8.4 & 2.6 Hz), 7.42–7.48(2H,m), 7.56(1H,td,J=8.0 & 0.8 Hz), 7.72(1H,dd,J=8.0 & 2.0 Hz), 8.35(1H,dd,J=6.0 & 0.8 Hz), 10.85(1H,s).

Reference Example 24

A mixture of 2-(5-bromo-2, α-dihydroxybenzyl) pyridine N-oxide (2.50 g), activated manganese dioxide (12.5 g) and chloroform (60 ml) was stirred for 16 hours at room temperature. The manganese dioxide was filtered off, and the filtrate was concentrated. The concentrate was recrystallized from ethyl acetate to give 2-(5-bromo-2-hydroxybenzoyl) pyridine N-oxide (1.26 g, m.p. 160°–162° C.), whose spectrum data are shown below.

$^1$H-NMR(CDCl$_3$); δ6.97(1H,d,J=9.2 Hz), 7.36–7.49(4H, m), 7.59(1H,dd,J=9.2 & 2.6 Hz), 8.28(1H,dd,J=9.2 & 2.6 Hz), 11.2–11.6(1H,br.s).

In accordance with the procedures in Reference Example 22 and Reference Example 24, Compound E-22 shown in Table 16 was produced.

Reference Example 25

To a solution of 3-bromopyridine (17.8 g) in chloroform (500 ml) was portionwise added m-perbenzoic acid (28.0 g) at 0° C. The mixture was warmed up to room temperature, which was stirred for 3 hours. To the reaction mixture was added an aqueous solution of sodium hydrogensulfite, which was stirred for 30 minutes, followed by addition of an aqueous solution of sodium hydroxide and chloroform for extraction. The organic layer was dried (anhydrous magnesium sulfate), followed by concentration. To the concentrate were added trimethylsilyl nitrile (50.0 g), triethylamine (60 ml) and acetonitrile (130 ml). The mixture was heated for 8 hours under reflux. The solvent was distilled off. The residue was purified by means of a silica gel column chromatography (elution solvent: ethyl acetate/hexane) to give 3-bromo- 2-cyanopyridine (14.6 g) as an oily product, whose spectrum data are shown below.

$^1$H-NMR(CDCl$_3$); δ7.42(1H,dd,J=4.8 & 8.0 Hz), 8.04 (1H,dd,J=1.4 & 8.0 Hz), 8.67(1H,dd,J=1.4 & 4.8 Hz).

By substantially the same procedure as described above, 3,5-dichloro-2-cyanopyridine was produced from 3,5-dichloropyridine.

$^1$H-NMR(CDCl$_3$); δ7.91(1H,d,J=2.0 Hz), 8.58(1H,d,J=2.0 Hz).

Reference Example 26 (Production of Compound B-19)

A solution of methyl 3-hydroxy-2-naphthoate (7.01 g) in THF (200 ml) was cooled to 0° C., to which was added 60% sodium hydride (1.58 g) during 10 minutes. Then, the mixture was stirred for one hour at room temperature, to which was added dropwise chloromethyl methyl ether (2.8 ml). The mixture was then stirred for two hours, to which was added water to quench the reaction, followed by extraction with ethyl acetate. The organic layer was dried (anhydrous magnesium sulfate), and distilled off the solvent under reduced pressure. The residue was purified by means of a silica gel column chromatography (eluted with ethyl acetate/hexane) to give methyl 3-methoxymethoxy-2-naphthoate (7.11 g) (Compound B-19). The physical properties are shown in Table 7.

Reference Example 27 (Production of Compound A-21)

To a solution of 2-bromo-3-(β-trimethylsilylethoxymethoxy)pyridine (8.51 g) in THF (150 ml) was added dropwise at −78° C. a 1.7M t-butyl lithium pentane solution (35 ml) under argon atmosphere, then the mixture was stirred for 20 minutes. To the mixture was then added dropwise at −78° C. a solution of methyl 3-methoxymethoxy-2-naphthoate (6.68 g) in THF (50 ml). The mixture was warmed up to room temperature and stirred for 2 hours, to which was added water to quench the reaction, followed by extraction with ethyl acetate. The organic layer was dried (anhydrous magnesium sulfate), then the solvent was distilled off under reduced pressure. To the residue were added acetone (200 ml) and 1N sulfuric acid (36 ml), then the mixture was stirred for 5 hours at 50°–60° C. The reaction mixture was cooled by aeration, which was then neutralized with a saturated aqueous solution of sodium hydrogencarbonate, followed by extraction with chloroform. The organic layer was dried (anhydrous magnesium sulfate), then the solvent was distilled off under reduced pressure. The residue was purified by means of a silica gel column chromatography (eluted with ethyl acetate/hexane) to give 2-(3-hydroxy-2-naphthoyl)-3-hydroxypyridine (3.93 g) (Compound A-21). The physical properties and spectrum data are shown in Table 1 and Table 5.

Reference Example 28 (Production of Compound B-23)

A solution of 2-bromo-4-methoxymethoxymethylphenol methoxymethyl ether (11.18 g) in diethyl ether (400 ml) was cooled to −78° C. To the solution was added dropwise a 1.6M n-butyl lithium hexane solution (28 ml) under argon atmosphere. The mixture was stirred for one hour while maintaining the temperature, to which was added dropwise DMF (5 ml), followed by raising the temperature up to room temperature and stirring overnight. The reaction mixture was subjected to extraction with the addition of water and ethyl acetate. The organic layer was washed (a saturated aqueous saline solution) and dried (anhydrous magnesium sulfate). Then, the solvent was distilled off under reduced pressure, and the residue was purified by means of a silica gel column chromatography (eluted with ethyl acetate/hexane) to give 5-methoxymethoxymethyl salicylaldehyde methoxymethyl ether (7.23 g) (Compound B-23). The physical properties are shown in Table 7.

By substantially the same manner as above, Compounds B-29, B-32, B-45 and B-53 shown in Table 8 were produced.

Reference Example 29 (Production of Compound B-25)

To a mixture of carbon tetrabromide (56.58 g), triphenylphosphine (44.61 g) and zinc powder (11.18 g) was added dichloromethane (300 ml), and the mixture was stirred for 25 hours at room temperature. To the mixture was then added p-methoxymethoxybenzaldehyde (13.91 g), which was stirred for 30 hours. The reaction mixture was subjected to filtration through celite, and the filtrate was concentrated under reduced pressure. The residue was purified by means of a silica gel column chromatography (eluted with ethyl acetate/hexane) to give 4-(2,2-dibromoethenyl)phenol methoxymethyl ether (17.84 g) (Compound B-25). The physical properties are shown in Table 7.

Reference Example 30 (Production of Compound B-26)

A solution of 4-(2,2-dibromoethenyl)phenol methoxymethyl ether (16.56 g) in THF (350 ml) was cooled to −78° C., to which was added dropwise, under argon atmosphere, a 1.6M n-butyl lithium hexane solution (70 ml). The mixture was stirred for one hour under the same conditions, which was then warmed and stirred for one hour at room temperature. The reaction mixture was cooled with ice, to which was added dropwise trimethylchlorosilane (7.2 ml). The mixture was then stirred for 3 hours while warming up to room temperature, to which was added water to quench the reaction, followed by extraction with ethyl acetate. The organic layer was washed (a saturated aqueous saline solution) and dried (anhydrous magnesium sulfate), then the solvent was distilled off under reduced pressure. The residue was purified by means of a silica gel column chromatography (eluted with ethyl acetate/hexane) to give 4-(2-trimethylsilylethynyl)phenol methoxymethyl ether (10.76 g) (Compound B-26). The physical properties are shown in Table 8.

Reference Example 31 (Production of Compound B-27)

A solution of 4-(2-trimethylsilylethynyl)phenol methoxymethyl ether (6.08 g) in diethyl ether (450 ml) was cooled to −78° C., to which was added dropwise, under argon atmosphere, a 1.7M t-butyl lithium pentane solution (18 ml), and the mixture was stirred for one hour at the same temperature. To the reaction mixture was then added dropwise DMF(5 ml), followed by warming up to room temperature and stirring overnight. To the reaction mixture were added ethyl acetate and water, which was subjected to extraction. The organic layer was washed (a saturated aqueous saline solution) and dried (anhydrous magnesium sulfate), followed by distilling off the solvent under reduced pressure. The residue was purified by means of a silica gel column chromatography (eluted with ethyl acetate/hexane) to give 5-(2-trimethylsilylethynyl)-2- methoxymethoxybenzaldehyde (5.29 g) (Compound B-27). The physical properties are shown in Table 8.

Reference Example 32

In chloroform (500 ml) was dissolved p-hydroxybenzaldehyde (12.60 g), to which was added dropwise at room temperature a solution of bromine (6 ml) in chloroform (15 ml). The mixture was stirred at room temperature overnight, to which was added an aqueous solution of sodium hydrogensulfite, and the mixture was stirred for 30 minutes. The reaction mixture was subjected to extraction with chloroform. The organic layer was dried (anhydrous magnesium sulfate), then the solvent was distilled off under reduced pressure. To the residue were added ethylene glycol (10 ml), toluene (300 ml) and p-toluenesulfonic acid (0.57 g). The mixture was subjected to azeotropic dehydration overnight. The reaction mixture was cooled by aeration, neutralized with an aqueous solution of sodium hydrogencarbonate. Toluene was distilled off under reduced pressure, and the residue was subjected to extraction with ethyl acetate. The extract was washed (a saturated aqueous saline solution), dried (anhydrous magnesium sulfate) and, then the solvent was distilled off under reduced pressure. The residue was purified by means of a silica gel column chromatography (eluted with ethyl acetate/ hexane) to give 2-bromo-4-(1,3-dioxolan-2-yl)phenol (19.17 g), m.p. 84°-87° C.

Reference Example 33

To a solution of 2-[5-(1,3-dioxolan-2-yl)-2-methoxymethoxy-α-hydroxybenzyl]-3-semoxypyridine (4.41 g) in dichloromethane (250 ml) was added activated manganese dioxide (13.18 g), and the mixture was stirred overnight at room temperature. The reaction mixture was subjected to filtration through celite to remove manganese dioxide, and the filtrate was concentrated. The concentrate was purified by means of a silica gel column chromatography (eluted with ethyl acetate/hexane) to give 2-[5-(1,3-dioxolan-2-yl)-2-methoxymethoxybenzoyl]-3-semoxypyridine (2.66 g) as an oily product. The spectrum data are as follows:

$^1$H-NMR(CDCl$_3$): δ-0.01(9H,s), 0.88–0.96(2H,m), 3.19 (3H,s), 3.67–3.75(2H,m), 4.03–4.14(4H,m), 4.86(2H,s), 5.21(2H,s), 5.84(1H,s), 7.07(1H,d,J=8.6 Hz), 7.31–7.35(1H, m), 7.57–7.63(2H,m), 7.94(1H,d,J=2.4 Hz), 8.25(1H,dd,J= 1.2 & 4.6 Hz).

By substantially the same procedure as above, Compounds E-1, E-7, E-9, E-18, E-23, E-27, E-32, E-40, E-42, E-47 and F-11 shown in Table 16, Table 17 and Table 22 were produced.

Reference Example 34 (Production of Compound A-24)

In a mixture of water (10 ml) and acetic acid (50 ml) was dissolved 3-(2-methoxymethoxy-5-nitrobenzoyl)-3-semoxypyridine (4.31 g). To the solution was added iron powder (3.63 g) at room temperature during 15 minutes, and the mixture was stirred for further 2 hours. The reaction mixture was concentrated, which was neutralized with an aqueous solution of sodium hydrogencarbonate and subjected to filtration through celite. The filtrate was subjected to extraction by the addition of ethyl acetate. The organic layer was washed with a saturated aqueous saline solution and, then dried (anhydrous magnesium sulfate), followed by distilling off the solvent under reduced pressure. The residue was dissolved in dichloromethane (200 ml). The solution was cooled to 0° C., to which were added triethylamine (15 ml) and acetyl chloride (1.3 ml) successively. The mixture was warmed and stirred overnight at room temperature, to which were added water and chloroform for extraction. The organic layer was dried (anhydrous magnesium sulfate), then the solvent was distilled off under reduced pressure. The residue was purified by means of a silica gel column chromatography (eluted with ethyl acetate/hexane) to give a benzyl alcohol compound (2.01 g). The benzyl alcohol compound (2.01 g) was dissolved in dichloromethane (150 ml). To the solution was added activated manganese dioxide (6.32 g) at room temperature, and the mixture was stirred overnight. The reaction mixture was subjected to filtration through celite to remove manganese dioxide, then the filtrate was concentrated. To the concentrate were added acetone (100 ml) and 1N sulfuric acid (21 ml), and the mixture was stirred for 5 hours at 50°–60° C. The reaction mixture was cooled by aeration, which was neutralized with a saturated aqueous solution of sodium hydrogencarbonate, followed by extraction with chloroform. The organic layer was dried (anhydrous magnesium sulfate), then the solvent was distilled off under reduced pressure. The residue was purified by means of a silica gel column chromatography (eluted with ethyl acetate/hexane) to give 2-(5-acetamino-2-hydroxybenzoyl)-3-hydroxypyridine (0.88 g) (Compound A-24). The physical properties are shown in Table 1 and Table 5.

Reference Example 35 (Production of Compound B-31)

To a suspension of 5-methylsalicylic acid (3.92 g) and potassium carbonate (8.91 g) in DMF (50 ml) was added dropwise chloromethyl methyl ether (5.83 g) during 30 minutes. The mixture was stirred overnight at room temperature, to which was added ice-water to quench the reaction, followed by extraction with ethyl acetate. The organic layer was washed with water and dried (anhydrous magnesium sulfate), followed by distilling off the solvent under reduced pressure to leave methoxymethyl 2-methoxymethoxy-5-methyl benzoate (6.19 g) (B-31). The physical properties were shown in Table 8.

By substantially the same procedure as above, Compounds B-39, B-43, B-47 and B-51 shown in Table 8 were produced from 4-chloro-5-fluorosalicylic acid [m.p. 205° C. (decomp.)].

Reference Example 36 (Production of Compound B-33)

In ethyl orthoformate (1.2 l) was dissolved 4-chlorosalicylic acid (125 g), which was stirred for 38 hours. The solvent was distilled off, and the residue was dissolved in chloroform (850 ml), to which was added dropwise at room temperature a solution of bromine (41 ml) in chloroform (20 ml). The mixture was warmed up to 40° C. and stirred for 3 days, to which was added a solution of sodium hydrogensulfite, and the mixture was stirred for 20 minutes at room temperature. The reaction mixture was subjected to extraction with chloroform. The organic layer was dried (anhydrous magnesium sulfate), then the solvent was distilled off under reduced pressure. The residue was dissolved in DMF (800 ml), to which was added potassium carbonate (205.1 g). To the mixture was added dropwise chloromethyl methyl ether (83.5 ml) during 40 minutes. The mixture was stirred for 2.5 hours, which was subjected to filtration through celite. The filtrate was concentrated, which was subjected to extraction with the addition of ethyl acetate and water. The organic layer was washed with water and a saturated aqueous saline solution, successively, then dried (anhydrous magnesium sulfate), followed by distilling off the solvent under reduced pressure. The residue was purified by means of a silica gel column chromatography (eluted with ethyl acetate/hexane) to give ethyl 5-bromo-4-chloro-2-methoxymethoxybenzoate (161.4 g) (Compound B-33). The physical properties are shown in Table 8.

By substantially the same procedure as above, Compound B-36 shown in Table 8 was produced from 5-fluorosalicylic acid.

Reference Example 37 (Production of Compound B-34)

In THF (800 ml) was dissolved ethyl 5-bromo-4-chloro-2-methoxymethoxybenzoate (161.4 g). To the solution was added lithium aluminum hydride (19.2 g) at 0° C. over a period of 30 minutes, and the mixture was stirred for further 30 minutes. The reaction mixture was poured into a saturated aqueous saline solution, to which was added ethyl acetate, followed by subjecting the mixture to filtration with celite. The organic layer was washed with a saturated aqueous saline solution, dried (anhydrous magnesium sulfate), and concentrated. The concentrate was purified by means of a silica gel column chromatography (eluted with ethyl acetate/hexane) to give 5-bromo-4-chloro-2-methoxymethoxybenzyl alcohol (137.9 g) (Compound B-34). The physical properties are shown in Table 8.

By substantially the same procedure as above, Compounds B-37 and B-40 shown in Table 8 were produced.

Reference Example 38 (Production of Compound B-35)

To a solution of 5-bromo-4-chloro-2-methoxymethoxybenzyl alcohol (137.9 g) and triethylamine (105 ml) in dichloromethane (500 ml) was added at 0° C. methanesulfonyl chloride (45.5 ml) over a period of 30 minutes. The mixture was stirred overnight (13 hours), while warming up to room temperature. The reaction mixture was poured into water, to which was added dichloromethane for extraction. The extract solution was dried (anhydrous magnesium sulfate) and concentrated. To a suspension of the concentrate and sodium cyanide (51.4 g) in dichloromethane (40 ml) was added dropwise at 0° C. DMSO (300 ml). The mixture was then stirred for 3 hours at room temperature. The reaction mixture was poured into water, which was subjected to extraction with ethyl acetate. The extract solution was washed with water, dried (anhydrous magnesium sulfate) and concentrated. The concentrate was purified by means of a silica gel column chromatography (eluted with ethyl acetate/hexane) to give 5-bromo-4-chloro-2-methoxymethoxybenzyl cyanide (86.4 g) (Compound B-35). The physical properties are shown in [Table 6].

By substantially the same manner as above, Compounds B-38 and B-41 shown in Table 8 were produced.

Reference Example 39 (Production of Compound C-15)

To a suspension of 5-bromo-4-chloro-2-methoxymethoxybenzyl cyanide (10.4 g), 2-bromo-3-methoxymethoxy pyridine (7.81 g) and sodium p-toluenesulfinate (12.7 g) in THF (150 ml) was added, at room temperature, sodium hydride (3.63 g). The mixture was heated for 2 hours under reflux under argon atmosphere. The reaction mixture was cooled by aeration, which was poured into ice-water, followed by extraction with ethyl acetate. The organic layer was washed with a saturated aqueous saline solution, dried (anhydrous magnesium sulfate) and concentrated. The crystal obtained was washed with cyclohexane/isopropyl ether (5:1) to give 2-(5-bromo-4-chloro-α-cyano-2-methoxymethoxybenzyl)-3-methoxymethoxypyridine (10.9 g) (Compound C-15). The physical properties and spectrum data are shown in Table 9 and Table 12.

By substantially the same procedure as above, Compounds C-16, C-17 and C-18 shown in Table 9 were produced.

Reference Example 40

DMF (100 ml) was added to a mixture of 2-(5-bromo-4-chloro-α-cyano-2-methoxymethoxybenzyl)-3-methoxymethoxypyridine (10.1 g) and potassium carbonate (9.84 g). The mixture was stirred at room temperature overnight under oxygen atmosphere. The reaction mixture was poured into water, which was subjected to extraction with ethyl acetate. The organic layer was washed with a saturated aqueous saline solution, dried (anhydrous magnesium sulfate), and concentrated. The concentrate was purified by a silica gel column chromatography (eluted with ethyl acetate/hexane) to give 2-(5-bromo-4-chloro-2-methoxymethoxybenzoyl)-3-methoxymethoxypyridine (9.08 g, m.p. 70°–72° C.). The spectrum data are shown as follows:

$^1$H-NMR(CDCl$_3$); δ3.20(3H,s), 3.45(3H,s), 4.83(2H,s), 5.21(2H,s), 7.27(1H,s), 7.34(1H,dd,J=4.6 & 8.6 Hz), 7.58 (1H,dd,J=1.2 & 8.6 Hz), 7.98(1H,s), 8.24(1H,dd,J=1.2 & 4.6 Hz).

Compound C-16 was subjected to substantially the same reaction as above to give a mixture of 2-(5-bromo-4-fluoro-2-methoxymethoxybenzoyl)-3-methoxymethoxy pyridine (4-fluoro compound) and 2-(5-bromo-4-cyano-2-methoxymethoxybenzoyl)-3-methoxYmethoxypyridine (4-cyano compound) (about 4:1). The spectrum data are shown as follows: 4-fluoro compound:

$^1$H-NMR(CDCl$_3$); δ3.20(3H,s), 3.45(3H,s), 4.82(2H,s), 5.21(2H,s), 6.97(1H,d,J=8.0 Hz), 7.34(1H,dd,J=4.6 & 8.6 Hz), 8.6 Hz), 7.58(1H,dd,J=1.2 & 8.6 Hz), 8.00(1H,d,J=8.0 Hz), 8.25(1H,dd,J=1.2 & 4.6 Hz).4-cyano compound:

$^1$H-NMR(CDCl$_3$); δ3.23(3H,s), 3.48(3H,s), 4.89(2H,s), 5.26(2H,s), 7.39(1H,dd,J=4.4 & 8.4 Hz), 7.47(1H,s), 7.61–7.66(1H,m), 7.88(1H,s), 8.23–8.26(1H,m).

By substantially the same procedure as above, from Compound C-17, was obtained a mixture of 2-(4-chloro-5-fluoro-2-methoxymethoxybenzoyl)-3-methoxymethoxy pyridine (5-fluoro compound) and 2-(4-chloro-5-cyano-2-methoxymethoxybenzoyl)-3-methoxymethoxypyridine (5-cyano compound) (about 3:1). The spectrum data are shown as follows:5-fluoro compound:

$^1$H-NMR(CDCl$_3$); δ3.20(3H,s), 3.45(3H,s), 4.82(2H,s), 5.21(2H,s), 6.99(1H,d,J=10.8 Hz), 7.34(1H,dd,J=4.6 & 8.6 Hz), 7.58(1H,dd,J=1.2 & 8.6 Hz), 7.86(1H,d,J=8.6 Hz), 8.25(1H,dd,J=1.2 & 4.6 Hz).5-cyano compound:

$^1$H-NMR(CDCl$_3$); δ3.23(3H,s), 3.48(3H,s), 4.89(2H,s), 5.26(2H,s), 7.34–7.42(1H,m), 7.47(1H,s), 7.72(1H,s), 8.23–8.26(1H,m).

Reference Example 41 (production of Compound A-8)

To a solution of 2-(5-bromo-4-chloro-2-methoxymethoxybenzoyl)-3-methoxymethoxypyridine (7.73 g) in methanol (250 ml) was added hydrochloric acid (12.5 ml), which was stirred for 5 hours at 50° C. Methanol was distilled off under reduced pressure. To the residue was added ethyl acetate (5 ml), which was poured into water. Crystalline precipitate then formed was collected by filtration, washed with ethyl acetate 10 and dried to give 2-(5-bromo-4-chloro-2-hydroxybenzoyl)-3-hydroxypyridine (5.95 g) (Compound A-8).

By substantially the same procedure as above, from a mixture of the 4-fluoro compound and 4-cyano compound described in Reference Example 40, was obtained a mixture of Compound A-16 and 2-(5-bromo-4-cyano-2-hydroxybenzoyl)-3-hydroxypyridine (4-cyano compound) (about 4:1). The spectrum data of the 4-cyano compound are shown as follows:

$^1$H-NMR(CDCl$_3$); δ7.39(1H,s), 7.68(2H,d,J=3.0 Hz), 8.29(1H,t,J=3.0 Hz), 8.45(1H,s).

By substantially the same procedure as above, from a mixture of 5-fluoro compound and 5-cyano compound described in Reference Example 40, was obtained a mixture of Compound A-5 and 2-(4-chloro-5-cyano-2-hydroxybenzoyl)-3-hydroxypyridine (5-cyano compound) (about 3:1). The spectrum data of the 5-cyano compound are shown as follows:

$^1$H-NMR(CDCl$_3$); δ7.41(1H,s), 7.68(2H,d,J=3.0 Hz), 8.30(1H,t,J=3.0 Hz), 8.32(1H,s). Reference Example 42 (Production of Compound D-2)

To a solution of 2-bromo-3-(1,3-dioxolan-2-yl)pyridine (m.p. 35°–40° C.; 3.60 g) synthesized by a known method in THF (60 ml) was added, at −78° C. under argon atmosphere, a 1.6M n-butyl lithium hexane solution (10.8 ml). The mixture was stirred for 15 minutes at the same temperature, to which was then added a solution of 5-bromo-2-methoxymethoxybenzaldehyde (3.83 g) in THF (10 ml). The mixture was stirred for 15 minutes at the same temperature, then stirred for further 20 minutes while warming up to room temperature. The reaction mixture was poured into a saturated aqueous saline solution, which was subjected to extraction with ethyl acetate. The extract solution was washed with a saturated aqueous saline solution, dried (anhydrous sodium sulfate) and concentrated. The concentrate was purified by means of a silica gel column chromatography (eluent: ethyl acetate/hexane) to give 2-(5-bromo-α-hydroxy-2-methoxymethoxybenzyl)-3-(1,3-dioxolan-2-yl)pyridine (4.50 g) (Compound D-2). The physical properties and spectrum data are shown in Table 13 and Table 14.

By substantially the same procedure as above, Compounds D-7, D-8, D-9, D-11 and D-14 shown in Table 13 were produced.

Reference Example 43 (Production of Compound E-1)

DMF (2 ml) was added to a mixture of 2-(5-bromo-α-cyano-2-methoxymethoxybenzyl)-3-(1,3-dioxolan-2-yl) pyridine (120 mg) and potassium carbonate (102 mg), which was stirred for 80 hours at room temperature. The reaction mixture was poured into water, which was subjected to extraction with ethyl acetate. The extract solution was washed with water, dried (anhydrous sodium sulfate) and concentrated to give 2-(5-bromo-2-methoxy methoxy benzoyl)-3-(1,3-dioxolan-2-yl)pyridine (90 mg) (Compound E-1). The physical properties and spectrum data are shown in Table 16 and Table 18.

By substantially the same procedure as above, Compounds E-5 and E-34 shown in Table 16 and Table 17 were produced.

Reference Example 44 (Production of Compound E-2)

A mixture solution of 2-(5-bromo-2-methoxymethoxybenzoyl)-3-(1,3-dioxolan-2-yl)pyridine (4.27 g), hydrochloric acid (9 ml) and THF (81 ml) was stirred for 14 hours at room temperature. The reaction mixture was neutralized with an aqueous sodium hydroxide, followed by extraction with ethyl acetate. The extract solution was washed with a saturated aqueous saline solution, dried (anhydrous sodium sulfate) and concentrated. The concentrate was purified by means of a silica gel column chromatography (eluent: ethyl acetate/hexane) to give a mixture (3.22 g) of 2-(5-bromo-2-hydroxybenzoyl)-3-formylpyridine and 2-(5-bromo-2-hydroxybenzoyl)-3-(1,3-dioxolan-2-yl)pyridine (about 7:2). A mixture of the said mixture (3.22 g), ethylene glycol (560 mg), p-toluenesulfonic acid monohydrate (170 mg) and toluene (40 ml) was subjected to heating under reflux azeotropically. The reaction mixture was poured into water, which was subjected to extraction with ethyl acetate. The extract solution was washed with a saturated aqueous saline solution, dried (anhydrous sodium sulfate) and concentrated. The concentrate was purified by means of a silica gel column chromatography (eluent: ethyl acetate/hexane) to give 2-(5-bromo-2-hydroxybenzoyl)-3-(1,3-dioxolan-2-yl)pyridine (2.92 g) (Compound E-2). The physical properties and spectrum data are shown in Table 16 and Table 18.

By substantially the same procedure as above, Compounds E-19, E-33, E-41 and E-49 shown in Table 16 and Table 17 were produced.

Reference Example 45 (Production of Compound D-4)

Sixty % sodium hydride (656 mg) was added, at room temperature, to a mixture of 5-bromo-2-methoxymethoxybenzyl cyanide (3.50 g), 2-chloro-3-trifluoromethylpyridine (2.48 g), sodium p-toluenesulfinate (731 mg) and DMF (35 ml), followed by stirring for 30 minutes at the same temperature under argon atmosphere. The reaction mixture was poured into an aqueous saline solution, followed by extraction with ethyl acetate. The extract solution was washed with an aqueous saline solution, dried (anhydrous sodium sulfate) and concentrated. The concentrate was purified by means of a silica gel column chromatography (eluent: ethyl acetate/hexane) to give 2-(5-bromo-α-cyano-2-methoxymethoxybenzyl)-3-trifluoromethyl-pyridine (2.63 g) (Compound D-4). The physical properties and spectrum date are shown in Table 13 and Table 14.

By substantially the same procedure as above, Compounds D-5 and D-12 shown in Table 13 were produced.

Reference Example 46

To a mixture of a 1.6M n-butyl lithium hexane solution (35 ml) and diethyl ether (200 ml) was added, at −78° C. under argon atmosphere, a solution of 1,4-diazabicyclo[2,2,2]octane (6.35 g) in diethyl ether (200 ml), which was stirred for one hour at temperatures ranging from −70° to −50° C. To the mixture was added 3-fluoropyridine (5.00 g) at −70° C., and the mixture was stirred for one hour at temperatures ranging from −70° to −60° C. To the reaction mixture was added at −70° C. DMF (9.41 g). The mixture was stirred for one hour at temperatures ranging from −70° to −50° C., which was then poured into a saturated aqueous saline solution, followed by extraction with ethyl acetate/ chloroform (about 4:1). The extract solution was washed with a saturated aqueous saline solution, dried (anhydrous sodium sulfate), and concentrated. The concentrate was purified by means of a silica gel column chromatography (eluent: ethyl acetate/hexane) to give 3-fluoro-2-formylpyridine (2.75 g, m.p. 52°–53° C.). Reference Example 47 (Production of Compound D-6)

To a solution of 2,4-dibromo-1-methoxymethoxybenzene (3.50 g) in diethyl ether (50 ml) was added, at −78° C. under argon atmosphere, a 1.6M n-butyl lithium hexane solution (8.1 ml). The mixture was stirred for 20 minutes at the same temperature, to which was added a solution of 3-fluoro-2-formyl-pyridine (1.48 g) in THF (10 ml), followed by stirring for one hour at temperatures ranging from −78° to 60° C. The reaction mixture was poured into a saturated aqueous saline solution, followed by extraction with ethyl acetate. The extract solution was washed with a saturated aqueous saline solution, dried (anhydrous sodium sulfate) and concentrated. The concentrate was purified by means of a silica gel column chromatography (eluent: ethyl acetate/hexane) to give 2-(5-bromo-α-hydroxy-2-methoxymethoxybenzyl)-3-fluoropyridine (1.64 g) (Compound D-6). The physical properties and spectrum data are shown in Table 13 and Table 14.

Reference Example 48 (Production of Compound E-10)

A mixture of 2-(5-chloro-2-methoxymethoxybenzoyl)-3-(1,3-dioxolan-2-yl)pyridine (3.41 g), hydrochloric acid (5.0 ml) and THF (35 ml) was stirred for 27 hours at room temperature. The reaction mixture was neutralized with an aqueous solution of sodium hydroxide, followed by extraction with ethyl acetate. The extract solution was washed with a saturated aqueous saline solution, then the solvent was distilled off to leave 2-(5-chloro-2-hydroxybenzoyl)-3-formylpyridine (2.03 g) (Compound E-10). The physical properties and spectrum data are shown in Table 16 and Table 18.

By substantially the same procedure as above, Compounds E-15, E-24, E-35, E-37, E-43 and E-48 shown in Table 16 and Table 17 were produced.

In accordance with the-procedures in Reference Example 48 and Reference Example 52, Compound E-29 shown in Table 17.

Reference Example 49 (Production of Compound E-11)

To a suspension of 60% sodium hydride (348 mg) previously washed with hexane in DMF (25 ml) was added, at 0° C. under argon atmosphere, 2-(5-chloro-2-hydroxy-benzoyl)-3-formylpyridine (2.05 g), and the mixture was stirred for 40 minutes at the same temperature. To the mixture was then added 80% chloromethyl methyl ether (867 mg), which was stirred for 40 minutes at the same temperature. The reaction mixture was poured into water, followed by extraction with ethyl acetate. The extract solution was washed with water, dried (anhydrous sodium sulfate), and concentrated to give 2-(5-chloro-2-methoxymethoxybenzoyl)-3-formylpyridine (2.34 g) (Compound E-11). The physical properties and spectrum data are shown in Table 16 and Table 19.

By substantially the same procedure as above, Compounds E-16, E-25, E-30, E-38 and E-44 shown in Table 16 and Table 17 were produced.

Reference Example 50 (Production of Compound E-12)

To a mixture of 2-(5-chloro-2-methoxymethoxy-benzoyl)-3-formylpyridine (2.34 g), hydroxylamine hydrochloride (532 mg) and triethylamine (775 mg) was added acetonitrile (30 ml), which was stirred for 1.5 hour at room temperature. The reaction mixture was concentrated, which was partitioned with ethyl acetate/water. The organic layer was washed with a saturated aqueous saline solution, dried (anhydrous sodium sulfate), and concentrated to give 2-(5-chloro-2-methoxymethoxybenzoyl)-3-hydroxylminomethylpyridine (2.39 g). A mixture of this compound and acetic anhydride (15 ml) was heated for one hour under reflux, followed by distilling off acetic anhydride under reduced pressure. The residue was purified by means of 10 a silica gel column chromatography (eluent: ethyl acetate/hexane) to give 2-(5-chloro-2-methoxymethoxybenzoyl)-3-cyanopyridine (1.51 g) (Compound E-12).

Likewise, Compounds E-39, E-45 and E-46 were produced. The physical properties and spectrum data are shown in Table 16, Table 17, Table 19, Table 21a and Table 21b.

Reference Example 51 (Production of Compound E-13)

A mixture of 2-(5-chloro-2-methoxymethoxybenzoyl)-3-cyanopyridine (1.50 g), hydrochloric acid (2.5 ml) and THF (17.5 ml) was stirred for 13 hours at room temperature. The reaction mixture was neutralized with an aqueous solution of sodium hydroxide, followed by extraction with ethyl acetate. The extract solution was washed with a saturated aqueous saline solution and dried (anhydrous sodium sulfate), which was purified by means of a silica gel column chromatography (eluent: ethyl acetate/hexane) to give 2-(5-chloro-2-hydroxybenzoyl)-3-cyanopyridine (1.10 g) (Compound E-13). The physical properties and spectrum data are shown in Table 16 and Table 19.

In accordance with the procedures in Reference Example 50 and Reference Example 51, Compounds E-17, E-26 and E-31 shown in Table 16 and Table 17 were produced.

Reference Example 52 (Production of Compound E-14)

To a solution of 2-bromo-3-(1,3-dioxolan-2-yl)pyridine (3.50 g) in THF (50 ml) was added, at −78° C. under argon atmosphere, a 1.6M n-butyl lithium hexane solution (10.5 ml), which was stirred for 20 minutes. This reaction mixture was added, at the same temperature under argon atmosphere, to a solution of methoxymethyl 2-methoxymethoxy-5-methylbenzoate (3.66 g) in THF (50 ml). The mixture was stirred for 40 minutes, then for further one hour while warming up to room temperature. The reaction mixture was poured into a saturated aqueous saline solution, followed by extraction with ethyl acetate. The extract solution was washed with a saturated aqueous saline solution, dried (anhydrous sodium sulfate) and concentrated. The concentrate was purified by means of a silica gel column chromatography (eluent: ethyl acetate/hexane) to give 3-(1,3-dioxolan-2-yl)-2-(2-methoxymethoxy-5-methylbenzoyl)pyridine (2.06 g) (Compound E-14). The physical properties and spectrum data are shown in Table 16 and Table 19.

By substantially the same procedure as above, Compounds E-20 and E-36 shown in Table 16 and Table 17 were produced.

Reference Example 53 (Production of Compound F-1)

A solution of 2-bromo-4-chloro-5-fluorophenol methoxymethylether (17.65 g) in diethyl ether (400 ml) was cooled to −78° C. To the solution was added dropwise, under argon atmosphere, 1.6M n-butyllithium hexane solution (45 ml). The mixture was stirred for one hour under the same conditions, followed by dropwise addition of 2-cyano-3-trimethylsilyloxypyridine (13.18 g) at −78° C. The cooling bath was then removed, and the reaction mixture was stirred overnight while raising the temperature to room temperature. The reaction was suspended by the addition of methanol (50 ml). Then the solvent was distilled off. To the residue were added methanol (300 ml) and conc. hydrochloric acid (7 ml). The mixture was stirred for 2 hours at room temperature. The reaction mixture was neutralized with an aqueous solution of potassium carbonate, which was subjected to extraction with ethyl acetate. The extract solution was dried (anhydrous magnesium sulfate), then the solvent was distilled off under reduced pressure. The residue was purified by means of a silica gel column chromatography (elution with ethyl acetate/hexane) to afford 2-(5-chloro-4-fluoro-2-methoxymethoxybenzoyl)-3-hydroxypyridine (9.18 g) (Compound F-1). Physico-chemical properties and spectrum data are shown in Table 22 and Table 23.

Reference Example 54 (Production of Compound F-2)

In accordance with the method in Reference Example 35, 2-(5-chloro-4-fluoro-2-methoxymethoxybenzoyl)-3-hydroxypyridine (9.15 g) was subjected to methoxymethylation to give 2-(5-chloro-4-fluoro-2-methoxymethoxybenzoyl)-3-methoxymethoxypyridine (9.82 g) (Compound F-2). The physico-chemical properties and spectrum data are shown in Table 22 and Table 23.

In accordance with the methods of Reference Examples 53 and 54, Compound F-10 shown in Table 22 was produced.

Reference Example 55 (Production of Compound F-3)

A mixture of 2-(5-chloro-4-fluoro-2-methoxymethoxybenzoyl)-3-methoxymethoxypyridine (1.98 g), a 50% aqueous solution of dimethylamine (20 ml) and DMF (50 ml) was stirred overnight at room temperature. The reaction mixture was subjected to extraction with ethyl acetate. The organic layer was washed with water and a saturated aqueous saline solution, successively, which was then dried (anhydrous magnesium sulfate). The solvent was distilled off, and the residue was purified by means of a silica gel column chromatography (ethyl acetate/hexane) to afford 2-(5-chloro-4-dimethylamino-2-methoxymethoxybenzoyl)-3-methoxymethoxypyridine (1.82 g) (Compound F-3).

By using a 40% aqueous solution of methyl amine, in place of a 50% aqueous solution of dimethylamine, 2-(5-chloro-2-methoxymethoxy-4-methylaminobenzoyl)-3-methoxymethoxypyridine was obtained (Compound F-4).

Likewise, by using a 15% aqueous solution of methyl mercaptan sodium, the reaction was allowed to proceed in ethanol to afford 2-(5-chloro-2-methoxymethoxy-4-methylthiobenzoyl)-3-methoxymethoxypyridine (Compound F-5).

Likewise, the reaction was allowed to proceed in an ethanol solution of sodium hydroxide to give 2-(5-chloro-4-ethoxy-2-methoxymethoxybenzoyl)-3-methoxymethoxypyridine (Compound F-6).

In a mixture solvent of benzylamine, potassium carbonate and DMF, the reaction was allowed to proceed at 60° C. overnight, followed by processing the reaction mixture similarly to afford 2-(4-benzylamino-5-chloro-2-methoxymethoxybenzoyl)-3-methoxymethoxypyridine (Compound F-7).

In potassium cyanide and DMSO, the reaction was allowed to proceed at 40° C. overnight, followed by processing the reaction mixture similarly to afford 2-(5-chloro-4-cyano-2-methoxymethoxybenzoyl)-3-methoxypyridine (Compound F-8).

Likewise, Compounds E-42 and F-12 were produced. Physico-chemical properties and spectrum data of Compounds F-4 to F-8 and F-12 are shown in Table 22 and Table 23.

Physical properties and spectrum data of Compound E-42 are shown in Table 17 and Table 21a.

Reference Example 56 (Production of Compound F-9).

By using DMSO/water (10:1), in place of DMF in Reference Example 40, 2-(5-bromo-α-cyano-4-fluoro-2-methoxymethoxybenzyl)-3-benzyloxypyridine (2.53 g) was subjected to oxidative decyanation to afford 2-(5-bromo-4-fluoro-2-methoxymethoxybenzoyl)-3-benzyloxypyridine (2.46 g) (Compound F-9). Physico-chemical properties and spectrum data are shown in Table 22 and Table 23.

Reference Example 57

To a solution of 2-bromo-3-formylpyridine (2.51 g) in methanol (40 ml) was added, at room temperature, sodium borohydride (255 mg). The mixture was stirred for 15 minutes at the same temperature. The reaction mixture was concentrated, to which was added water, followed by subjecting the mixture to extraction. The extract solution was washed with a saturated aqueous saline solution, dried (anhydrous sodium sulfate), which was then concentrated to afford 2-bromo-3-hydroxymethylpyridine (2.40 g). To a mixture of this compound (2.40 g), iodomethane (5.44 g) and DMF (25 ml) was added, at room temperature, 60% sodium hydride (613 mg), and the mixture was stirred for 30 minutes at the same temperature. To the reaction mixture was poured water, which was subjected to extraction with ethyl acetate. The extract solution was washed with water, which was dried (anhydrous sodium sulfate), followed by concentration. The residue was purified by means of a silica gel column chromatography (eluent: ethyl acetate/hexane) to afford 2-bromo-3-methoxymethylpyridine (2.34 g) as a yellow liquid product.

Reference Example 58 (Production of Compound D-10)

Instead of addition of DMF in Reference Example 46, a THF solution of 2-methoxymethoxy-5-trifluoromethoxybenzaldehyde was added. The mixture was processed in substantially the same manner to afford 3-fluoro-2-(α-hydroxy-2-methoxymethoxy-5-trifluoromethoxybenzyl)pyridine (2.38 g) (Compound D-10). Physico-chemical properties and spectrum data are shown in Table 13 and Table 15.

Reference Example 59 (Production of Compound E-28)

A mixture of 3-fluoro-2-(2-methoxymethoxy-5-trifluoromethoxybenzoyl)pyridine (2.26 g), potassium cyanide (525 mg) and DMF (20 ml) was stirred for 8 minutes at 150° C. The reaction mixture was cooled with ice, which was then poured into an aqueous saline solution, followed by extraction with ethyl acetate. The extract solution was washed with an aqueous saline solution, dried (anhydrous sodium sulfate) and concentrated. The residue was purified by means of a silica gel column chromatography (eluent: ethyl acetate/hexane) to afford 3-cyano-2-(2-methoxymethoxy-5-trifluoromethoxymethoxybenzoyl) pyridine (0.57 g) (Compound E-28). Physico-chemical properties and spectrum data are shown in Table 17 and Table 20.

Reference Example 60 (Production of Compound D-13)

In acetic acid (300 ml) was dissolved 3-chloro-2-(5-chloro-a-cyano-2-methoxymethoxybenzyl)-5-nitropyridine (15.0 g). To the solution were added water (10 ml) and powdery iron (11.4 g). The mixture was stirred for 2 hours at room temperature. The solvent was distilled off under reduced pressure. To the residue were added ethyl acetate and an aqueous solution of sodium carbonate. Insolubles were filtered off by using celite. The organic layer was washed with water and a saturated aqueous saline solution, successively, which was then dried (anhydrous magnesium sulfate), followed by concentration. The concentrate was purified by means of a silica gel column chromatography (eluent: ethyl acetate/hexane) to afford 5-amino-3-chloro-2-(5-chloro-α-cyano-2-methoxymetho-xybenzyl)pyridine (12.4 g) (Compound D-13). Physico-chemical properties and spectrum data are shown in Table 13 and Table 15.

Reference Example 61 (Production of Compound B-48)

A mixture of 5-bromo-4-fluorosalicylic acid (17.77 g) and cuprous cyanide (9.86 g) in 1-methyl-2-pyrrolidone (100 ml) was heated under reflux for 3 hours under argon atmosphere. To the reaction mixture were added ferric chloride hexahydrate (34.0 g), conc. HCl (9 ml) and water (120 ml). The mixture was stirred at room temperature for 30 minutes, and extracted with ethyl acetate. The extract was washed in turn with a saturated aqueous solution of potassium hydrogensulfate and a saturated brine, dried (anhydrous magnesium sulfate), and evaporated in vacuo. To the residue were added DMF (200 ml) and potassium carbonate (62.7 g). Chloromethyl methyl ether (26 ml) was added dropwise to the mixture, and then the mixture was stirred overnight at room temperature. The reaction was quenched with ice-water, and the mixture was extracted with ethyl acetate. The ethyl acetate was dried (anhydrous magnesium sulfate), and evaporated in vacuo. The residue chromatographed on silica gel using ethyl acetate/hexane as eluent to give methoxymethyl 5-cyano-4-fluoro-2-methoxymethoxybenzoate (16.6 g) (Compound B-48), whose physical properties are shown in Table 8.

Reference Example 62 (Production of Compound B-49)

Lithium aluminum hydride (2.39 g) was added portion-wise to a solution of methoxymethyl 5-cyano-4-fluoro-2-methoxymethoxybenzoate (16.6 g) in diethyl ether (500 ml) at −30° C., and the mixture was stirred for 30 minutes. The reaction mixture was poured into a saturated brine, to which was added ethyl acetate, followed by filtration through celite. The organic layer was washed with a saturated brine, dried (anhydrous magnesium sulfate), and concentrated. The residue was chromatographed on silica gel using ethyl 10 acetate/hexane as eluent to give 5-cyano-4-fluoro-2-methoxymethoxybenzyl alcohol (10.0 g) (Compound B-49). The physical properties are shown in Table 8.

Reference Example 63 (Production of Compound B-50)

To a solution of 5-cyano-4-fluoro-2-methoxymethoxybenzyl alcohol (10.0 g) in dichloromethane (500 ml) was added activated manganese dioxide (31.4 g). The mixture was stirred overnight at room temperature, and filtered through celite to remove manganese dioxide. The filtrate was condensed under reduced pressure to give a solid, which was washed with hexane to yield 5-cyano-4-fluoro-2-methoxymethoxybenzaldehyde (8.01 g) (Compound B-50). The physical properties was shown in Table 8.

Reference Example 64 (Production of Compound A-31)

A mixture of Compound F-12 (0.23 g), trifluoroacetic acid (0.2 ml) and dichloromethane (25 ml) was stirred overnight at room temperature, and then neutralized with a saturated aqueous solution of sodium hydrogencarbonate. The mixture was condensed under reduced pressure, and extracted with chloroform. The chloroform was dried (anhydrous magnesium sulfate), evaporated in vacuo, and washed with diisopropyl ether to give 2-(4,5-dicyano-2-hydroxybenzoyl)-3-hydroxypyridine (0.12 g) (Compound A-12). The physical properties and spectrum data are shown in Table 2 and Table 6.

Reference Example 65 (Production of Compound D-15)

In accordance with procedures successively in Reference Example 60, 61, 62 and 42 using ethyl 5-bromo-4-chlorosalicylate as starting material, 2-(4-chloro-5-cyano-α-hydroxy-2-methyoxymethoxybenzyl-3-(1,3-dioxolan-2-yl) pyridine was produced (Compound D-15). The physical properties and spectrum data are shown in Table 13 and Table 15.

TABLE 1

| Cpd. No. | R' | R" | Formula | m.p. (°C.) physical property |
|---|---|---|---|---|
| A-1 | Br | H | $C_{12}H_8BrNO_3$ | 143–145 |
| A-2 | $CF_3$ | H | $C_{13}H_8F_3NO_3$ | 152–153 |
| A-3 | Cl | H | $C_{12}H_8ClNO_3$ | 154–155 |
| A-4 | Me | H | $C_{13}H_{11}NO_3$ | 137–138 |
| A-5 | F | Cl | $C_{12}H_7ClFNO_3$ | 167–168 |
| A-6 | H | F | $C_{12}H_8FNO_3$ | 128.5–129 |
| A-7 | MeO | H | $C_{13}H_{11}NO_4$ | 93–93.5 |
| A-8 | Br | Cl | $C_{12}H_7BrClNO_3$ | 188–190 |
| A-9 | $NO_2$ | H | $C_{12}H_8N_2O_5 \cdot \frac{1}{8}H_2O$ | 216–220 |
| A-10 | Br | MeO | $C_{13}H_{10}BrNO_4 \cdot \frac{1}{4}H_2O$ | 179–180.5 |
| A-11 | H | MeO | $C_{13}H_{11}NO_4 \cdot \frac{1}{8}H_2O$ | 106–108 |
| A-12 | CN | H | $C_{13}H_8N_2O_3 \cdot \frac{1}{4}H_2O$ | 182–183 |
| A-13 | $NO_2$ | MeO | $C_{13}H_{10}N_2O_6$ | 240–244 |
| A-14 | Br | Me | $C_{13}H_{10}BrNO_3 \cdot \frac{1}{4}H_2O$ | 139–141 |
| A-15 | $NO_2$ | Me | $C_{13}H_{10}N_2O_5$ | 241–245 |
| A-16 | Br | F | $C_{12}H_7BrFNO_3 \cdot \frac{1}{4}H_2O$ | 205–209 |

TABLE 1-continued

[Structure: pyridine-N with 3-OH and C(=O) linked to benzene bearing 2-OH, R' at 5-position, R" at 4-position]

| Cpd. No. | R' | R" | Formula | m.p. (°C.) physical property |
|---|---|---|---|---|
| A-17 | Et | H | $C_{14}H_{13}NO_3$ | 55–57 |
| A-18 | Me | Me | $C_{14}H_{13}NO_3$ | 119–120 |
| A-19 | F | Me | $C_{13}H_{10}FNO_3 \cdot \frac{1}{4}H_2O$ | 90–91 |
| A-20 | Me | F | $C_{13}H_{10}FNO_3 \cdot \frac{1}{3}H_2O$ | 129.5–130 |
| A-21 | —CH=CH—CH=CH— | | $C_{16}H_{11}NO_3$ | 142–143 |
| A-22 | $CH_2OH$ | H | $C_{13}H_{11}NO_4$ | 156–158 |
| A-23 | $Me_3SiC\equiv C$ | H | $C_{17}H_{17}NO_3Si \cdot \frac{1}{8}H_2O$ | 101–102.5 |
| A-24 | AcNH | H | $C_{14}H_{12}N_2O_4$ | 165–167 |

TABLE 2

| Cpd. No. | R' | R" | Formula | m.p. (°C.) physical property |
|---|---|---|---|---|
| A-25 | Cl | $Me_2N$ | $C_{14}H_{13}ClN_2O_3 \cdot 2/5H_2O$ | 112–113 |
| A-26 | Cl | EtO | $C_{14}H_{12}ClNO_4$ | 181–182.5 |
| A-27 | Cl | MeNH | $C_{13}H_{11}ClN_2O_3 \cdot 1/4H_2O$ | 151–152 |
| A-28 | Cl | MeS | $C_{13}H_{10}ClNO_3S$ | 157.5 159 |
| A-29 | Cl | BnNH | $C_{19}H_{15}ClN_2O_3$ | 141–141.5 |
| A-30 | Cl | CN | $C_{13}H_7ClN_2O_3$ | 235–237 |
| A-31 | CN | CN | $C_{14}H_7N_3O_3$ | 255(dec.) |

Bn: benzyl

TABLE 3

| Cpd. No. | $^1$H-NMR (CDCl$_3$; TMS internal standard, ppm) | IR (KBr; cm$^{-1}$) |
|---|---|---|
| A-1 | 6.96(1H, d, J=9.0Hz), 7.54–7.61(1H, m), 7.60(2H, d, J=2.8Hz), 8.28(1H, t, J=2.8Hz), 8.45(1H, d, J=2.4Hz), 12.56(1H, s). | 3440, 1600, 1580, 1440, 1315, 1280, 1250, 1165. |
| A-2 | 7.14(1H, d, J=8.8Hz), 7.63(2H, d, J=3.0Hz), 7.71(1H, dd, J=2.4&8.8Hz), 8.28(1H, t, J=3.0Hz), 8.63–8.64(1H, m). | 3400, 3030, 1605, 1435, 1315, 1275, 1250, 1150, 1130, 1090. |
| A-3 | 7.01(1H, d, J=9.0Hz), 7.45(1H, dd, J=2.8&9.0Hz), 7.60(2H, d, J=2.8Hz), 8.28(1H, t, J=2.8Hz), 8.32(1H, d, J=2.8Hz), 12.55(1H, s). | 3450, 1605, 1590, 1460, 1435, 1315, 1250, 1165. |
| A-4 | 2.33(3H, s), 6.97(1H, d, J=8.4Hz), 7.34(1H, dd, J=3.0&8.4Hz), 7.56(2H, d, J=3.4Hz), 8.08(1H, d, J=3.0Hz), 8.27(1H, t, J=3.4Hz), 12.62(1H, s). | 3450, 2900, 1780, 1600, 1460, 1430, 1320, 1285, 1270, 1170. |
| A-5 | 7.11(1H, d, J=6.2Hz), 7.62(2H, d, J=3.0Hz), 8.21(1H, d, J=11.0Hz), 8.27(1H, t, J=3.0Hz), 12.59(1H, s). | 3450, 1600, 1430, 1245, 1150. |
| A-6 | 6.63–6.74(2H, m), 7.58(2H, d, J=2.8Hz), 8.26(1H, t, J=2.8Hz), 8.45–8.53(1H, m) 12.61(1H, s). | 3450, 1810, 1600, 1465, 1440, 1420, 1320, 1180. |
| A-7 | 3.83(3H, s), 7.00(1H, d, J=8.8Hz), 7.17(1H, dd, J=.8&7.7Hz), 7.57(2H, d, J=2.6Hz), 7.84(1H, d, J=2.8Hz), 8.27(1H, t, J=2.6Hz), 12.70(1H, s). | 3430, 2990, 1600, 1465, 1435, 1320, 1275, 1260, 1215, 1160, 1115, 1080, 1020. |
| A-8 | 7.19(1H, s), 7.63(2H, d, J=3.0Hz), 8.26(1H, t, J=3.0Hz), 8.56(1H, s), 12.63(1H, br. s). | 3430, 3080, 1600, 1575, 1440, 1420, 1245, 1155. |
| A-9 | *6.99(1H, d, J=9.0Hz), 7.47(1H, dd, J=1.6&8.6Hz), 7.54(1H, dd, J=4.0&8.6Hz), 8.16(1H, dd, J=1.6&4.0Hz), 8.23(1H, dd, J=2.8&9.0Hz), 8.33(1H, d, J=2.8Hz). | 3430, 3080, 1600, 1490, 1440, 1410, 1320, 1250, 1210, 1100, 1055. |

TABLE 4

| Cpd. No. | $^1$H-NMR (CDCl$_3$; TMS internal standard, ppm) | IR (KBr; cm$^{-1}$) |
| --- | --- | --- |
| A-10 | 3.96(3H, s), 6.50(1H, s), 7.56(2H, d, J=3.0Hz), 8.25(1H, t, J=3.0Hz), 8.75(1H, s). | 3440, 1625, 1590, 1560, 1435, 1405, 1220. |
| A-11 | 3.88(3H, s), 6.47–6.56(2H, m), 7.50–7.52(2H, m), 8.25(1H, t, J=3.0Hz), 8.57(1H, d, J=9.2Hz), 12.65(1H, s). | 3440, 3070, 3000, 2630, 1620, 1590, 1450, 1420, 1355, 1320, 1220, 1180. |
| A-12 | 7.12(1H, d, J=8.6Hz), 7.66(2H, d, J=3.0Hz), 7.71(1H, dd, J=2.2&8.6Hz), 8.29(1H, t, J=3.0Hz), 8.73(1H, d, J=2.2Hz), 12.53(1H, s). | 3400, 2210, 1610, 1440, 1315, 1245, 1150. |
| A-13 | 4.03(3H, s), 6.58(1H, s), 7.64(2H, d, J=2.8Hz), 8.28(1H, t, J=2.8Hz), 9.31(1H, s), 12.74(1H, s). | 3450, 1605, 1525, 1450, 1330, 1235. |
| A-14 | 2.41(3H, s), 6.95(1H, s), 7.58(2H, d, J=3.0Hz), 8.26(1H, t, J=3.0Hz), 8.53(1H, s), 12.66(1H, s). | 3450, 1820, 1600, 1430, 1395, 1245, 1155. |
| A-15 | 2.67(3H, s), 6.95(1H, s), 7.66(2H, d, J=2.8Hz), 8.29(1H, t, J=2.8Hz), 9.24(1H, s), 12.66(1H, s). | 3450, 3080, 1600, 1440, 1325, 1300, 1255, 1240, 1155. |
| A-16 | 6.80(1H, d, J=10.0Hz), 7.62(2H, d, J=2.8Hz), 8.26(1H, t, J=2.8Hz), 8.62(1H, d, J=8.4Hz), 12.64(1H, s). | 3430, 3080, 1595, 1445, 1410, 1250, 1180. |
| A-17 | 1.24(3H, t, J=7.6Hz), 2.64(2H, q, J=7.6Hz), 6.99(1H, d, J=8.0Hz), 7.37(1H, dd, J=8.0&2.2Hz), 7.55(2H, d, J=2.6Hz), 8.10(1H, d, J=2.2Hz), 8.26(1H, t, J=2.6Hz), 12.64(1H, s). | 3450, 2970, 1800, 1600, 1480, 1440, 1400, 1320, 1270, 1170, 1140. |

TABLE 5

| Cpd. No. | $^1$H-NMR (CDCl$_3$; TMS internal standard, ppm) | IR (KBr; cm$^{-1}$) |
| --- | --- | --- |
| A-18 | 2.24(3H, s), 2.29(3H, s), 6.85(1H, s), 7.53–7.54(2H, m), 8.10(1H, s), 8.24–8.27(1H, m), 12.72(1H, s). | 3050, 2960, 2940, 1840, 1625, 1440, 1400. |
| A-19 | 2.31(3H, s), 6.86(1H, d, J=6.6Hz), 7.56(1H, d, J=2.8Hz), 8.15(1H, d, J=11.8Hz), 8.27(1H, t, J=2.8Hz), 12.58(1H, s). | 3430, 1800, 1610, 1590, 1460, 1430, 1400. |
| A-20 | 2.24(3H, s), 6.68(1H, d, J=11.0Hz), 7.56–7.58(2H, m), 8.23–8.25(2H, m), 12.69(1H, s). | 3450, 1800, 1620, 1590, 1470, 1410. |
| A-21 | 5.30(1H, s), 7.28–7.36(1H, m), 7.39(1H, s), 7.47–7.55(1H, m), 7.57 (2H, d, J=2.8Hz), 7.67–7.72(1H, m), 7.85–7.89(1H, m), 8.34(1H, t, J=2.8Hz), 8.94(1H, s), 12.29(1H, s). | 3450, 1625, 1595, 1440. |
| A-22 | 4.67(2H, s), 7.07(1H, d, J=8.4Hz), 7.54–7.59(3H, m), 8.26–8.31(2H, m), 2.59(1H, s). | 3450, 1600, 1430. |
| A-23 | 0.25(9H, s), 6.98(1H, d, J=8.6Hz), 7.27(1H, dd, J=2.6&3.4Hz), 7.55–7.60 (3H, m), 8.45(1H, d, J=2.2Hz), 12.64(1H, s). | 3400, 2950, 2145, 1585, 1430. |
| A-24 | 2.18(3H, s), 7.04(1H, d, J=8.8Hz), 7.16(1H, br. s), 7.57(2H, d, J=3.0Hz), 7.81(1H, dd, J=2.8&7.7Hz), 8.26–8.29(2H, m), 12.57(1H, s). | 3450, 3300, 1645, 1635, 1480, 1440. |
| A-25 | 3.00(6H, s), 6.47(1H, s), 7.52(2H, d, J=2.8Hz), 8.24(1H, t, J=2.8Hz), 8.58(1H, s), 12.79(1H, s). | 3440, 1620, 1595, 1445, 1250. |

TABLE 6

| Cpd. No. | $^1$H-NMR (CDCl$_3$; TMS internal standard, ppm) | IR (KBr; cm$^{-1}$) |
| --- | --- | --- |
| A-26 | 1.52(3H, t, J=3.0Hz), 4.18(2H, q, J=3.0Hz), 6.49(1H, s), 7.55(2H, d, J=2.8Hz), 8.25(1H, t, J=2.8Hz), 8.61(1H, s), 12.77(1H, s). | 3450, 1620, 1590, 1455, 1210. |
| A-27 | 2.99(3H, d, J=5.0Hz), 5.13(1H, br. d), 6.14(1H, s), 7.47(2H, d, J=2.6Hz), 8.24(1H, t, J=2.6Hz), 8.79(1H, s), 12.74(1H, s). | 3410, 1630, 1590, 1440. |
| A-28 | 2.52(3H, s), 6.75(1H, s), 7.58(2H, d, J=2.8Hz), 8.27(1H, t, J=2.8Hz), 8.46 (1H, s), 12.75(1H, s). | 3440, 1585, 1420. |
| A-29 | 4.76(2H, d, J=5.4Hz), 5.43(1H, m), 6.19(1H, s), 7.32–7.49(7H, m), 8.24(1H, dd, J=2.4&3.4Hz), 8.79(1H, s), 12.74(1H, s). | 3400, 1620, 1590, 1445. |
| A-30 | 7.40(1H, s), 7.58(2H, d, J=3.0Hz), 8.29(1H, t, J=3.0Hz), 8.32(1H, s), 12.45(1H, s). | 3450, 2240, 1595, 1450. |
| A-31 | 7.47(1H, s), 7.74(2H, d, J=3.0Hz), 8.31(1H, t, J=3.0Hz), 8.70(1H, s), 12.44(1H, s). | |

*measured with DMSO-d$_6$

TABLE 7

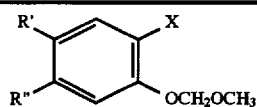

| Cpd. No. | R' | R" | X | Formula | m.p. (°C.) physical property |
|---|---|---|---|---|---|
| B-1 | Me | H | Br | C₉H₁₁BrO₂ | oil |
| B-2 | F | Cl | Br | C₈H₇BrClFO₂ | oil |
| B-3 | H | F | Br | C₈H₈BrFO₂ | oil |
| B-4 | H | H | MeO | CHO | C₁₀H₁₂O₄ | 55-56 |
| B-5 | MeO | H | CHO | C₁₀H₁₂O₄ | oil |
| B-7 | H | Me | CHO | C₁₀H₁₂O₃ | oil |
| B-8 | CN | H | CHO | C₁₀H₉NO₃ | 55-56 |
| B-9 | Br | MeO | CHO | C₁₀H₁₁BrO₄ | 61-63 |
| B-10 | Br | Me | CHO | C₁₀H₁₁BrO₃ | 47-48 |
| B-11 | NO₂ | MeO | CHO | C₁₀H₁₁NO₆ | 63-65 |
| B-12 | NO₂ | Me | CHO | C₁₀H₁₁NO₅ | oil |
| B-13 | Br | H | CHO | C₉H₉BrO₃ | oil |
| B-14 | Et | H | H | C₁₀H₁₄O₂ | oil |
| B-15 | Br | F | CHO | C₉H₈BrFO₃ | oil |
| B-16 | Me | Me | Br | C₁₀H₁₃BrO₂ | oil |
| B-17 | F | Me | Br | C₉H₁₀BrFO₂ | oil |
| B-18 | Me | F | Br | C₉H₁₀BrFO₂ | oil |
| B-19 | —CH=CH—CH=CH— | | CO₂Me | C₁₄H₁₄O₄ | oil |
| B-20 | CHO | H | Br | C₉H₉BrO₃ | oil |
| B-21 | CH₂OH | H | Br | C₉H₁₁BrO₃ | oil |
| B-22 | MeOCH₂OCH₂ | H | Br | C₁₁H₁₅BrO₄ | oil |
| B-23 | MeOCH₂OCH₂ | H | CHO | C₁₂H₁₆O₅ | oil |
| B-24 | CHO | H | H | C₉H₁₀O₃ | oil |
| B-25 | Br₂C=CH | H | H | C₁₀H₁₀Br₂O₂ | oil |

TABLE 8

| Cpd. No. | R' | R" | X | Formula | m.p. (°C.) physical property |
|---|---|---|---|---|---|
| B-26 | Me₃SiC≡C | H | H | C₁₃H₁₈O₂Si | oil |
| B-27 | Me₃SiC≡C | H | CHO | C₁₃H₁₈O₂Si | oil |
| B-28 | 1,3-dioxolan-2-yl | H | Br | C₁₁H₁₃BrO₄ | oil |
| B-29 | 1,3-dioxolan-2-yl | H | CHO | C₁₂H₁₄O₅ | oil |
| B-30 | Br | H | Br | C₈H₈Br₂O₂ | oil |
| B-31 | Me | H | CO₂CH₂OMe | C₁₂H₁₆O₅ | oil |
| B-32 | Cl | F | CHO | C₉H₈ClFO₈ | oil |
| B-33 | Br | Cl | CO₂Et | C₁₁H₁₂BrClO₄ | oil |
| B-34 | Br | Cl | CH₂OH | C₉H₁₀BrClO₃ | oil |
| B-35 | Br | Cl | CH₂CN | C₁₀H₉BrClNO₂ | oil |
| B-36 | Br | F | CO₂Et | C₁₁H₁₂BrFO₄ | oil |
| B-37 | Br | F | CH₂OH | C₉H₁₀BrFO₃ | oil |
| B-38 | Br | F | CH₂CN | C₁₀H₉BrFNO₂ | 79-81 |
| B-39 | F | Cl | CO₂CH₂OMe | C₁₁H₁₂ClFO₅ | oil |
| B-40 | F | Cl | CH₂OH | C₉H₁₀ClFO₃ | oil |
| B-41 | F | Cl | CH₂CN | C₁₀H₉ClFNO₂ | oil |
| B-42 | Cl | F | Br | C₇H₇BrClFO₂ | oil |
| B-43 | Br | H | CO₂CH₂OMe | C₁₁H₁₃BrO₅ | oil |
| B-44 | CF₃O | H | Br | C₉H₈BrF₃O₃ | oil |
| B-45 | CF₃O | H | CHO | C₁₀H₉F₃O₄ | oil |
| B-46 | MeO | H | CO₂CH₂OMe | C₁₂H₁₆O₆ | oil |
| B-47 | NO₂ | H | CHO | C₉H₉NO₅ | 68 |
| B-48 | CN | F | CO₂CH₂OMe | C₁₂H₁₂FNO₅ | oil |
| B-49 | CN | F | CH₂OH | C₁₀H₁₀FNO₃ | oil |
| B-50 | CN | F | CHO | C₁₀H₈FNO₃ | 96-98 |
| B-51 | F | H | CO₂CH₂OMe | C₁₁H₁₃FO₅ | oil |
| B-52 | CF₃ | H | Br | C₉H₈BrF₃O₂ | oil |
| B-53 | CF₃ | H | CHO | C₁₀H₉F₃O₃ | oil |

TABLE 9

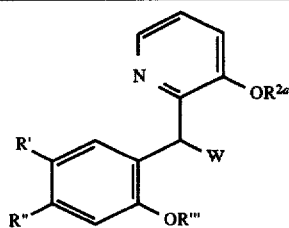

| Cpd. No. | R' | R" | R'" | $R^{2a}$ | W | Formula | m.p. (°C.) physical property |
|---|---|---|---|---|---|---|---|
| C-1 | MeO | H | MOM | SEM | OH | $C_{21}H_{31}NO_6Si$ | oil |
| C-2 | Br | Cl | MOM | SEM | OH | $C_{20}H_{27}BrClNO_5Si$ | oil |
| C-3 | Br | MeO | MOM | SEM | OH | $C_{21}H_{30}BrNO_6Si$ | oil |
| C-4 | $NO_2$ | H | MOM | SEM | OH | $C_{20}H_{28}N_2O_7Si$ | oil |
| C-5 | H | MeO | MOM | SEM | OH | $C_{21}H_{31}NO_6Si$ | oil |
| C-6 | CN | H | MOM | SEM | OH | $C_{21}H_{28}N_2O_5Si$ | oil |
| C-7 | $NO_2$ | MeO | MOM | SEM | OH | $C_{21}H_{30}N_2O_8Si$ | oil |
| C-8 | Br | Me | MOM | SEM | OH | $C_{21}H_{30}BrNO_5Si$ | oil |
| C-9 | $NO_2$ | Me | MOM | SEM | OH | $C_{21}H_{30}N_2O_7Si$ | oil |
| C-10 | Br | F | MOM | SEM | OH | $C_{20}H_{27}BrFNO_5Si$ | oil |
| C-11 | MOM—$OCH_2$ | H | MOM | SEM | OH | $C_{23}H_{35}NO_7Si$ | oil |
| C-12 | $Me_3SiC\equiv C$ | H | MOM | SEM | OH | $C_{25}H_{37}NO_5Si_2$ | oil |
| C-13 | 1,3-dioxolan-2-yl | H | MOM | SEM | OH | $C_{23}H_{33}NO_7Si$ | oil |
| C-14 | Br | H | MOM | MOM | OH | $C_{17}H_{17}BrN_2O_4$ | 92–93 |
| C-15 | Br | Cl | MOM | MOM | CN | $C_{17}H_{16}BrClN_2O_4$ | 144.5–146 |
| C-16 | Br | F | MOM | MOM | CN | $C_{17}H_{16}BrFN_2O_4$ | 101–102 |
| C-17 | F | Cl | MOM | MOM | CN | $C_{17}H_{16}ClFN_2O_4$ | 94–95 |
| C-18 | Br | F | MOM | Bn | CN | $C_{22}H_{18}BrFN_2O_3$ | oil |
| C-19 | CN | F | MOM | SEM | OH | $C_{21}H_{27}FN_2O_5Si$ | oil |

MOM: $CH_2OCH_3$, SEM: $CH_2OCH_2CH_2SiMe_3$, Bn: benzyl

TABLE 10

| Cpd. No. | $^1$H-NMR ($CDCl_3$; TMS internal standard, ppm) | IR (KBr; $cm^{-1}$) |
|---|---|---|
| C-1 | −0.07(9H, s), 0.74–0.83(2H, m), 3.25–3.53(2H, m), 3.48(3H, s), 3.66(3H, s), 5.01 (1H, d, J=7.0Hz), 5.12(1H, d, J=7.0Hz), 5.14(2H, s), 6.27(1H, s), 6.52(1H, d, J=3.0Hz), 6.70(1H, dd, J=3.0&8.8Hz), 7.04(1H, d, J=8.8Hz), 7.21(1H, dd, J=4.6&8.4Hz), 7.37(1H, dd, J=1.4&8.4Hz), 8.27(1H, dd, J=1.4&4.6Hz). | 3400, 2950, 2900, 1740, 1600, 1460, 1435, 1320, 1270, 1165. |
| C-2 | −0.06(9H, s), 0.80(2H, t, J=8.2Hz), 3.28–3.54(2H, m), 3.42(3H, s), 5.05(1H, d, J=7.2Hz), 5.15(1H, d, J=7.2Hz), 5.16(2H, s), 5.48(1H, d, J=6.6Hz), 6.16(1H, d, J=6.6Hz), 7.20(1H, s), 7.22(1H, s), 7.24(1H, dd, J=4.6&8.2Hz), 7.40(1H, dd, J=1.2&8.2Hz), 8.26(1H, dd, J=1.2&4.6Hz). | 3400, 2950, 2900, 1735, 1585, 1575, 1440, 1250, 1155, 1085. |
| C-3 | −0.07(9H, s), 0.80(2H, t, J=8.0Hz), 3.29–3.55(2H, m), 3.46(3H, s), 3.84(3H, s), 5.04 (1H, d, J=6.8Hz), 5.14(1H, d, J=6.8Hz), 5.20(2H, s), 5.44(1H, d, J=6.6Hz), 6.17(1H, d, J=6.6Hz), 6.73(1H, s), 7.09(1H, s), 7.22(1H, dd, J=4.8&8.2Hz), 7.39(1H, dd, J=1.0&8.2Hz), 8.27(1H, dd, J=1.0&4.8Hz). | 3450, 2950, 1600, 1575, 1490, 1455, 1300, 1250, 1150, 1135, 1090, 1010. |
| C-4 | −0.09(9H, s), 0.78(2H, t, J=8.2Hz), 3.25–3.52(2H, m), 3.41(3H, s), 5.06(1H, d, J=7.2Hz), 5.14(1H, d, J=7.2Hz), 5.28(2H, s), 5.59(1H, d, J=6.4Hz), 6.25(1H, d, J=6.4Hz), 7.18(1H, d, J=9.2Hz), 7.26(1H, dd, J=4.8&8.2Hz), 7.42(1H, dd, J=1.2&8.2Hz), 7.98(1H, d, J=2.8Hz), 8.11 (1H, dd, J=2.8&9.2Hz), 8.30(1H, dd, J=1.2&4.8Hz). | 3380, 2950, 1735, 1590, 1520, 1340, 1250, 1160. |
| C-5 | −0.07(9H, s), 0.79(2H, t, J=8.0Hz), 3.26–3.54(2H, m), 3.45(3H, s), 3.74(3H, s), 5.00(1H, d, J=6.8Hz), 5.11(1H, d, J=6.8Hz), 5.20(2H, s), 5.37(1H, d, J=6.8Hz), 6.23(1H, d, J=6.8Hz), 6.41(1H, dd, J=2.6&8.4Hz), 6.68(1H, d, J=2.6Hz), 6.84(1H, d, J=8.4Hz), 7.20(1H, dd, J=4.8&8.0Hz), 7.37(1H, dd, J=1.2&8.0Hz), 8.26(1H, dd, J=1.2&4.8Hz). | 3400, 2950, 2900, 1735, 1610, 1585, 1505, 1445, 1400, 1290, 1260, 1250, 1215, 1150. |

TABLE 11

| Cpd. No. | $^1$H-NMR ($CDCl_3$; TMS internal standard, ppm) | IR (KBr; $cm^{-1}$) |
|---|---|---|
| C-6 | −0.07(9H, s), 0.79(2H, t, J=8.0Hz), 3.24–3.55(2H, m), 3.41(3H, s), 5.04(1H, d, J=7.2Hz), 5.13(1H, d, J=7.2Hz), 5.26(2H, s), 6.22(1H, br. s) 7.16(1H, d, J=8.8Hz), 7.26(1H, dd, | 3400, 2950, 2900, 2225, 1735, 1605, 1490, 1445, |

TABLE 11-continued

| Cpd. No. | ¹H-NMR (CDCl₃; TMS internal standard, ppm) | IR (KBr; cm⁻¹) |
|---|---|---|
|  | J=4.8&8.4Hz), 7.31(1H, d, J=2.Hz), 7.41(1H, dd, J=1.6&8.4Hz), 7.49(1H, dd, J=2.2&8.8Hz), 8.28(1H, dd, J=1.6&4.8Hz). | 1250, 1150, 1080, 1040. |
| C-7 | −0.08(9H, s), 0.81(2H, t, J=8.2Hz), 3.33–3.59(2H, m), 3.41(3H, s), 3.93(3H, s), 5.08(1H, d, J=7.0Hz), 5.14(1H, d, J=7.0Hz), 5.24(1H, d, J=7.0Hz), 5.28(1H, d, J=7.0Hz), 5.50(1H, br. s), 6.14(1H, br. s), 6.78(1H, s), 7.24(1H, dd, J=4.6&8.2Hz), 7.41(1H, dd, J=1.2&8.2Hz), 7.72(1H, s), 8.27(1H, dd, J=1.2&4.6Hz). | 3380, 2950, 2900, 1735, 1620, 1580, 1520, 1450, 1340, 1280, 1150, 1095, 1060, 1000. |
| C-8 | −0.07(9H, s), 0.80(2H, t, J=8.2Hz), 2.30(3H, s), 3.27–3.53(2H, m), 3.44(3H, s), 5.04 (1H, d, J=7.0Hz), 5.14(1H, d, J=7.0Hz), 5.17(2H, s), 5.43(1H, d, J=6.8Hz), 6.18(1Hd, J=6.8Hz), 6.98(1H, s), 7.09(1H, s), 7.22(1H, dd, J=4.8&8.4Hz), 7.38(1H, dd, J=1.4&8.4Hz). 8.26(1H, dd, J=1.4&4.8Hz). | 3400, 2960, 2900, 1740, 1580, 1485, 1450, 1370, 1250, 1140, 1080. |
| C-9 | −0.09(9H, s), 0.80(2H, t, J=8.2Hz), 2.59(3H, s), 3.29–3.49(2H, m), 3.40(3H, s), 5.07(1H, d, J=7.2Hz), 5.15(1H, d, J=7.2Hz), 5.26(2H, s), 5.51(1H, d, J=6.8Hz), 6.20(1H, d, J=6.8Hz), 6.98(1H, s), 7.25(1H, dd, J=4.6&8.4Hz), 7.42(1H, dd, J=1.2&8.4Hz), 7.83(1H, s), 8.28(1H, dd, J=1.2&4.6Hz). | 3400, 2950, 2900, 1735, 1615, 1575, 1515, 1450, 1335, 1250, 1150, 1090. |
| C-10 | −0.07(9H, s), 0.79(2H, t, J=8.2Hz), 3.26–3.563(2H, m), 3.42(3H, s), 5.04(1H, d, J=7.0Hz), 5.15(1H, d, J=7.0Hz), 5.16(2H, s), 5.50(1H, d, J=6.4Hz), 6.17(1H, d, J=6.4Hz), 6.94(1H, d, J=10.4Hz), 7.12(1H, d, J=7.8Hz), 7.18–7.27(1H, m), 7.34–7.42(1H, m), 8.25–8.27(1H, m). | 3380, 2950, 2900, 1735, 1590, 1575, 1485, 1465, 1250, 1150, 1090. |
| C-11 | −0.07(9H, s), 0.79(2H, t, J=8.0Hz), 3.24–3.54(2H, m), 3.33(3H, s), 3.43(3H, s), 4.42 (2H, s), 4.60(2H, s), 4.99(1H, d, J=7.2Hz), 5.09(1H, d, J=7.2Hz), 5.19(2H, s), 5.42(1H, d, 6.8Hz), 6.29(1H, d, J=6.8Hz), 6.98–7.24(4H, m), 7.37(1H, dd, J=1.2&8.2Hz), 8.27(1H, dd, J=1.2&4.6Hz). |  |

TABLE 12

| Cpd. No. | ¹H-NMR (CDCl₃; TMS internal standard, ppm) | IR (KBr; cm⁻¹) |
|---|---|---|
| C-12 | −0.07(9H, s), 0.19(9H, s), 0.78(2H, t, J=8.6Hz), 3.33–3.52(2H, m), 3.42(3H, s), 4.50 (1H, d, J=8.8Hz), 5.12(1H, d, J=7.2Hz), 5.26(2H, s), 6.23(1H, s), 7.01(1H, d, J=8.8Hz), 7.11(1H, d, J=2.0Hz), 7.19–7.47(3H, m), 8.28(1H, dd, J=1.2&4.6Hz). |  |
| C-13 | −0.07(9H, s), 0.79(2H, t, J=8.4Hz), 3.26–3.49(2H, m), 3.40(3H, s), 3.90–4.08(4H, m), 4.99(1H, d, J=7.2Hz), 5.08(1H, d, J=7.2Hz), 5.17(1H, d, J=6.8Hz), 5.21(1H, d, J=6.8Hz), 5.66(1H, s), 6.27(1H, s), 7.06–7.46(5H, m), 8.27(1H, dd, J=1.2&4.6Hz). |  |
| C-14 | 3.35(3H, s), 3.36(3H, s), 5.15–5.21(4H, m), 5.92(1H, s), 7.00(1H, d, J=8.8Hz), 7.24 (1H, dd, J=4.6&8.4Hz), 7.37(1H, dd, J=2.4&8.8Hz), 7.45(1H, dd, J=1.4&8.4Hz), 7.49(1H, d, J=2.4Hz), 8.28(1H, dd, J=1.4&4.6Hz). | 2240, 1580, 1580. |
| C-15 | 3.35(3H, s), 3.40(3H, s), 5.12(1H, d, J=6.8Hz), 5.17(1H, d, J=6.8Hz), 5.23(2H, s), 5.87 (2H, s), 7.22–7.29(2H, m), 7.47(1H, dd, J=1.2&8.8Hz), 7.62(1H, s), 8.27(1H, dd, J=1.2&4.6Hz), |  |
| C-16 | 3.36(3H, s), 3.39(3H, s), 5.14(1H, d, J=7.0Hz), 5.18(1H, d, J=7.0Hz), 5.21(1H, dJ=7.0Hz), 5.25(1H, d, J=7.0Hz), 5.89(2H, s), 6.98(1H, d, J=10.0Hz), 7.26(1H, dd, J=4.6&8.4Hz), 7.47 (1H, dd, J=1.4&8.4Hz), 7.56(1H, d, J=7.6Hz), 8.28(1H, dd, J=1.4&4.6Hz). |  |
| C-17 | 3.36(3H, s), 3.38(3H, s), 5.13(1H, d, J=7.0Hz), 5.17(1H, d, J=7.0Hz), 5.20(1H, d, J=7.0Hz), 5.24(1H, d, J=7.0Hz), 5.88(1H, s), 6.99(1H, d, J=10.6Hz), 7.25(1H, dd, J=4.6&8.4Hz), 7.41 (1H, d, J=8.2Hz), 7.46(1H, dd, J=1.4&8.4Hz), 8.28(1H, dd, J=1.4&6.4Hz). |  |
| C-18 | 3.25(3H, s), 4.98(2H, s), 5.02(1H, d, J=11.4Hz), 5.09(1H, d, J=11.4Hz), 5.96(1H, s), 6.93(1H, d, J=10.2Hz), 7.22–7.40(8H, m), 7.47(1H, d, J=7.6Hz), 8.25–8.28(1H, m). |  |
| C-19 | −0.06(9H, s), 0.81(2H, t, J=8.0Hz), 3.29–3.55(2H, m), 3.41(3H, s), 5.06(1H, d, J=7.0Hz), 5.14(1H, d, J=7.0Hz), 5.24(2H, s), 5.49(1H, d, J=6.6Hz), 6.16(1H, d, J=6.6Hz), 6.96(1H, d, J=11.0Hz), 7.22–7.29(2H, m), 7.42(1H, dd, J=1.2&8.2Hz), 8.27(1H, dd, J=1.2&4.6Hz). |  |

TABLE 13

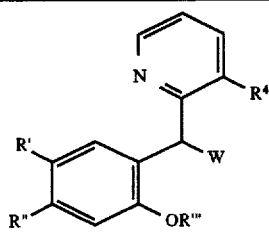

| Cpd. No. | R' | R" | R''' | R⁴ | W | Formula | m.p. (°C.) physical property |
|---|---|---|---|---|---|---|---|
| D-1 | Br | H | H | H | OH | $C_{12}H_{10}BrNO_2$ | 126–127 |
| D-2 | Br | H | MOM | 1,3-dioxolan-2-yl | OH | $C_{17}H_{18}BrNO_5$ | oil |
| D-3 | Br | H | MOM | 1,3-dioxolan-2-yl | CN | $C_{18}H_{17}BrN_2O_4$ | oil |
| D-4 | Br | H | MOM | $CF_3$ | CN | $C_{16}H_{12}BrF_3N_2O_2$ | 95–96 |
| D-5 | Cl | H | MOM | Cl | CN | $C_{15}H_{12}Cl_2N_2O_2$ | oil |
| D-6 | Br | H | MOM | F | OH | $C_{14}H_{13}BrFNO_3$ | oil |
| D-7 | Cl | H | MOM | 1,3-dioxolan-2-yl | OH | $C_{17}H_{18}ClNO_5$ | oil |
| D-8 | Cl | F | MOM | 1,3-dioxolan-2-yl | OH | $C_{17}H_{17}ClFNO_5$ | oil |
| D-9 | CN | H | MOM | 1,3-dioxolan-2-yl | OH | $C_{18}H_{18}N_2O_5$ | oil |
| D-10 | $CF_3O$ | H | MOM | F | OH | $C_{15}H_{13}F_4NO_4$ | 87–88 |
| D-11 | $NO_2$ | H | MOM | 1,3-dioxolan-2-yl | OH | $C_{17}H_{18}N_2O_7$ | 116–117 |
| D-12 | Cl | H | MOM | 3-Cl-5-$NO_2$ | CN | $C_{15}H_{11}Cl_2N_3O_4$ | 147–148 |
| D-13 | Cl | H | MOM | 5-$NH_2$-3-Cl | CN | $C_{15}H_{13}Cl_2N_3O_2$ | 142–143 |
| D-14 | $CF_3$ | H | MOM | 1,3-dioxolan-2-yl | OH | $C_{18}H_{18}F_3NO_5$ | oil |
| D-15 | CN | Cl | MOM | 1,3-dioxolan-2-yl | OH | $C_{18}H_{17}ClN_2O_5$ | 130–131 |

MOM: $CH_2OCH_3$

TABLE 14

| Cpd. No. | ¹H-NMR (CDCl₃; TMS internal standard, ppm) | IR (KBr; cm⁻¹) |
|---|---|---|
| D-1 | 2.8–4.0(2H, br. s), 5.98(1H, s), 6.83(1H, d, J=8.4Hz), 7.24–7.30(2H, m), 7.49–7.54(1H, dt, J=1.6&8.7Hz), 8.48(1H, m). | |
| D-2 | 3.38(3H, s), 3.89–4.47(4H, m), 5.14(2H, s), 5.38(1H, d, J=6.8Hz), 5.80(1H, s), 6.40(1H, d, J=6.8Hz), 6.98(1H, d, J=8.8Hz), 7.28–7.34(2H, m), 7.93(1H, dd, J=1.8&7.6Hz), 8.62(1H, dd, J=1.8&4.8Hz). | |
| D-3 | 3.33(3H, s), 4.00–4.09(4H, m), 5.13&5.17(2H, ABq, J=7.0Hz), 5.96(1H, s), 6.10(1H, s), 6.98 (1H, d, J=8.8Hz), 7.30(1H, dd, J=4.8&7.8Hz), 7.38(1H, dd, J=2.4&8.8Hz), 7.55(1H, d, J=2.4Hz), 7.91(1H, dd, J=1.6&7.8Hz), 8.65(1H, dd, J=1.6&4.8Hz). | |
| D-4 | 3.33(3H, s), 5.12&5.16(2H, ABq, J=7.0Hz), 7.02(1H, d, J=8.8Hz), 7.41(1H, dd, J=2.4&8.8Hz), 7.47(1H, m), 7.57(1H, d, J=2.4Hz), 8.05(1H, dd, J=1.2&8.0Hz), 8.87(1H, m). | 2250, 1580, 1480, 1320. |
| D-5 | 3.39(3H, s), 5.18&5.22(2H, ABq, J=7.0Hz), 6.11(1H, s), 7.08(1H, d, J=8.8Hz), 7.24–7.34(3H, m), 7.74(1H, dd, J=1.6&8.0Hz), 8.60(1H, dd, J=1.6&4.8Hz). | |
| D-6 | 3.41(3H, s), 4.99(1H, d, J=7.0Hz), 5.17(2H, s), 6.34(1H, dd, J=1.0&7.0Hz), 7.01(1H, dt, J= 1.0&9.2Hz), 7.29–7.42(4H, m), 8.44(1H, dt, J=1.6&4.4Hz). | |
| D-7 | 3.39(3H, s), 3.89–4.07(4H, m), 5.136(1H, s), 5.140(1H, s), 5.79(1H, s), 6.41(1H, s), 7.02 (1H, d, J=8.8Hz), 7.07(1H, d, J=2.6Hz), 7.16(1H, dd, J=2.6&8.8Hz), 7.31(1H, dd, J=4.8&7.6Hz), 7.93(1H, dd, J=1.8&7.6Hz), 8.62(1H, dd, J=1.8&4.8Hz). | |
| D-8 | 3.38(3H, s), 3.89–4.08(4H, m), 5.13(2H, s), 5.35(1H, br. s), 5.78(1H, s), 6.37(1H, br. s), 6.95(1H, d, J=11.0Hz), 7.12(1H, d, J=8.4Hz), 7.32(1H, dd, J=4.8&7.8Hz), 7.93(1H, dd, J= 18&7.8Hz), 8.62(1H, dd, J=1.8&4.8Hz). | |

TABLE 15

| Cpd. No. | ¹H-NMR (CDCl₃; TMS internal standard, ppm) | IR (KBr; cm⁻¹) |
|---|---|---|
| D-9 | 3.34(3H, s), 3.86–4.14(4H, m), 5.18&5.23(2H, ABq, J=7.0Hz), 5.27(1H, d, J=6.8Hz), 5.81(1H, s), 6.41(1H, d, J=6.8Hz), 7.13(1H, d, J=8.6Hz), 7.33(1H, dd, J=4.8&8.0Hz), 7.46(1H, d, J= 2.2Hz), 7.52(1H, dd, J=2.2&8.6Hz), 7.92(1H, dd, J=1.8&8.0Hz), 8.61(1H, dd, J=1.8&4.8Hz). | |
| D-10 | 3.41(3H, s), 4.98(1H, d, J=7.4Hz), 5.18(2H, s), 6.34(1H, dd, J=1.2&7.4Hz), 7.04–7.14(3H, m), 7.24–7.41(2H, m), 8.44(1H, dt, J=1.4&4.4Hz). | |

TABLE 15-continued

| Cpd. No. | 1H-NMR (CDCl3; TMS internal standard, ppm) | IR (KBr; cm⁻¹) |
|---|---|---|
| D-11 | 3.33(3H, s), 3.90–4.08(4H, m), 5.21&5.25(2H, ABq, J=6.6Hz), 5.29(1H, d, J=6.6Hz), 5.85(1H, s), 6.44(1H, d, J=6.6Hz), 7.16(1H, d, J=9.6Hz), 7.33(1H, dd, J=4.8&8.0Hz), 7.93(1H, dd, J=1.8&8.0Hz), 8.10–8.17(2H, m), 8.63(1H, dd, J=1.8&4.8Hz). | |
| D-12 | 3.40(3H, s), 5.19(2H, s), 6.17(1H, s), 7.10(1H, d, J=8.8Hz), 7.30(1H, dd, J=2.6&8.8Hz), 7.37(1H, d, J=2.6Hz), 8.55(1H, d, J=2.2Hz), 9.37(1H, d, J=2.2Hz). | 2260, 1595, 1525, 1490, 1355. |
| D-13 | 3.42(3H, s), 3.90(2H, br. s), 5.20(2H, s), 5.96(1H, s), 6.99(1H, d, J=2.6Hz), 7.06(1H, d, J=8.8Hz), 7.23(1H, dd, J=2.6&8.8Hz), 7.29(1H, d, J=2.6Hz), 8.03(1H, d, J=2.6Hz). | 2250, 1590, 1485. |
| D-14 | 3.32(3H, s), 3.87–4.07(4H, m), 5.17(2H, s), 5.39(1H, br. d, J=6.0Hz), 5.76(1H, s), 6.42 (1H, br. d, J=6.0Hz), 7.14(1H, d, J=9.2Hz), 7.30(1H, dd, J=4.8&8.0Hz), 7.46–7.51(2H, m), 7.92(1H, dd, J=1.8&8.0Hz), 8.62(1H, dd, J=1.8&4.8Hz). | |
| D-15 | 3.33(3H, s), 3.91–4.09(4H, m), 5.16, 5.21(2H, ABq, J=7.0Hz), 5.83(1H, s), 6.35(1H, br. s), 7.21(1H, d), 7.33(1H, dd, J=4.8&7.8Hz), 7.48(1H, s), 7.93(1H, dd, J=1.8&7.8Hz), 8.61 (1H, dd, J=1.8&4.8Hz). | 3600–3300, 2950, 2890, 2230, 1600, 1470. |

TABLE 16

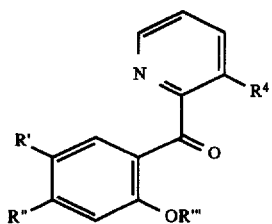

| Cpd. No. | R' | R" | R'" | R⁴ | Formula | m.p. (°C.) physical property |
|---|---|---|---|---|---|---|
| E-1 | Br | H | MOM | 1,3-dioxolan-2-yl | C₁₇H₁₆BrNO₅ | oil |
| E-2 | Br | H | H | 1,3-dioxolan-2-yl | C₁₅H₁₂BrNO₄ | 91–91.5 |
| E-3 | Br | H | MOM | CF₃ | C₁₅H₁₁BrF₃NO₃ | oil |
| E-4 | Br | H | H | CF₃ | C₁₃H₇BrF₃NO₂ | 98–100 |
| E-5 | Cl | H | MOM | Cl | C₁₄H₁₁Cl₂NO₃ | oil |
| E-6 | Cl | H | H | Cl | C₁₂H₇Cl₂NO₂ | 120–121 |
| E-7 | Br | H | MOM | F | C₁₄H₁₁BrFNO₃ | oil |
| E-8 | Br | H | H | F | C₁₂H₇BrFNO₂ | 110–112 |
| E-9 | Cl | H | MOM | 1,3-dioxdlan-2-yl | C₁₇H₁₆ClNO₅ | oil |
| E-10 | Cl | H | H | CHO | C₁₃H₈ClNO₃ | 132–133 |
| E-11 | Cl | H | MOM | CHO | C₁₅H₁₂ClNO₄ | oil |
| E-12 | Cl | H | MOM | CN | C₁₅H₁₁ClN₂O₃ | oil |
| E-13 | Cl | H | H | CN | C₁₃H₇ClN₂O₂ | 158.5–159.5 |
| E-14 | Me | H | MOM | 1,3-dioxolan-2-yl | C₁₈H₁₉NO₅ | oil |
| E-15 | Me | H | H | CHO | C₁₄H₁₁NO₃ | 134–135 |
| E-16 | Me | H | MOM | CHO | C₁₆H₁₅NO₄ | oil |
| E-17 | Me | H | H | CN | C₁₄H₁₀N₂O₂ | 137–138 |
| E-18 | Cl | F | MOM | 1,3-dioxolan-2-yl | C₁₇H₁₅ClFNO₅ | oil |
| E-19 | Cl | F | H | 1,3-dioxolan-2-yl | C₁₅H₁₁ClFNO₄ | morph. |
| E-20 | Br | H | MOM | Boc-NH | C₁₉H₂₁BrN₂O₅ | oil |
| E-21 | Br | H | H | NH₂ | C₁₂H₉BrN₂O₂ | 129-130 |
| E-22 | Br | H | H | MOM | C₁₄H₁₂BrNO₃ | oil |
| E-23 | CN | H | MOM | 1,3-dioxolan-2-yl | C₁₈H₁₆N₂O₅ | 134–136 |
| E-24 | CN | H | H | CHO | C₁₄H₈N₂O₃ | 174–175 |
| E-25 | CN | H | MOM | CHO | C₁₆H₁₂N₂O₄ | 149–150 |
| E-26 | CN | H | H | CN | C₁₄H₇N₃O₂ | 192–194 |

TABLE 17

| Cpd. No. | R' | R'' | R''' | R⁴ | Formula | m.p. (°C.) physical property |
|---|---|---|---|---|---|---|
| E-27 | CF₃O | H | MOM | F | $C_{15}H_{11}F_4NO_4$ | oil |
| E-28 | CF₃O | H | MOM | CN | $C_{16}H_{11}F_3N_2O_4$ | oil |
| E-29 | MeO | H | H | CHO | $C_{14}H_{11}NO_4$ | 108–109 |
| E-30 | MeO | H | MOM | CHO | $C_{16}H_{15}NO_5$ | oil |
| E-31 | MeO | H | MOM | CN | $C_{16}H_{14}N_2O_4$ | oil |
| E-32 | NO₂ | H | MOM | 1, 3-dioxolan-2-yl | $C_{17}H_{16}N_2O_7$ | 135–136 |
| E-33 | NO₂ | H | H | 1, 3-dioxolan-2-yl | $C_{15}H_{12}N_2O_6$ | 136–137 |
| E-34 | Cl | H | MOM | 5-NH₂-3-Cl | $C_{14}H_{12}Cl_2N_2O_3$ | 181–182 |
| E-35 | Cl | H | H | 5-NH₂-3-Cl | $C_{12}H_8Cl_2N_2O_2$ | 201–202 |
| E-36 | F | H | MOM | 1, 3-dioxolan-2-yl | $C_{17}H_{16}FNO_5$ | 99–101 |
| E-37 | F | H | H | CHO | $C_{13}H_8FNO_3$ | 145–146 |
| E-38 | F | H | MOM | CHO | $C_{15}H_{12}FNO_4$ | 70–71 |
| E-39 | F | H | MOM | CN | $C_{15}H_{11}FN_2O_3$ | 100–101 |
| E-40 | CF₃ | H | MOM | 1, 3-dioxolan-2-yl | $C_{18}H_{16}F_3NO_5$ | oil |
| E-41 | CF₃ | H | H | 1, 3-dioxolan-2-yl | $C_{16}H_{12}F_3NO_4$ | 96–97 |
| E-42 | Cl | CN | MOM | 1, 3-dioxolan-2-yl | $C_{18}H_{15}ClN_2O_5$ | oil |
| E-43 | Cl | CN | H | CHO | $C_{14}H_7ClN_2O_3$ | 178–180 |
| E-44 | Cl | CN | MOM | CHO | $C_{16}H_{11}ClN_2O_4$ | 134–135 |
| E-45 | Cl | CN | MOM | CH=NOH | $C_{16}H_{12}ClN_3O_4$ | 206–209 (dec.) |
| E-46 | Cl | CN | MOM | CN | $C_{16}H_{10}ClN_3O_3$ | 176–178 |
| E-47 | CN | Cl | MOM | 1, 3-dioxolan-2-yl | $C_{18}H_{15}ClN_2O_5$ | oil |
| E-48 | CN | Cl | H | CHO | $C_{14}H_7ClN_2O_3$ | 194–196 |
| E-49 | CN | Cl | H | 1, 3-dioxolan-2-yl | $C_{16}H_{11}ClN_2O_4$ | oil |

MOM: CH₂OCH₃, Boc: benzyloxycarbonyl

TABLE 18

| Cpd. No. | ¹H-NMR (CDCl₃; TMS internal standard, ppm) | IR (KBr; cm⁻¹) |
|---|---|---|
| E-1 | 3.18(3H, s), 3.96–4.10(4H, m), 4.80(2H, s), 6.25(1H, s), 7.03(1H, d, J=8.6Hz), 7.41(1H, dd, J=4.8&8.0Hz), 7.56(1H, dd, J=2.4&8.6Hz), 7.87(1H, d, J=2.4Hz), 8.08(1H, dd, J=1.6&8.0Hz), 8.55(1H, dd, J=1.6&4.8Hz). | |
| E-2 | 3.94–3.97(4H, m), 6.09(1H, s), 6.96(1H, d, J=9.0Hz), 7.43(1H, d, J=2.6Hz), 7.51(1H, dd, J=4.8&8.0Hz), 7.56(1H, dd, J=2.6&9.0Hz), 8.07(1H, dd, J=1.6&8.0Hz), 8.69(1H, dd, J=1.6&4.8Hz), 11.83(1H, s). | 3600–3300, 2880, 1640, 1610, 1460. |
| E-3 | 3.13(3H, s), 4.75(2H, s), 7.03(1H, d, J=8.8Hz), 7.52(1H, m), 7.61(1H, dd, J=2.4&8.8Hz), 8.07(1H, d, J=2.4Hz), 8.12(1H, m), 8.73(1H, m). | |
| E-4 | 7.00(1H, d, J=8.8Hz), 7.27(1H, d, J=2.6Hz), 7.61(1H, dd, J=2.6&8.8Hz), 7.66(1H, m), 8.19 (1H, dd, J=0.8&8.0Hz), 8.90(1H, dd, J=1.0&4.8Hz), 11.58(1H, s) | 3600–3300, 1630, 1580, 1460, 1320. |
| E-5 | 3.20(3H, s), 4.82(2H, s), 7.08(1H, d, J=9.2Hz), 7.34(1H, dd, J=4.8&8.0Hz), 7.45(1H, dd, J=2.6&9.2Hz), 7.80–7.85(2H, m), 8.48(1H, dd, J=1.6&4.8Hz). | |
| E-6 | 7.04(1H, d, J=8.8Hz), 7.20(1H, d, J=2.6Hz), 7.43–7.50(2H, m), 7.90(1H, dd, J=1.4&8.0Hz), 8.62(1H, dd, J=1.6&4.8Hz), 11.70(1H, s). | 3300–3100, 3060, 1640, 1470. |
| E-7 | 3.23(3H, s), 4.87(2H, s), 7.07(1H, d, J=8.8Hz), 7.47(1H, dt, J=4.4&8.6Hz), 7.52–7.61(2H, m), 7.81(1H, d, J=2.4Hz), 8.45(1H, dt, J=1.4&4.4Hz). | |
| E-8 | 6.99(1H, d, J=9.0Hz), 7.52–7.70(4H, m), 8.58(1H, dt, J=1.6&4.4Hz), 11.82(1H, s). | 3600–3300, 3080, 1630, 1440, 1330. |
| E-9 | 3.18(3H, s), 4.00–4.08(4H, m), 4.80(2H, s), 6.26(1H, s), 7.09(1H, d, J=9.0Hz), 7.38–7.44 (2H, m), 7.73(1H, d, J=2.6Hz), 8.08(1H, dd, J=1.8&8.8Hz), 8.55(1H, dd, J=1.8&4.8Hz). | |

TABLE 19

| Cpd. No. | ¹H-NMR (CDCl₃; TMS internal standard, ppm) | IR (KBr; cm⁻¹) |
|---|---|---|
| E-10 | 7.07(1H, dd, J=0.6&8.4Hz), 7.45–7.52(2H, m), 7.70(1H, dd, J=4.8&8.0Hz), 8.40(1H, dd, J=1.8& 8.0Hz), 8.91(1H, dd, J=1.8&4.8Hz), 10.16(1H, s), 11.71(1H, s). | 3600–3300, 1700, 1620, 1460. |
| E-11 | 3.16(3H, s), 4.80(2H, s), 7.13(1H, d, J=9.0Hz), 7.48(1H, dd, J=2.6&9.0Hz), 7.57(1H, dd, J=4.8&8.0Hz), 7.77(1H, d, J=2.6Hz), 8.37(1H, dd, J=1.8&8.0Hz), 8.75(1H, dd, J=1.8&4.8Hz). | |
| E-12 | 3.24(3H, s), 4.86(2H, s), 7.14(1H, d, J=8.8Hz), 7.48(1H, dd, J=2.6&8.8Hz), 7.57(1H, dd, J=4.8&7.8Hz), 7.68(1H, d, J=2.6Hz), 8.19(1H, dd, J=1.8&7.8Hz), 8.77(1H, dd, J=1.8&4.8Hz). | |
| E-13 | 7.07(1H, d, J=9.2Hz), 7.52(1H, dd, J=2.6&9.2Hz), 7.68(1H, dd, J=4.8&8.0Hz), 7.73(1H, d, J=2.6Hz), 8.25(1H, dd, J=1.8&8.0Hz), 8.93(1H, dd, J=1.8&4.8Hz), 11.66(1H, s). | 3600–3300, 3060, 2240, 1620, 1460. |
| E-14 | 2.34(3H, s), 3.17(3H, s), 3.96–4.12(4H, m), 4.77(2H, s), 6.23(1H, s), 7.02(1H, d, J=8.6Hz), | |

TABLE 19-continued

| Cpd. No. | 1H-NMR (CDCl3; TMS internal standard, ppm) | IR (KBr; cm−1) |
|---|---|---|
|  | 7.28(1H, m), 7.39(1H, dd, J=4.8&7.8Hz), 7.59(1H, d, J=2.2Hz), 8.07(1H, m), 8.55(1H, dd, J=1.4&4.8Hz). |  |
| E-15 | 2.21(3H, s), 7.01(1H, d, J=8.6Hz), 7.16(1H, dd, J=0.8&2.2Hz), 7.37(1H, dd, J=2.2&8.6Hz), 7.66(1H, m), 8.40(1H, dd, J=1.6&8.7Hz), 8.90(1H, dd, J=1.6&4.8Hz), 10.14(1H, s), 11.62(1H, s). | 3600–3300, 2850, 1640, 1565. |
| E-16 | 2.37(3H, s), 3.14(3H, s), 4.77(2H, s), 7.06(1H, d, J=8.4Hz), 7.34(1H, m), 7.53(1H, m), 7.64(1H, d, J=2.2Hz), 8.36(1H, dd, J=1.8&8.0Hz), 8.75(1H, dd, J=1.8&4.8Hz), 10.33(1H, s). |  |
| E-17 | 2.24(3H, s), 7.01(1H, d, J=8.4Hz), 7.33–7.41(2H, m), 7.64(1H, dd, J=4.8&8.0Hz), 8.22(1H, dd, J=1.8&8.0Hz), 8.91(1H, dd, J=1.8&4.8Hz), 11.53(1H, s). | 3600–3300, 3060, 2230, 1630, 1480. |
| E-18 | 3.20(3H, s), 3.99–4.06(4H, m), 4.79(2H, s), 6.22(1H, s), 6.99(1H, d, J=10.6Hz), 7.41(1H, dd, J=4.8&8.0Hz), 7.85(1H, d, J=8.4Hz), 8.07(1H, dd, J=1.8&8.0Hz), 8.55(1H, dd, J=1.8&4.8Hz). |  |
| E-19 | 3.97(4H, m), 6.10(1H, s), 6.85(1H, d, J=10.2Hz), 7.44(1H, d, J=8.4Hz), 7.52(1H, dd, J=4.8&7.8Hz), 8.09(1H, dd, J=1.6&7.8Hz), 8.69(1H, dd, J=1.6&4.8Hz), 12.12(1H, br. s). |  |

TABLE 20

| Cpd. No. | 1H-NMR (CDCl3; TMS internal standard, ppm) | IR (KBr; cm−1) |
|---|---|---|
| E-20 | 1.55(9H, s), 3.31(3H, s), 4.97(2H, s), 7.12(1H, d, J=8.6Hz), 7.41(1H, dd, J=4.&8.8Hz), 7.47–7.56(2H, m), 8.23(1H, dd, J=1.4&4.4Hz), 8.87(1H, dd, J=1.4&8.8Hz). |  |
| E-21 | 6.26(2H, br. s), 6.91(1H, d, J=8.8Hz), 7.20(1H, dd, J=1.6&8.4Hz), 7.34(1H, dd, J=4.0&8.4Hz), 7.50(1H, dd, J=2.6&8.8Hz), 8.03(1H, dd, J=1.6&4.0Hz), 8.23(1H, d, J=2.6Hz). | 3600–3350, 3300, 1610. |
| E-22 | 3.35(3H, s), 4.59(2H, s), 6.97(1H, dd, J=1.0&8.4Hz), 7.49(1H, dd, J=4.8&7.8Hz), 7.54–7.60(2H, m), 7.95–8.00(1H, m), 8.63(1H, dd, J=1.4&4.8Hz), 11.99(1H, s). |  |
| E-23 | 3.21(3H, s), 4.02–4.09(4H, m), 4.94(2H, s), 6.31(1H, s), 7.23(1H, d, J=8.8Hz), 7.42(1H, dd, J=4.8&8.0Hz), 7.74(1H, dd, J=2.&8.8Hz), 8.01(1H, d, J=2.2Hz), 8.12(1H, dd, J=1.8&8.0Hz), 8.55(1H, dd, J=1.8&4.8Hz). |  |
| E-24 | 7.19(1H, d, J=8.8Hz), 7.72–7.79(2H, m), 7.92(1H, d, J=2.Hz), 8.42(1H, dd, J=1.8&8.0Hz), 8.93(1H, dd, J=1.8&4.8Hz), 10.16(1H, s), 12.23(1H, s). | 3600–3300, 2230, 1690, 1620. |
| E-25 | 3.19(3H, s), 4.94(2H, s), 7.28(1H, d, J=8.4Hz), 7.60(1H, m), 7.80(1H, dd, J=2.2&8.4Hz), 8.06(1H, d, J=2.2Hz), 8.38(1H, dd, J=1.6&8.0Hz), 8.74(1H, dd, J=1.6&4.8Hz), 10.39(1H, s). | 3600–3300, 3040, 2950, 2220, 1700, 1660, 1600, 1490. |
| E-26 | *7.04(1H, d, J=8.8Hz), 7.83(1H, dd, J=4.8&8.0Hz), 7.88(1H, dd, J=2.2&8.8Hz), 8.03(1H, d, J=2.2Hz), 8.56(1H, dd, J=1.6&8.0Hz), 8.86(1H, dd, J=1.6&4.8Hz), 11.43(1H, br. s). | 3600–3300, 3090, 2220, 1630, 1610. |
| E-27 | 3.24(3H, s), 4.88(2H, s), 7.19(1H, d, J=9.2Hz), 7.32–7.38(1H, m), 7.42–7.62(3H, m), 8.45(1H, dt, J=1.6&4.8Hz). |  |
| E-28 | 3.25(3H, s), 4.88(2H, s), 7.21(1H, d, J=9.2Hz), 7.35–7.42(1H, m), 7.55–7.61(2H, m), 8.19(1H, dd, J=1.8&8.0Hz), 8.77(1H, dd, J=1.8&4.8Hz). |  |

TABLE 21

| Cpd. No. | 1H-NMR (CDCl3; TMS internal standard, ppm) | IR (KBr; cm−1) |
|---|---|---|
| E-29 | 3.67(3H, s), 6.93(1H, d, J=3.2Hz), 7.05(1H, d, J=9.2Hz), 7.20(1H, dd, J=3.2&9.2Hz), 7.66(1H, m), 8.40(1H, dd, J=1.8&8.0Hz), 8.93(1H, dd, J=1.8&4.8Hz), 10.16(1H, s), 11.46(1H, s). | 3600–3300, 1700, |
| E-30 | 3.15(3H, s), 3.85(3H, s), 4.70(2H, s), 7.10–7.11(2H, m), 7.37(1H, t, J=1.6Hz), 7.54(1H, dd, J=4.8&8.0Hz), 8.36(1H, dd, J=1.8&8.0Hz), 8.75(1H, dd, J=1.8&4.8Hz), 10.31(1H, s). |  |
| E-31 | 3.22(3H, s), 3.84(3H, s), 4.77(2H, s), 7.10–7.12(2H, m), 7.28–7.30(1H, m), 7.54(1H, dd, J=4.8&8.0Hz), 8.17(1H, dd, J=1.8&8.0Hz), 8.78(1H, dd, J=1.8&4.8Hz). |  |
| E-32 | 3.23(3H, s), 4.03–4.10(4H, m), 4.99(2H, s), 6.36(1H, s), 7.26(1H, d, J=9.2Hz), 7.46(1H, dd, J=4.8&8.0Hz), 8.14(1H, dd, J=1.8&8.0Hz), 8.36(1H, dd, J=1.8&9.2Hz), 8.56(1H, dd, J=1.8&4.8Hz), 8.60(1H, d, J=2.8Hz). |  |
| E-33 | 3.92–3.99(4H, m), 6.18(1H, s), 7.16(1H, d, J=8.8Hz), 7.56(1H, dd, J=4.8&8.0Hz), 8.10–8.14(1H, m), 8.33–8.40(2H, m), 8.70(1H, dd, J=1.8&4.8Hz), 12.55(1H, s). | 3600–3300, 1650, 1470, 1340. |
| E-34 | 3.30(3H, s), 4.10(2H, br. s), 4.94(2H, s), 7.04(1H, d, J=2.4Hz), 7.10(1H, d, J=8.8Hz), 7.38(1H, dd, J=2.7&8.8Hz), 7.54(1H, d, J=2.7Hz), 7.91(1H, d, JU=2.4Hz). | 1645, 1575. |
| E-35 | 4.17(2H, br. s), 7.00(1H, d, J=8.6Hz), 7.10(1H, d, J=2.4Hz), 7.43(1H, dd, J=2.5&8.6Hz), 7.48(1H, d, J=2.5Hz), 8.02(1H, d, J=2.4Hz), 11.91(1H, s). | 1620, 1615, 1575. |

*measured with DMSO-d6

TABLE 21a

| Cpd. No. | $^1$H-NMR (CDCl$_3$; TMS internal standard, ppm) | IR (KBr; cm$^{-1}$) |
|---|---|---|
| E-36 | 3.20(3H, s), 3.97–4.12(4H, m), 4.77(2H, s), 6.26(1H, s), 7.08–7.24(2H, m), 7.42(1H, dd, J=4.8&7.8Hz), 7.49(1H, br. dd, J=2.8&8.8Hz), 8.09(1H, dd, J=1.6&7.8Hz), 8.56(1H, dd, J=1.6&4.8Hz). | |
| E-37 | 7.08(1H, dd, J=4.&9.0Hz), 7.18–7.35(2H, m), 7.69(1H, dd, J=4.8&7.8Hz), 8.40(1H, dd, J=1.6&7.8Hz), 8.90(1H, dd, J=1.6&4.8Hz), 10.16(1H, s), 11.57(1H, s). | 3600–3300, 3100, 1700, 1620, 1570, 1470. |
| E-38 | 3.17(3H, s), 4.76(2H, s), 7.12–7.29(2H, m), 7.50–7.60(2H, m), 8.36(1H, dd, J=1.8&7.6 Hz), 8.75(1H, dd, J=1.8&4.8Hz), 10.33(1H, d, J=0.6Hz). | |
| E-39 | 3.24(3H, s), 4.83(2H, s), 7.12–7.29(2H, m), 7.40–7.46(1H, m), 7.57(1H, dd, J=4.8&8.0 Hz), 8.18(1H, dd, J=1.8&8.0Hz), 8.77(1H, dd, J=1.8&4.8Hz). | 3600–3300, 3080, 2230, 1680, 1670, 1490. |
| E-40 | 3.19(3H, s), 4.01–4.08(4H, m), 4.89(2H, s), 6.29(1H, s), 7.23(1H, br. d, J=8.6Hz), 7.42 (1H, dd, J=4.8&7.8Hz), 7.69–7.74(1H, m), 8.05(1H, br. d, J=2.4Hz), 8.07–8.13(1H, m), 8.55(1H, dd, J=1.8&4.8Hz). | |
| E-41 | 3.87–4.02(4H, m), 6.11(1H, s), 7.15(1H, d, J=8.6Hz), 7.53(1H, dd, J=4.8&8.0Hz), 7.61–7.66(1H, m), 7.71(1H, dd, J=2.6&8.6Hz), 8.10(1H, dd, J=1.4&8.0Hz), 8.69(1H, dd, J=1.4&4.8Hz), 12.22(1H, s). | 3600–3300, 2890, 1640. |
| E-42 | 3.22(3H, s), 4.00–4.10(4H, m), 4.87(2H, s), 6.36(1H, s), 7.46(1H, dd, J=4.8&8.0Hz), 7.48(1H, s), 7.75(1H, s), 8.11–8.16(1H, m), 8.54(1H, dd, J=1.6&4.8Hz). | 2950, 2900, 2230, 1730, 1680, 1480. |

*measured with DMSO-d$_6$

TABLE 21b

| Cpd. No. | $^1$H-NMR (CDCl$_3$; TMS internal standard, ppm) | IR (KBr; cm$^{-1}$) |
|---|---|---|
| E-43 | 7.45(1H, s), 7.68(1H, s), 7.77(1H, dd, J=4.8&8.0Hz), 8.43(1H, dd, J=1.6&8.0Hz), 8.94 (1H, dd, J=1.6&4.8Hz), 10.17(1H, s), 11.77(1H, s). | 3600–3300, 2240, 1700, 1630. |
| E-44 | 3.21(3H, s), 4.88(2H, s), 7.53(1H, s), 7.58–7.65(1H, m), 7.80(1H, s), 8.37(1H, dd, J=1.6&8.0Hz), 8.74(1H, dd, J=1.6&4.8Hz), 10.43(1H, d, J=0.6Hz). | 3600–3100, 2900, 2240, 1700, 1680. |
| E-45 | *2.85(3H, s), 4.88(2H, s), 7.53(1H, dd, J=5.0&7.8Hz), 7.56(1H, s), 8.00(1H, dd, J=1.6&7.8Hz), 8.05(1H, s), 8.17(1H, s), 8.55–8.58(2H, m). | 3600–3300, 3300–2600, 2240, 1480, 1370. |
| E-46 | *3.11(3H, s), 5.14(2H, s), 7.81(1H, dd, J=4.8&8.0Hz), 7.94(1H, s), 8.61 (1H, dd, J=1.4&8.0Hz), 8.89(1H, dd, J=1.4&4.8Hz). | 3600–3300, 3100, 3050, 2240, 1690, 1380. |
| E-47 | 3.23(3H, s), 4.01–4.09(4H, m), 4.94(2H, s), 6.30(1H, s), 7.31(1H, s), 7.45(1H, dd, J=4.8&8.0Hz), 8.01(1H, s), 8.12(1H, dd, J=1.8&8.0Hz), 8.54(1H, dd, J=1.8&4.8Hz). | |
| E-48 | *7.19(1H, s), 7.79(1H, dd, J=4.8&7.6Hz), 8.20(1H, s), 8.31(1H, dd, J=1.8&7.6Hz), 8.82 (1H, dd, J=1.8&4.8Hz), 10.16(1H, s), 11.80–12.10(1H, br. s). | 3600–3300, 3200–3000, 2230, 1690. 1630, 1460. |
| E-49 | 3.88–4.03(4H, m), 6.15(1H, s), 7.21(1H, s), 7.56(1H, dd, J=4.8&8.0Hz), 7.79(1H, s), 8.09–8.14(1H, m), 8.69(1H, dd, J=1.4&4.8Hz), 12.51(1H, br. s). | |

*measured with DMSO-d$_6$

TABLE 22

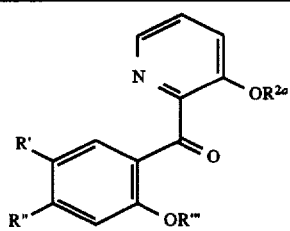

| Cpd. No. | R' | R" | R'" | R$^2$ | Formula | m.p. (°C.) physical property |
|---|---|---|---|---|---|---|
| F-1 | Cl | F | MOM | H | C$_{14}$H$_{11}$ClFNO$_4$ | oil |
| F-2 | Cl | F | MOM | MOM | C$_{16}$H$_{15}$ClFNO$_5$ | oil |
| F-3 | Cl | Me$_2$N | MOM | MOM | C$_{18}$H$_{21}$ClN$_2$O$_5$ | oil |

TABLE 22-continued

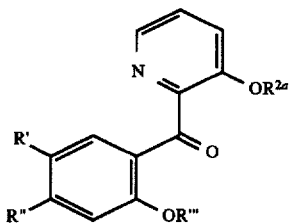

| Cpd. No. | R' | R" | R'" | R² | Formula | m.p. (°C.) physical property |
|---|---|---|---|---|---|---|
| F-4 | Cl | MeNH | MOM | MOM | $C_{17}H_{19}ClN_2O_5$ | 125–126 |
| F-5 | Cl | MeS | MOM | MOM | $C_{17}H_{18}ClNO_5S$ | 72–73 |
| F-6 | Cl | EtO | MOM | MOM | $C_{18}H_{20}ClNO_5$ | 93.5–94 |
| F-7 | Cl | BnNH | MOM | MOM | $C_{23}H_{23}ClN_2O_5$ | oil |
| F-8 | Cl | CN | MOM | MOM | $C_{17}H_{15}ClN_2O_5$ | oil |
| F-9 | Br | F | MOM | Bn | $C_{21}H_{17}BrFNO_4$ | oil |
| F-10 | F | F | MOM | MOM | $C_{16}H_{15}F_2NO_5$ | 91–92 |
| F-11 | CN | F | MOM | SEM | $C_{21}H_{25}FN_2O_5Si$ | oil |
| F-12 | CN | CN | MOM | SEM | $C_{22}H_{25}N_3O_5Si$ | oil |

MOM: $CH_2OCH_3$, Bn: benzyl

TABLE 23

| Cpd. No. | ¹H-NMR (CDCl₃; TMS internal standard, ppm) |
|---|---|
| F-1 | 3.39(3H, s), 5.05(2H, s), 7.13(1H, d, J=10.6Hz), 7.42(2H, d, J=3.0Hz), 7.49(1H, d, J=8.0Hz), 8.21(1H, t, J=3.0Hz), 11.55(1H, s). |
| F-2 | 3.21(3H, s), 4.82(2H, s), 5.21(2H, s), 6.99(1H, d, J=10.6Hz), 7.34(1H, dd, J=4.6&8.6Hz), 7.59(1H, dd, J=1.2&7.86(1H, d, J=8.6Hz), 8.25(1H, dd, J=1.2&4.6Hz). |
| F-3 | 2.92(6H, s), 3.22(3H, s), 3.44(3H, s), 4.79(2H, s), 5.19(2H, s), 6.68(1H, s), 7.29(1H, dd, J=4.6&8.4Hz), 7.55(1H, dd, J=1.2& 8.4Hz), 7.86(1H, s), 8.24(1H, dd, J=1.2&4.6Hz). |
| F-4 | 2.94(3H, d, J=5.2Hz), 3.20(3H, s), 3.42(3H, s), 4.93(1H, br. d), 5.16(2H, s), 6.26(1H, s), 7.25(1H, dd, J=4.6&8.4Hz), 7.51(1H, dd, J=1.2&8.4Hz), 7.90(1H, s), 8.23(1H, dd, J=1.2&2.4Hz). |
| F-5 | 2.48(3H, s), 3.23(3H, s), 3.45(3H, s), 4.82(2H, s), 5.20(2H, s), 6.91(1H, s), 7.32(1H, dd, J=4.6&8.6Hz), 7.57(1H, dd, J=1.2& 8.6Hz), 7.80(1H, s), 8.25(1H, dd, J=1.2&4.6Hz). |
| F-6 | 1.49(3H, t, J=7.0Hz), 3.22(3H, s), 3.43(3H, s), 4.13(2H, q, J=7.0Hz), 4.79(2H, s), 5.18(2H, s), 6.69(1H, s), 7.29(1H, dd, J=4.8& 8.4Hz), 7.55(1H, dd, J=1.4&8.4Hz), 7.90(1H, s), 8.24(1H, dd, J=1.4&8.4Hz). |
| F-7 | 3.12(3H, s), 3.40(3H, s), 4.42(2H, d, J=4.3Hz), 4.65(2H, s), 5.15(2H, s), 5.28(1H, br. t), 6.32(1H, s), 7.21–7.36(6H, m), 7.50 (1H, dd, J=1.4&8.4Hz), 7.91(1H, s), 8.21(1H, dd, J=1.4&4.6Hz). |
| F-8 | 3.23(3H, s), 3.49(3H, s), 4.89(2H, s), 5.26(2H, s), 7.36–7.43(1H, m), 7.47(1H, s), 7.61–7.66(1H, m), 7.73(1H, s), 8.23–8.26 (1H, m). |
| F-9 | 3.17(3H, s), 4.78(2H, s), 5.11(2H, s), 6.90(1H, d, J=10.2Hz), 7.21–7.38(7H, m), 7.94(1H, d, J=8.0Hz), 8.23(1H, dd, J=2.2&3.8Hz). |
| F-10 | 3.21(3H, s), 3.45(3H, s), 4.77(2H, s), 5.21(2H, s), 7.01(1H, dd, J=6.4&11.8Hz), 7.34(1H, dd, J=4.6&8.6Hz), 7.58(1H, dd, J=1.2& 8.6Hz), 7.67(1H, dd, J=9.2&10.4Hz), 8.25(1H, dd, J=1.2&4.6Hz). |
| F-11 | 0.00(9H, s), 0.89–0.97(2H, m), 3.23(3H, s), 3.70–3.78(2H, m), 4.95(2H, s), 5.27(2H, s), 7.01(1H, d, J=10.8Hz), 7.37(1H, dd, J=4.6& 8.6Hz), 7.64(1H, dd, J=1.2&8.6Hz), 7.99(1H, d, J=7.4Hz), 8.23(1H, dd, J=1.2&4.6Hz). |
| F-12 | 0.01(9H, s), 0.90–0.98(2H, m), 3.26(3H, s), 3.74–3.82(2H, m), 5.02(2H, s), 5.32(2H, s), 7.41(1H, dd, J=4.4&8.6Hz), 7.57(1H, s), 7.68(1H, dd, J=1.4&8.6Hz), 7.93(1H, s), 8.20(1H, dd, J=1.4&4.4Hz). |

EXAMPLE 1 (Production of Compounds 40 and 41)

In ethanol (50 ml) were dissolved 2-(4-chloro-5-fluoro-2-hydroxybenzoyl)-3-hydroxypyridine (2.81 g) and triethylamine (20 ml). To the solution was added O-t-5 butylhydroxylamine hydrochloride (1.63 g). The mixture was heated for 5 hours under reflux. The solvent was distilled off under reduced pressure. To the residue were added chloroform and water for extraction. The extract was dried (anhydrous magnesium sulfate), then the solvent was distilled off under reduced pressure. The residue was purified by means of a silica gel column chromatography, eluting with ethyl acetate/hexane to give (Z)-2-(4-chloro-5-fluoro-2-hydroxybenzoyl)-3-hydroxypyridine O-t-butyloxime (2.35 g) and (E)-2-(4-chloro-5-fluoro-2-hydroxybenzoyl)-3-hydroxypyridine O-t-butyloxime (1.03 g) (Compounds 40 and 41). By substantially the same procedure as described above, Compounds 1 to 7, 9 to 10, 12 to 14, 16 to 30, 36 to 39, 42 to 44, 60 to 62, 68, 70, 83 to 86, 106 to 114, 116, 128, 130, 131, 148 to 151, 153 and 154, 157 to 164, 174, 178, 179 and 194 were produced.

Physical properties and spectrum data of these compounds and compounds obtained in the following Examples are shown in Table 24 to Table 59.

EXAMPLE 2 (Production of Compounds 34 and 35)

A mixture of 2-bromo-4,5-difluorophenol (7.27 g) and 2-methoxypropene (10 ml) was stirred for one hour at room temperature, followed by adding diethyl ether (75 ml) and cooling to −78° C. To the mixture was added dropwise, under argon atmosphere, a 1.6M solution of n-butyl lithium hexane solution (25 ml), followed by stirring for one hour. To the reaction mixture was then added dropwise 2-cyano- 3-trimethylsilyloxypyridine (7.01 g). The cooling bath was removed, and the mixture was stirred for 3 hours while warming up to room temperature. To the reaction mixture was added ethanol (10 ml) to quench the reaction. The solvent was distilled off under reduced pressure. To the residue were added triethylamine (20 ml), O-t-butylhydroxylamine hydrochloride (3.06 g) and ethanol (50 ml). The mixture was heated for 5 hours under reflux. The solvent was distilled off. To the residue were added chloroform and water for extraction. The organic layer was dried (anhydrous magnesium sulfate), and the solvent was distilled off under reduced pressure. The residue was purified by means of a silica gel column chromatography (eluted with ethyl acetate/hexane) to give (Z)-2-(4,5-difluoro-2-hydroxybenzoyl)-3-hydroxypyridine O-t-butyloxime (5.19 g) and (E)-2-(4,5-difluoro-2-hydroxybenzoyl)-3-hydroxypyridine O-t-butyloxime (1.49 g) (Compounds 34 and 35).

By substantially the same procedure as described above, Compounds 8, 11, 15, 32 to 33 and 36 to 37 were produced.

EXAMPLE 3 (Production of Compound 56)

To a solution of (Z)-2-(4-chloro-5-fluoro-2-hydroxybenzoyl)-3-hydroxypyridine O-t-butyloxime (0.82 g) in chloroform (30 ml) was added 70% m-chloroperbenzoic acid (1.01 g) at 0° C. The mixture was warmed up to room temperature and stirred for 5 hours. To the reaction mixture was added an aqueous solution of sodium hydrogensulfite to quench the reaction. The reaction mixture was subjected to extraction with chloroform. The organic layer was dried (anhydrous magnesium sulfate). The solvent was distilled off under reduced pressure. The residue was purified by means of a silica gel column chromatography to give (Z)-2-(4-chloro-5-fluoro-2-hydroxybenzoyl)-3-hydroxypyridine N-oxide O-t-butyloxime (0.79 g) (Compound 56).

By substantially the same procedure as described above, Compounds 48 to 55, 57 to 59, 63 to 67, 69, 89 to 104, 118 to 127, 129, 132, 133, 169, 171 to 173, 175, 177, 193 and 195 were produced.

EXAMPLE 4 (Production of Compound 45)

(Z)-2-(5-bromo-2-hydroxybenzoyl)-3-hydroxypyridine O-t-butyloxime (0.86 g) was dissolved in ethanol (20 ml), to which was added 2N-HCl (1.4 ml). The mixture was stirred for one hour at room temperature, then the solvent was distilled off under reduced pressure. The residue was crystallized with ethyl acetate to give (Z)-2-(5-bromo-2-hydroxybenzoyl)-3-hydroxypyridine O-t-butyloxime hydrochloride (0.31 g) (Compound 45).

EXAMPLE 5 (Production of Compound 46)

Pyridine (0.30 ml) was dissolved in chloroform (10 ml). To the solution was added acetic anhydride (0.18 ml), and the mixture was stirred for 50 minutes. To the reaction mixture was then added (Z)-2-(2-hydroxy-5-trifluoromethylbenzoyl)-3-hydroxypyridine O-t-butyloxime (0.21 g), and the mixture was stirred for 3 hours at room temperature. To the reaction mixture were added water and chloroform for extraction. The organic layer was dried (anhydrous magnesium sulfate), followed by distilling off the solvent under reduced pressure. The residue was purified by means of a silica gel column chromatography (eluted with ethyl acetate/hexane, then with ethyl acetate/THF) to give (Z)-3-acetoxy-2-(2-hydroxy-5-trifluoromethylbenzoyl) pyridine O-t-butyloxime (0.20 g) (Compound 46).

By substantially the same procedure as described above, Compound 168 was produced.

EXAMPLE 6 (Production of Compound 47)

(Z)-2-(5-bromo-2-hydroxybenzoyl)-3-hydroxypyridine O-t-butyloxime (1.66 g) was dissolved in pyridine (10 ml). To the solution was added sulfur pyridinium trioxide (1.02 g), and the mixture was stirred for 3 hours at room temperature. Insolubles were filtered off by using a small amount of silica gel. From the filtrate, the solvent was distilled off under reduced pressure. The residue was crystallized from ethyl acetate to give (Z)-2-(5-bromo-2-hydroxybenzoyl)-3-hydroxypyridine O-t-butyloxime 3-sulfuric acid pyridinium salt (1.14 g) (Compound 47).

EXAMPLE 7 (Production of Compound 31)

2-(2-Hydroxybenzoyl)-3-hydroxypyridine (9.01 g) was dissolved in acetic acid (50 ml), to which were added dropwise at 0° C. sulfuric acid (20 ml) and nitric acid (4.5 ml) successively. The mixture was stirred for one hour at room temperature, followed by neutralization with an aqueous solution of sodium hydroxide. Thus neutralized solution was subjected to extraction with ethyl acetate. The organic layer was dried (anhydrous magnesium sulfate), then the solvent was distilled off under reduced pressure. To the residue were added triethylamine (30 ml), O-t-butyl hydroxylamine hydrochloride (5.00 g) and ethanol (60 ml). The mixture was refluxed for 5 hours, then the solvent was distilled off. To the residue were added chloroform and water for extraction. The organic layer was dried (anhydrous magnesium sulfate), then the solvent was distilled off under reduced pressure. The residue was purified by subjecting to a silica gel column chromatography, eluting with ethyl acetate/hexane to give (Z)-2-(2-hydroxy-3-nitrobenzoyl)-3-hydroxypyridine O-t-butyloxime (1.28 g) (Compound 31).

Example 8 (Production of Compound 71)

To a solution of (Z)-2-(5-cyano-2-hydroxybenzoyl)-3-hydroxypyridine O-t-butyloxime (0.98 g) in ethanol (20 ml) were added at 0° C. 6N NaOH (0.15 ml) and 30% aqueous solution of hydrogen peroxide (1.5 ml). The mixture was stirred for 2 hours at temperatures ranging from 50° to 60° C. The reaction mixture was cooled by aeration, which was then neutralized with a saturated aqueous solution of potassium hydrogensulfate, then the solvent was concentrated. The concentrate was subjected to extraction with chloroform and dried (anhydrous magnesium sulfate), followed by distilling off the solvent. The residue was recrystallized from chloroform to give (Z)-2-(5-carbamoyl-2-hydroxybenzoyl)-3-hydroxypyridine O-t-butyloxime (0.42 g) (Compound 71).

Example 9 (Production of Compound 75)

A mixture of 2,4-dibromophenol (5.0 g) and 2-methoxypropene (4 ml) was stirred for one hour at room temperature, to which was added diethyl ether (50 ml). The mixture was cooled to −78° C. under argon atmosphere, to which was added dropwise a 1.6M n-butyl lithium hexane solution (14 ml), followed by stirring for one hour at the same temperature. To the reaction mixture was then added dropwise 2-cyanopyridine (2.1 ml). The cooling bath was removed, and the reaction mixture was stirred for 3 hours while warming up to room temperature. To the reaction mixture was added ethanol (10 ml), followed by stirring for several minutes. Then, the solvent was distilled off under reduced pressure. To the residue were added triethylamine (20 ml), O-t-butylhydroxylamine hydrochloride (2.5 g) and ethanol (50 ml). The mixture was heated for 5 hours under reflux, then the solvent was distilled off. To the residue were added chloroform and water for extraction. The organic layer was dried (anhydrous magnesium sulfate), then the solvent was distilled off under reduced pressure. The residue was purified by subjecting to a silica gel column chromatography, eluting with ethyl acetate/hexane to give (Z)-2-(5-bromo-2-hydroxybenzoyl)pyridine O-t-butyloxime (4.24 g) (Compound 75).

By substantially the same procedure as described above, Compounds 72 to 73, 77 and 82 were produced.

Example 10 (Production of Compound 81)

Employing 3-bromo-2-cyanopyridine (5.88 g) in place of 2-cyanopyridine in the production of Compound 75 in Example 9, substantially the same reaction as in Example 9 was conducted to give (Z)-2-(5-bromo-2-hydroxybenzoyl)-3-bromopyridine O-t-butyloxime (3.74 g) (Compound 81) from 2,4-dibromophenol (8.01 g).

By substantially the same procedure as described above, Compounds 74, 78 to 80 were produced.

EXAMPLE 11 (Production of Compound 87)

2-(2-Hydroxybenzoyl)pyridine (14.1 g) was dissolved in acetic acid (70 ml). To the solution were added dropwise, under ice-cooling, sulfuric acid (15 ml) and nitric acid (10 ml), successively. The mixture was then stirred for 2 hours at room temperature, which was neutralized with an aqueous solution of sodium hydroxide, followed by extraction with ethyl acetate. The organic layer was dried (anhydrous magnesium sulfate), then the solvent was distilled off under reduced pressure. To the residue were added triethylamine (30 ml), O-t-butylhydroxylamine hydrochloride (10.0 g) and ethanol (80 ml). The mixture was heated for 5 hours under reflux, then the solvent was distilled off. To the residue were added chloroform and water for extraction. The organic layer was dried (anhydrous magnesium sulfate), then the solvent was distilled off under reduced pressure. The residue was purified by means of a silica gel column chromatography (eluted with ethyl acetate/hexane) to give (Z)-2-(2-(2-hydroxy-5-nitrobenzoyl)pyridine O-t-butyloxime (6.17 g) (Compound 87).

EXAMPLE 12 (Production of Compound 76)

(Z)-2-(5-bromo-2-hydroxybenzoyl)pyridine O-t-butyloxime (12.7 g) was dissolved in DMF (100 ml). To the solution was added cuprous cyanide (4.64 g), and the mixture was heated, under argon atmosphere, for 3 hours under reflux. To the reaction mixture was added a solution of ethylenediamine (30 ml) in water (20 ml). The mixture was stirred for 30 minutes at room temperature, followed by extraction with ethyl acetate. The organic layer was dried (anhydrous magnesium sulfate), then the solvent was distilled off. The residue was purified by means of a silica gel column chromatography, eluting with ethyl acetate/hexane, to give (Z)-2-(5-cyano-2-hydroxybenzoyl)pyridine O-t-butyloxime (4.31 g) (Compound 76).

EXAMPLE 13 (Production of Compound 88)

A mixture of 2-(5-bromo-2-hydroxybenzoyl)pyridine [produced by oxidation of 5-bromo-2-hydroxy-α-(2-pyridyl)benzyl alcohol obtained in Reference Example 22 with activated manganese dioxide, m.p. 71°–73° C.; 0.80 g], neopentylamine (0.50 g), boron trifluoride diethyl ether (35 ul) and toluene (15 ml) was stirred for 100 minutes at room temperature. The reaction mixture was poured into an aqueous saline solution, followed by extraction with ethyl acetate. The organic layer was washed with a saturated aqueous saline solution, dried (anhydrous sodium sulfate) and concentrated. The concentrate was purified by means of a silica gel column chromatography (eluted with ethyl acetate/hexane) to give (Z)-2-[(5-bromo-2-hydroxy)-α-neopentyliminobenzyl] pyridine (0.53 g) (Compound 88).

EXAMPLE 14 (Production of Compound 105)

Employing 2-(5-bromo-2-hydroxybenzoyl)pyridine N-oxide (0.35 g) in place of 2-(5-bromo-2-hydroxybenzoyl)pyridine in the production of Compound 88 in Example 13, substantially the same reaction as in Example 13 was allowed to proceed, followed by purification by means of a silica gel column chromatography (eluted with ethyl acetate/hexane) to give (Z)-2-[(5-bromo-2-hydroxy)-α-neopentyliminobenzyl]pyridine N-oxide (0.25 g) (Compound 105).

EXAMPLE 15 (Production of Compound 115)

In methanol (50 ml) was dissolved 2-[2-hydroxy-5-(2-trimethylsilylethynyl)benzoyl]-3-hydroxypyridine O-t-butyl oxime (0.70 g). To the solution was added potassium carbonate (0.1 g) at room temperature, followed by heating for 3 hours under reflux. The reaction mixture was cooled by aeration, then the solvent was distilled off. To the residue were added chloroform and water for extraction. The organic layer was dried (anhydrous magnesium sulfate), then the solvent was distilled off under reduced pressure. The residue was purified by means of a silica gel column chromatography (eluted with ethyl acetate/hexane) to give (Z)-2-(5-ethynyl-2-hydroxybenzoyl)-3-hydroxypyridine O-t-butyloxime (0.21 g) (Compound 115).

EXAMPLE 16 (Production of Compound 117)

In ethanol (50 ml) were dissolved 2-[2-methoxymethoxy-5-(1,3-dioxolan-2-yl)benzoyl]-3-semoxypyridine (2.66 g) and pyrrolidine (5 ml). To the solution was added O-t-butylhydroxylamine hydrochloride (1.28 g), and the mixture was heated for 5 hours under reflux. The reaction mixture was cooled by aeration, then the solvent was distilled off, followed by addition of chloroform and water for extraction. The organic layer was dried (anhydrous magnesium sulfate), then the solvent was distilled off under reduced pressure. To the residue were added acetone (100 ml) and 1N-sulfuric acid (10 ml). The mixture was stirred for 5 hours at temperatures ranging from 50° to 60° C. The reaction mixture was cooled by aeration, then neutralized with a saturated aqueous solution of sodium hydrogencarbonate, followed by extraction with ethyl acetate. The organic layer was dried (anhydrous magnesium sulfate), then the solvent was distilled off under reduced pressure. The residue was purified by means of a silica gel column chromatography (eluted with ethyl acetate/hexane) to give (Z)-2-(5-formyl-2-hydroxybenzoyl)-3-hydroxypyridine (0.83 g) (Compound 117).

EXAMPLE 17 (Production of Compound 134)

A solution of 2-(5-bromo-2-hydroxybenzoyl)-3-(1,3-dioxolan-2-yl)pyridine (2.92 g), O-t-butyl-hydroxylamine hydrochloride (2.09 g) and pyrrolidine (1.78 g) in n-propanol (40 ml) was heated for 2 hours under reflux. The reaction mixture was concentrated, to which was added water, followed by subjecting the mixture to extraction with ethyl acetate. The extract solution was washed with a saturated aqueous saline solution, dried (anhydrous sodium sulfate), and concentrated. The concentrate was purified by means of a silica gel column chromatography (eluent: ethyl acetate/hexane) to give (Z)-2-(5-bromo-2-hydroxybenzoyl)-3-(1,3-dioxolan-2-yl)pyridine O-t-butyloxime (2.81 g) (Compound 134).

By substantially the same procedure as above, Compounds 146, 187, 191, 198 and 204 were produced.

EXAMPLE 18 (Production of Compound 135)

A mixture of (Z)-2-(5-bromo-2-hydroxybenzoyl)-3-(1,3-dioxolan-2-yl)pyridine O-t-butyloxime (2.81 g), p-toluenesulfonic acid monohydrate (1.27 g), acetone (70 ml) and water (30 ml) was heated for 16 hours under reflux. The reaction mixture was concentrated, to which was added water, followed by extraction with ethyl acetate. The extract solution was washed with a saturated aqueous saline solution, dried (anhydrous sodium sulfate), and concentrated. The concentrate was purified by means of a silica gel column chromatography (eluent: ethyl acetate/hexane) to give (Z)-2-(5-bromo-2-hydroxybenzoyl)-3-formylpyridine O-t-butyloxime (2.33 g) (Compound 135).

Likewise, Compounds 199 and 205 were produced.

EXAMPLE 19 (Production of Compound 136)

To a solution of (Z)-2-(5-bromo-2-hydroxybenzoyl)-3-formylpyridine O-t-butyloxime (340 mg) in methanol (3 ml) was added at 0° C. sodium borohydride (17 mg). The mixture was stirred for 20 minutes at the same temperature. The reaction mixture was concentrated, to which was added water, followed by neutralization with an aqueous solution of potassium hydrogensulfate. The solution neutralized was subjected to extraction with ethyl acetate. The extract solution was washed with a saturated aqueous saline solution, dried (anhydrous sodium sulfate), and concentrated. The concentrate was purified by means of a silica gel column chromatography (eluent: ethyl acetate/hexane) to give (Z)-2-(5-bromo-2-hydroxybenzoyl)-3-hydroxymethylpyridine O-t-butyloxime (292 mg) (Compound 136).

By substantially the same procedure as described above, Compound 188 was produced.

EXAMPLE 20 (Production of Compound 137)

To a solution of diethylaminosulfatrifluoride (416 mg) in dichloromethane (12 ml) was added, at −78° C. under argon atmosphere, a solution of (Z)-2-(5-bromo-2-hydroxybenzoyl)-3-hydroxymethylpyridine O-t-butyloxime (653 mg) in dichloromethane (12 ml), during 10 minutes. The mixture was stirred for 20 minutes while warming up to room temperature, then the reaction mixture was poured into an aqueous saline solution, followed by extraction with ethyl acetate. The extract solution was washed with a saturated aqueous saline solution, dried (anhydrous sodium sulfate), and concentrated. The concentrate was purified by means of a silica gel column chromatography (eluent: ethyl acetate/hexane) to give (Z)-2-(5-bromo-2-hydroxybenzoyl)-3-fluoromethylpyridine O-t-butyloxime (150 mg) (Compound 137).

EXAMPLE 21 (Production of Compound 138)

To a solution of (Z)-2-(5-bromo-2-hydroxybenzoyl)-3-formylpyridine O-t-butyloxime (500 mg) in acetone (4 ml) was added, at room temperature, Jones reagent (1 ml), and the mixture was stirred for 30 minutes. To the reaction mixture was added diethyl ether. Insolubles then formed were filtered off. To the filtrate was added a small volume of isopropyl alcohol, and the mixture was concentrated. The concentrate was purified by means of a silica gel column chromatography (eluent: diethyl ether) to give (Z)-2-(5-bromo-2-hydroxybenzoyl)nicotinic acid O-t-butyloxime (240 mg (Compound 138).

EXAMPLE 22 (Compound 139)

To a solution of (Z)-2-(5-bromo-2-hydroxybenzoyl)nicotinic acid O-t-butyloxime (540 mg) and DMF (0.02 ml) in THF (6 ml) was added, at room temperature, oxalyl chloride (0.33 ml). The mixture was stirred for 2 hours at the same temperature and then concentrated, which was dissolved in THF (2 ml). To the solution was added ethanol (8 ml) at room temperature. The mixture was stirred for 1.5 hour at the same temperature and concentrated. To the concentrate was added water, followed by extraction with ethyl acetate. The extract solution was washed with a saturated aqueous saline solution, dried (anhydrous sodium sulfate), and concentrated. The concentrate was purified by means of a silica gel column chromatography (eluent: ethyl acetate/hexane) to give ethyl(Z)-2-(5-bromo-2-hydroxybenzoyl)nicotinate O-t-butyloxime (403 mg) (Compound 139).

EXAMPLE 23 (Production of Compound 140)

Sixty % sodium hydride (170 mg) was washed with hexane, to which was added, at room temperature under argon atmosphere, DMSO (3.0 ml). This mixture was stirred for 30 minutes at 80° C., which was then stirred for 10 minutes while cooling to room temperature. To the reaction mixture was added, at room temperature, a solution of methyltriphenyl phosphonium bromide (1.52 g) in DMSO (5.0 ml). The mixture was stirred for 20 minutes at the same temperature, to which was added a solution of (Z)-2-(5-bromo-2-hydroxybenzoyl)-3-formylpyridine O-t-butyloxime (400 mg) in DMSO (3.0 ml). The mixture was stirred for further 30 minutes at room temperature, which was poured into water and neutralized with an aqueous solution of potassium hydrogensulfate, followed by extraction with ethyl acetate. The extract solution was washed with water, dried (anhydrous sodium sulfate), and concentrated. The concentrate was purified by means of a silica gel column chromatography (eluent: ethyl acetate/hexane) to give (Z)-2-(5-bromo-2-hydroxybenzoyl)-3-ethenylpyridine O-t-butyloxime (267 mg) (Compound 140).

EXAMPLE 24 (Production of Compound 141)

To a solution of diethylaminosulfatrifluoride (1.18 g) in dichloromethane (10 ml) was added, at room temperature, a solution of (Z)-2-(5-bromo-2-hydroxybenzoyl)-3-formylpyridine O-t-butyloxime (1.10 g) in dichloromethane (5.0 ml). The mixture was stirred for 1.5 hour at the same temperature, which was poured into water, followed by extraction with ethyl acetate. The extract solution was washed with a saturated aqueous saline solution, dried (anhydrous sodium sulfate), and concentrated. The concentrate was purified by means of a silica gel column chromatography (eluent: ethyl acetate/hexane) to give (Z)-2-(5-bromo-2-hydroxybenzoyl)-3-difluoromethylpyridine O-t-butyloxime (258 mg) (Compound 141).

EXAMPLE 25 (Production of Compound 142)

A solution of (Z)-2-(5-bromo-2-hydroxybenzoyl)-3-formylpyridine O-t-butyloxime (300 mg), hydroxylamine hydrochloride (66 mg) and triethylamine (177 mg) in ethanol (5 ml) was heated for 2.5 hours under reflux. The reaction mixture was concentrated, to which was added water, followed by extraction with ethyl acetate. The extract solution was washed with a saturated aqueous saline solution, dried (anhydrous sodium sulfate), and concentrated. The concentrate was purified by means of a silica gel column chromatography (eluent: ethyl acetate/hexane) to give 2-(5-bromo-2-hydroxybenzoyl)-3hydroxylminomethylpyridine (Z)-O-t-butyloxime (215 mg) (Compound 142).

Likewise, Compound 200 was produced.

EXAMPLE 26 (Production of Compound 143)

A mixture of 2-(5-bromo-2-hydroxybenzoyl)-3-hydroxylminomethylpyridine (Z)-O-t-butyloxime (702 mg) and acetic anhydride (7 m) was heated for 18 hours under reflux. The reaction mixture was concentrated, and the concentrate was purified by means of a silica gel column chromatography (eluent: ethyl acetate/hexane) to give (Z)-2-(2-acetoxy-5-bromobenzoyl)-3-cyanopyridine O-t-butyloxime (640 mg) as an oily substance. To a solution of this oily substance (640 mg) in ethanol (6 ml) was added, at room temperature, a solution of sodium carbonate (814 mg) in water (3 ml). The mixture was stirred for 8 hours at the same temperature, which was neutralized with an aqueous solution of potassium hydrogensulfate, followed by extraction with ethyl acetate. The extract solution was washed with a saturated aqueous saline solution, dried (anhydrous sodium sulfate), and concentrated. The concentrate was purified by means of silica gel column chromatography (eluent: ethyl acetate/hexane) to give (Z)-2-(5-bromo-2-hydroxybenzoyl)-3-cyanopyridine O-t-butyloxime (540 mg) (Compound 143).

Likewise, Compound 201 was produced.

In accordance with Example 25 and Example 26, Compounds 156, 189, 190 and 206 were produced.

EXAMPLE 27 (Production of Compound 144)

A mixture of (Z)-2-(5-bromo-2-hydroxybenzoyl)-3-cyanopyridine O-t-butyloxime (630 mg), 2N sodium hydroxide (7 ml), a 30% aqueous solution of hydrogen peroxide (7 peroxide (7 ml) and THF (28 ml) was stirred for 14 hours at room temperature. The reaction mixture was neutralized with hydrochloric acid, followed by extraction with ethyl acetate. The extract solution was washed with a saturated aqueous saline solution, dried (anhydrous sodium sulfate), and concentrated. The concentrate was purified by means of a silica gel column chromatography to give (Z)-2-(5-bromo-2-hydroxybenzoyl)-3-carbamoylpyridine O-t-butyloxime (392 mg) (Compound 144).

EXAMPLE 28 (Production of Compound 145)

A solution of (Z)-2-(5-bromo-2-hydroxybenzoyl)-3-cyanopyridine O-t-butyloxime (350 mg) and 50% m-chloroperbenzoic acid (710 mg) in chloroform (5 ml) was stirred for 6 hours at 50° C. The reaction mixture was cooled by aeration, which was poured into an aqueous solution of sodium sulfite. The mixture was stirred and subjected to extraction with chloroform. The extract solution was washed successively with a saturated aqueous solution of sodium hydrogencarbonate and a saturated aqueous saline solution, dried (anhydrous sodium sulfate), and concentrated. The concentrate was purified by means of a silica gel column chromatography (eluent: ethyl acetate/hexane) to give (Z)-2-(5-bromo-2-hydroxybenzoyl)-3-cyanopyridine N-oxide O-t-butyloxime (120 mg) (Compound 145).

EXAMPLE 29 (Production of Compound 152)

A mixture of 2-(5-chloro-2-hydroxybenzoyl)-3-cyanopyridine (217 mg), O-t-butylhydroxylamine hydrochloride (158 mg), pyrrolidine (149 mg) and n-propanol (4.0 ml) was heated for 30 minutes under reflux. The reaction mixture was poured into a saturated aqueous saline solution, which was subjected to extraction with ethyl acetate. The extract solution was washed successively with an aqueous solution of potassium hydrogensulfate and a saturated aqueous saline solution, dried (anhydrous sodium sulfate), and concentrated. The concentrate was purified by means of a silica gel column chromatography (eluent: ethyl acetate/ hexane) to give (Z)-2-(5-chloro-2-hydroxybenzoyl)-3-carbamoylpyridine O-t-butyloxime (251 mg) (Compound 152).

EXAMPLE 30 (production of Compound 155)

A solution of 2-(5-chloro-4-fluoro-2-hydroxybenzoyl)-3-(1,3-dioxolan-2-yl)pyridine (1.45 g), O-t-butylhydroxylamine hydrochloride (1.69 g) and pyrrolidine (9.56 g) in n-propanol (20 ml) was heated for 1.5 hour under reflux. The reaction mixture was concentrated, to which was added water, followed by extraction with ethyl acetate. The extract solution was washed with a saturated aqueous saline solution, dried (anhydrous sodium sulfate), and concentrated. The concentrate was purified by means of a silica gel column chromatography (eluent: ethyl acetate/hexane) to give a mixture (540 mg) of (Z)-2-(5-chloro-4-fluoro-2-hydroxybenzoyl)-3-(1,3-dioxolan-2-yl)pyridine O-t-butyloxime and (Z)-2-[5-chloro-2-hydroxy-4-(pyrrolidin-1-yl)benzoyl]-3-(1,3-dioxolan-2-yl)pyridine O-t-butyloxime (about 2:1). A mixture of this mixture (470 mg), p-toluenesulfonic acid monohydrate (162 mg), acetone (9.0 ml) and water (3.5 ml) was heated for 14 hours under reflux. The reaction mixture was concentrated, to which was added water, followed by extraction with ethyl acetate. The extract solution was washed with a saturated aqueous saline solution, dried (anhydrous sodium sulfate), and concentrated to leave an oily substance. This oily substance was dissolved in chloroform (2.0 ml), to which was added, at room temperature, 50% m-chloroperbenzoic acid (75 mg). The mixture was stirred for 8 minutes at the same temperature, which was then poured into an aqueous solution of sodium sulfite, followed by extraction with ethyl acetate. The extract solution was washed with a saturated aqueous saline solution, dried (anhydrous sodium sulfate), and concentrated. The concentrate was purified by means of a silica gel column chromatography (eluent: ethyl acetate/hexane) to give (Z)-2-(5-chloro-4-fluoro-2-hydroxybenzoyl)-3-formylpyridine O-t-butyloxime (230 mg) (Compound 155).

EXAMPLE 31 (Production of Compounds 165, 166)

A mixture of 2-(5-chloro-2-hydroxy-4-methylthiobenzoyl)-3-hydroxypyridine O-t-butyloxime (0.51 g; E/Z=1:1.4), sodium metaperiodate (0.36 g), water (30 ml) and methanol (50 ml) was stirred for 8 hours at 50° C. The reaction mixture was cooled by aeration, which was subjected to extraction with ethyl acetate. The organic layer was washed with water and a saturated aqueous saline solution, successively, which was dried (anhydrous magnesium sulfate), followed by distilling off the solvent under reduced pressure. The residue was purified by means of a silica gel column chromatography (eluted with ethyl acetate/hexane) to give 2-(5-chloro-2-hydroxy-4-methylsulfinylbenzoyl)-3-hydroxypyridine O-t-butyloxime (Z compound; 0.17 g, E compound; 0.18 g) (Compounds 165, 166).

EXAMPLE 32 (Production of Compound 167)

A mixture of 2-(5-chloro-2-hydroxy-4-methylthiobenzoyl)-3-hydroxypyridine O-t-butyloxime (1.82 g; E/Z=1:1.4), 70% m-chloroperbenzoic acid (10.08 g) and chloroform (50 ml) was stirred for 8 hours at room temperature. To the reaction mixture was added an aqueous solution of sodium hydrogensulfite to suspend the reaction, which was subjected to extraction with ethyl acetate. The organic layer was washed with a saturated sodium hydrogencarbonate, water and saturated aqueous saline solution, successively, which was dried (anhydrous magnesium sulfate), followed by distilling off the solvent under reduced pressure. The residue was recrystallized from ethyl acetate to give 2-(5-chloro-2-hydroxy-4-methylsulfonylbenzoyl)-3-hydroxypyridine N-oxide O-t-butyloxime (1.54 g; E/Z=1/1) (Compound 167).

EXAMPLE 33 (Production of Compound 170)

Using pivaloyl chloride in place of anhydrous acetic acid in Example 5, substantially the same reaction was conducted to give (Z)-2-(5-bromo-4-fluoro-2-hydroxybenzoyl)-3-pivaloyloxypyridine O-t-butyloxime (Compound 170).

EXAMPLE 34 (Compound 192)

A mixture of 2-(5-bromo-4-fluoro-2-methoxymethoxybenzoyl)-3-benzyloxypyridine (2.46 g), conc. hydrochloric acid (0.5 ml) and methanol (50 ml) was refluxed for 5 hours. The reaction mixture was cooled by aeration, followed by extraction with ethyl acetate. The organic layer was washed with water and a saturated aqueous saline solution, successively, which was dried (anhydrous magnesium sulfate), followed by distilling off the solvent under reduced pressure. The residue was subjected to reflux together with O-t-butyl hydroxylamine hydrochloride (1.23 g), triethylamine (10 ml) and ethanol (50 ml). The reaction mixture was cooled by aeration, followed by extraction with ethyl acetate. The organic layer was washed with water and a saturated aqueous saline solution, successively, which was dried (anhydrous magnesium sulfate). The solvent was distilled off under reduced pressure, and the residue was purified by means of a silica gel column chromatography (eluted with ethyl acetate/hexane) to give 3-benzyloxy-2-(5-bromo-4-fluoro-2-hydroxybenzoyl)pyridine O-t-butyloxime (1.98 g; E/Z=3/1) (Compound 192). The spectrum data are shown as follows:

$^1$H-NMR(CDCl$_3$): δ1.28 & 1.31 (combinedly 9H,s), 5.10 & 5.15 (combinedly 2H,s), 6.76(1H,d,J=10.0 Hz), 6.77–6.84 & 7.17–7.38 (combinedly 9H,m), 8.19 & 8.33–8.36 (combinedly 1H, each dd(J=1.6 & 4.2 Hz),m), 10.27 & 11.60 (combinedly 1H,s).

EXAMPLE 35 (Production of Compound 176)

A mixture of 2-(4,5-difluoro-2-methoxymethoxybenzoyl)-3-methoxymethoxy pyridine (7.18 g), potassium cyanide (4.47 g) and DMSO (100 ml) was stirred at 34°–40° C. overnight. To the reaction mixture were added ethyl acetate and water for extraction. The organic layer was washed with water and a saturated aqueous saline solution, successively, which was then dried (anhydrous magnesium sulfate), followed by distilling off the solvent under reduced. The residue was purified by means of a silica gel column chromatography (eluted with ethyl acetate/hexane) to give a mixture (7.05 g) of 2-(4-cyano-5-fluoro-2-methoxymethoxybenzoyl)-3-methoxymethoxypyridine and the starting compound (5:1). To this mixture (6.98 g) were added methanol (100 ml) and conc. hydrochloric acid (5 ml), which was stirred at 60° C. overnight. The reaction mixture was cooled by aeration, which was neutralized with a saturated aqueous solution of sodium hydrogencarbonate, followed by extraction with chloroform. The organic solvent was dried (anhydrous magnesium sulfate). The solvent was distilled under reduced pressure. The residue was washed with isopropylether to give 2-(4-cyano-5-fluoro-2-hydroxybenzoyl)-3-hydroxypyridine as crude crystals (4.59 g). This crude crystalline product was, without further purification subjected to reaction, in accordance with the method in Example 1, to lead to its oxime to give (Z)-2-(4-cyano-5-fluoro-2-hydroxybenzoyl)-3-hydroxyoyridine O-t-butyloxime (2.46 g) (Compound 176).

EXAMPLE 36 (Production of Compound 180)

Using ethanol, in place of n-propanol in Example 17, (Z)-2-(5-bromo-2-hydroxybenzoyl)-3-methoxymethylpyridine O-t-butyloxime (60 mg) (Compound 180) was produced from 2-(5-bromo-2-hydroxybenzoyl)-3-methoxymethylpyridine (80 mg).

EXAMPLE 37 (Production of Compounds 181 and 182)

Without using triethylamine in Example 1, (Z)-3-cyano-2-(5-cyano-2-hydroxybenzoyl)pyridine O-t-butyloxime (0.29 g) (Compound 181) and the (E) compound (0.42 g) (Compound 182) were produced from 3-cyano-2-(5-cyano-2-hydroxybenzoyl)pyridine (0.68 g).

EXAMPLE 38 (Production of Compounds 183 and 184)

In accordance with Example 37, (Z)-3-cyano-2-(2-hydroxy-5-trifluoromethoxybenzoyl)pyridine O-t-butyloxime (0.17 g) (Compound 183) and the (E) compound (0.25 g) (Compound 184) were produced from 3-cyano-2-(2-methoxymethoxy-5-trifluoromethoxybenzoyl)pyridine (0.54 g) all at once.

Likewise, Compounds 186, 187, 196, 197, 202 and 203 were produced.

EXAMPLE 39

A mixture of Compound F-11 (2.0 g), 1N-sulfuric acid (5 ml) and acetone (50 ml) was heated under reflux for 5 hours, air-cooled, and neutralized with a saturated aqueous solution of sodium hydrogencarbonate. The mixture was extracted with chloroform, and the organic layer was dried (anhydrous magnesium sulfate) and concentrated. To the residue were added triethylamine (2 ml), O-t-butylhydroxylamine hydrochloride (1.16 g) and ethanol (20 ml). The mixture was heated under reflux for 5 hours. The solvent was evaporated under reduced pressure, and to the residue were added chloroform and water. The chloroform was dried (anhydrous magnesium sulfate) and concentrated under reduced pressure. The residue was chromatographed on silica gel using ethyl acetate/hexane as eluent to give (Z)-2-(5-cyano-4-fluoro-2-hydroxybenzoyl)-3-hydroxypyridine O-t-butyloxime (0.63 g).

TABLE 24

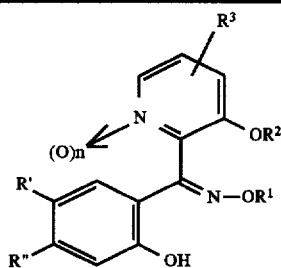

| Cpd. No. | R' | R" | R¹ | R² | R³ | n | geometrical isomerism | Formula | m.p. (°C.) physical property |
|---|---|---|---|---|---|---|---|---|---|
| 1 | CF$_3$ | H | Me | H | H | 0 | E | C$_{14}$H$_{11}$F$_3$N$_2$O$_3$ | 141–143 |
| 2 | CF$_3$ | H | Me | H | H | 0 | Z | C$_{14}$H$_{11}$F$_3$N$_2$O$_3$ | 235–236.5 |
| 3 | CF$_3$ | H | H | H | H | 0 | Z | C$_{13}$H$_9$F$_3$N$_2$O$_3$ | 172–173.5 |
| 4 | CF$_3$ | H | t-Bu | H | H | 0 | Z | C$_{17}$H$_{17}$F$_3$N$_2$O$_3$ | 205–206 |
| 5 | CF$_3$ | H | allyl | H | H | 0 | Z | C$_{16}$H$_{13}$F$_3$N$_2$O$_3$ | 133–134 |
| 6 | Br | H | t-Bu | H | H | 0 | Z | C$_{16}$H$_{17}$BrN$_2$O$_3$ | 218–219 |
| 7 | Br | H | t-Bu | H | H | 0 | E + Z | C$_{16}$H$_{17}$BrN$_2$O$_3$ | 154–155 |
| 8 | F | H | t-Bu | H | H | 0 | Z | C$_{16}$H$_{17}$FN$_2$O$_3$ | 223–224 |
| 9 | CN | H | t-Bu | H | H | 0 | Z | C$_{17}$H$_{17}$N$_3$O$_3$·1/5H$_2$O | 244–248 |
| 10 | CN | H | t-Bu | H | H | 0 | E | C$_{17}$H$_{17}$N$_3$O$_3$·1/5H$_2$O | 172–174 |
| 11 | H | H | t-Bu | H | H | 0 | Z | C$_{16}$H$_{18}$N$_2$O$_3$ | 207–209 |
| 12 | Br | H | Bn | H | H | 0 | Z | C$_{19}$H$_{15}$BrN$_2$O$_3$ | 202–204 |
| 13 | Cl | H | t-Bu | H | H | 0 | E | C$_{16}$H$_{17}$ClN$_2$O$_3$ | 170–171 |
| 14 | Cl | H | t-Bu | H | H | 0 | E + Z | C$_{16}$H$_{17}$ClN$_2$O$_3$ | 162–163.5 |
| 15 | CF$_3$O | H | t-Bu | H | H | 0 | E + Z | C$_{17}$H$_{17}$F$_3$N$_2$O$_4$ | 135–136 |
| 16 | Br | H | i-Bu | H | H | 0 | Z | C$_{16}$H$_{17}$BrN$_2$O$_3$ | 155–156 |
| 17 | Br | H | i-Bu | H | H | 0 | E + Z | C$_{16}$H$_{17}$BrN$_2$O$_3$ | 93.5–95 |
| 18 | Br | H | n-Bu | H | H | 0 | Z | C$_{16}$H$_{17}$BrN$_2$O$_3$ | 152–153 |
| 19 | Br | H | i-Pr | H | H | 0 | Z | C$_{15}$H$_{15}$BrN$_2$O$_3$ | 192–194 |
| 20 | Br | H | Et | H | H | 0 | Z | C$_{14}$H$_{13}$BrN$_2$O$_3$ | 190–192 |
| 21 | Br | H | n-Bu | H | H | 0 | E + Z | C$_{16}$H$_{17}$BrN$_2$O$_3$ | 98–101 |
| 22 | Br | H | n-Hex | H | H | 0 | E + Z | C$_{18}$H$_{21}$BrN$_2$O$_3$ | 82–84 |

TABLE 25

| Cpd. No. | R' | R" | R¹ | R² | R³ | n | geometrical isomerism | Formula | m.p. (°C.) physical property |
|---|---|---|---|---|---|---|---|---|---|
| 23 | Me | H | t-Bu | H | H | 0 | Z | C$_{17}$H$_{20}$N$_2$O$_3$ | 223–224.5 |
| 24 | Me | H | t-Bu | H | H | 0 | E | C$_{17}$H$_{20}$N$_2$O$_3$ | 144–145 |
| 25 | MeO | H | t-Bu | H | H | 0 | Z | C$_{17}$H$_{20}$N$_2$O$_4$ | 230–231 |
| 26 | MeO | H | t-Bu | H | H | 0 | E | C$_{17}$H$_{20}$N$_2$O$_4$ | 102–103.5 |
| 27 | NO$_2$ | H | t-Bu | H | H | 0 | Z | C$_{16}$H$_{17}$N$_3$O$_5$ | 254–255 |
| 28 | NO$_2$ | H | t-Bu | H | H | 0 | E + Z | C$_{16}$H$_{17}$N$_3$O$_5$ | 157–161 |
| 29 | H | MeO | t-Bu | H | H | 0 | Z | C$_{17}$H$_{20}$N$_2$O$_4$ | 199–202 |
| 30 | H | F | t-Bu | H | H | 0 | Z | C$_{16}$H$_{17}$FN$_2$O$_3$ | 209–211 |
| 31 | 3-NO$_2$ | H | t-Bu | H | H | 0 | Z | C$_{16}$H$_{17}$N$_3$O$_5$ | 209–210 |
| 32 | Cl | Cl | t-Bu | H | H | 0 | Z | C$_{16}$H$_{16}$Cl$_2$N$_2$O$_3$·½H$_2$O | 187–188.5 |
| 33 | Cl | Cl | t-Bu | H | H | 0 | E | C$_{16}$H$_{16}$Cl$_2$N$_2$O$_3$·½H$_2$O | 125–126.5 |
| 34 | F | F | t-Bu | H | H | 0 | Z | C$_{16}$H$_{16}$F$_2$N$_2$O$_3$ | 226–227 |
| 35 | F | F | t-Bu | H | H | 0 | E | C$_{16}$H$_{16}$F$_2$N$_2$O$_3$ | 132–133 |
| 36 | Cl | F | t-Bu | H | H | 0 | Z | C$_{16}$H$_{16}$ClFN$_2$O$_3$ | 191–191.5 |
| 37 | Cl | F | t-Bu | H | H | 0 | E | C$_{16}$H$_{16}$ClFN$_2$O$_3$ | 127–128 |
| 38 | Br | Cl | t-Bu | H | H | 0 | Z | C$_{16}$H$_{16}$BrClN$_2$O$_3$ | 189–190 |
| 39 | Br | Cl | t-Bu | H | H | 0 | E | C$_{16}$H$_{16}$BrClN$_2$O$_3$ | 154–155 |
| 40 | F | Cl | t-Bu | H | H | 0 | Z | C$_{16}$H$_{16}$ClFN$_2$O$_3$ | 211–212 |
| 41 | F | Cl | t-Bu | H | H | 0 | E | C$_{16}$H$_{16}$ClFN$_2$O$_3$ | 124–125 |
| 42 | Br | MeO | t-Bu | H | H | 0 | E + Z | C$_{17}$H$_{19}$BrN$_2$O$_4$ | 158–162 |
| 43 | Br | MeO | t-Bu | H | H | 0 | Z | C$_{17}$H$_{19}$BrN$_2$O$_4$ | 219–221 |
| 44 | NO$_2$ | MeO | t-Bu | H | H | 0 | Z | C$_{17}$H$_{19}$N$_3$O$_6$·¼H$_2$O | 223–224 |
| 45 | Br | H | t-Bu | H | H | 0 | Z | C$_{16}$H$_{17}$BrN$_2$O$_3$·HCl·½H$_2$O | 209–211 |
| 46 | CF$_3$ | H | t-Bu | Ac | H | 0 | Z | C$_{19}$H$_{19}$F$_3$N$_2$O$_4$ | 83–85 |
| 47 | Br | H | t-Bu | SO$_3$⁻PyH⁺ | H | 0 | Z | C$_{21}$H$_{22}$BrN$_2$O$_6$S·3/2H$_2$O | 115–120 |
| 48 | CF$_3$ | H | H | H | H | 1 | E | C$_{13}$H$_9$F$_3$N$_2$O$_4$ | 234 (dec.) |
| 49 | CF$_3$ | H | H | H | H | 1 | Z | C$_{13}$H$_9$F$_3$N$_2$O$_4$ | 252 (dec.) |
| 50 | CF$_3$ | H | Me | H | H | 1 | E | C$_{14}$H$_{11}$F$_3$N$_2$O$_4$ | 242 (dec.) |

TABLE 26

| Cpd. No. | R' | R" | R¹ | R² | R³ | n | geometrical isomerism | Formula | m.p. (°C.) physical property |
|---|---|---|---|---|---|---|---|---|---|
| 51 | $CF_3$ | H | t-Bu | H | H | 1 | E | $C_{17}H_{17}F_3N_2O_4$ | 222–224 |
| 52 | H | H | t-Bu | H | H | 1 | Z | $C_{16}H_{18}N_2O_4$ | 230 (dec.) |
| 53 | Br | H | t-Bu | H | H | 1 | E | $C_{16}H_{17}BrN_2O_4$ | 257 (dec.) |
| 54 | F | H | t-Bu | H | H | 1 | E | $C_{16}H_{17}FN_2O_4$ | 280.5 (dec.) |
| 55 | CN | H | t-Bu | H | H | 1 | E | $C_{17}H_{17}N_3O_4$ | 243–245 |
| 56 | F | Cl | t-Bu | H | H | 1 | Z | $C_{16}H_{16}ClFN_2O_4$ | 262 (dec.) |
| 57 | F | Cl | t-Bu | H | H | 1 | E | $C_{16}H_{16}ClFN_2O_4$ | 220 (dec.) |
| 58 | Cl | F | t-Bu | H | H | 1 | Z | $C_{16}H_{16}ClFN_2O_4$ | 253–256 |
| 59 | F | F | t-Bu | H | H | 1 | Z | $C_{16}H_{16}F_2N_2O_4$ | 255–258 |
| 60 | H | F | t-Bu | H | H | 0 | E | $C_{16}H_{17}FN_2O_3$ | 98–100 |
| 61 | Br | Me | t-Bu | H | H | 0 | Z | $C_{17}H_{19}BrN_2O_3 \cdot \frac{1}{4}H_2O$ | 187–191 |
| 62 | Br | Me | t-Bu | H | H | 0 | E | $C_{17}H_{19}BrN_2O_3 \cdot \frac{1}{4}H_2O$ | 141–142 |
| 63 | Br | H | t-Bu | H | H | 1 | Z | $C_{16}H_{17}BrN_2O_4 \cdot \frac{1}{4}H_2O$ | 235 (dec.) |
| 64 | $NO_2$ | H | t-Bu | H | H | 1 | Z | $C_{16}H_{17}N_3O_6 \cdot \frac{1}{4}H_2O$ | >300 |
| 65 | CN | H | t-Bu | H | H | 1 | Z | $C_{17}H_{17}N_3O_4 \cdot \frac{1}{4}H_2O$ | 290 (dec.) |
| 66 | Me | H | t-Bu | H | H | 1 | Z | $C_{17}H_{20}N_2O_4$ | 253–256 |
| 67 | Br | Me | t-Bu | H | H | 1 | Z | $C_{17}H_{19}BrN_2O_4 \cdot \frac{1}{4}H_2O$ | 263 (dec.) |
| 68 | Br | F | t-Bu | H | H | 0 | Z | $C_{16}H_{16}BrFN_2O_3 \cdot \frac{1}{2}H_2O$ | 198–200 |
| 69 | Br | F | t-Bu | H | H | 1 | Z | $C_{16}H_{16}BrFN_2O_4 \cdot \frac{1}{4}H_2O$ ($C_{16}H_{16}BrFN_2O_4$) | 248–252 (258.5–260) |
| 70 | Et | H | t-Bu | H | H | 0 | Z | $C_{18}H_{22}N_2O_3$ | 212–212.5 |
| 71 | $CONH_2$ | H | t-Bu | H | H | 0 | Z | $C_{17}H_{19}N_3O_4 \cdot \frac{3}{4}H_2O$ | 264–268 |

Bu: butyl, Hex: hexyl, Bn: benzyl, Py: pyridyl

TABLE 27

| Cpd. No. | R' | R" | R¹ | R² | R³ | n | geometrical isomerism | Formula | m.p. (°C.) physical property |
|---|---|---|---|---|---|---|---|---|---|
| 106 | Me | Me | t-Bu | H | H | 0 | Z | $C_{18}H_{22}N_2O_3 \cdot 1/4H_2O$ | 194–196 |
| 107 | Me | Me | t-Bu | H | H | 0 | E | $C_{18}H_{22}N_2O_3 \cdot 1/8H_2O$ | 146–147 |
| 108 | —CH=CH—CH=CH— | | t-Bu | H | H | 0 | Z | $C_{20}H_{20}N_2O_3 \cdot 1/8H_2O$ | 219–221 |
| 109 | —CH=CH—CH=CH— | | t-Bu | H | H | 0 | E | $C_{20}H_{20}N_2O_3$ | 211–213 |
| 110 | Br | F | t-Bu | H | H | 0 | E | $C_{16}H_{16}BrFN_2O_3$ | 86–89 |
| 111 | Me | F | t-Bu | H | H | 0 | Z | $C_{17}H_{19}FN_2O_3$ | 190–191.5 |
| 112 | $CH_2OH$ | H | t-Bu | H | H | 0 | E + Z | $C_{17}H_{20}N_2O_4$ | 135–139 |
| 113 | AcNH | H | t-Bu | H | H | 0 | E + Z | $C_{18}H_{21}N_3O_4 \cdot 1/4H_2O$ | 231–235 |
| 114 | F | Me | t-Bu | H | H | 0 | Z | $C_{17}H_{19}FN_2O_3$ | 203–204 |
| 115 | CH≡C | H | t-Bu | H | H | 0 | Z | $C_{18}H_{18}N_2O_3 \cdot 1/4H_2O$ | 196 (dec.) |
| 116 | $Me_3SiC$≡C | H | t-Bu | H | H | 0 | E + Z | $C_{21}H_{16}N_2O_3Si$ | 210–214 |
| 117 | CHO | H | t-Bu | H | H | 0 | Z | $C_{17}H_{18}N_2O_4$ | 212–215 |
| 118 | $NO_2$ | MeO | t-Bu | H | H | 1 | Z | $C_{17}H_{19}N_3O_7$ | >300 |
| 119 | Br | Cl | t-Bu | H | H | 1 | Z | $C_{16}H_{16}BrClN_2O_4$ | 253–255 |
| 120 | Br | Cl | t-Bu | H | H | 1 | E | $C_{16}H_{16}BrClN_2O_4$ | 232–235 |
| 121 | Br | MeO | t-Bu | H | H | 1 | Z | $C_{17}H_{19}BrN_2O_5 \cdot EtOH$ | 178–179 |
| 122 | Cl | Cl | t-Bu | H | H | 1 | Z | $C_{16}H_{16}Cl_2N_2O_4$ | 240–241 |
| 123 | Cl | H | t-Bu | H | H | 1 | Z | $C_{16}H_{17}ClN_2O_4$ | 278–280 |
| 124 | Cl | H | t-Bu | H | H | 1 | E | $C_{16}H_{17}ClN_2O_4$ | 269 (dec.) |
| 125 | Me | Me | t-Bu | H | H | 1 | Z | $C_{18}H_{22}N_2O_4 \cdot 1/4H_2O$ | 278 (dec.) |
| 126 | Me | F | t-Bu | H | H | 1 | Z | $C_{17}H_{19}FN_2O_4 \cdot 4/5H_2O$ | 135–138 |
| 127 | F | Me | t-Bu | H | H | 1 | Z | $C_{17}H_{19}FN_2O_4$ | 273 (dec.) |
| 128 | Br | CN | t-Bu | H | H | 0 | Z | $C_{17}H_{16}BrN_3O_3$ | 188.5–190 |
| 129 | Br | CN | t-Bu | H | H | 1 | Z | $C_{17}H_{16}BrN_3O_4$ | 299 (dec.) |
| 130 | CN | Cl | t-Bu | H | H | 0 | Z | $C_{17}H_{16}ClN_3O_3$ | 218–219 |
| 131 | CN | Cl | t-Bu | H | H | 0 | E | $C_{17}H_{16}ClN_3O_3 \cdot 1/5H_2O$ | 191–193 |
| 132 | CN | Cl | t-Bu | H | H | 1 | Z | $C_{17}H_{16}ClN_3O_4$ | 292 (dec.) |
| 133 | CN | Cl | t-Bu | H | H | 1 | E | $C_{17}H_{16}ClN_3O_4 \cdot 1/4H_2O$ | 284 (dec.) |

TABLE 28

| Cpd. No. | $^1$H-NMR (CDCl$_3$; TMS internal standard, ppm) | IR (KBr; cm$^{-1}$) |
|---|---|---|
| 1 | *3.93(3H, s), 7.08–7.12(2H, m), 7.33(2H, d, J=3.0Hz), 7.58–7.66(1H, m), 8.12(1H, t, J=3.0Hz), | 3100, 2940, 1620, 1580, 1420, 1335, 1315, 1295, 1150, 1110, 1070, 1040. |
| 2 | 4.09(3H, s), 7.18(1H, d, J=8.8Hz), 7.29–7.33(1H, m), 7.45–7.61(3H, m), 8.12(1H, dd, J=1.6&4.4Hz), 10.56(1H, s). | 3100, 2945, 1620, 1585, 1515, 1440, 1335, 1315, 1165, 1105, 1045. |
| 3 | *6.49(1H, br. s), 7.13(1H, m), 7.36(2H, br. s), 7.57–7.61(1H, m), 8.17(1H, br. s). | 3100, 2800, 1620, 1580, 1350, 1320, 1280, 1260, 1195, 1160, 1120, 1080. |
| 4 | *1.28(9H, s), 6.99–7.02(1H, m), 7.15(1H, d, J=8.4Hz), 7.35(2H, m), 7.60–7.65(1H, m), 8.13–8.16(1H, m). | 2950, 2600, 1625, 1600, 1370, 1340, 1320, 1290, 1260, 1200, 1160, 1100, 1075, 1010. |
| 5 | 4.80(2H, d, J=6.2Hz), 5.34–5.47(22H, m), 5.93–6.18(2H, m), 7.09(1H, d, J=9.2Hz), 7.15(1H, m), 7.41–7.53(3H, m), 8.34–8.36(1H, m). | 3650, 3070, 2940, 1625, 1605, 1460, 1345, 1320, 1290, 1260, 1200, 1150, 1120, 1080, 1005. |
| 6 | 1.43(9H, s), 6.91(1H, d, J=8.6Hz), 6.98(1H, d, J=2.4Hz), 7.30–7.50(3H, m), 8.33(1H, dd, J=1.4&4.0Hz). | 3400, 2980, 2925, 1615, 1570, 1470, 1455, 1360, 1295, 1280, 1190, 1105, 1005. |
| 7 | 1.41&1.44(comb. 9H, each s), 6.89–7.48(5H), 8.12&8.35 (comb. 1H, each dd, J=1.6&4.6Hz, J=1.8&4.2Hz). | 1590, 1570, 1490, 1470, 1450, 1440, 1400, 1385, 1365, 1300, 1190, 1105, 1040, 1010. |
| 8 | 1.44(9H, s), 6.55–6.61(1H, m), 6.95–6.99(2H, m), 7.39(1H, dd, J=4.0&8.4Hz), 7.47(1H, dd, J=1.0&8.4Hz), 8.34(dd, J=1.0, 4.0Hz, 1H). | 3050, 2970, 1590, 1570, 1485, 1395, 1385, 1295, 1240, 1170. | comb.: combinedly

TABLE 29

| Cpd. No. | $^1$H-NMR (CDCl$_3$; TMS internal standard, ppm) | IR (KBr; cm$^{-1}$) |
|---|---|---|
| 9 | 1.45(9H, s), 6.48(1H, s), 7.07(1H, d, J=8.4Hz), 7.29(1H, d, J=2.2Hz), 7.40–7.56(3H, m), 8.35(1H, dd, J=1.8&4.4Hz), 12.18(1H, s). | 3400, 2975, 2560, 2220, 1615, 1595, 1575, 1490, 1455, 1360, 1295, 1260, 1185, 1000. |
| 10 | 1.41(9H, s), 7.15(1H, d, J=8.4Hz), 7.30(1H, dd, J=4.6&8.4Hz), 7.48(1H, dd, J=1.4&8.4Hz), 7.61(1H, dd, J=2.2&8.4Hz), 7.69(1H, d, J=2.2Hz), 8.11(1H, dd, J=1.4&4.6Hz), 10.81(1H, s). | 3390, 3060, 2970, 2220, 1680, 1600, 1435, 1365, 1290, 1240, 1180, 1020. |
| 11 | 1.43(9H, s), m 6.74–6.85(2H, m), 7.02(1H, d, J=8.2Hz), 7.22–7.50(3H, m) 8.32–8.34(1H, m). | 2970, 1585, 1460, 1360, 1245, 1240, 1185, 1005. |
| 12 | *5.20(2H, s), 6.77(1H, d, J=2.4Hz), 6.88(1H, d, J=8.8Hz), 7.36(8H, br. s), 8.14–8.25(2H, m), 10.38(1H, br. s), 10.58(1H, br. s). | 2930, 2640, 1580, 1470, 1455, 1300, 1280, 1245, 1110, 1005. |
| 13 | 1.41(9H, s), 7.04(1H, d, J=9.6Hz), 7.23–7.32(3H, m), 7.44(1H, dd, J=1.4&8.2Hz), 8.13(1H, dd, J=1.4&6.4Hz). | 3220, 2975, 1615, 1580, 1490, 1440, 1405, 1365, 1320, 1300, 1275, 1240, 1185, 1120, 1040, 1015. |
| 14 | 1.42&1.44(comb. 9H, each s), 6.96&7.04(comb. 1H, each d, J=8.8Hz, J=2.4Hz), 7.19–7.49(comb. 4H, m), 8.13&8.35(comb. 1H, each dd, J=1.4&4.6Hz, J=1.6&4.2Hz). | 1585, 1570, 1475, 1440, 1365, 1295, 1185, 1010. |
| 15 | 1.40&1.45(comb. 9H, each s), 6.76–7.50(5H, m), 8.13&8.35(comb. 1H, each dd, J=1.4&4.6Hz, J=1.6&4.0Hz), 11.03(1H, s). | 3000, 2980, 2630, 1580, 1490, 1460, 1445, 1365, 1300, 1250, 1220, 1200, 1155, 1040. |

TABLE 30

| Cpd. No. | $^1$H-NMR (CDCl$_3$; TMS internal standard, ppm) | IR (KBr; cm$^{-1}$) |
|---|---|---|
| 16 | 0.91(6H, d, J=6.6Hz), 1.96–2.18(1H, m), 4.10(2H, d, J=6.8Hz), 6.91(1H, d, J=8.8Hz), 6.97(1H, d, J=2.2Hz), 7.32–7.47(3H, m), 8.32–8.34(1H, m). | 3000, 2960, 1570, 1470, 1455, 1300, 1280, 1240, 1105, 1020. |
| 17 | 0.92&0.97(comb. 6H, each d, J=7.0Hz, J=6.6Hz), 2.00–2.20(1H, m), 4.06&4.11(comb. 1H, each d, J=7.0Hz, J=7.0Hz), 6.89–7.02(1H, m), 7.24–7.44(4H, m), 8.12&8.35(comb. 1H, each dd, J=1.2&4.4Hz, J=1.8&4.4Hz), 10.72(1H, s). | 3150, 2960, 2580, 1615, 1585, 1470, 1440, 1300, 1280, 1240, 1025. |
| 18 | 0.92(3H, t, J=7.4Hz), 1.27–1.42(2H, m), 1.61–1.81(2H, m), 4.34(2H, t, J=6.6Hz), 6.91(1H, d, J=8.8Hz), 6.98(1H, d, J=2.2Hz), 7.32–7.48(3H, m), 8.34(1H, dd, J=1.4&4.0Hz). | 3000, 2600, 1575, 1470, 1455, 1300, 1280, 1245, 1000. |
| 19 | 1.37(6H, d, J=6.2Hz), 4.61–4.73(1H, m), 6.91(1H, d, J=8.8Hz), 7.01(1H, d, J=2.4Hz), 7.35(1H, dd, J=2.4&8.8Hz), 7.40(1H, dd, J=4.2, 8.4Hz), 7.47(1H, dd, J=1.6&8.4Hz), 8.35(1H, dd, J=1.6&4.2Hz). | 2970, 1570, 1470, 1300, 1280, 1110, 1015. |
| 20 | 1.38(3H, t, J=7.0Hz), 4.40(2H, q, J=7.0Hz), 6.91(1H, d, J=8.8Hz), 6.98(1H, d, J=2.6Hz), 7.35(1H, dd, J=2.6&8.8Hz), 7.39(1H, dd, J=4.2&8.4Hz), 7.45(1H, dd, J=1.8&8.4Hz), 8.34(1H, dd, J=1.8&4.2Hz). | 3400, 2975, 2950, 2590, 1615, 1580, 1480, 1385, 1305, 1280, 1245, 1200, 1040, 1015. |

TABLE 31

| Cpd. No. | ¹H-NMR (CDCl₃; TMS internal standard, ppm) | IR (KBr; cm⁻¹) |
|---|---|---|
| 21 | 0.92–0.99(3H, m), 1.36–1.77(4H, m), 4.25–4.34(2H, m), 6.88–7.02(1H, m), 7.24–7.31(1H, m), 7.40–7.47(3H, m). 8.12&8.34–8.36(comb. 1H, in order dd, m, J=1.6, 4.6Hz), 10.73(1H, s). | 3070, 2950, 2600, 1580, 1490, 1440, 1400, 1300, 1280, 1240, 1200, 1060, 1015. |
| 22 | 0.80–0.94(3H, m), 1.21–1.80(8H, m), 4.24–4.36(2H, m), 6.89–7.02&7.26–7.48(comb. 5H, m), 8.12&8.35(comb. 1H, each dd, J=1.6&4.6Hz, J=1.6&4.0Hz), 10.74(1H, s). | 3050, 2930, 2850, 2600, 1575, 1470, 1460, 1300, 1280, 1240, 1200, 1000. |
| 23 | 1.43(9H, s), 2.16(3H, s), 6.44(1H, br. s), 6.60(1H, d, J=1.8Hz), 6.93(1H, d, J=8.4Hz), 7.08(1H, dd, J32 1.8&8.4Hz), 7.36(1H, dd, J=4.2&8.4Hz), 7.44(1H, dd, J=1.6&8.4Hz), 8.35(1H, dd, J=1.6&4.2Hz), 10.86(1H, s). | 2980, 2930, 2640, 1580, 1490, 1475, 1370, 1300, 1290, 1240, 1190, 1115, 1010. |
| 24 | 1.41(9H, s), 2.29(3H, s), 7.01(1H, d, J=8.4Hz), 7.08–7.26(3H, m), 7.41(1H, dd, J=1.4&8.4Hz), 8.13(1H, dd, J=1.4&4.6Hz), 11.23(1H, s), | 3250, 2970, 1610, 1580, 1500, 1440, 1360, 1295, 1260, 1240, 1190, 1040. |
| 25 | 1.44(9H, s), 3.64(3H, s), 6.40(1H, d, J=2.8Hz), 6.44(1H, s), 6.89(1H, dd, J=2.8&9.0Hz), 6.97(1H, d, J=9.0Hz), 7.37(1H, dd, J=4.4&8.4Hz), 7.44(1H, dd, J=2.6&8.4Hz), 8.35(1H, dd, J=2.6&4.4Hz), 10.64(1H, s). | 3400, 2980, 2640, 1580, 1490, 1465, 1370, 1300, 1280, 1240, 1195, 1015. |

TABLE 32

| Cpd. No. | ¹H-NMR (CDCl₃; TMS internal standard, ppm) | IR (KBr; cm⁻¹) |
|---|---|---|
| 26 | 1.42(9H, s), 3.75(3H, s), 6.84(1H, d, J=2.8Hz), 6.94(1H, dd, J=2.8&8.8Hz), 7.04(1H, d, J=8.8Hz), 7.23(1H, dd, J=4.&8.4Hz), 7.41(1H, dd, J=1.4&8.4Hz), 8.13(1H, dd, J=1.4&4.4Hz), 8.50(1H, s), 11.21(1H, s). | 3250, 2975, 1585, 1505, 1440, 1365, 1295, 1240, 1210, 1185, 1040. |
| 27 | 1.47(9H, s), 7.09(1H, d, J=9.2Hz), 7.45(1H, dd, J=4.0&8.0Hz), 7.53(1H, dd, J=1.6&8.0Hz), 7.97(1H, d, J=2.6Hz), 8.17(1H, dd, J=2.6&9.2Hz), 8.36(1H, dd, J=1.6&4.0Hz). | 3420, 2980, 2570, 1630, 1590, 1575, 1475, 1460, 1340, 1295. |
| 28 | 1.42&1.47(comb. 9H, each s), 7.08&7.15(comb. 1H, each d, J=9.2Hz, J=9.2Hz), 7.29–7.37(1H, m), 7.46–7.52(1H, m), 7.97&8.10–8.13 (comb. 1H, m), 8.19–8.25(1H, m), 10.81&11.83–11.88(comb. 1H, m). | 3430, 2980, 1620, 1595, 1525, 1495, 1440, 1345, 1295. |
| 29 | 1.43(9H, s), 3.80(3H, s), 6.35(1H, s), 6.35(1H, dd, J=2.6&8.8Hz), 6.54(1H, d, J=2.6Hz), 6.73(1H, d, J=8.8Hz), 7.35(1H, dd, J=4.2&8.4Hz), 7.43(1H, dd, J=1.6&8.4Hz), 8.36(1H, dd, J=1.6&4.2Hz), 11.14(1H, s). | 3410, 2975, 2600, 1630, 1580, 1520, 1460, 1360, 1290, 1185, 1160. |
| 30 | 1.43(9H, s), 6.39(1H, s), 6.45–6.55(1H, m), 6.72(1H, dd, J=2.4&10.2Hz), 6.84(1H, dd, J=6.6&8.8Hz), 7.37(1H, dd, J=4.4&8.6Hz), 7.45(1H, dd, J=1.8&8.6Hz), 8.35(1H, dd, J=1.8&4.4Hz), 11.41(1H, d, J=1.6Hz). | 3400, 2975, 2600, 1620, 1600, 1575, 1510, 1460, 1385, 1360, 1260. |
| 31 | 1.47(9H, s), 7.0591(1H, dd, J=7.6&8.4Hz), 7.33(1H, dd, J=4.2&8.2Hz), 7.45(1H, dd, J=1.4&8.2Hz), 7.79(1H, dd, J=1.8&7.6Hz), 8.14(1H, dd, J=1.8&8.4Hz), 8.19(1H, dd, J=1.4&4.2Hz), 11.07(1H, br. s). | 3080, 2970, 2925, 2600, 1600, 1570, 1530, 1455, 1360, 1350, 1335, 1290, 1260. |

TABLE 33

| Cpd. No. | ¹H-NMR (CDCl₃; TMS internal standard, ppm) | IR (KBr; cm⁻¹) |
|---|---|---|
| 32 | 1.43(9H, s), 6.98(1H, s), 7.13(1H, s), 7.37–7.52(2H, m), 8.31–8.33(1H, m). | 1600, 1480, 1440, 1400, 1365, 1290, 1260, 1245. |
| 33 | 1.41(9H, s), 7.22(1H, s), 7.28(1H, dd, J=4.6&8.4Hz), 7.43(1H, s), 7.45(1H, dd, J=1.4&8.4Hz), 8.12(1H, dd, J=1.4&4.6Hz), 10.93(1H, br. s). | 3100, 2980, 1600, 1480, 1440, 1400, 1365, 1295, 1245, 1200, 1180. |
| 34 | 1.44(9H, s), 6.39(1H, br. s), 6.73(1H, dd, J=9.2&11.6Hz), 6.81(1H, dd, J=7.0&11.6Hz), 7.40(1H, dd, J=3.8&8.0Hz), 7.46(1H, dd, J=1.2&8.0Hz), 8.36(1H, dd, J=1.2&3.8Hz), 11.18–11.30(1H, br. s). | 2980, 2940, 2600, 1620, 1570, 1520, 1460, 1365, 1300, 1260, 1180. |
| 35 | 1.41(9H, s), 6.89(1H, dd, J=7.0&11.6Hz), 7.12–7.31(2H, m), 7.41–7.48(1H, m), 8.12(1H, dd, J=1.4&4.8Hz), 10.99(1H, s). | 3075, 2975, 1620, 1535, 1440, 1365, 1300, 1200, 1180, 1010. |
| 36 | 1.44(9H, s), 6.43(1H, br. s), 6.82(1H, d, J=10.6Hz), 6.95(1H, d, J=8.4Hz), 7.41(1H, dd, J=4.4&8.4Hz), 7.48(1H, dd, J=1.8&8.4Hz), 8.35(1H, dd, J=1.8&4.4Hz). | 3400, 2980, 2600, 1580, 1500, 1490, 1455, 1380, 1370, 1300, 1200, 1165, 1010. |
| 37 | 1.41(9H, s), 6.90(1H, d, J=10.2Hz), 7.28(1H, dd, J=4.&8.4Hz), 7.39(1H, d, J=8.4Hz), 7.45(1H, dd, J=1.6&8.4Hz), 8.12(1H, dd, J=1.6&4.4Hz), 10.97(1H, s). | 3100, 2980, 1740, 1610, 1510, 1440, 1420, 1365, 1300, 1250, 1200, 1180, 1050, 1010. |
| 38 | 1.44(9H, s), 6.52(1H, br. s), 7.14(2H, s), 7.40(1H, dd, J=4.4&8.4Hz), 7.47(1H, dd, J=1.8&7.4Hz), 8.33(1H, dd, J=1.8&4.4Hz). | 3400, 2970, 2760, 2600, 1605, 1575, 1460, 1360, 1300, 1200, 1120, 1040, 1020. |

TABLE 34

| Cpd. No. | $^1$H-NMR (CDCl$_3$; TMS internal standard, ppm) | IR (KBr; cm$^{-1}$) |
|---|---|---|
| 39 | 1.41(9H, s), 6.71(1H, s), 7.22(1H, s), 7.28(1H, dd, J=4.6&8.4Hz), 7.45(1H, dd, J=1.6&8.4Hz), 7.58(1H, s), 8.11(1H, dd, J=1.6&4.6Hz), 10.92(1H, s). | 3400, 3120, 2980, 1595, 1480, 1440, 1380, 1365, 1240, 1015. |
| 40 | 1.44(9H, s), 6.44(1H, s), 6.71(1H, d, J=10.2Hz), 7.06(1H, d, J=6.6Hz), 7.41(1H, dd, J=4.2&8.4Hz), 7.47(1H, dd, J=1.4&8.4Hz), 8.35(1H, dd, J=1.4&4.2Hz), 11.17(1H, br. s). | 3400, 2980, 2600, 1580, 1495, 1365, 1300, 1255, 1180, 1040, 1010. |
| 41 | 1.41(9H, s), 7.13(1H, d, J=3.0Hz), 7.17(1H, s), 7.28(1H, dd, J=4.6&8.4Hz), 7.45(1H, dd, J=1.4&8.4Hz), 8.12(1H, dd, J=1.4&4.6Hz), 10.98(1H, s). | 3300, 2980, 1615, 1585, 1500, 1440, 1415, 1295, 1180, 1045. |
| 42 | 1.42(9H, br. s), 3.92(3H, br. s), 6.55&6.62(comb. 1H, each s), 7.01&7.53(comb. 1H, each s), 7.23–7.31(1H, m), 7.36–7.47(1H, m) 8.12&8.35–8.37(comb. 1H, each dd, m, J=1.4&4.4Hz), 10.30&11.16 (comb. 1H, each s). | 3400, 3150, 2975, 1615, 1585, 1440. |
| 43 | 1.43(9H, s), 3.90(3H, s), 6.38(1H, s), 6.57(1H, s), 7.01(1H, s), 7.38(1H, dd, J=4.0&8.4Hz), 7.45(1H, dd, J=1.8&8.4Hz), 8.36(1H, dd, J=1.8&4.0Hz), 11.36(1H, s). | 3400, 2975, 2600, 1620, 1590, 1570, 1500, 1455, 1365, 1350, 1275, 1200, 1110, 1045. |
| 44 | 1.45(9H, s), 3.98(3H, s), 6.51(1H, br. s), 6.63(1H, s), 7.43(1H, dd, J=4.0&8.4Hz), 7.49(1H, dd, J=2.&8.4Hz), 7.78(1H, s), 8.35(1H, dd, J=2.&4.0Hz), 12.42(1H, s). | 3430, 2980, 2680, 1635, 1535, 1460, 1315, 1280, 1210. |

TABLE 35

| Cpd. No. | $^1$H-NMR (CDCl$_3$; TMS internal standard, ppm) | IR (KBr; cm$^{-1}$) |
|---|---|---|
| 45 | *1.28(9H, s), 6.82–6.86(1H, m), 7.11–7.26(1H, m), 7.37–7.51(1H, m) 7.5–7.75(2H, m), 8.26–8.34(1H, m). | 3400, 2975, 2560, 1555, 1460, 1365, 1315, 1285, 1240, 1185, 1040, 1015. |
| 46 | 1.30(9H, s), 2.19(3H, s), 6.95(1H, d, J=1.8Hz), 7.10(1H, d, J=8.8Hz), 7.44–7.51(2H, m), 7.69(1H, dd, J=1.2&8.2Hz), 8.62(1H, dd, J=1.2&4.6Hz), 11.48(1H, s). | 3430, 2990, 2940, 1780, 1770, 1625, 1600, 1500, 1450, 1345, 1200, 1155, 1015. |
| 47 | *1.27(9H, s), 6.86(1H, br. s), 6.91(1H, d, J=8.8Hz), 7.41(1H, d, J=8.8Hz), 7.52–7.55(1H, m), 8.00–8.03(2H, m), 8.11–8.13(1H, m), 8.35(1H, m), 8.51–8.55(1H, m), 8.90(2H, d, J=5.1Hz). | 3430, 3070, 2980, 1640, 1615, 1540, 1475, 1440, 1365, 1280, 1115, 1040, 1010. |
| 48 | *6.91–6.97(1H, m), 7.16–7.22(1H, m), 7.40–7.44(1H, m), 7.47–7.61 (2H, m), 8.05–8.09(1H, m), 11.28(1H, br. s), 12.08(1H, br. s). | 3450, 1620, 1580, 1500, 1440, 1340, 1320, 1280, 1200, 1160, 1120, 1025. |
| 49 | *7.05(2H, m), 7.24(1H, m), 7.39(1H, dd, J=6.6&8.6Hz), 7.56–7.59(1H, m), 7.56–7.59(1H, m), 8.00(1H, d, J=6.6Hz), 10.99(1H, br. s), 11.89 (1H, br. s), 12.13(1H, br. s). | 1620, 1580, 1500, 1435, 1345, 1320, 1290, 1250, 1200, 1160, 1125, 1080, 1025. |
| 50 | *3.92(3H, s), 6.93–6.98(1H, m), 7.18(1H, m), 7.40–7.54(3H, m), 8.04–8.07(1H, m). | 3125, 2400, 1625, 1580, 1505, 1435, 1325, 1285, 1250, 1205, 1160, 1120, 1040, 1025. |
| 51 | *1.25(9H, br. s), 6.88–7.05(1H, m), 7.15–7.28(1H, m), 7.37–7.75(3H, m), 8.02–8.22(1H, m). | 2990, 1625, 1590, 1580, 1325, 1290, 1265, 1115, 1025. |

TABLE 36

| Cpd. No. | $^1$H-NMR(CDCl$_3$; TMS internal standard, ppm) | IR(KBr; cm$^{-1}$) |
|---|---|---|
| 52 | *1.26(9H, s), 6.80–7.00(3H, m), 7.23–7.38(2H, m), 7.88–7.91(1H, m). | 3075, 2975, 2500, 1615, 1600, 1565, 1415, 1365, 1245, 1200, 1030, 1005. |
| 53 | *1.25(9H, s), 6.74(1H, d, J=8.4Hz), 7.12–7.45(4H, m), 8.00–8.06(1H, m), 11.14(1H, br. s). | 2970, 1570, 1480, 1425, 1240, 1200, 1035. |
| 54 | *1.27(9H, s), 6.65–6.71(1H, m), 6.88–7.17(3H, m), 7.33–7.41(1H, m), 7.94(1H, d, J=6.4Hz). | 3075, 2970, 1600, 1565, 1485, 1430, 1240, 1230, 1200, 1185, 1160, 1030, 1000. |
| 55 | *1.26(9H, s), 6.88–6.94(1H, m), 7.16–7.21(1H, m), 7.39–7.47(1H, m), 7.57–7.62(2H, m), 8.01–8.07(1H, m). | 2225, 1610, 1580, 1490, 1440, 1360, 1260, 1360, 1260, 1200, 1015. |
| 56 | *1.26(9H, s), 6.97–7.08(3H, m), 7.36(1H, dd, J=6.6 & 8.8Hz), 7.95(1H, d, J=6.6Hz), 10.94–11.15(1H, br. s). | 3420, 2980, 1625, 1575, 1495, 1480, 1435, 1365, 1335, 1250, 1200, 1035, 1020. |
| 57 | *1.25(9H, s), 6.94(1H, d, J=6.6Hz), 7.14–7.19(2H, m), 7.42(1H, dd, J=6.6 * 8.8Hz), 8.01–8.04(1H, m), 11.24(1H, br. s). | 3400, 2990, 2520, 1620, 1575, 1490, 1480, 1430, 1360, 1210, 1025. |
| 58 | *1.25(9H, s), 6.90(1H, m), 7.04(1H, d, J=8.4Hz), 7.08–7.13(1H, m), | 3440, 2970, 2600, 1610, 1570, 1500, |

TABLE 36-continued

| Cpd. No. | ¹H-NMR(CDCl₃; TMS internal standard, ppm) | IR(KBr; cm⁻¹) |
|---|---|---|
| | 7.33–7.41(1H, m), 7.96(1H, d, J=6.0Hz), 8.28(1H, br. s). | 1430, 1200, 1035. |
| 59 | *1.25(9H, s), 6.89–7.03(3H, m), 7.36(1H, dd, J=6.2 & 8.6Hz), 7.94(1H, d, J=6.2Hz), 11.16(1H, br. s). | 3430, 2970, 2750, 1620, 1565, 1520, 1430, 1200, 1035. |
| 60 | 1.41(9H, s), 6.66(1H, m), 6.80(1H, d, J=2.6 & 10.6Hz), 7.22–7.35(2H, m), 7.43(1H, dd, J=1.4 & 8.4Hz), 8.12(1H, dd, J=1.4 & 4.8Hz), 10.02(1H, s), 11.13(1H, s) | 3400, 2980, 2600, 1620, 1590, 1435, 1300, 1255, 1010. |

TABLE 37

| Cpd. No. | ¹H-NMR (CDCl₃; TMS internal standard, ppm) | IR (KBr; cm⁻¹) |
|---|---|---|
| 61 | 1.43(9H, s), 2.34(3H, s), 6.41(1H, s), 6.91(1H, s), 7.00(1H, s), 7.38(1H, dd, J=4.0&8.4Hz), 7.45(1H, dd, J=1.8&8.4Hz), 8.35(1H, dd, J=1.8&4.0Hz), 11.08(1H, s). | 3400, 2970, 2580, 1620, 1585, 1570, 1460, 1365, 1295, 1260, 1180, 1110. |
| 62 | 1.42(9H, s), 2.39(3H, s), 6.99(1H, s), 7.21–7.28(1H, m), 7.42(1H, dd, J=1.6&8.6Hz), 7.48(1H, s), 8.10–8.12(1H, m), 9.39(1H, s), 11.08(1H, s). | 3400, 3200, 2980, 1615, 1585, 1570, 1440, 1395. |
| 63 | *1.25(9H, s), 6.84(1H, d, J=8.8Hzx), 6.98(1H, d, J=8.4Hz), 7.07(1H, d, J=2.6Hz), 7.30–7.42(2H, m), 7.91(1H, d, J=5.8Hz), 11.27(1H, br. s). | 3430, 2980, 1575, 1480, 1435, 1205, 1040. |
| 64 | *1.27(9H, s), 7.02(1H, d, J=9.0Hz), 7.08(1H, d, J=8.6Hz), 7.41(1H, dd, J=6.4&8.6Hz), 8.01(1H, d, J=6.4Hz), 8.02(1H, d, J=3.0Hz), 8.16(1H, dd, J=3.0&9.0Hz). | 3430, 2980, 2600, 1630, 1595, 1565, 1535, 1480, 1430, 1340, 1205, 1030. |
| 65 | *1.26(9H, s), 7.01(1H, d, J=8.6Hz), 7.06(1H, d, J=8.6Hz), 7.39(1H, dd, J=6.4&8.6Hz), 7.49(1H, d, J=2.0Hz), 7.70(1H, dd, J=2.0&8.6Hz), 7.98(1H, d, J=6.4HJz), 11.00(1H, br. s), 12.10(1H, br. s). | 3420, 2980, 2500, 2225, 1735, 1605, 1570, 1490, 1430, 1200, 1035. |
| 66 | *1.25(9H, s), 2.15(3H, s), 6.64(1H, d, J=1.4Hz), 6.81(1H, d, J=8.2Hz), 6.98(1H, d, J=8.4Hz), 7.07(1H, dd, J=1.4&8.4Hz), 7.34(1H, dd, J=6.4&8.2Hz), 7.92(1H, d, J, =6.4Hz), 10.78(1H, br. s). | 3410, 2980, 1575, 1495, 1435, 1255, 1205, 1040. |
| 67 | *1.25(9H, s), 2.29(3H, s), 6.92–7.02(3H, m), 7.36(1H, m), 7.95(1H, t, J=6.8Hz), 1.096(1H, br. s). | 3430, 2980, 1625, 1570, 1430, 1365, 1200, 1035. |

TABLE 38

| Cpd. No. | ¹H-NMR (CDCl₃; TMS internal standard, ppm) | IR (KBr; cm⁻¹) |
|---|---|---|
| 68 | 1.44(9H, s), 6.46(1H, s), 6.80(1H, d, J=9.8Hz), 7.08(1H, d, J=8.0Hz), 7.40(1H, dd, J=4.0&8.6Hz), 7.47(1H, dd, J=1.6*8.6Hz), 8.34(1H, dd, J=1.6&4.0Hz), 11.67(1H, s). | |
| 69 | *1.25(9H, s), 6.89(1H, d, J=10.4Hz), 7.05(1H, d, J=8.6Hz), 7.22(1H, d, J=8.0Hz), 7.38(1H, dd, J=6.4&8.6Hz), 7.97(1H, d, J=6.4Hz), 11.02(1H, br. s) 11.67(1H, br. s). | 3420, 3080, 2990, 2650, 1620, 1600, 1585, 1500, 1490, 1435, 1215, 1080, 1060, 1045. |
| 70 | 1.09(3H, t, J=7.6Hz), 1.43(9H, s), 2.46(2H, q, J=7.6Hz), 6.39(1H, br. s), 6.62(1H, d, J=1.8Hz), 6.95(1H, d, J=8.0Hz), 7.11(1H, dd, J=1.8&8.0Hz), 7.36(1H, dd, J=4.2&8.8Hz), 7.44(1H, dd, J=1.4&8.8Hz), 8.34(1H, dd, J=1.4&4.2Hz), 10.85(1H, s). | 3400, 2975, 2930, 2600, 1580, 1490, 1455, 1370, 1300, 1260, 1190, 1115, 1000. |
| 71 | *1.27(9H, s), 6.98(1H, d, J=8.4Hz), 7.13(1H, br. s), 7.32(1H, d, J=2.2Hz), 7.33(2H, d, J=3.0Hz), 7.81(1H, dd, J=2.&8.4Hz), 8.14(1H, t, J=3.0Hz), 10.11(1H, s), 11.55(1H, s). | 3470, 3200, 2990, 1675, 1605, 1460, 1380, 1300, 1000. |

*measured with DMSO-d₆

TABLE 39

| Cpd. No. | ¹H-NMR(CDCl₃; TMS internal standard, ppm) | IR(KBr; cm⁻¹) |
|---|---|---|
| 106 | 1.43(9H, s), 2.06(3H, s), 6.37(1H, s), 6.53(1H, s), 7.35(1H, dd, J=4.4 & 4.8Hz), 7.44(1H, dd, J=1.6 & 8.4Hz), 8.35(1H, dd, J=1.6 & 4.4Hz), 10.71(1H, s). | 3450, 2975, 1575, 1450. |
| 107 | 1.42(9H, s), 2.19(3H, s), 2.26(3H, s), 6.91(1H, s), 7.04(1H, s), 7.21(1H, dd, J=4.4 & 8.2Hz), 7.39(1H, dd, J=1.4 & 8.2Hz), 8.13(1H, dd, J=1.4 & 4.4Hz), 8.41(1H, br. s), 11.28(1H, s). | 3200, 2970, 1620, 1580, 1500, 1435. |

TABLE 39-continued

| Cpd. No. | ¹H-NMR(CDCl₃; TMS internal standard, ppm) | IR(KBr; cm⁻¹) |
|---|---|---|
| 108 | 1.46(9H, s), 6.46(1H, s), 7.18–7.69(8H, m), 8.35–8.38(1H, m), 10.99(1H, s), | 3400, 2970, 2910, 1630, 1570, 1450. |
| 109 | 1.40(9H, s), 7.21–7.50(5H, m), 7.73–7.78(2H, m), 7.83(1H, s), 8.12(1H, dd, J=1.4 & 4.4Hz), 8.55(1H, s), 11.22(1H, s). | 3300, 2960, 1625, 1440. |
| 110 | 1.41(9H, s), 6.88(1H, d, J=9.8Hz), 7.28(1H, dd, J=4.6 & 8.0Hz), 7.45(1H, dd, J=1.4 & 8.0Hz), 7.53(1H, d, J=7.8Hz), 8.11(1H, dd, J=1.4 & 4.6Hz), 10.40(1H, s), 10.95(1H, s). | 3400, 2970, 2700, 1600, 1435, 1410. |
| 111 | 1.43(9H, s), 2.07(3H, s), 6.39(1H, s), 6.61–6.72(2H, m), 7.37(1H, dd, J=4.2 & 8.6Hz), 7.45(1H, dd, J=1.4 & 6.8Hz), 8.35(1H, dd, J=1.4 & 4.2Hz), 11.15(1H, s). | 3400, 2975, 2600, 1600, 1575, 1450. |
| 112 | 1.41 & 1.44(comb. 9H, each s), 4.4 & 4.61(comb. 2H, each d, botjh J=5.0Hz), 6.82–7.45(5H, m), 8.09–8.12 & 8.32–8.35(comb. 1H, each m), 11.12 & 11.13 (comb. 1H, each s). | 3400, 3150, 2970, 1435. |

TABLE 40

| Cpd. No. | ¹H-NMR (CDCl₃; TMS internal standard, ppm) | IR (KBr; cm⁻¹) |
|---|---|---|
| 113 | 1.42&1.59(comb. 9H, each s), 2.04&2.11(comb. 3H, each s), 6.91–7.54 (5H, m), 8.10&8.32(comb. 1H, each dd, both J=1.6&4.6Hz), 10.99&11.12 (comb. 1H, each s). | 3400, 3050, 2970, 1650, 1560, 1490, 1435. |
| 114 | 1.43(9H, s), 2.23(3H, s), 6.37(1H, s), 6.50(1H, d, J=10.6Hz), 6.82(1H, d, J=6.8Hz), 7.36–7.47(2H, m), 8.3–8.4(1H, m), 10.73(1H, s). | 3400, 2970, 2600, 1575, 1500, 1450. |
| 115 | 1.43(9H, s), 2.90(1H, s), 6.96(1H, d, J=8.4Hz), 7.04(1H, d, J=2.0Hz), 7.35–7.50(3H, m), 8.33(1H, dd, J=1.4&4.4Hz). | 3430, 3250, 2960, 2550, 2100, 1595, 1575, 1485. |
| 116 | 0.19&0.22(comb. 9H, each s), 1.41&1.43(comb. 9H, each s), 6.93–7.49 (6H, m), 8.13&8.35(comb. 1H, each dd, in order J=1.4&4.4Hz, J=1.6&4.2Hz). | 3400, 2960, 2600, 2150, 1600, 1485, 1440. |
| 117 | 1.46(9H, s), 7.14(1H, d, J=8.6Hz), 7.43(1H, dd, J=4.4&8.4Hz), 7.48–7.53(2H, m), 7.83(1H, dd, J=2.&8.6Hz), 8.36(1H, dd, J=1.8&4.4Hz), 9.75(1H, s). | 3400, 2970, 2600, 1690, 1590. |
| 118 | *1.26(9H, s), 3.92(3H, s), 6.74(1H, s), 7.09(1H, d, J=8.8Hz), 7.42(1H, dd, J=6.2& 8.8Hz), 7.74(1H, s), 8.02(1H, d, J=6.2Hz), 11.15(1H, br. s), 12.54(1H. br. s). | 3400, 2970, 2600, 1620, 1525, 1440, 1360, 1260, 1200, 1150. |
| 119 | *1.25(9H, s), 7.04(1H, d, J=8.6Hz), 7.12(1H, s), 7.32(1H, s), 7.38(1H, dd, J=6.4& 8.6Hz), 7.96(1H, d, J=6.4Hz), 11.02(1H, br. s), 11.48(1H, br. s). | 3400, 3100, 2970, 1605, 1565, 1415. |
| 120 | *1.25(9H, s), 7.03(1H, s), 7.13–7.21(1H, m), 7.39–7.51(2H, m), 8.00–8.06(1H, m), 11.14–11.61(2H, m). | 3400, 2970, 2500, 1570, 1430. |

TABLE 41

| Cpd. No. | ¹H-NMR (CDCl₃; TMS internal standard, ppm) | IR (KBr; cm⁻¹) |
|---|---|---|
| 121 | *1.06(3H, t, J=7.0Hz), 1.24(9H, s), 3.42–3.47(2H, m), 3.84(3H, s), 4.33(1H, br. s), 6.66(1H, s), 6.96(1H, s), 7.02(1H, d, J=8.6Hz), 7.36(1H, dd, J=6.6&8.6Hz), 7.95(1H, d, J=6.6Hz), 10.92(1H, br. s), 11.32(1H, br. s). | 3400, 2960, 2600, 1620, 1425. |
| 122 | *1.25(9H, s), 7.04(1H, dJ=8.8Hz), 7.13(1H, s), 7.20(1H, s), 7.38(1H, dd, J=6.6& J=6.6&8.8Hz), 7.97(1H, d, J=6.6Hz), 10.98(1H, s), 11.49(1H, s). | 3400, 3100, 2960, 2500, 1610, 1565, 1425. |
| 123 | *1.26(9H, s), 6.89–6.94(2H, m), 7.02(1H, d, J=8.6Hz), 7.29(1H, dd, J=2.8&8.8Hz), 7.37(1H, dd, J=6.6&8.6Hz), 7.95(1H, d, J=6.6Hz), 10.94(1H, s), 11.09(1H, s). | 3400, 2970, 2600, 1565, 1475, 1425. |
| 124 | *1.24(9H, s), 6.78(1H, d, J=9.4Hz), 7.13–7.23(3H, m), 7.42(1H, dd, J=6.2&8.6Hz), 8.02(1H, d, J=5.6Hz), 11.13(1H, s). | 3400, 2960, 2520, 1565, 1480, 1400. |
| 125 | *1.24(9H, s), 2.04(3H, s), 2.17(3H, s), 6.55(1H, s), 6.74(1H, s), 6.97(1H, d, J=8.6Hz), 7.33(1H, dd, J=6.4&8.6Hz), 7.91(1H, d, J=6.4Hz), 10.66–10.75(1H, m). | 3400, 3080, 2970, 2600, 1560, 1385, 1305, 1280, 12 |
| 126 | *1.24(9H, s), 2.08(3H, s), 6.80(1H, d, J=8.4Hz), 7.00(1H, d, J=8.4Hz), 7.35(1H, dd, J=6.6&8.4Hz), 7.94(1H, d, J=6.6Hz). | 3430, 2970, 2600, 1610, 1425. |
| 127 | *1.26(9H, s), 2.20(3H, s), 6.57(1H, d, J=10.2Hz), 6.82(1H, d, J=6.6Hz), 7.00(1H, d, J=8.6Hz), 7.35(1H, ddJ=6.4&8.6Hz), 7.93(1H, d, J=6.3Hz), 10.85(1H, s). | 3400, 2960, 2600, 1565, 1425. |
| 128 | 1.45(9H, s), 6.58(1H, s), 7.25(1H, s), 7.30(1H, s), 7.4(1H, dd, J=4.0&8.4Hz), 7.50(1H, dd, J=1.8&8.4Hz), 8.32(1H, dd, J=1.8&4.0H), 12.05(1H, s). | 3400, 2970, 2600, 2225, 1575. |

TABLE 42

| Cpd. No. | $^1$H-NMR (CDCl$_3$; TMS internal standard, ppm) | IR (KBr, cm$^{-1}$) |
|---|---|---|
| 129 | *1.26(9H, s), 7.04(1H, d, J=8.6Hz), 7.34–7.42(2H, m), 7.50(1H, s), 7.96(1H, d, J=6.0Hz), 11.01(1H, s), 11.64(1H, s). | |
| 130 | 1.46(9H, s), 6.54(1H, s), 7.11(1H, s), 7.31(1H, s), 7.44(1H, dd, J=4.2&8.4Hz), 7.51(1H, dd, J=1.8&8.4Hz), 8.33(1H, dd, J=1.8&4.2Hz), 11.99(1H, s) | 3350, 2975, 2590, 2230, 1565, 1480, 1455, 1365, 1320, 1295. EI-MS; 345(M$^+$). |
| 131 | 1.41(9H, s), 7.31(1H, dd, J=4.6&8.6Hz), 7.39(1H, s), 7.46(1H, s), 7.48(1H, dd, J=1.6&8.6Hz), 8.12(1H, dd, J=1.6&4.6Hz), 10.2–10.3(1H, br. s), 10.70(1H, s). | 3400, 2970, 2230, 1580, 1480, 1440, 1390, 1360, 1290, 1240, |
| 132 | *1.26(9H, s), 7.03(1H, d, J=8.4Hz), 7.37(1H, dd, J=6.4&8.4Hz), 7.385(1H, s), 7.39(1H, s), 7.95(1H, d, J=6.4Hz). | 3420, 2970, 2230, 1565, 1480, 1425, 1365, 1240, 1205, 1030. |
| 133 | *1.24(9H, s), 7.12(1H, d, J=8.4Hz), 7.31(1H, s), 7.39(1H, dd, J=6.2&8.4Hz), 7.41(1H, s), 8.00(1H, d, J=6.2Hz). | 3420, 3120, 2980, 2230, 1575, 1470, 1440, 1360, 1315, 1255, 1200, 1020. |

*measured with DMSO-d$_6$

TABLE 43

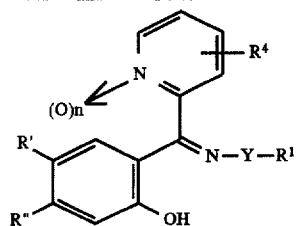

| Cpd. No. | R' | R" | R$^1$ | R$^4$ | Y | n | geometrical isomerism | Formula | m.p. (°C.) physical property |
|---|---|---|---|---|---|---|---|---|---|
| 72 | H | H | t-Bu | H | O | 0 | E | C$_{16}$H$_{18}$N$_2$O$_2$ | 76–77 |
| 73 | CF$_3$ | H | t-Bu | H | O | 0 | E + Z | C$_{17}$H$_{17}$F$_3$N$_2$O$_2$ | 172–176 |
| 74 | CF$_3$ | H | t-Bu | 3-OMe | O | 0 | E + Z | C$_{18}$H$_{19}$F$_3$N$_2$O$_3$ | 113–114 |
| 75 | Br | H | t-Bu | H | O | 0 | Z | C$_{16}$H$_{17}$BrN$_2$O$_2$ | 118–119 |
| 76 | CN | H | t-Bu | H | O | 0 | Z | C$_{17}$H$_{17}$N$_3$O$_2$.3/4H$_2$O | 141–142 |
| 77 | Cl | Cl | t-Bu | H | O | 0 | Z | C$_{16}$H$_{16}$Cl$_2$N$_2$O$_2$ | 96–97.5 |
| 78 | Br | H | t-Bu | 3-Cl | O | 0 | Z | C$_{16}$H$_{16}$BrClN$_2$O$_2$ | 155–156 |
| 79 | Br | H | t-Bu | 3-Me | O | 0 | Z | C$_{17}$H$_{19}$BrN$_2$O$_2$ | oil |
| 80 | Br | H | t-Bu | 3,5-diCl | O | 0 | Z | C$_{16}$H$_{15}$BrCl$_2$N$_2$O$_2$ | 150–152 |
| 81 | Br | H | t-Bu | 3-Br | O | 0 | Z | C$_{16}$H$_{16}$Br$_2$N$_2$92 | 171–172 |
| 82 | F | F | t-Bu | H | O | 0 | Z | C$_{16}$H$_{16}$F$_2$N$_2$O$_2$ | 107–107.5 |
| 83 | F | Cl | t-Bu | H | O | 0 | Z | C$_{16}$H$_{16}$ClFN$_2$O$_2$ | 99–100.5 |
| 84 | F | Cl | t-Bu | H | O | 0 | E | C$_{16}$H$_{16}$ClFN$_2$O$_2$ | 135.5–137 |
| 85 | Br | Cl | t-Bu | H | O | 0 | Z | C$_{16}$H$_{16}$BrClN$_2$O$_2$ | 170–172 |
| 86 | Br | Cl | t-Bu | H | O | 0 | E | C$_{16}$H$_{16}$BrClN$_2$O$_2$ | 161–163 |
| 87 | NO$_2$ | H | t-Bu | H | O | 0 | Z | C$_{16}$H$_{17}$N$_3$O$_4$ | 213–215 |
| 88 | Br | H | t-Bu | H | CH$_2$ | 0 | Z | C$_{17}$H$_{19}$BrN$_2$O | 127–128 |
| 89 | Br | H | t-Bu | H | O | 1 | Z | C$_{16}$H$_{17}$BrN$_2$O$_3$ | 165–166 |
| 90 | CF$_3$ | H | t-Bu | H | O | 1 | E + Z | C$_{17}$H$_{17}$F$_3$N$_2$O$_3$ | 203–205 |

TABLE 44

| Cpd. No. | R' | R" | R$^1$ | R$^4$ | Y | n | geometrical isomerism | Formula | m.p. (°C.) physical property |
|---|---|---|---|---|---|---|---|---|---|
| 91 | CF$_3$ | H | t-Bu | 3-OMe | O | 1 | E + Z | C$_{18}$H$_{19}$F$_3$N$_2$O$_4$ | 183–185 |
| 92 | NO$_2$ | H | t-Bu | H | O | 1 | Z | C$_{16}$H$_{17}$N$_3$O$_5$ | 236–237 |
| 93 | F | H | t-Bu | H | O | 1 | Z | C$_{16}$H$_{17}$FN$_2$O$_3$ | 175–176.5 |
| 94 | CN | H | t-Bu | H | O | 1 | Z | C$_{17}$H$_{17}$N$_3$O$_3$.¼H$_2$O | 216–218 |
| 95 | Cl | Cl | t-Bu | H | O | 1 | Z | C$_{16}$H$_{16}$Cl$_2$N$_2$O$_3$ | 166–168 |
| 96 | Br | H | t-Bu | 3-Cl | O | 1 | Z | C$_{16}$H$_{16}$BrClN$_2$O$_3$ | 167–169 |

TABLE 44-continued

| Cpd. No. | R' | R" | R$^1$ | R$^4$ | Y | n | geometrical isomerism | Formula | m.p. (°C.) physical property |
|---|---|---|---|---|---|---|---|---|---|
| 97 | Br | H | t-Bu | 3-Me | O | 1 | Z | C$_{17}$H$_{19}$BrN$_2$O$_3$ | 164–166 |
| 98 | Br | H | t-Bu | 3-Br | O | 1 | Z | C$_{16}$H$_{16}$Br$_2$N$_2$O$_3$ | 183–184 |
| 99 | Br | H | t-Bu | 3,4-diCl | O | 1 | Z | C$_{16}$H$_{15}$BrCl$_2$N$_2$O$_3$ | 170–171 |
| 100 | F | F | t-Bu | H | O | 1 | Z | C$_{16}$H$_{16}$F$_2$N$_2$O$_3$ | 192–193 |
| 101 | Br | Cl | t-Bu | H | O | 1 | Z | C$_{16}$H$_{16}$BrClN$_2$O$_3$ | 175–176 |
| 102 | Br | Cl | t-Bu | H | O | 1 | E | C$_{16}$H$_{16}$BrClN$_2$O$_3$ | 163–164.5 |
| 103 | F | Cl | t-Bu | H | O | 1 | Z | C$_{16}$H$_{16}$ClFN$_2$O$_3$ | 181–182 |
| 104 | F | Cl | t-Bu | H | O | 1 | E | C$_{16}$H$_{16}$ClFN$_2$O$_3$·¼H$_2$O | 216–220 |
| 105 | Br | H | t-Bu | H | CH$_2$ | 1 | Z | C$_{17}$H$_{19}$BrN$_2$O$_2$ | 157–158 |

TABLE 45

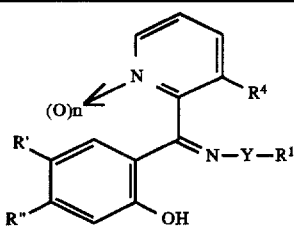

| Cpd. No. | R' | R" | R$^1$ | R$^4$ | Y | n | geometrical isomerism | Formula | m.p. (°C.) physical property |
|---|---|---|---|---|---|---|---|---|---|
| 134 | Br | H | t-Bu | 1,3-dioxolan-2-yl | O | 0 | Z | C$_{19}$H$_{21}$BrN$_2$O$_4$ | 175–177 |
| 135 | Br | H | t-Bu | CHO | O | 0 | Z | C$_{17}$H$_{17}$BrN$_2$O$_3$ | 120–121 |
| 136 | Br | H | t-Bu | CH$_2$OH | O | 0 | Z | C$_{17}$H$_{19}$BrN$_2$O$_3$ | 189–190 |
| 137 | Br | H | t-Bu | CH$_2$F | O | 0 | Z | C$_{17}$H$_{18}$BrFN$_2$O$_2$ | 134–135 |
| 138 | Br | H | t-Bu | CO$_2$H | O | 0 | Z | C$_{17}$H$_{17}$BrN$_2$O$_4$ | amorph. |
| 139 | Br | H | t-Bu | CO$_2$Et | O | 0 | Z | C$_{19}$H$_{21}$BrN$_2$O$_4$ | 113–114 |
| 140 | Br | H | t-Bu | CH$_2$=CH | O | 0 | Z | C$_{18}$H$_{19}$BrN$_2$O$_2$ | 108–109 |
| 141 | Br | H | t-Bu | CHF$_2$ | O | 0 | Z | C$_{17}$H$_{17}$BrF$_2$N$_2$O$_2$ | 118–120 |
| 142 | Br | H | t-Bu | CH=NOH | O | 0 | Z | C$_{17}$H$_{18}$BrN$_3$O$_3$ | 213.5–214.5 |
| 143 | Br | H | t-Bu | CN | O | 0 | Z | C$_{17}$H$_{16}$BrN$_3$O$_2$ | 149–150 |
| 144 | Br | H | t-Bu | CONH$_2$ | O | 0 | Z | C$_{17}$H$_{18}$BrN$_3$O$_3$ | 211(dec.) |
| 145 | Br | H | t-Bu | CN | O | 1 | Z | C$_{17}$H$_{16}$BrN$_3$O$_3$ | 164–165 |
| 146 | Br | H | t-Bu | CF$_3$ | O | 0 | Z | C$_{17}$H$_{16}$BrF$_3$N$_2$O$_2$ | 122.5–123 |
| 147 | Cl | H | t-Bu | Cl | O | 0 | Z | C$_{16}$H$_{16}$Cl$_2$N$_2$O$_2$ | 147–149 |
| 148 | Br | H | t-Bu | F | O | 0 | Z | C$_{16}$H$_{16}$BrFN$_2$O$_2$ | 115.5–116 |
| 149 | Br | H | t-Bu | F | O | 0 | E | C$_{16}$H$_{16}$BrFN$_2$O$_2$ | 137–138 |
| 150 | Cl | H | t-Bu | CN | O | 0 | Z | C$_{17}$H$_{16}$ClN$_3$O$_2$ | 141–142 |
| 151 | Cl | H | t-Bu | CN | O | 0 | E | C$_{17}$H$_{16}$ClN$_3$O$_2$ | 158.5–159 |
| 152 | Cl | H | t-Bu | CONH$_2$ | O | 0 | Z | C$_{17}$H$_{18}$ClN$_3$O$_3$ | 198–201 |
| 153 | Me | H | t-Bu | CN | O | 0 | Z | C$_{18}$H$_{19}$N$_3$O$_2$ | 130–131 |
| 154 | Me | H | t-Bu | CN | O | 0 | E | C$_{18}$H$_{19}$N$_3$O$_2$ | oil |
| 155 | Cl | F | t-Bu | CHO | O | 0 | Z | C$_{17}$H$_{16}$ClFN$_2$O$_3$ | amorph. |
| 156 | Cl | F | t-Bu | CN | O | 0 | Z | C$_{17}$H$_{15}$ClFN$_3$O$_2$ | 111–113 |

TABLE 46

| Cpd. No. | $^1$H-NMR (CDCl$_3$; TMS internal standard, ppm) | IR (KBr; cm$^{-1}$) |
|---|---|---|
| 72 | 1.32(9H, s), 6.67–6.77(2H, m), 7.02(1H, d, J=7.8Hz), 7.19–7.41(3H, m), 7.82(1H, dt, J=1.6&7.8Hz), 8.75–8.78(1H, m), 11.26(1H, br. s). | 2970, 1620, 1585, 1560, 1460, 1435, 1360, 1250, 1240, 1180, 1150, 1005. |
| 74 | 1.31(9H, s), 3.83(3H, s), 6.95(1H, br. s), 7.07(1H, d, J=8.8Hz), 7.32–7.48(3H, m), 8.35–8.37(1H, m), 11.72(1H, br. s). | 2985, 1625, 1600, 1460, 1365, 1340, 1320, 1295, 1280, 1160, 1130, 1100, 1075, 1005. |
| 75 | 1.32(9H, s), 6.82(1H, d, J=2.4Hz), 6.90(1H, d, J=8.6Hz), 7.28–7.42 (3H, m), 7.83(1H, dt, J=1.8&8.0Hz), 8.76(1H, m), 11.30(1H, br. s). | 2960, 2920, 1610, 1580, 1560, 1470, 1360, 1280, 1245, 1040, 1005. |

TABLE 46-continued

| Cpd. No. | ¹H-NMR (CDCl₃; TMS internal standard, ppm) | IR (KBr; cm⁻¹) |
|---|---|---|
| 76 | 1.34(9H, s), 7.07(1H, d, J=8.6Hz), 7.12(1H, d, J=2.0Hz), 7.04–7.53 (3H, m), 7.87(1H, dt, J=1.8&7.8Hz), 8.77–8.80(1H, m), 12.00(1H, br. s). | 2970, 2925, 2220, 1610, 1595, 1585, 1485, 1360, 1295, 1265, 1040, 1015. |
| 77 | 1.32(9H, s), 6.81(1H, s), 7.12(1H, s), 7.26–7.44(2H, m), 7.84(1H, dt, J=1.8&8.0Hz), 8.74–8.78(1H, m). | 2980, 1615, 1580, 1560, 1460, 1430, 1365 1325, 1265, 1225, 1180, 1130, 1040, 1010. |
| 78 | 1.32(9H, s), 6.65(1H, d, J=2.2Hz), 6.93(1H, d, J=8.6Hz), 7.30–7.42 7.85(1H, dd, J=1.4&8.2Hz), 8.67(1H, dd, J=1.4&4.6Hz). | 3060, 2990, 1615, 1590, 1570, 1475, 1425, 1365, 1280, 1250, 1015. |
| 79 | 1.31(9H, s), 2.21(3H, s), 6.62(1H, d, J=2.4Hz), 6.68(1H, d, J=8.8Hz), 7.27–7.35(2H, m), 7.63–7.66(1H, m), 8.56–8.58(1H, m), 11.22(1H, br. s). | 3400, 3100, 2980, 1580, 1490, 1475, 1365, 1280, 1245, 1180, 1165, 1010. |
| 80 | 1.32(9H, s), 6.63(1H, d, J=2.4Hz), 6.94(1H, d, J=8.8Hz), 7.34(1H, dd, J=2.4&8.8Hz), 7.88(1H, d, J=2.2Hz), 8.63(1H, d, J=2.2Hz). | 3060, 2980, 2900, 1615, 1590, 1560, 1475, 1430, 1365, 1280, 1250, 1175, 1065, 1010. |
| 81 | 1.33(9H, s), 6.63(1H, d, J=2.4Hz), 6.934(1H, d, J=8.8Hz), 7.27–7.35 (2H, m), 8.02(1H, dd, J=1.4&8.2Hz), 8.71(1H, dd, J=1.4&4.6Hz). | 3450, 2980, 1570, 1475, 1365, 1280, 1250, 1010. |

TABLE 47

| Cpd. No. | ¹H-NMR (CDCl₃; TMS internal standard, ppm) | IR (KBr; cm⁻¹) |
|---|---|---|
| 82 | 1.32(9H, s), 6.57(1H, dd, J=8.8&11.6Hz), 6.80(1H, dd, J=7.0&11.6Hz), 7.26–7.43(2H, m), 7.83(1H, dt, J=1.6&7.6Hz), 8.74–8.77(1H, m), 11.34(1H, s). | 2990, 1635, 1615, 1590, 1565, 1520, 1465, 1440, 1390, 1365, 1350, 1300, 1260, 1205, 1185, 1160, 1130, 1040, 1010. |
| 83 | 1.32(9H, s), 6.54(1H, d, J=10.2Hz), 7.04(1H, d, J=6.4Hz), 7.36–7.44 (2H, m), 7.83(1H, dt, J=1.8&7.8Hz), 8.74–8.77(1H, m), 11.20(1H, s). | 3450, 2980, 1620, 1590, 1495, 1465, 1365, 1195, 1035, 1005. |
| 84 | 1.38(9H, s), 7.02(1H, d, J=9.8Hz), 7.10(1H, d, J=6.6Hz), 7.37(1H, q, J=4.6Hz), 7.83–7.84(2H, m), 8.49–8.52(1H, m), 10.88(1H, s). | 2980, 2550, 1600, 1485, 1425, 1380, 1360, 1190. |
| 86 | 1.38(9H, s), 7.19(1H, s), 7.34–7.41(1H, m), 7.47(1H, s), 7.82–7.86 (2H, m), 8.49–8.52(1H, m). | |
| 88 | 0.97(9H, s), 3.07(2H, s), 6.75(1H, d, J=2.4Hz), 6.80(1H, d, J=8.8Hz), 7.37(1H, dt, J=1.0&7.6Hz), 7.35(1H, dd, J=2.4&8.8Hz), 7.46(1H, m), 7.90(1H, dt, J=1.6&7.6Hz), 8.81(1H, m). | 2960, 1610, 1580, 1480. |
| 89 | 1.33(9H, s), 6.86(1H, d, J=2.4Hz), 6.92(1H, d, J=8.8Hz), 7.23–7.26 (1H, m), 7.33(1H, dd, J=2.4&8.8Hz), 7.38–7.43(2H, m), 8.35–8.38(1H, m), | 3060, 2980, 1615, 1585, 1470, 1420, 1265, 1250, 1160, 1000. |
| 90 | 1.31&1.34(comb. 9H, each s), 7.02–7.13(1H, m), 7.23–7.28(2H, m), 7.33–7.64(3H, m), 8.25–8.39(1H, m), 10.10&11.29(comb. 1H, each s). | |
| 91 | 1.33(9H, s), 3.84(3H, s), 6.97(1H, d, J=8.8Hz), 7.06–7.11(2H, m), 7.31–7.39(1H, m), 7.46–7.50(1H, m), 8.05(1H, d, J=6.6Hz). | 3075, 2975, 1615, 1600, 1555, 1425, 1365, 1350, 1315, 1280, 1260, 1230, 1160, 1105, 1090, 1070, 1010. |

TABLE 48

| Cpd. No. | ¹H-NMR (CDCl₃; TMS internal standard, ppm) | IR (KBr; cm⁻¹) |
|---|---|---|
| 92 | 1.35(9H, s), 7.09)1H, d, J=9.0Hz), 7.29–7.32(1H, m), 7.44–7.48(2H, m), 7.76(1H, d, J=2.6Hz), 8.16(1H, dd, J=2.6&9.0Hz), 8.36–8.40(1H, m). | 3090, 2970, 1595, 1485, 1430, 1320, 1300, |
| 93 | 1.33(9H, s), 6.44–6.50(1H, m), 6.96–6.99(2H, m), 7.23–7.28(1H, m), 7.39–7.43(2H, m), 8.37–7.41(1H, m). | 3080, 2960, 1630, 1565, 1490, 1480, 1420, 1360, 1265, 1245, 1230, 1180, 1145, 1000. |
| 94 | 1.34(9H, s), 7.06–7.11(2H, m), 7.23–7.28(1H, m), 7.42–7.47(2H, m), 7.52(1H, dd, J=2.0&8.6Hz), 8.35–8.39(1H, m), 11.50(1H, br. s). | 2970, 2400, 2220, 1600, 1500, 1420, 1200, 1180, 1120. |
| 95 | 1.32(9H, s), 6.82(1H, s), 7.13(1H, s), 7.21–7.24(1H, m), 7.38–7.43 (2H, m), 8.33–8.37(1H, m). | 2970, 2400, 1590, 1420, 1380, 1360, 1320, 1280, 1270, 1220, 1185, 1160, 1130. |
| 96 | 1.34(9H, s), 6.83(1H, d, J=2.4Hz), 6.93(1H, d, J=8.8Hz), 7.30–7.37 (2H, m), 7.43(1H, dd, J=1.2&8.4Hz), 8.26(1H, dd, J=1.2&6.2Hz). | 3440, 3110, 3070, 2980, 1615, 1585, 1480, 1410, 1365, 1285, 1270, 1165, 1010. |
| 97 | 1.33(9H, s), 2.15(3H, s), 6.85(1H, d, J=2.4Hzx), 6.92(1H, d, J=8.8Hz), 7.21–7.38(3H, m), 8.21(1H, m), 10.94(1H, br. s). | 3430, 3080, 3060, 2980, 1610, 1600, 1585, 1470, 1365, 1290, 1275, 1175, 1160, 1050. |
| 98 | 1.35(9H, s), 6.85(1H, d, J=2.4Hz), 6.94(1H, d, J=8.8Hz), 7.24–7.31 (1H, m), 7.35(1H, dd, J=2.4&8.8Hz), 7.58(1H, dd, J=1.0&8.4Hz), 8.30(1H, dd, J=1.0&6.6Hz), 10.63(1H, br. s). | 3430, 2980, 1615, 1595, 1475, 1410, 1365, 1275, 1265. |
| 99 | 1.35(9H, s), 6.79(1H, d, J=2.4Hz), 6.93(1H, d, J=8.8Hz), 7.35(1H, dd, J=2.4&8.8Hz), 7.43(1H, d, J=1.4Hz), 8.28(1H, d, J=1.4Hz). | 3430, 3070, 2975, 1590, 1580, 1535, 1465, 1365, 1280, 1160, 1010. |
| 100 | 1.32(9H, s), 6.57(1H, dd, J=8.8&11.2Hz), 6.82(1H, dd, J=6.8&11.2Hz), 7.21–7.25(1H, m), 7.37–7.42(1H, m), 8.33–8.37(1H, m), 10.86(1H, s). | 2980, 1640, 1620, 1520, 1480, 1425, 1250, 1200, 1185, 1130, 1010. |

TABLE 49

| Cpd. No. | ¹H-NMR (CDCl₃; TMS internal standard, ppm) | IR (KBr; cm⁻¹) |
|---|---|---|
| 101 | 1.32(9H, s), 6.98(1H, s), 7.15(1H, s), 7.22–7.25(1H, m), 7.36–7.47 (2H, m), 8.35–8.38(1H, m). | 3430, 2980, 2430, 1585, 1490, 1420, 1220. |
| 102 | 1.32(9H, s), 7.11(1H, s), 7.19(1H, s), 7.38–7.54(3H, m), 8.28–8.31 (1H, m). | 3060, 2975, 1720, 1580, 1420, 1210, 1050. |
| 103 | 1.33(9H, s), 6.55(1H, d, J=9.8Hz), 7.06(1H, d, J=6.2Hz), 7.22–7.24 (1H, m), 7.38–7.43(2H, m), 8.33–8.37(1H, m), 10.71(1H, s). | 2975, 2500, 1600, 1505, 1420, 1185. |
| 104 | 1.25(9H, s), 6.94(1H, d, J=6.6Hz), 7.14–7.19(2H, m), 7.42(1H, dd, J=6.6&8.8Hz), 8.01–8.04(1H, m), 11.24(1H, br. s). | 3400, 2990, 2520, 1620, 1575, 1490, 1480, 1430, 1360, 1210, 1025. |
| 105 | 1.00(9H, s), 2.92&3.32(2H, ABq, J=14.4Hz), 6.81(1H, d, J=2.2Hz), 6.92(1H, d, J=8.8Hz), 7.22&7.35–7.52(3H, m), 8.37(1H, m). | 2960, 1610, 1480. |

TABLE 50

| Cpd. No. | ¹H-NMR (CDCl₃; TMS internal standard, ppm) | IR (KBr; cm⁻¹) |
|---|---|---|
| 134 | 1.30(9H, s), 3.86–4.14(4H, m), 5.72(1H, s), 6.68(1H, d, J=2.6Hz), 6.90(1H, d, J=8.8Hz), 7.30(1H, dd, J=2.6&8.8Hz), 7.44(1H, dd, J=4.8&8.0Hz), 8.03(1H, dd, J=1.6&8.0Hz), 8.74(1H, dd, J=1.6&4.8Hz), 11.13(1H, s). | 3600–3300, 2980, 1580, 1480. |
| 135 | 1.28(9H, s), 6.75(1H, d, J=2.4Hz), 6.96(1H, d, J=8.8Hz), 7.36(1H, dd, J=2.4&8.8Hz), 7.61(1H, m), 8.38(1H, dd, J=1.8&8.0Hz), 8.99(1H, dd, J=1.8&4.8Hz), 9.89(1H, s), 10.96(1H, s). | 3600–3300, 2980, 1700, 1480. |
| 136 | 1.32(9H, s), 2.12(1H, dd, J=5.2&7.2Hz), 4.50(1H, dd, J=7.2&13.2Hz), 4.59(1H, dd, J=5.2&13.2Hz), 6.63(1H, d, J=2.4Hz), 6.92(1H, d, J=8.8Hz), 7.33(1H, dd, J=2.4&8.8Hz), 7.47(1H, dd, J=4.8&8.0Hz), 8.00(1H, dd, J=1.6&8.0Hz), 8.71(1H, dd, J=1.6&4.8Hz), 11.08(1H, s). | 3600–3300, 2980, 1580, 1460. |
| 137 | 1.31(9H, s), 5.17(1H, dd, J=11.8&47.2Hz), 6.65(1H, d, J=2.6Hz), 6.92(1H, d, J=8.8Hz), 7.32(1H, dd, J=2.6&7.7Hz), 7.49(1H, dd, J=4.8&7.6Hz), 7.94–7.99(1H, m), 8.75(1H, m), 11.03(1H, s). | 3600–3300, 2980, 1580, 1470. |
| 138 | 1.23(9H, s), 6.70(1H, d, J=2.2Hz), 6.92(1H, dJ=8.8Hz), 7.31(1H, dd, J=2.&8.8Hz), 7.53(1H, dd, J=4.8&8.0Hz), 8.42(1H, dd, J=1.6&8.0Hz), 8.93(1H, dd, J=1.6&4.8Hz), 9.4–11.6(2H, br. s). | 3600–3300, 2980, 1720, 1580, 1470. EI-MS; 394(M+1), 392(M−1). |
| 139 | 1.16(3H, t, J=7.2Hz), 1.24(9H, s), 4.23(2H, q, J=7.2Hz), 6.74(1H, d, J=2.4Hz), 6.92 (1H, d, J=8.8Hz), 7.31(1H, dd, J=2.4&8.8Hz), 7.51(1H, dd, J=4.8&8.0Hz), 8.40(1H, dd, J=1.8&8.0Hz), 8.89(1H, dd, J=1.8&4.8Hz), 11.10(1H, s). | 3600–3300, 2980, 1725, 1475, 1280. |

TABLE 51

| Cpd. No. | ¹H-NMR (CDCl₃; TMS internal standard, ppm) | IR (KBr; cm⁻¹) |
|---|---|---|
| 140 | 1.29(9H, s), 5.36(1H, d, J=11.0Hz), 5.81(1H, d, J=17.2Hz), 6.52(1H, dd, J=11.0&17.2Hz), 6.65(1H, d, J=2.4Hz), 6.91(1H, d, J=8.8Hz), 7.30(1H, dd, J=2.4&8.8Hz), 7.39(1H, dd, J=4.8&8.0Hz), 8.00(1H, dd, J=1.4&8.0Hz), 8.64(1H, dd, J=1.6&4.8Hz), 11.19(1H, s). | 3600–3300, 2980, 1470. |
| 141 | 1.31(9H, s), 6.53(1H, t, J=55.0Hz), 6.63(1H, d, J=2.4Hz), 6.93(1H, d, J=8.8Hz), 7.34(1H, dd, J=2.4&8.8Hz), 7.56(1H, dd, J=4.8&8.0Hz), 8.13(1H, m), 8.88(1H, br. d, J=4.8Hz), 10.90(1H, s). | 3600–3300, 2980, 1570, 1470. |
| 142 | 1.30(9H, s), 6.70(1H, d, J=2.2Hz), 6.92(1H, d, J=8.8Hz), 7.33(1H, dd, J=2.2&8.8Hz), 7.46(1H, dd, J=4.8&8.0Hz), 7.91(1H, s), 8.29(1H, dd, J=1.6&8.0Hz), 8.77(1H, dd, J=1.6&4.8Hz). | 3600–3300, 3160, 3070, 2980, 2860, 2790, 1470. |
| 143 | 1.36(9H, s), 6.63(1H, d, J=2.2Hz), 6.96(1H, d, J=8.8Hz), 7.35(1H, dd, J=2.2&8.8Hz), 7.57(1H, dd, J=5.2&8.0Hz), 8.15(1H, dd, J=1.8&8.0Hz), 8.98(1H, dd, J=1.8&5.2Hz), 9.6–11.4(1H, br. s). | 3600–3300, 3060, 2980, 2240, 1565, 1480. |
| 144 | 1.32(9H, s), 5.4–5.8&6.1–6.4(comb. 2H, each br. s), 6.67(1H, d, J=2.6Hz), 6.92 (1H, d, J=8.8Hz), 7.34(1H, dd, J=4.8&8.0Hz), 8.20(1H, dd, J=1.8&8.0Hz), 8.86(1H, dd, J=1.8&4.8Hz), 10.89(1H, s). | 3420, 3250–3100, 2980, 1670. |
| 145 | 1.37(9H, s), 6.77(1H, d, J=2.4Hz), 6.96(1H, d, J=8.8z), 7.38(1H, dd, J=2.4&8.8Hz), 7.53(1H, dd, J=6.6&8.0Hz), 7.65(1H, dd, J=1.2&8.0Hz), 8.49(1H, dd, J=1.2&6.6Hz), 10.38(1H, br. s). | 3600–3300, 2970, 2240, 1420. |

TABLE 52

| Cpd. No. | ¹H-NMR (CDCl₃; TMS internal standard, ppm) | IR (KBr; cm⁻¹) |
|---|---|---|
| 146 | 1.28(9H, s), 6.53(1H, d, J=2.6Hz), 6.92(1H, d, J=8.8Hz), 7.32(1H, dd, J=2.6&8.8Hz), 7.57(1H, m), 8.13(1H, dd, J=1.0&8.0Hz), 8.95(1H, dd, J=1.0&4.8Hz), 10.94(1H, s). | 3600–3300, 2980, 1470. 1470. |
| 147 | 1.32(9H, s), 6.51(1H, d, J=2.6Hz), 6.97(1H, d, J=8.8Hz), 7.19(1H, dd, J=2.6&8.8Hz), 7.38(1H, dd, J=4.8&8.2Hz), 7.84(1H, dd, J=1.4&8.2Hz), 8.66(1H, dd, J=1.4&4.8Hz), 10.8–11.2(1H, br. s). | 3600–3300, 2970, 1560, 1470. |
| 148 | 1.32(9H, s), 6.81(1H, d, J=2.6Hz), 6.923(1H, d, J=8.6Hz), 7.33(1H, dd, J=2.6&8.6Hz), 7.46(1H, dt, J=4.4&8.6Hz), 7.56(1H, dt, J=1.6&8.6Hz), 8.60(1H, dt, J=1.6&4.4Hz), 11.06(1H, s). | 3600–3300, 2970, 1580, 1470, 1450. |
| 149 | 1.39(9H, s), 6.94(1H, d, J=8.8Hz), 7.21(1H, d, J=2.6Hz), 7.34–7.42(2H, m), 7.58(2H, dt, J=1.4&8.8Hz), 8.40(1H, dt, J=1.4&4.6Hz), 9.47(1H, s). | 3600–3300, 2970, 1600, 1440, 1410. |
| 150 | 1.37(9H, s), 6.47(1H, d, J=2.4Hz), 7.00(1H, d, J=8.8Hz), 7.22(1H, dd, J=2.4&8.8Hz), 7.57(1H, dd, J=4.8&8.0Hz), 8.15(1H, dd, J=1.8&8.0Hz), 8.98(1H, dd, J=1.8&4.8Hz), 10.80(1H, s). | 3600–3300, 3070, 2970, 2240, 1470, 1440. |
| 151 | 1.47(9H, s), 7.02(1H, d, J=8.8Hz), 7.05(1H, d, J=2.6Hz), 7.30(1H, dd, J=2.6&8.8Hz), 7.49(1H, dd, J=4.8&8.0Hz), 8.16(1H, dd, J=1.8&7.0Hz), 8.57(1H, s), 8.74(1H, d, J=1.8&4.8Hz). | 3600–3100, 2990, 2970, 2250, 1570, 1490, 1410. |
| 152 | 1.32(9H, s), 5.5–5.7&6.1–6.3(comb. 1H, each br. s), 6.52(1H, d, J=2.6Hz), 6.97 (1H, d, J=8.8Hz), 7.20(1H, dd, J=2.6&8.8Hz), 7.52(1H, dd, J=4.8&7.8Hz), 8.19(1H, dd, J=1.8&7.8Hz), 8.86(1H, dd, J=1.8&4.8Hz), 10.86(1H, s). | 3600–3300, 3170, 2970, 1690, 1480. |

TABLE 53

| Cpd. No. | ¹H-NMR (CDCl₃; TMS internal standard, ppm) | IR (KBr; cm⁻¹) |
|---|---|---|
| 153 | 1.36(9H, s), 2.12(3H, s), 6.27(1H, m), 6.95(1H, d, J=8.2Hz), 7.08(1H, dd, J=1.8&8.2Hz), 7.54(1H, dd, J=4.8&8.0Hz), 8.13(1H, dd, J=1.8&8.0Hz), 8.97(1H, dd, J=1.8&4.8Hz), 10.6(1H, s). | 3600–3300, 2980, 2230, 1480. |
| 154 | 1.47(9H, s), 2.23(3H, s), 6.76(1H, br. d, J=2.2Hz), 6.98(1H, d, J=8.4Hz), 7.16(1H, dd, J=2.2&8.4Hz), 7.44(1H, dd, J=4.8&8.0Hz), 7.89(1H, s), 8.13(1H, dd, J=1.8&8.0Hz), 8.74(1H, dd, J=1.8&4.8Hz). | 3600–3300, 2980, 2230, 1580. |
| 155 | 1.28(9H, s), 6.68(1H, d, J=8.0Hz), 6.87(1H, d, J=10.4Hz), 7.61(1H, m), 8.37(1H, dd, J=1.8&8.0Hz), 8.98(1H, dd, J=1.8&4.8Hz), 9.89(1H, s), 11.20(1H, br. s). | |
| 156 | 1.36(9H, s), 6.56(1H, d, J=8.0Hz), 6.86(1H, d, J=10.4Hz), 7.58(1H, dd, J=4.8&8.0Hz), 8.16(1H, dd, J=1.8&8.0Hz), 8.99(1H, dd, J=1.8&4.8Hz), 11.08(1H, d, J=1.6Hz). | 3600–3300, 2980, 2240, 1600, 1500, 1170. |

TABLE 54

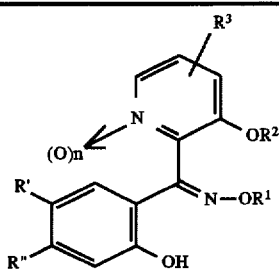

| Cpd. No. | R' | R" | R¹ | R⁴ | Y | n | geometrical isomerism | Formula | m.p. (°C.) physical property |
|---|---|---|---|---|---|---|---|---|---|
| 157 | Cl | Me₂N | t-Bu | H | H | 0 | Z | C₁₉H₂₂ClN₃O₃·¼H₂O | 217–219 |
| 158 | Cl | Me₂N | t-Bu | H | H | 0 | E | C₁₉H₂₂ClN₃O₃·¼H₂O | 126.5–128 |
| 159 | Cl | MeNH | t-Bu | H | H | 0 | E + Z | C₁₇H₂₀ClN₃O₃ | 123–126 |
| 160 | Cl | EtO | t-Bu | H | H | 0 | Z | C₁₈H₂₁ClN₂O₄ | 198–199 |
| 161 | Cl | EtO | t-Bu | H | H | 0 | E | C₁₈H₂₁ClN₂O₄ | 89–90 |
| 162 | Cl | BnNH | t-Bu | H | H | 0 | Z | C₂₃H₂₄ClN₃O₃ | 222.5–223 |
| 163 | Cl | BnNH | t-Bu | H | H | 0 | E | C₂₃H₂₄ClN₃O₃ | 174.5–176 |
| 164 | Cl | MeS | t-Bu | H | H | 0 | E + Z | C₁₇H₁₉ClN₂O₃S | 156–158 |
| 165 | Cl | MeSO | t-Bu | H | H | 0 | Z | C₁₇H₁₉ClN₂O₄S | 242–243 |
| 166 | Cl | MeSO | t-Bu | H | H | 0 | E | C₁₇H₁₉ClN₂O₄S | 218–219 |

TABLE 54-continued

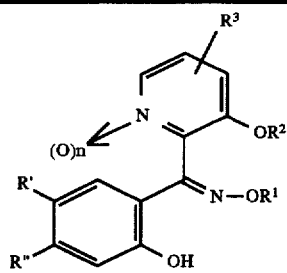

| Cpd. No. | R' | R" | R$^1$ | R$^4$ | Y | n | geometrical isomerism | Formula | m.p. (°C.) physical property |
|---|---|---|---|---|---|---|---|---|---|
| 167 | Cl | MeSO$_2$ | t-Bu | H | H | 1 | E + Z | C$_{17}$H$_{19}$ClN$_2$O$_6$S | 295(dec.) |
| 168 | Br | F | t-Bu | Ac | H | 0 | Z | C$_{18}$H$_{18}$BrFN$_2$O$_4$ | 129–130 |
| 169 | Br | F | t-Bu | Ac | H | 1 | Z | C$_{18}$H$_{18}$BrFN$_2$O$_5$ | 137–138 |
| 170 | Br | F | t-Bu | Pv | H | 0 | Z | C$_{21}$H$_{24}$BrFN$_2$O$_4$ | 110–111 |
| 171 | Br | F | t-Bu | Pv | H | 1 | Z | C$_{21}$H$_{24}$BrFN$_2$O$_5$ | 158–159 |
| 172 | Br | F | t-Bu | Bn | H | 1 | Z | C$_{23}$H$_{22}$BrFN$_2$O$_4$ | 160–162 |
| 173 | Br | F | t-Bu | Bn | H | 1 | E | C$_{23}$H$_{22}$BrFN$_2$O$_4$ | 164–165 |
| 174 | Cl | CN | t-Bu | W | H | 0 | Z | C$_{17}$H$_{16}$ClN$_3$O$_3$·1/5H$_2$O | 206–208 |
| 175 | Cl | CN | t-Bu | H | H | 1 | Z | C$_{17}$H$_{16}$ClN$_3$O$_4$·1/5H$_2$O | 296(dec.) |
| 176 | F | CN | t-Bu | H | H | 0 | Z | C$_{17}$H$_{16}$FN$_3$O$_3$·1/5H$_2$O | 254–256 |
| 177 | F | CN | t-Bu | H | H | 1 | Z | C$_{17}$H$_{16}$FN$_3$O$_4$ | 265–267 |
| 192 | CN | F | t-Bu | H | H | 0 | Z | C$_{17}$H$_{16}$FN$_3$O$_3$·1/2H$_2$O | 190–191.5 |
| 193 | CN | F | t-Bu | H | H | 1 | Z | C$_{17}$H$_{16}$FN$_3$O$_4$ | 279(dec.) |
| 194 | CN | CN | t-Bu | H | H | 0 | Z | C$_{18}$H$_{16}$N$_4$O$_3$ | 211–213 |
| 195 | CN | CN | t-Bu | H | H | 1 | Z | C$_{18}$H$_{16}$N$_4$O$_4$ | 297(dec.) |

Bn: benzyl, Pv: pivaloyl

TABLE 55

| Cpd. No. | $^1$H-NMR (CDCl$_3$; TMS internal standard, ppm) | IR (KBr; cm$^{-1}$) |
|---|---|---|
| 157 | 1.43(9H, s), 2.84(6H, s), 6.37(1H, s), 6.66(1H, s), 6.80(1H, s), 7.38(1H, dd, J=4.4&8.8Hz), 7.45(1H, dd, J=1.8&8.8Hz), 8.37(1H, dd, J=1.8&4.4Hz), 11.08(1H, s). | 3400, 2970, 2600, 1620, 1500, 1300. |
| 158 | 1.43(9H, s), 2.88(6H, s), 6.75(1H, s), 7.22–7.45(3H, m), 8.12–8.14(1H, m), 9.91(1H, s), 11.22(1H, s). | 3350, 2960, 2650, 1610, 1440. |
| 159 | 1.41&1.43(comb. 9H, s), 2.90–2.94(3H, m), 4.55(1H, br. s), 6.25, 6.29, 6.35, 6.68, 7.39, 9.90, 11.10&11.38(comb. 4H, all s), 7.20–7.46(2H, m), 8.11–8.14& 8.36–8.38(comb. 1H, m). | 3400, 2970, 2925, 1625, 1520, 1440. |
| 160 | 1.43(9H, s), 1.47(3H, t, J=6.8Hz), 4.11(2H, q, J=6.8Hz), 6.33(1H, s), 6.57(1H, s), 6.84(1H, s), 7.38(1H, dd, J=4.0&8.4Hz), 7.45(1H, dd, J=1.8&8.4Hz), 8.36(1H, dd, J=1.8&4.0Hz), 11.25(1H, s). | 3400, 2975, 2625, 1620, 1360, 1190. |
| 161 | 1.42(9H, s), 1.50(3H, t, J=7.0Hz), 4.14(2H, q, J=7.0Hz), 6.65(1H, s), 7.26(1H, dd, J=4.6&8.2Hz), 7.37(1H, s), 7.44(1H, dd, J=1.4&8.2Hz), 8.12(1H, dd, J=1.4&4.6Hz), 10.22(1H, br. s), 11.19(1H, s). | 3200, 2980, 2600, 1610, 1440, 1415. |
| 162 | 1.40(9H, s), 4.42(2H, d, J=5.6Hz), 4.95(1H, m), 6.26(1H, s), 6.31(1H, s), 6.71(1H, s), 7.30–7.46(7H, m), 8.38(1H, dd, J=1.6&4.2Hz), 11.07(1H, s). | 3400, 2970, 2640, 1625. |
| 163 | 1.43(9H, s), 4.41(2H, d, J=5.4Hz), 4.87(1H, m), 6.37(1H, s), 7.20–7.42(8H, m), 8.10–8.14(1H, m), 9.93(1H, s), 11.37(s, 1H). | 3410, 2975, 1610, 1515, 1430. |
| 164 | 1.42&1.44(comb. 9H, s), 2.48&2.50(comb. 3H, s), 6.38, 6.78, 6.84, 6.87, 7.33, 10.06, 11.10&11.28 (comb. 4H, all s), 7.24–7.29(2H, m), 8.12&8.36(comb. 1H, each dd, J=1.6&4.4Hz, J=1.8&4.2Hz). | 2980, 2600, 1610, 1570, 1460, 1360. |

TABLE 56

| Cpd. No. | $^1$H-NMR (CDCl$_3$; TMS internal standard, ppm) | IR (KBr; cm$^{-1}$) |
|---|---|---|
| 165 | 1.45(9H, s), 2.79(3H, s), 6.83(1H, s), 6.92(1H, s), 7.41(1H, dd, J=4.0&8.4Hz), 7.46–7.51(2H, m), 8.34(1H, dd, J=1.6&4.0Hz), 11.61(1H, s). | 3130, 2970, 1580, 1460, 1440, 1360. |
| 166 | 1.39(9H, s), 2.88(3H, s), 7.18–7.26(2H, m), 7.37–7.41(1H, m), 7.77(1H, s), 8.09– | 3200, 2980, 1580, 1440, |

TABLE 56-continued

| Cpd. No. | ¹H-NMR (CDCl₃; TMS internal standard, ppm) | IR (KBr; cm⁻¹) |
|---|---|---|
|  | 8.12(1H, m), 9.70(1H, s), 11.01(1H, s). | 1385. |
| 167 | *1.27(9H, br. s), 3.33(3H, br. s), 6.99–7.16(1H, m), 7.31–7.54(3H, m), 7.89–8.03 (1H, m). | 3420, 2975, 2650, 1570, 1435, 1315. |
| 168 | 1.28(9H, s), 2.20(3H, s), 6.79–6.85(2H, m), 7.49(1H, dd, J=4.8&8.4Hz), 7.69(1H, dd, J=1.4&8.4Hz), 8.63(1H, dd, J=1.4&4.8Hz), 11.34(1H, s). | 3410, 2980, 1775, 1440. |
| 169 | 1.30(9H, s), 2.17(3H, s), 6.82(1H, d, J=9.8Hz), 6.93(1H, d, J=7.8Hz), 7.29–7.34 (1H, m), 7.40–7.47(1H, m), 8.26(1H, d, J=6.8Hz), 10.95(1H, s). | 3420, 3080, 2980, 2600, 1780, 1600, 1425. |
| 170 | 1.15(9H, s), 1.28(9H, s), 6.78–6.83(2H, m), 7.48(1H, dd, J=4.6&8.4Hz), 7.66(1H, dd, J=1.4&8.4Hz), 8.64(1H, dd, J=1.4&4.6Hz), 11.39(1H, s). | 3060, 2960, 1755, 1615, 1580, 1485, 1435, 1360. |
| 171 | 1.12(9H, s), 1.32(9H, s), 6.81(1H, d, J=9.8Hz), 6.94(1H, d, J=7.6Hz), 7.27(1H, dd, J=1.0&8.6Hz), 7.42(1H, dd, J=6.6&8.6Hz), 8.26(1H, dd, J=1.0&6.6Hz), 11.01(1H, s). | 3430, 2980, 2500, 1760, 1600, 1420. |
| 172 | 1.31(9H, s), 5.15(2H, s), 6.80(1H, d, J=10.0Hz), 6.91–6.99(2H, m), 7.20–7.37(6H, m), 8.00–8.03(1H, m), 11.26(1H, s). | 3430, 2970, 1740, 1600, 1480, 1425. |
| 173 | 1.26(9H, s), 5.15(2H, s), 6.69(1H, d, J=10.2Hz), 7.10(1H, dd, J=0.6&8.8Hz), 7.23–7.48(7H, m), 7.99(1H, dd, J=0.6&6.2Hz), 10.92(1H, s). | 3450, 2970, 1600, 1580, 1475, 1425. |
| 174 | 1.46(9H, s), 6.55(1H, s), 7.10(1H, s), 7.31(1H, s), 7.44(1H, dd, J=4.2&8.4Hz), 7.51(1H, dd, J=1.8&8.4Hz), 8.33(1H, dd, J=1.8&4.2Hz), 11.99(1H, s). | 3400, 2980, 2600, 2230, 1570, 1455, 1365. |

TABLE 57

| Cpd. No. | ¹H-NMR (CDCl₃; TMS internal standard, ppm) | IR (KBr; cm⁻¹) |
|---|---|---|
| 175 | *1.26(9H, s), 7.01–7.07(1H, m), 7.34–7.45(3H, m), 7.94–7.97(1H, m). | 3400, 2975, 2600, 2230, 1570, 1425. |
| 176 | 1.46(9H, s), 6.48(1H, s), 6.84(1H, d, J=9.6Hz), 7.23(1H, d, J=5.4Hz), 7.44(1H, dd, J=4.0&8.4Hz), 7.50(1H, dd, J=1.8&8.4Hz), 8.34(1H, dd, J=1.8&4.0Hz), 11.59(1H, s). | 3400, 2980, 2500, 2230, 1570, 1460. |
| 177 | *1.26(9H, s), 7.00(1H, d, J=8.4Hz), 7.22(1H, d, J=10.0Hz), 7.30–7.39(2H, m), 7.92 (1H, d, J=5.6Hz), 10.96(1H, s), 11.11(1H, s). | 3200, 3100, 2980, 2600, 2240, 1575, 1430. |
| 192 | 1.45(9H, s), 6.55(1H, s), 6.81(1H, d, J=10.4Hz), 7.29(1H, d, J=7.4Hz), 7.45(1H, dd, J=4.2&8.4Hz), 7.51(1H, dd, J=1.8&8.4Hz), 8.34(1H, dd, J=1.8&4.2Hz), 12.77(1H, s). | 3600, 2975, 2630, 2220, 1610, 1495. |
| 193 | *1.25(9H, s), 6.93–7.12(2H, m), 7.38–7.45(1H, m), 7.64(1H, d, J=7.6Hz), 8.03(1H, d, J=6.8Hz), 11.10(1H, s). | 3450, 2970, 2630, 2225, 1610, 1500, 1425. |
| 194 | 1.47(9H, s), 6.63(1H, s), 7.38(1H, s), 7.46–7.57(3H, m), 8.33(1H, dd, J=1.8&4.0Hz). | 3400, 2970, 2620, 2225, 1575, 1365, 1295. |
| 195 | *1.27(9H, s), 7.07(1H, d, J=8.0Hz), 7.40(1H, dd, J=6.4&8.0Hz), 7.49(1H, s), 7.90 (1H, s), 7.98(1H, d, J=6.4Hz), 11.11(1H, s). | 3430, 2975, 2650, 2225, 1600, 1580, 1440, 1415. |

*measured with DMSO-d₆

TABLE 58

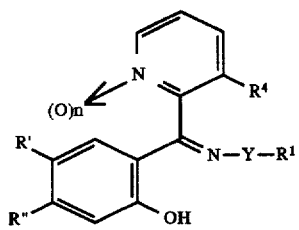

| Cpd. No. | R' | R" | R¹ | R⁴ | Y | n | geometrical isomerism | Formula | m.p. (°C.) physical property |
|---|---|---|---|---|---|---|---|---|---|
| 178 | Br | H | t-Bu | NH₂ | O | 0 | Z | C₁₆H₁₈BrN₃O₂ | 189–190 |
| 179 | Br | H | t-Bu | NH₂ | O | 0 | E | C₁₆H₁₈BrN₃O₂ | 156–156.5 |
| 180 | Br | H | t-Bu | MeOCH₂ | O | 0 | Z | C₁₉H₂₁BrN₂O₃ | 132–133 |
| 181 | CN | H | t-Bu | CN | O | 0 | Z | C₁₈H₁₆N₄O₂ | 162 |
| 182 | CN | H | t-Bu | CN | O | 0 | E | C₁₈H₁₆N₄O₂ | 210.5–211 |
| 183 | CF₃O | H | t-Bu | CN | O | 0 | Z | C₁₈H₁₆F₃N₃O₃ | 168–169 |
| 184 | CF₃O | H | t-Bu | CN | O | 0 | E | C₁₈H₁₆F₃N₃O₃ | 140–141 |
| 185 | MeO | H | t-Bu | CN | O | 0 | Z | C₁₈H₁₉N₃O₃ | 111–112 |

TABLE 58-continued

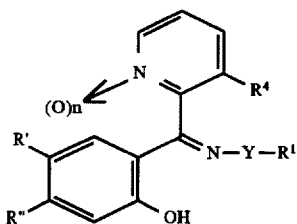

| Cpd. No. | R' | R" | R¹ | R⁴ | Y | n | geometrical isomerism | Formula | m.p. (°C.) physical property |
|---|---|---|---|---|---|---|---|---|---|
| 186 | MeO | H | t-Bu | CN | O | 0 | E | $C_{18}H_{19}N_3O_3$ | 143–144 |
| 187 | $NO_2$ | H | t-Bu | 1,3-dioxolan-2-yl | O | 0 | Z | $C_{19}H_{21}N_3O_6$ | 155–156 |
| 188 | $NO_2$ | H | t-Bu | CHO | O | 0 | Z | $C_{17}H_{17}N_3O_5$ | 168–169 |
| 189 | $NO_2$ | H | t-Bu | CH=NOH | O | 0 | Z | $C_{17}H_{18}N_4O_5$ | 226–230 |
| 190 | $NO_2$ | H | t-Bu | CN | O | 0 | Z | $C_{17}H_{16}N_4O_4$ | 156–157 |
| 191 | Cl | H | t-Bu | 5-$NH_2$-3-Cl | O | 0 | Z | $C_{16}H_{17}Cl_2N_3O_2$ | 187–188 |
| 196 | F | H | t-Bu | CN | O | 0 | Z | $C_{17}H_{16}FN_3O_2$ | 128–129 |
| 197 | F | H | t-Bu | CN | O | 0 | E | $C_{17}H_{16}FN_3O_2$ | 111–112 |
| 198 | $CF_3$ | H | t-Bu | 1,3-dioxolan-2-yl | O | 0 | Z | $C_{20}H_{21}F_3N_2O_4$ | 114–115 |
| 199 | $CF_3$ | H | t-Bu | CHO | O | 0 | Z | $C_{18}H_{17}F_3N_2O_3$ | 114–115 |
| 200 | $CF_3$ | H | t-Bu | CH=NOH | O | 0 | Z | $C_{18}H_{18}F_3N_3O_3$ | 207–210(sub.) |
| 201 | $CF_3$ | H | t-Bu | CN | O | 0 | Z | $C_{18}H_{16}F_3N_3O_2$ | 164–165 |
| 202 | Cl | CN | t-Bu | CN | O | 0 | Z | $C_{18}H_{15}ClN_4O_2$ | 188–189 |
| 203 | Cl | CN | t-Bu | CN | O | 0 | E | $C_{18}H_{15}ClN_4O_2$ | 165–166 |
| 204 | CN | Cl | t-Bu | 1,3-dioxolan-2-yl | O | 0 | Z | $C_{20}H_{20}ClN_3O_4$ | 115–116 |
| 205 | CN | Cl | t-Bu | CHO | O | 0 | Z | $C_{18}H_{16}ClN_3O_3.0.5H_2O$ | 192–193 |
| 206 | CN | Cl | t-Bu | CN | O | 0 | Z | $C_{18}H_{15}ClN_4O_2$ | 144–145 |

TABLE 59

| Cpd. No. | ¹H-NMR (CDCl₃; TMS internal standard, ppm) | IR (KBr; cm⁻¹) |
|---|---|---|
| 178 | 1.36(9H, s), 3.77(2H, s), 6.84(1H, d, J=2.4Hz), 6.89(1H, d, J=8.8Hz), 7.12(1H, dd, J=2.4&8.2Hz), 7.21(1H, dd, J=4.8&8.2Hz), 7.31(1H, dd, J=2.4&8.8Hz), 8.17(1H, dd, J=1.4&4.8Hz), 11.24(1H, s). | 3450, 3340, 3210, 2970, 1640, 1580, 1450. |
| 179 | 1.36(9H, s), 5.30(2H, br. s), 6.95(1H, d, J=8.8Hz), 7.07–7.18(2H, m), 7.32–7.39(2H, m), 7.92(1H, dd, J=2.0&4.0Hz), 11.04(1H, br. s). | 3460, 3340, 2970, 1600, 1450. |
| 180 | 1.31(9H, s), 3.32(3H, s), 4.27&4.40(2H, ABq, J=13.2Hz), 6.65(1H, d, J=2.2Hz), 6.91 (1H, d, J=8.8Hz), 7.31(1H, dd, J=2.2&8.8Hz), 7.42(1H, dd, J=4.8&7.8Hz), 7.92–7.97 (1H, m), 8.67(1H, dd, J=1.8&4.8Hz), 11.14(1H, s). | 3600–3300, 2970, 1565, 1470. |
| 181 | 1.38(9H, s), 6.90(1H, d, J=2.0Hz), 7.12(1H, d, J=8.6Hz), 7.54(1H, dd, J=2.0&8.6Hz), 7.61(1H, dd, J=6.0&8.0Hz), 8.18(1H, dd, J=1.8&8.0Hz), 8.99(1H, dd, J=1.8&5.0Hz), 11.45(1H, s). | 3600–3300, 2980, 2220, 1610, 1480. |
| 182 | 1.45(9H, s), 7.12(1H, d, J=8.8Hz), 7.50–7.57(2H, m), 7.59(1H, dd, J=2.0&8.8Hz), dd, J=1.8&8.0Hz), 8.73(1H, dd, J=1.8&5.0Hz), 9.97(1H, s). | 3600–3300, 3070, 2980, 2230, 1500. |
| 183 | 1.38(9H, s), 6.40(1H, d, J=2.6Hz), 7.06(1H, d, J=9.2Hz), 7.13–7.19(1H, m), 7.57(1H, dd, J=5.0&8.0Hz), 8.16(1H, dd, J=1.6&8.0Hz), 8.98(1H, dd, J=1.6&5.0Hz), 10.84(1H, s). | 3600–3300, 3070, 2980, 2230, 1560, 1490. |
| 184 | 1.45(9H, s), 7.03–7.09(2H, m), 7.17–7.23(1H, m), 7.51(1H, dd, J=4.8&8.0Hz), 8.19 (1H, dd, J=1.8&8.0Hz), 8.73(1H, dd, J=1.8&4.8Hz), 9.32(1H, s). | 3600–3300, 2970, 2240, 1570, 1500. |
| 185 | 1.36(9H, s), 3.63(3H, s), 6.06(1H, d, J=3.0Hz), 6.87(1H, dd, J=3.0&9.0Hz), 6.99(1H, d, J=9.0Hz), 7.52(1H, dd, J=5.0&7.8Hz), 8.12(1H, dd, J=1.8&7.8Hz), 8.95(1H, dd, J= 1.8&5.0Hz), 10.34(1H, s). | 3600–3300, 3080, 2990, 2240, 1570, 1490. |

TABLE 60

| Cpd. No. | ¹H-NMR (CDCl₃; TMS internal standard, ppm) | IR (KBr; cm⁻¹) |
|---|---|---|
| 186 | 1.47(9H, s), 3.71(3H, s), 6.54(1H, d, J=3.0Hz), 6.93(1H, dd, J=3.0&8.8Hz), 7.02(1H, d, J=8.8Hz), 7.45(1H, dd, J=5.0&8.0Hz), 7.88(1H, s), 8.13(1H, dd, J=1.8&8.0Hz), 8.74 (1H, dd, J=1.8&5.0Hz). | 3450, 3340, 3210, 2970, 1640, 1510. |

TABLE 60-continued

| Cpd. No. | ¹H-NMR (CDCl₃; TMS internal standard, ppm) | IR (KBr; cm⁻¹) |
|---|---|---|
| 187 | 1.33(9H, s), 3.82–4.12(4H, m), 5.81(1H, s), 7.08(1H, d, J=8.8Hz), 7.48(1H, dd, J=4.8& 7.8Hz), 7.58(1H, d, J=2.8Hz), 8.03–8.08(1H, m), 8.13(1H, dd, J=2.8&8.8Hz), 8.75(1H, dd, J=1.8&4.8Hz), 12.03(1H, s). | 3600–3300, 2980, 1630, 1530, 1340. |
| 188 | 1.31(9H, s), 7.14(1H, d, J=9.0Hz), 7.63–7.69(2H, m), 8.18(1H, dd, J=2.6&9.0Hz), 8.40 (1H, dd, J=1.8&7.6Hz), 9.00(1H, dd, J=1.8&4.8Hz), 9.92(1H, d, J=0.8Hz), 11.84(1H, s). | 3600–3300, 2980, 1710, 1340. |
| 189 | 1.33(9H, s), 7.11(1H, d, J=9.0Hz), 7.49(1H, m), 7.63(1H, d, J=3.0Hz), 7.75(1H, br. s), 7.92(1H, s), 8.15(1H, dd, J=3.0&9.0Hz), 8.29(1H, dd, J=1.6&8.0Hz), 8.77(1H, dd, J=1.6 &4.8Hz), 11.98(1H, br. s). | |
| 190 | 1.40(9H, s), 7.14(1H, d, J=9.2Hz), 7.55(1H, d, J=2.4Hz), 7.62(1H, dd, J=4.8&8.0Hz), 8.15–8.21(2H, m), 9.01(1H, dd, J=1.8&4.8Hz), 11.69(1H, s). | 3600–3300, 2980, 2230, 1630, 1520, 1340. |
| 191 | 1.33(9H, s), 3.97(2H, br. s), 6.62(1H, d, J=2.6Hz), 6.95(1H, d, J=8.8Hz), 7.10(1H, d, J=2.6Hz), 7.17(1H, dd, J=2.6&8.8Hz), 8.09(1H, d, J=2.6Hz), 11.14 (1H, s). | 1635, 1585, 1465. |
| 196 | 1.37(9H, s), 6.20–6.27(1H, m), 6.97–7.02(2H, m), 7.55(1H, dd, J=4.8&8.0Hz), 8.14 (1H, dd, J=1.8&8.0), 8.97(1H, dd, J=1.8&4.8Hz), 10.58(1H, s). | 3600–3300, 2980, 2240, 1560, 1480. |
| 197 | 1.47(9H, s), 6.75–6.82(1H, m), 6.98–7.12(2H, m), 7.48(1H, dd, J=4.8&8.0Hz), 8.15 (1H, dd, J=1.8&8.0Hz), 8.32(1H, s), 8.74(1H, dd, J=1.8&4.8Hz). | 3600–3100, 2980, 2240, 1500, 1430. |

TABLE 60a

| Cpd. No. | ¹H-NMR (CDCl₃; TMS internal standard, ppm) | IR (KBr; cm⁻¹) |
|---|---|---|
| 198 | 1.32(9H, s), 3.78–4.12(4H, m), 5.77(1H, s), 6.85(1H, br. d, J=1.0Hz), 7.09(1H, br. d, J=8.8Hz), 7.42–7.49(2H, m), 8.04(1H, dd, J=1.8&7.8Hz), 8.74(1H, dd, J=1.8&4.8 Hz), 11.54(1H, s). | 3600–3300, 2970, 1630, 1600, 1580, 1500. |
| 199 | 1.30(9H, s), 6.93(1H, br. d, J=1.8Hz), 7.15(1H, br. d, J=8.8Hz), 7.52(1H, br. dd, J=1.8&8.8Hz), 7.59–7.66(1H, m), 8.38(1H, dd, J=1.8&8.0Hz), 8.98(1H, dd, J=1.8& 4.8Hz), 9.91(1H, s), 11.37(1H, s). | 3600–3300, 2980, 1700, 1620, 1600, 1580. |
| 200 | 1.32(9H, s), 6.89(1H, br. d, J=2.2Hz), 7.12(1H, br. d, J=8.6Hz), 7.43–7.56(3H, m), 7.94(1H, s), 8.30(1H, dd, J=1.6&8.2Hz), 8.77(1H, dd, J=1.6&4.8Hz), 11.49(1H, s). | |
| 201 | 1.38(9H, s), 6.80(1H, br. d, J=1.8Hz), 7.14(1H, br. d, J=8.8Hz), 7.51(1H, br. dd, J=1.8&8.8Hz), 7.58(1H, dd, J=4.8&8.0Hz), 8.16(1H, dd, J=1.8&8.0Hz), 8.98(1H, dd, J=1.8&4.8Hz), 11.24(1H, s). | 3600–3300, 2980, 2240, 1630, 1600, 1500. |
| 202 | 1.39(9H, s), 6.69(1H, s), 7.35(1H, s), 7.61(1H, dd, J=4.8&8.0Hz), 8.18(1H, dd, J=1.8&8.0Hz), 8.99(1H, dd, J=1.8&4.8Hz), 11.02(1H, s). | 3600–3300, 2980, 2230, 1480, 1430, 1370. |
| 203 | 1.44(9H, s), 7.30(1H, s), 7.37(1H, s), 7.55(1H, dd, J=4.8&8.0Hz), 8.21(1H, dd J=1.8&8.0Hz), 8.73(1H, dd, J=1.8&4.8Hz), 9.66(1H, s). | 3600–3300, 2980, 2240, 1480, 1370. |
| 204 | 1.31(9H, s), 3.82–4.10(4H, m), 5.76(1H, s), 6.93(1H, s), 7.13(1H, s), 7.48(1H, dd, J=4.8&8.2Hz), 8.05(1H, dd, J=1.6&8.2Hz), 8.73(1H, dd, J=1.6&4.8Hz), 11.88–12.00(1H, br. s). | 3600–3300, 2980, 2230, 1610, 1580, 1480. |
| 205 | 1.29(9H, s), 7.03(1H, s), 7.19(1H, s), 7.63–7.69(1H, m), 8.38(1H, dd, J=1.8&7.6 Hz), 8.99(1H, dd, J=1.8&4.8Hz), 9.88(1H, d, J=0.6Hz), 11.78(1H, br. s). | 3600–3300, 2980, 2230, 1700, 1600, 1580. |
| 206 | 1.38(9H, s), 6.91(1H, s), 7.19(1H, s), 7.62(1H, dd, J=4.8&8.0Hz), 8.18(1H, dd, J=1.6&8.0Hz), 8.99(1H, dd, J=1.6&4.8Hz), 11.62(1H, s). | 3600–3300, 2980, 2230, 1610, 1480. |

The following are Experimental Examples showing the pharmacological effects of the Compound [I].

Experimental Example 1

Vasorelaxation activity in a specimen of rat aorta Effects on contraction caused by tetraethylammonium chloride (TEA) and barium chloride (BaCl₂)

Method

Male Wister rats (10 to 13 week old were employed for the experiment. After dehematization, the aorta was excised and a ring specimen (5 mm length) was prepared. The specimen was suspended in a bath filled with oxygenated (95% O₂-5%CO₂) Krebs solution (36° C.). The ring specimen was fixed at one end and the other end was connected to a transducer (Nippon Koden) for recording tension to determine the tension. After a stabilization period of one hour, TEA (30–45 mM) and BaCl₂ (0.3 mM) were added to the bath to cause vasoconstriction. After the constriction had reached a steady state (after about 15 minutes), a test compound was added to the bath and its relaxation activity was measured.

Results

The results are shown in Table 61, Table 62 and Table 63 in terms of the inhibitory ratio of the test compound. As a result, it is apparent that the compounds of this invention show vasorelaxation activity.

Experimental Example 2

Vasorelaxation activity in a specimen of rat aorta Effects on contraction caused by potassium chloride (KCl)

Method

The same experiment was conducted as in Experiment 1, excepting the use of KCl (80 ml) instead of TEA and BaCl₂

Results

The results are shown in Table 64 and Table 65 in terms of the inhibitory ratio of the test compound. As a result, it is apparent that the compounds of this invention show vasorelaxation activity based on potassium channel opening activity.

Experimental Example 3

Hypotensive activity in rats (Tail Cuff Method)

Method

Spontaneously hypertensive rats (SHR, male, 20 to 23 week old) were warmed up to 36° C. The blood pressure at the tail aorta was measured by the tail cuff method. The blood pressure was measured three times, i.e. before oral administration of the test compound, two hours after the administration and five hours after the administration. The test compound was orally administered in the state of a suspension in gum arabic.

Results

Maximal, hypotensive effect against the blood pressure before the administration is shown as % pre. in Table 66. As a result, it is apparent that the compounds of this invention show hypotensive activity.

Experimental Example 4

Action of increasing coronary blood flow in anesthetized dogs (Administration into coronary artery) Method: Beagle dogs (10 to 12 kg body weight) were anesthetized with pentobarbital and subjected to thoractomy under artificial respiration. A by-pass fitted with an electromagnetic flowmeter (Nippon Koden) was prepared between the left coronary artery and left carotid artery,and the volume of coronary blood flow was measured. The test compound was dissolved in a 50% aqueous physiological saline solution of polyethylene glycol, a 50% aqueous physiological saline solution of DMF or solely DMF, and injected into the coronary artery through the bypass (30 ug/day).

Results

Maximal change rate against the value measured before the administration (% of basal flow) and the duration period [shown in terms of the time ($T_{1/2}$) in which the activity is reduced to half] are shown in Table 67. As a result, it is apparent that the compounds of this invention show action of increasing coronary blood flow.

TABLE 61

| Compound No. | constriction inhibitory ratio (%) | | |
|---|---|---|---|
| | 1 μM | 3 μM | 10 μM |
| 4 | 38 | 79 | |
| 6 | 62 | 82 | |
| 8 | 16 | 93 | |
| 14 | 71 | 90 | |
| 18 | | 41 | 63 |
| 19 | 58 | 95 | |
| 32 | 87 | 100 | |
| 34 | 54 | 59 | |
| 36 | 81 | 80 | |
| 38 | 92 | 100 | |
| 40 | 85 | 72 | |
| 43 | | 63 | 75 |
| 56 | 100 | | |
| 58 | 84 | 94 | |
| 59 | 6 | 100 | |
| 89 | | 55 | 85 |
| 95 | 59 | 71 | |
| 100 | 52 | 100 | |
| 101 | 71 | 65 | |
| 103 | | 29 | 47 |
| 105 | 46 | 87 | |

TABLE 62

| Compound No. | constriction inhibitory ratio (%) | | |
|---|---|---|---|
| | 1 μM | 3 μM | 10 μM |
| 9 | | 22 | 82 |
| 30 | 4 | 50 | 92 |
| 61 | 54 | 100 | |
| 63 | 13 | 61 | 100 |
| 64 | | 43 | 100 |
| 67 | 32 | 89 | 100 |
| 68 | 92 | | |
| 69 | 100 | | |
| 106 | 2 | 56 | 100 |
| 111 | 81 | 92 | |
| 114 | 65 | 89 | |
| 117 | 10 | 52 | 99 |
| 119 | 69 | 71 | |
| 121 | 3 | 57 | 82 |
| 122 | 100 | | |
| 123 | | 52 | 91 |
| 125 | | 25 | 78 |
| 127 | 8 | 85 | 100 |
| 147 | 100 | | |

TABLE 63

| Compound No. | constriction inhibitory ratio (%) | | |
|---|---|---|---|
| | 1 μM | 3 μM | 10 μM |
| 128 | 100 | | |
| 129 | 100 | | |
| 130 | 100 | | |
| 132 | 100 | | |
| 160 | 100 | | |
| 174 | 100 | | |
| 175 | 100 | | |
| 176 | 100 | | |
| 177 | 50 | 100 | |

TABLE 64

| Compound No. | constriction inhibitory ratio (%) | | |
|---|---|---|---|
| | 1 μM | 3 μM | 10 μM |
| 4 | −2 | 7 | |
| 6 | 5 | 17 | |
| 8 | −9 | −2 | |
| 14 | 2 | 11 | |
| 19 | −5 | 6 | |
| 32 | −2 | 11 | |
| 34 | 4 | 18 | |
| 36 | 0 | 4 | |
| 38 | 0 | 1 | |
| 40 | 0 | 0 | |
| 43 | | 0 | 5 |
| 58 | 0 | 0 | |
| 89 | | 11 | 32 |
| 95 | 3 | 12 | |
| 100 | 4 | 11 | |
| 101 | 3 | 25 | |
| 105 | 4 | 28 | |

TABLE 65

| Compound No. | constriction inhibitory ratio (%) | | |
|---|---|---|---|
| | 1 μM | 3 μM | 10 μM |
| 9 | | 0 | 10 |
| 30 | | 1 | 18 |

TABLE 65-continued

| Compound No. | constriction inhibitory ratio (%) | | |
|---|---|---|---|
| | 1 μM | 3 μM | 10 μM |
| 61 | 4 | 7 | |
| 63 | 0 | 0 | 0 |
| 64 | | 0 | 4 |
| 67 | 0 | 0 | 0 |
| 68 | 4 | | |
| 69 | 0 | | |
| 106 | 0 | 5 | 39 |
| 111 | 0 | 0 | |
| 114 | 0 | 0 | |
| 117 | 4 | 12 | 32 |
| 119 | 5 | 6 | |
| 121 | | 0 | 0 |
| 122 | 0 | | |
| 123 | | 0 | 0 |
| 125 | | 1 | 8 |
| 127 | | 0 | 0 |
| 147 | 16 | | |
| 129 | 18 | | |
| 160 | 18 | | |
| 175 | 4 | | |
| 177 | 0 | 0 | |

TABLE 66

| Compound No. | dose (mg/kg) | after 2 hours (%) | after 5 hours (%) |
|---|---|---|---|
| 32 | 10 | 19 | 18 |
| 34 | 10 | 27 | 10 |
| 36 | 10 | 42 | 30 |
| 38 | 10 | 29 | 13 |
| 40 | 10 | 30 | 11 |
| 105 | 30 | 59 | 44 |
| 56 | 10 | 51 | 42 |
| 58 | 10 | 55 | 45 |
| | 1 | 35 | 19 |
| 59 | 10 | 45 | 54 |
| | 1 | 22 | 10 |
| 63 | 10 | 42 | 54 |
| 67 | 10 | 28 | 35 |
| 69 | 1 | 26 | 19 |
| 101 | 3 | 10 | 11 |
| 119 | 1 | 48 | 29 |
| 122 | 1 | 30 | 24 |
| 123 | 1 | 37 | 12 |

TABLE 67

| Compound No. | Basal flow(%) | duration ($T_{1/2}$, min) |
|---|---|---|
| 6 | 224 | 1.5 |
| 14 | 170 | 1.6 |
| 23 | 117 | 1.2 |
| 27 | 120 | 2.1 |
| 32 | 269 | 3.0 |
| 34 | 255 | 3.7 |
| 36 | 319 | 4.8 |
| 38 | 168 | 4.7 |
| 40 | 227 | 2.8 |
| 43 | 100 | 1.7 |
| 56 | 176 | 27.3 |
| 58 | 202 | 47.7 |
| 59 | 145 | 15.1 |
| 61 | 105 | 2.0 |
| 63 | 78 | 2.4 |
| 67 | 92 | 8.9 |
| 95 | 164 | 4.0 |
| 100 | 114 | 3.3 |
| 101 | 85 | 7.9 |
| 103 | 127 | 3.0 |

TABLE 67-continued

| Compound No. | Basal flow(%) | duration ($T_{1/2}$, min) |
|---|---|---|
| 105 | 119 | 2.9 |
| 128 | 298 | 6.2 |
| 129* | 366 | 42.9 |
| 130 | 310 | 4.4 |
| 132 | 288 | 71.8 |
| 171* | 71 | 23.4 |
| 174* | 274 | 4.4 |
| 175* | 265 | 34.3 |
| 176* | 210 | 1.8 |
| 177* | 184 | 9.8 |

*10 μg/dog administration

The present invention provides novel pyridine derivatives having potassium.channel opening activity and useful as therapeutic agents of circulatory diseases such as angina pectoris, hypertension, etc.

What is claimed is:

1. A compound of the formula

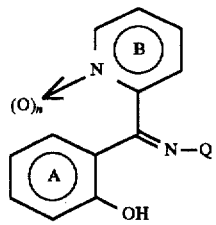

wherein the ring A stands for a benzene ring optionally substituted, in addition to the hydroxy group, with 1 to 3 substituents selected from the group consisting of (1) a halogen, (2) cyano group, (3) nitro group, (4) an acyl group derived from a carboxylic acid, sulfinic acid or sulfonic acid, (5) (i) an amino group optionally substituted with 1 or 2 substituents selected from a $C_{1-6}$ alkyl, $C_{1-6}$ alkoxy, halogeno-$C_{1-4}$ alkyl, $C_{3-6}$ cycloalkyl, hydroxyl, carbamoyl, phenyl, phenyl-$C_{1-4}$ alkyl, $C_{1-6}$ alkanoyl, nitroxy-$C_{2-4}$ alkanoyl, $C_{3-6}$ cycloalkylcarbonyl, benzoyl, phenyl-$C_{2-4}$ alkanoyl, $C_{1-6}$ alkoxy-carbonyl, nitroxy-$C_{1-4}$ alkoxycarbonyl, phenoxycarbonyl, phenyl-$C_{1-4}$ alkoxycarbonyl, $C_{1-6}$ alkylsulfinyl, nitroxy-$C_{1-4}$ alkylsulfinyl, $C_{3-6}$ cycloalkylsulfinyl, phenylsulfinyl, $C_{1-6}$ alkylsulfonyl, nitroxy-$C_{1-4}$ alkylsulfonyl, $C_{3-6}$ cycloalkylsulfonyl, $C_{1-6}$ alkoxysulfonyl and phenylsulfonyl, or (ii) a cyclic amino group, (6) a $C_{1-6}$ alkoxy group optionally substituted with 1 to 3 substituents selected from a $C_{1-4}$ alkoxy, phenyl, phenoxy, hydroxyl, nitro, nitroxy, halogen, halogeno-$C_{1-4}$ alkoxy and cyano, (7) a $C_{1-6}$ alkoxy-carbonyl, nitroxy-$C_{1-4}$ alkoxycarbonyl, $C_{3-6}$ cycloalkoxy-carbonyl, phenyl-$C_{1-4}$ alkoxycarbonyl, carbamoyl, $C_{1-6}$ alkylaminocarbonyl, $C_{3-6}$ cycloalkylaminocarbonyl, nitroxy-$C_{1-4}$ alkylaminecarbonyl, cyclic aminocarbonyl, anilinocarbonyl or phenyl-$C_{1-4}$ alkylaminocarbonyl group, (8) a $C_{1-6}$ alkoxysulfinyl, $C_{3-6}$ cycloalkoxysulfinyl, phenyl-$C_{1-4}$ alkoxysulfinyl, sulfimamoyl, $C_{1-6}$ alkylaminosulfinyl, $C_{3-6}$ cycloalkylaminosulfinyl, nitroxy-$C_{1-4}$ alkylaminosulfinyl, cyclic aminosulfinyl, anilinosulfinyl, phenyl-$C_{1-4}$ alkylaminosulfinyl, $C_{1-6}$ alkoxysulfonyl, $C_{3-6}$ cycloalkoxysulfonyl, phenyl-$C_{1-4}$ alkoxysulfonyl, sulfamoyl, $C_{1-6}$ alkylaminosulfonyl, $C_{3-6}$ cycloalkylaminosulfonyl, nitroxy-$C_{1-4}$ alkylaminosulfonyl, cyclic aminosulfonyl, anilinosulfonyl or phenyl-$C_{1-4}$ alkylaminosulfonyl group, (9) a mercapto group optionally substituted with a $C_{1-6}$ alkyl, nitroxy $C_{1-4}$ alkyl, $C_{3-6}$ cycloalkyl, phenyl, phenyl $C_{1-4}$ alkyl or halogeno-$C_{1-4}$ alkyl group, (10)(a) a $C_{1-6}$ alkyl, $C_{2-6}$ alkenyl, $C_{2-6}$ alkynyl or $C_{3-6}$ cycloalkyl group optionally substituted with 1 to 3 substituents selected from (i) a $C_{1-4}$ alkoxy, (ii) a phenyl optionally substituted with 1 to 3 substituents selected from the group consisting of a $C_{1-4}$ alkyl, $C_{1-4}$ alkoxy, hydroxyl, nitro, halogen, halogeno-$C_{1-4}$ alkyl, cyano and halogeno-$C_{1-4}$ alkoxy, (iii) a phenoxy, (iv) a hydroxyl, (v) nitro, (vi) nitroxy, (vii) a halogen, (viii) a halogeno-$C_{1-6}$ alkoxy and (ix), cyano, or (b) an iminomethyl group optionally substituted with (i) a hydroxyl, (ii) an amino, (iii) a $C_{1-6}$ alkyl, (iv) a $C_{3-6}$ cycloalkyl, (v) a $C_{1-6}$ alkoxy, (vi) a $C_{3-6}$ cycloalkoxy, (vii) a phenyl-$C_{1-4}$ alkyl and (viii) a phenyl-$C_{1-4}$ alkoxy,

(11) (i) —CH=CH—CH—CH=CH— optionally substituted with 1 to 3 substituents selected from a $C_{1-4}$ alkyl, $C_{1-4}$ alkoxy, nitro, halogen, $CH_3$, $C_{1-4}$ alkoxycarbonyl and cyano, (ii) —$(CH_2)_a$— wherein a denotes 3 or 4, or (iii) —$(CH_2)_b$—CO—, wherein b denotes 2 or 3, and

(12) =N—O—N=, the ring B stands for a pyridine ring optionally substituted with 1 to 2 substituents selected from the group consisting of (1) a halogen, (2) cyano group, (3) (i) an amino group optionally substituted with 1 or 2 substituents selected from a $C_{1-6}$ alkyl, $C_{1-6}$ alkoxy, halogeno-$C_{1-4}$ alkyl, $C_{3-6}$ cycloalkyl, hydroxyl, carbamoyl, phenyl, phenyl $C_{1-4}$ alkyl, $C_{1-6}$ alkanoyl, nitroxy-$C_{2-4}$ alkanonyl, $C_{3-6}$ cycloalkylcarbonyl, benzoyl, phenyl $C_{2-4}$ alkanoyl, $C_{1-6}$ alkoxy-carbonyl, nitroxy-$C_{1-4}$ alkoxycarbonyl, phenoxycarbonyl, phenyl-$C_{1-4}$ alkoxycarbonyl, $C_{1-6}$ alkylsulfinyl, nitroxy-$C_{1-4}$ alkylsulfinyl, $C_{3-6}$ cycloalkylsulfinyl, phenylsulfinyl, $C_{1-6}$ alkylsulfonyl, nitroxy-$C_{1-4}$ alkoxysulfonyl, $C_{3-6}$ cycloalkylsulfonyl, $C_{1-6}$ alkoxysulfonyl and phenylsulfonyl, or (ii) a cyclic amino group, (4) (i) an acyl group derived from a carboxylic acid, sulfinic acid or sulfonic acid, or (ii) 1,3-dioxolan-2-yl group, (5) a $C_{1-6}$ alkoxy-carbonyl, nitroxy-$C_{1-4}$ alkoxycarbonyl, $C_{3-6}$ cycloalkoxy-carbonyl, phenyl-$C_{1-4}$ alkoxycarbonyl, carbamoyl, $C_{1-6}$ alkylaminocarbonyl, $C_{3-6}$ cycloalkylaminocarbonyl, nitroxy $C_{1-4}$ alkylaminocarbonyl, cyclic aminocarbonyl, anilinocarbonyl or phenyl-$C_{1-4}$ alkylaminocarbonyl group, (6) a $C_{1-6}$ alkoxy group optionally substituted with 1 to 3 substituents selected from a $C_{1-4}$ alkoxy, phenyl, phenoxy, hydroxyl, nitro, nitroxy, halogen, halogeno-$C_{1-4}$ alkoxy and cyano-,-, (7) a mercapto group optionally substituted with a $C_{1-6}$ alkyl, nitroxy-$C_{1-4}$ alkyl, $C_{3-6}$ cycloalkyl, phenyl, phenyl-$C_{1-4}$ alkyl or halogeno-$C_{1-4}$ alkyl group, (8) (a) a $C_{1-6}$ alkyl, $C_{2-6}$ alkenyl, $C_{2-6}$ alkynyl or $C_{3-6}$ cycloalkyl group optionally substituted with 1 to 3 substituents selected from (i) a $C_{1-4}$ alkoxy, (ii) a phenyl optionally substituted with 1 to 3 substituents selected from the group consisting of a $C_{1-4}$ alkyl, $C_{1-4}$ alkoxy, hydroxyl, nitro, halogen, halogeno-$C_{1-4}$ alkyl, cyano and halogeno-$C_{1-4}$ alkoxy, (iii) a phenoxy, (iv) a hydroxyl, (v) nitro, (vi) nitroxy, (vii) a halogen, (viii) a halogeno-$C_{1-4}$ alkoxy and (ix) cyano, or (b) an iminomethyl group optionally substituted with (i) a hydroxyl, (ii) an amino, (iii) a $C_{1-6}$ alkyl, (iv) a $C_{3-6}$ cycloalkyl, (v) a $C_{1-6}$ alkoxy, (vi) a $C_{3-6}$ cycloalkoxy, (vii) a phenyl-$C_{1-4}$ alkyl and (viii) a phenyl-$C_{1-4}$ alkoxy, and (9) $OR^2$ wherein $R^2$ stands for H or a hydroxyl-protecting group, Q represents hydroxyl, $OQ^1$ or $Q^1$ wherein $Q^1$ represents benzyl, $C_{1-10}$ alkyl, $C_{3-10}$ alkenyl, $C_{3-10}$ alkynyl, $C_{3-8}$ cycloalkyl or $C_{5-8}$ cycloalkenyl each of which groups are unsubstituted or are substituted with 1 to 3 substituents selected from the group consisting of (i) halogen, (ii) halogeno-$C_{1-4}$ alkyl, (iii) $C_{1-4}$ alkoxy and (iv) phenyl which is unsubstituted or is substituted with 1 to 3 substituents selected from the group consisting of $C_{1-4}$ alkyl, $C_{1-4}$ alkoxy, hydroxyl, nitro, halogen, halogeno-$C_{1-4}$ alkyl, cyano and halogeno-$C_{1-4}$ alkoxy, and n is 0 or 1, or a pharmaceutically acceptable salt thereof.

2. A compound as claimed in claim 1, which is a compound of the formula

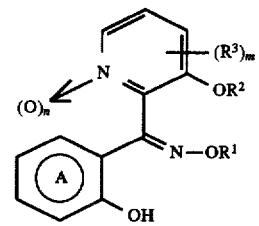

wherein the ring A is as defined in claim 1, $R^1$ is hydrogen or is benzyl, $C_{1-10}$ alkyl, $C_{3-10}$ alkenyl, $C_{3-10}$ alkynyl, $C_{3-8}$ cycloalkyl or $C_{5-8}$ cycloalkenyl each of which groups are unsubstituted or are substituted with 1 to 3 substituents selected from the group consisting of (i) halogen, (ii) halogeno-$C_{1-4}$ alkyl, (iii) $C_{1-4}$ alkoxy and (iv) phenyl which is unsubstituted or is substituted with 1 to 3 substituents selected from the group consisting of $C_{1-4}$ alkyl, $C_{1-4}$ alkoxy, hydroxyl, nitro, halogen, halogeno-$C_{1-4}$ alkyl, cyano and halogeno-$C_{1-4}$ alkoxy, $R^2$ is hydrogen or a hydroxy-protecting group, $R^3$ is halogen, cyano, $C_{1-4}$ alkoxy, $C_{1-4}$ alkyl or halogeno-$C_{1-4}$ alkyl, and m and n each is 0 or 1.

3. A compound as claimed in claim 1, which is a compound of the formula

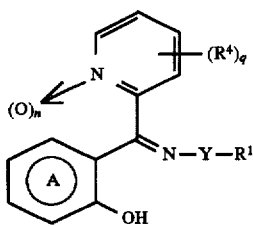

wherein the ring A is as defined in claim 1, $R^1$ is hydrogen or is $C_{1-10}$ alkyl, $C_{3-10}$ alkenyl, $C_{3-10}$ alkynyl, $C_{3-8}$ cycloalkyl or $C_{5-8}$ cycloalkenyl group optionally substituted with 1 to 3 substituents selected from the group consisting of (i) a halogen, (ii) a halogeno-$C_{1-4}$ alkyl, (iii) a $C_{1-4}$ alkoxy and (iv) a phenyl optionally substituted with 1 to 3 substituents selected from the group consisting of a $C_{1-4}$ alkyl, $C_{1-4}$ alkoxy, hydroxyl, nitro, halogeno, halogeno-$C_{1-4}$ alkyl, cyano and halogeno-$C_{1-4}$ alkoxy, $R^4$ is (1) a halogen, (2) a cyano group, (3) an amino group, (4) a $C_{1-8}$ alkanoyl, $C_{3-8}$ cycloalkylcarbonyl, benzoyl, $C_{1-6}$ alkylsulfinyl group, a $C_{3-6}$ cycloalkylsulfinyl group, a $C_{3-6}$ cycloalkylsulfonyl group, a phenylsulfonyl group or a 1,3-dioxolan-2-yl group, (5) a carboxyl, carbamoyl or $C_{1-4}$ alkoxy-carbonyl group, (6) a $C_{1-4}$ alkoxy group, (7) a $C_{1-4}$ alkylthio group, or (8) a $C_{1-4}$ alkyl, $C_{2-4}$ alkynyl or $C_{2-4}$ alkenyl group optionally substituted with a hydroxyl, a hydroxylmino, a halogen or a $C_{1-4}$ alkoxy, Y is O or $CH_2$, n is 0 or 1, and q is 0, 1 or 2.

4. A pharmaceutical composition for the treatment of cardiovascular disease which comprises, an effective amount of a compound or pharmaceutically acceptable salt as defined in claim 1 and a pharmaceutically acceptable carrier therefor.

5. A method for the treatment of angina pectoris or hypertension which comprises administering to a mammal in need of such treatment an effective amount of a compound or pharmaceutically acceptable salt thereof as defined in claim 1.

6. A compound as claimed in claim 1, wherein the acyl group substituent on the benzene ring stands for a $C_{1-8}$ alkanoyl, $C_{3-6}$ cycloalkyl-carbonyl, benzoyl, $C_{1-6}$ slkylsulfinyl, $C_{3-6}$ cycloalkylsulfinyl, phenylsulfinyl, $C_{1-6}$ alkylsulfonyl, $C_{3-6}$ cycloalkylsulfonyl or phenylsulfonyl group optionally substituted with a nitroxy or phenyl.

7. A compound as claimed in claim 1, wherein the substituent on the benzene ring is selected from the group consisting of (i) a halogen, (ii) cyano group, (iii) nitro group, (iv) a $C_{1-8}$ alkanoyl, $C_{3-6}$ cycloalkylcarbonyl, benzoyl, $C_{1-6}$ alkylsulfinyl, $C_{3-6}$ cycloalkylsulfinyl, phenylsulfinyl, $C_{1-6}$ alkylsulfonyl, $C_{3-6}$ cycloalkylsulfonyl or phenylsulfonyl group, (v) an amino group which may be substituted with a $C_{1-6}$ alkyl, (vi) a $C_{1-4}$ alkoxy group which may be substituted with a $C_{1-4}$ halogen, (vii) a $C_{1-4}$ alkylthio group and (viii) a alkyl, $C_{2-4}$ alkenyl or $C_{2-6}$ alkynyl group which may be substituted with a halogen.

8. A compound as claimed in claim 1, wherein the benzene ring is substituted with a halogen and/or cyano.

9. A compound as claimed in claim 1, wherein the ring A stands for

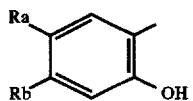

wherein Ra stands for a halogen, cyano group, nitro group, a $C_{1-10}$ acyl group, a $C_{1-4}$ alkoxy group, a halogeno-$C_{1-4}$ alkoxy group, a $C_{1-4}$ alkylthio group, a halogeno-$C_{1-4}$ alkyl group or a $C_{1-4}$ hydrocarbon group; and Rb stands for H, a halogen, cyano group, nitro group, a $C_{1-10}$ acyl group, an amino group, a $C_{1-4}$ alkylamino group, a $C_{1-4}$ alkoxy group, a $C_{1-4}$ alkylthio group, $C_{1-4}$ hydrocarbon group or halogeno-$C_{1-4}$ alkyl group.

10. A compound as claimed in claim 9, wherein Ra stands for a halogen, cyano group, nitro group, a $C_{1-8}$ alkanoyl group, a $C_{3-6}$ cycloalkyl-carbonyl group, a benzoyl group, a $C_{1-6}$ alkylsulfinyl group, a $C_{3-6}$ cycloalkylsulfinyl group, a phenylsulfinyl group, a $C_{1-6}$ alkylsulfonyl group, a $C_{3-6}$ cycloalkylsulfonyl group, a phenylsulfonyl group, a $C_{1-4}$ alkoxy group, a halogeno-$C_{1-4}$ alkoxy group, a $C_{1-4}$ alkylthio group, a halogeno-$C_{1-4}$ alkyl group, a $C_{2-4}$ alkynyl group or a $C_{2-4}$ alkenyl group; and Rb stands for H, a halogen, cyano group, nitro group, a $C_{1-8}$ alkanoyl group, a $C_{3-6}$ cycloalkylcarbonyl group, a benzoyl group, a $C_{1-6}$ alkylsulfinyl group, a $C_{3-6}$ cycloalkylsulfinyl group, a phenylsulfinyl group, a $C_{1-6}$ alkylsulfonyl group, a $C_{3-6}$ cycloalkylsulfonyl group, a phenylsulfonyl group, an amino group, a $C_{1-4}$ alkylamino group, a $C_{1-4}$ alkoxy group, a $C_{1-4}$ alkylthio group, a halogeno-$C_{1-4}$ alkyl group, a $C_{1-4}$ alkyl group, a $C_{2-4}$ alkynyl group or a $C_{2-4}$ alkenyl.

11. A compound as claimed in claim 1, wherein the benzene ring may be substituted with 1 to 3 electron-attracting groups.

12. A compound as claimed in claim 1, wherein the ring A stands for

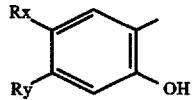

wherein Rx and Ry each stands for an electron-attractive group.

13. A compound as claimed in claim 12, wherein the electron-attracting group stands for a halogen, cyano group, nitro group, trifluoromethyl group, pentafluoroethyl group, trifluoromethoxy group, pentafluoroethoxy group or a $C_{1-10}$ acyl group.

14. A compound as claimed in claim 13, wherein the $C_{1-10}$ acyl group stands for a $C_{1-8}$ alkanoyl group, $C_{3-6}$ cycloalkylcarbonyl group, benzoyl group, $C_{1-6}$ alkylsulfinyl group, $C_{1-6}$ alkylsulfonyl group, $C_{3-6}$ cycloalkylsulfonyl group or phenylsulfonyl group.

15. A compound as claimed in claim 1, wherein the acyl group substituent on the pyridine ring stands for a $C_{1-8}$ alkanoyl, $C_{3-6}$ cycloalkylcarbonyl, benzoyl, $C_{1-6}$ alkylsulfinyl, $C_{3-6}$ cycloalkylsulfinyl, phenylsulfinyl group, $C_{1-6}$ alkylsulfonyl, $C_{3-4}$ cycloalkylsulfonyl or phenylsulfonyl group optionally be substituted with a nitroxy or phenyl.

16. A compound as claimed in claim 1, wherein the substituent on the ring B is selected from the group consisting of (1) a halogen, (2) cyano group, (3) an amino group, (4) a $C_{1-10}$ acyl or 1,3-dioxolan-2-yl group, (5) a carboxyl, carbamoyl or $C_{1-4}$ alkoxy-carbonyl group, (6) a $C_{1-4}$ alkoxy group, (7) a $C_{1-4}$ alkylthio group, (8) a $C_{1-4}$ hydrocarbon group optionally substituted with a hydroxyl, hydroxylmino, halogen or $C_{1-4}$ alkoxy and (9) $OR^2$ wherein $R^2$ stands for H or a hydroxyl-protecting group.

17. A compound as claimed in claim 1, wherein substituent on the ring B is selected from the group consisting of (1) a halogen, (2) cyano group, (3) an amino group, (4) a $C_{1-8}$ alkanoyl, $C_{3-6}$ cycloalkylcarbonyl, benzoyl, $C_{1-6}$ alkylsulfinyl, $C_{3-6}$ cycloalkylsulfonyl, phenylsulfonyl or 1,3-dioxolan-2-yl group, (5) a carboxyl, carbamoyl or $C_{1-4}$ alkoxy-carbonyl group (6) a $C_{1-4}$ alkoxy group, (7) a $C_{1-4}$ alkylthio group, (8) a $C_{1-4}$ alkyl group, a $C_{2-4}$ alkynyl group or a $C_{2-4}$ alkenyl group optionally substituted with a hydroxy, hydroxylmino, halogen or $C_{1-4}$ alkoxy and (9) $OR^2$ wherein $R^2$ stands for H or a hydroxyl-protecting group.

18. A compound as claimed in claim 1, wherein the ring B stands for

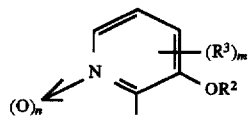

wherein $R^2$ stands for H or a hydroxyl-protecting group; $R^3$ stands for a halogen, cyano, $C_{1-4}$ alkoxy, $C_{1-4}$ alkyl or halogeno-$C_{1-4}$ alkyl group; and m and n each denotes 0 or 1.

19. A compound as claimed in claim 18, wherein m is 0.

20. A compound as claimed in claim 1, wherein the ring B stands for a pyridine ring optionally substituted with 1 or 2 substituents selected from a halogen, $C_{1-4}$ alkoxy, $C_{1-4}$ alkyl, halogeno-$C_{1-4}$ alkyl and $OR^2$ wherein $R^2$ stands for H or a hydroxyl-protecting group.

21. A compound as claimed in claim 1, which is a Z-isomer.

22. A compound as claimed in claim 2, wherein $R^3$ stands for a halogen, $C_{1-4}$ alkoxy, $C_{1-4}$ alkyl or halogeno-$C_{1-4}$ alkyl group.

23. A compound as claimed in claim 2, wherein $R^1$ stands for H, a $C_{1-10}$ alkyl, $C_{3-10}$ alkenyl, $C_{3-10}$ alkynyl, $C_{3-8}$ cycloalkyl, $C_{5-8}$ cycloalkenyl or benzyl group.

24. A compound as claimed in claim 2, wherein $R^1$ is t-butyl group.

25. A compound as claimed in claim 2, wherein m is 0.

26. A compound as claimed in claim 2, wherein the ring A stands for

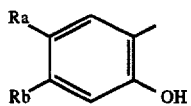

wherein Ra stands for a halogen, cyano group, nitro group, a $C_{1-10}$ acyl group, a $C_{1-4}$ alkoxy group, a halogeno-$C_{1-4}$ alkoxy group, $C_{1-4}$ alkylthio group, a halogeno-$C_{1-4}$ alkyl group or a $C_{1-4}$ hydrocarbon group; and Rb stands for H, a halogen, cyano group, nitro group, a $C_{1-10}$ acyl group, an amino group, a $C_{1-4}$ alkylamino group, a $C_{1-4}$ alkoxy group, a $C_{1-4}$ alkylthio group, a $C_{1-4}$ hydrocarbon group or a halogeno-$C_{1-4}$ alkyl group.

27. A compound as claimed in claim 26, wherein Ra stands for a halogen, cyano group, nitro group, a $C_{3-8}$ alkanoyl group, a $C_{3-6}$ cycloalkyl-carbonyl group, a benzoyl group, a $C_{1-6}$ alkylsulfinyl group, a $C_{3-6}$ cycloalkylsulfinyl group, a phenylsulfinyl group, a $C_{1-6}$ alkylsulfonyl group, a $C_{3-6}$ cycloalkylsulfonyl group, a phenylsulfonyl group, a $C_{1-4}$ alkoxy group, a halogeno-$C_{1-4}$ alkoxy group, a $C_{1-4}$ alkylthio group, a halogeno-$C_{1-4}$ alkyl group, a $C_{2-4}$ alkynyl group or a $C_{2-4}$ alkenyl group; and Rb stands for H, a halogen, cyano group, nitro group, a $C_{1-8}$ alkanoyl group, a $C_{3-6}$ cycloalkylcarbonyl group, a benzoyl group, a $C_{1-6}$ alkylsulfinyl group, a $C_{3-6}$ cycloalkylsulfinyl group, a phenylsulfinyl group, a $C_{1-6}$ alkylsulfonyl group, a $C_{3-6}$ cycloalkylsulfonyl group, a phenylsulfonyl group, an amino group, a $C_{1-4}$ alkylamino group, a $C_{1-4}$ alkoxy group, a $C_{1-4}$ alkylthio group, a halogeno-$C_{1-4}$ alkyl group, a $C_{1-4}$ alkyl group, a $C_{2-6}$ alkynyl group or a $C_{2-4}$ alkenyl group.

28. A compound as claimed in claim 26, wherein Ra stands for a halogen, cyano group, nitro group, a $C_{1-4}$ alkoxy group, a halogeno-$C_{1-4}$ alkyl group or a $C_{1-4}$ alkyl group; and Rb stands for H, a halogen or a $C_{1-4}$ alkyl group.

29. A compound as claimed in claim 3, wherein n denotes 1.

30. A compound as claimed in claim 1, wherein q denotes 0 or 1.

31. A compound as claimed in claim 1, wherein $R^4$ stands for a halogen, a $C_{1-6}$ alkyl group or a $C_{1-6}$ alkoxy group.

32. A compound as claimed in claim 1, wherein $R^1$ stands for a branched $C_{3-8}$ alkyl or cycloalkyl group.

33. A compound as claimed in claim 1, wherein $R^1$ is t-butyl group.

34. A compound as claimed in claim 1, wherein the ring A stands for

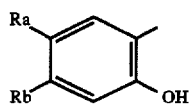

wherein Ra stands for a halogen, cyano group, nitro group, a $C_{1-10}$ acyl group, a $C_{1-4}$ alkoxy group, a halogeno-$C_{1-4}$ alkoxy group, a $C_{1-4}$ alkylthio group, a halogeno-$C_{1-4}$ alkyl group or a $C_{1-4}$ hydrocarbon group; and Rb stands for H, a halogen, cyano group, nitro group, a $C_{1-10}$ acyl group, an amino group, a $C_{1-4}$ alkylamino group, a $C_{1-4}$ alkoxy group, a $C_{1-4}$ alkylthio group, a $C_{1-4}$ hydrocarbon group or a halogeno-$C_{1-4}$ alkyl group.

35. A compound as claimed in claim 34, wherein Ra stands for a halogen, cyano group, nitro group, a $C_{1-8}$ alkanoyl group, a $C_{3-6}$ cycloalkyl-carbonyl group, a benzoyl group, a $C_{1-6}$ alkylsulfinyl group, a $C_{3-6}$ cycloalkylsulfinyl group, a phenylsulfinyl group, a $C_{1-6}$ alkylsulfonyl group, a $C_{3-6}$ cycloalkylsulfonyl group, a phenylsulfonyl group, a $C_{1-4}$ alkoxy group, a halogeno-$C_{1-4}$ alkoxy group, a $C_{1-4}$ alkylthio group, a halogeno-$C_{1-4}$ alkyl group, a $C_{2-4}$ alkynyl group or a $C_{2-4}$ alkenyl group; and Rb stands for H, a halogen, cyano group, nitro group, a $C_{1-8}$ alkanoyl group, a $C_{3-6}$ cycloalkylcarbonyl group, benzoyl group, a $C_{1-6}$ alkylsulfinyl group, a $C_{3-6}$ cycloalkylsulfinyl group, a phenylsulfinyl group, a $C_{1-6}$ alkylsulfonyl group, a $C_{3-6}$ cycloalkylsulfonyl group, a phenylsulfonyl group, an amino group, a $C_{1-4}$ alkylamino group, a $C_{1-4}$ alkoxy group, a $C_{1-4}$ alkylthio group, a halogeno $C_{1-4}$ alkyl group, a $C_{1-4}$ alkyl group, a $C_{2-4}$ alkynyl group or a $C_{2-4}$ alkenyl.

36. A compound as claimed in claim 34, wherein Ra stands for a halogen, cyano group, nitro group, a $C_{1-4}$ alkoxy group, a halogeno-$C_{1-4}$ alkyl group or a $C_{1-4}$ alkyl group; and Rb stands for H, a halogen or a $C_{1-4}$ alkyl group.

37. A compound as claimed in claim 1, which is (Z)-2-(5-chloro-4-fluoro-2-hydroxybenzoyl)-3-hydroxypyridine N-oxide O-t-butyloxime or its salt, (Z)-2-(5-bromo-4-chloro-2-hydroxybenzoyl)-3-hydroxypyridine N-oxide O-t-butyloxime or its salt, (Z)-2-(5-bromo-4-fluoro-2-hydroxybenzoyl)-3-hydroxypyridine N-oxide O-t-butyloxime or its salt, (Z)-2-(5-bromo-4-cyano-2-hydroxybenzoyl)-3-hydroxypyridine O-t-butyloxime or its salt,
(Z)-2-(5-bromo-4-cyano-2-hydroxybenzoyl)-3-hydroxypyridine N-oxide O-t-butyloxime or its salt,
(Z)-2-(5-chloro-4-cyano-2-hydroxybenzoyl)-3-hydroxypyridine N-oxide O-t-butyloxime or its salt,
(Z)-2-(5-cyano-4-chloro-2-hydroxybenzoyl)-3-hydroxypyridine N-oxide O-t-butyloxime or its salt,
(Z)-2-(5-fluoro-4-cyano-2-hydroxybenzoyl)-3-hydroxypyridine N-oxide O-t-butyloxime or its salt,
(Z)-2-(5-cyano-4-fluoro-2-hydroxybenzoyl)-3-hydroxypyridine N-oxide O-t-butyloxime or its salt, or
(Z)-2-(4,5-dicyano-2-hydroxybenzoyl)-3-hydroxypyridine N-oxide O-t-butyloxime or its salt.

38. A compound as claimed in claim 1, which is (Z)-2-(5-chloro-4-fluoro-2-hydroxybenzoyl)-3-acetoxypyridine N-oxide O-t-butyloxime or its salt,
(Z)-2-(5-bromo-4-chloro-2-hydroxybenzoyl)-3-acetoxypyridine N-oxide O-t-butyloxime or its salt,
(Z)-2-(5-bromo-4-fluoro-2-hydroxybenzoyl)-3-acetoxypyridine N-oxide O-t-butyloxime or its salt,
(Z)-2-(5-bromo-4-cyano-2-hydroxybenzoyl)-3-acetoxypyridine O-t-butyloxime or its salt,
(Z)-2-(5-bromo-4-cyano-2-hydroxybenzoyl)-3-acetoxypyridine N-oxide O-t-butyloxime or its salt,
(Z)-2-(5-chloro-4-cyano-2-hydroxybenzoyl)-3-acetoxypyridine N-oxide O-t-butyloxime or its salt,
(Z)-2-(5-cyano-4-chloro-2-hydroxybenoyl)-3-acetoxypyridine N-oxide O-t-butyloxime or its salt,
(Z)-2-(5-fluoro-4-cyano-2-hydroxybenzoyl)-3-acetoxypyridine N-oxide O-t-butyloxime or its salt,
(Z)-2-(5-cyano-4-fluoro-2-hydroxybenzoyl)-3-acetoxypyridine N-oxide O-t-butyloxime or its salt, or
(Z)-2-(4,5-dicyano-2-hydroxybenzoyl)-3-acetoxypyridine N-oxide O-t-butyloxime or its salt.

39. A compound as claimed in claim 1, which is (Z)-2-(5-chloro-4-fluoro-2-hydroxybenzoyl)-3-pivaloyloxypyridine N-oxide O-t-butyloxime or its salt,
(Z)-2-(5-bromo-4-chloro-2-hydroxybenzoyl)-3-pivaloyloxypyridine N-oxide O-t-butyloxime or its salt,
(Z)-2-(5-bromo-4-fluoro-2-hydroxybenzoyl)-3-pivaloyloxypyridine N-oxide O-t-butyloxime or its salt,
(Z)-2-(5-bromo-4-cyano-2-hydroxybenzoyl)-3-pivaloyloxypyridine O-t-butyloxime or its salt,
(Z)-2-(5-bromo-4-cyano-2-hydroxybenzoyl)-3-pivaloyloxypyridine N-oxide O-t-butyloxime or its salt,
(Z)-2-(5-chloro-4-cyano-2-hydroxybenzoyl)-3-pivaloyloxypyridine N-oxide O-t-butyloxime or its salt,
(Z)-2-(5-cyano-4-chloro-2-hydroxybenzoyl)-3-pivaloyloxypyridine N-oxide O-t-butyloxime or its salt,
(Z)-2-(5-fluoro-4-cyano-2-hydroxybenzoyl)-3-pivaloyloxypyridine N-oxide O-t-butyloxime or its salt,
(Z)-2-(5-cyano-4-fluoro-2-hydroxybenzoyl)-3-pivaloyloxypyridine N-oxide O-t-butyloxime or its salt, or
(Z)-2-(4,5-dicyano-2-hydroxybenzoyl)-3-pivaloyloxypyridine N-oxide O-t-butyloxime or its salt.

40. A compound as claimed in claim 1, said compound being (Z)-2-(5-bromo-4-fluoro-2-hydroxybenzoyl)-3-hydroxypyridine-N-oxide-O-t-butyloxime or its pharmaceutically acceptable salt.

* * * * *